(12) United States Patent
Glass et al.

(10) Patent No.: US 9,139,631 B2
(45) Date of Patent: Sep. 22, 2015

(54) METHODS AND COMPOSITIONS USING FGF23 VARIANT POLYPEPTIDES WITH REDUCED AGGREGATION AND CLEAVAGE

(71) Applicant: NOVARTIS AG, Basel (CH)

(72) Inventors: David Glass, Cambridge, MA (US); Shou-Ih Hu, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 13/743,770

(22) Filed: Jan. 17, 2013

(65) Prior Publication Data

US 2013/0122004 A1    May 16, 2013

Related U.S. Application Data

(62) Division of application No. 13/015,159, filed on Jan. 27, 2011, now abandoned.

(51) Int. Cl.
*A61K 38/18* (2006.01)
*C07K 14/50* (2006.01)
*A61K 38/00* (2006.01)

(52) U.S. Cl.
CPC .............. *C07K 14/50* (2013.01); *A61K 38/1825* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,408,038 A | 4/1995 | Smith et al. | |
| 5,541,094 A | 7/1996 | Anton et al. | |
| 7,060,479 B2 | 6/2006 | Dumas Milne Edwards et al. | |
| 7,217,798 B2 | 5/2007 | Hinton et al. | |
| 7,223,563 B2 | 5/2007 | Econs et al. | |
| 7,259,248 B2 | 8/2007 | Itoh et al. | |
| 7,745,406 B2 | 6/2010 | Econs et al. | |
| 2006/0160181 A1 | 7/2006 | Luethy et al. | |
| 2006/0281679 A1 | 12/2006 | Itoh et al. | |
| 2010/0298220 A1 | 11/2010 | Blaber et al. | |
| 2011/0195895 A1* | 8/2011 | Walker et al. | 514/4.8 |
| 2014/0323396 A1* | 10/2014 | Belouski et al. | 514/5.1 |

OTHER PUBLICATIONS

Goetz et al. (Mol. Cell. Biol. 27(9): 3417-3428, 2007).*
Beenken et al. (Adv. Exp. Med. Biol. 728: 1-24, 2012).*
Goetz et al.; "Molecular Insights into the Klotho-Dependent, Endocrine Mode of Action of Fibroblast Growth Factor 19 Subfamily Members"; Molecular and Cellular Biology; 27(9):3417-3428 (2007).
Hessell et al.; "Fc receptor but not complement binding is important in antibody protection against HIV"; Nature—Letters; 449:101-105 (2007).
Kurosu et al.; "Regulation of Fibroblast Growth Factor-23 Signaling by Klotho"; The Journal of Biological Chemistry; 281(10):6120-6123 (2006).
Lode et al.; "Gene therapy with a single chain interleukin 12 fusion protein induces T cell-dependent protective immunity in a syngeneic model of murine neuroblastoma"; Proc. Natl. Acad. Sci. USA; 95:2475-2480 (1998).
Ray; "Klotho Gets Around"; Science STKE; 2006(365):tw416 (2006)[Abstract].
Razzaque; "Therapeutic potential of klotho—FGF23 fusion polypeptides: WO2009095372"; Expert Opin. Ther. Patents; 20(6):1-5 (2010).
Tohyama et al.; "Klotho Is a Novel Beta-Glucuronidase Capable of Hydrolyzing Steroid Beta-Glucuronides"; The Journal of Biological Chemistry; 279(11):9777-9784 (2004).
Torres et al.; "Klotho: An antiaging protein involved in mineral and vitamin D metabolism"; Kidney International; 71:730-737 (2007).
Urakawa et al.; "Klotho converts canonical FGF receptor into a specific receptor for FGF23"; Nature—Letters; 444:770-774 (2006).
Wu et al.; "Co-receptor Requirements for Fibroblast Growth Factor-19 Signaling"; The Journal of Biological Chemistry; 282(40):29069-29072 (2007).
The ADHR Consortium; "Autosomal dominant hypophosphataemic rickets is associated with mutations in FGF23"; Nature Genetics; 26:345-348 (2000).
Bai et al.; "The Autosomal Dominant Hypophosphatemic Rickets R176Q Mutation in Fibroblast Growth Factor 23 Resists Proteolytic Cleavage and Enhances in Vivo Biological Potency"; The Journal of Biological Chemistry; 278(11):9843-9849 (2003).
Bai et al.; "Transgenic Mice Overexpressing Human Fibroblast Growth Factor 23 (R176Q) Delineate a Putative Role for Parathyroid Hormone in Renal Phosphate Wasting Disorders"; Endocrinology; 145(11):5269-5279 (2004).
Bai et al.; "Klotho ablation converts the biochemical and skeletal alterations in FGF23 (R176Q) transgenic mice to a Klotho-deficient phenotype"; Am. J. Physiol. Endocrinol. Metab.; 296:E79-E88 (2009).

(Continued)

*Primary Examiner* — Christine J Saoud
(74) *Attorney, Agent, or Firm* — Frank Wu

(57) ABSTRACT

The present disclosure is directed to methods, kits and compositions for preventing or treating age-related conditions or metabolic disorders. The fusion polypeptides of the disclosure include FGF23 or an active fragment thereof. In one embodiment, the fusion polypeptide comprises (a) a polypeptide comprising fibroblast growth factor 23 (FGF23), or a functionally active variant or derivative thereof, wherein FGF23 has a mutation at one or more of the positions Q156, C206 and C244; and (b) either a modified Fc fragment having decreased affinity for Fc-gamma-receptor and/or increased serum half-life, or a polypeptide comprising at least one extracellular subdomain of a Klotho protein, or a functionally active variant or derivative thereof; and, optionally (c) a linker. In another embodiment, the fusion polypeptide comprises a FGF (such as FGF23), or a functionally active variant or derivative thereof; and a modified Fc fragment, or a functionally active variant or derivative thereof. In various embodiments of the fusion polypeptides, FGF23 has mutations which decrease aggregation and protease-mediated cleavage.

8 Claims, 30 Drawing Sheets

(56) References Cited

OTHER PUBLICATIONS

Ben-Dov et al.; "The parathyroid is a target organ for FGF23 in rats"; The Journal of Clinical Investigation—Research Article; 117(12):4003-4008 (2007).

Berndt et al.; "Biological activity of FGF-23 fragments"; Pflugers Arch—Eur. J. Physiol.; 454:615-623 (2007).

Carpenter et al.; "Circulating Levels of Soluble Klotho and FGF23 in X-Linked Hypophosphatemia: Circadian Variance, Effects of Treatment, and Relationship to Parathyroid Status"; J. Clin. Endocrinol. Metab.; 95:E352-E357 (2010).

Drueke et al.; "Klotho spins the thread of life-what does Klotho do to the receptors of fibroblast growth factor-23 (FGF23)?"; Nephrol Dial. Transplant.; 22:1524-1526 (2007).

Kuro-O; "Overview of the FGF23-Klotho axis"; Pediatr. Nephrol.; 25:583-590 (2010).

Shimada et al.; "Mutant FGF-23 responsible for autosomal dominant hypophosphatemic rickets is resistant to proteolytic cleavage and causes hypophosphatemia in vivo"; Endocrinology; 143(8):3179-3182 (2002).

Strewler; "FGF23, hypophosphatemia, and rickets: Has phosphatonin been found?"; PNAS—Commentary; 98(11):5945-5946 (2001).

Urakawa et al; "Klotho converts canonical FGF receptor into a specific receptor for FGF23"; Nature; 444:770-774 (2006)[Supplemental Data List; Supplemental Figures 1-6; Supplemental Discussion; Supplemental Methods and Supplemental Table].

White et al.; "Autosomal-dominant hypophosphatemic rickets (ADHR) mutations stabilize FGF-23"; Kidney International; 60:2079-2086 (2001).

Yu et al.; "FGF23 and disorders of phosphate homeostasis"; Cytokine & Growth Factor Reviews; 16:221-232 (2005).

\* cited by examiner

▨ : Klotho (extracellular domain) or active fragment of Klotho;

▨ : FGF23 (R179Q), FGF23, FGF 19, FGF21; ▨ : linker; ▯ : IgG signal peptide.

Figure 2

Human Klotho nucleic acid sequence (NM_004795) (SEQ ID NO: 1)
Protein coding region: 9-3047

```
   1 cgcgcagcat gccgccagc gcccgccgc gccgccgcg gccgccgccg ccgtcgctgt
  61 cgctgctgct ggtgctgctg ggctgggcg gccgccgcct gcgtgcggag ccgggcgacg
 121 gcgcgcagac ctgggccgt ttctcgcgg ctcctgccc cgaggccgcg ggctcttcc
 181 agggcaactt ccccgacgg ttcctctggg ccgtgggcag cgccgcctac cagacggagg
 241 gcggctggca gcagcacggc aagggtgcgt ccatctggga tacgttcacc caccacccc
 301 tggcacccc gggagactcc cggaacgcca gtctgcggtt gggcgcccg tgccgctgc
 361 agccgccac cggggacgta gccagcgaca gctacaacaa cgtcttccgc gacacggagg
 421 cgctgcgcga gctcggggtc actcactacc gcttctccat ctcgtgggcg cgagtgctcc
 481 ccaatggcag cgcagggtc cccaaccgag aggggtgcg ctactacgg cgcctgctgg
 541 agcggctgcg ggagctgggc gtgcagccg tggtcacct gtaccactgg gacctgccc
 601 agcgcctgca ggacgcctac ggcggctggg ccaaccgcgc cctggccgac acttcaggg
 661 attacgcgga gctctgcttc cgccacttcg gcggtcaggt caagtactgg atcaccatcg
 721 acaaccccta cgtggtggcc tggcacggct acgccacggg gcgcctggcc ccggcatcc
 781 ggggcagccc gcggctcggg tacctggtgg cgcacaacct cctcctggct catgccaaag
 841 tctggcatct ctacaatact tctttccgtc ccactcaggg aggtcaggtg tccattgcc
 901 taagctctca ctggatcaat cctcgaagaa tgaccgacca cagcatcaaa gaatgtcaaa
 961 aatctctgga ctttgtacta ggttggttg ccaacccgt atttattgat ggtgactatc
1021 ccgagagcat gaagaataac ctttcatcta tctgcctga ttttactgaa tctgagaaaa
1081 agttcatcaa aggaactgct gacttttg ctctttgctt tggacccacc ttgagttttc
1141 aacttttgga ccctcacatg aagttccgcc aattggaatc tccaacctg aggcaactgc
1201 tttcctggat tgaccttgaa tttaaccatc ctcaaatatt tattgtggaa aatggctggt
1261 ttgtctcagg gaccaccaag agagatgatg ccaaatatat gtattaccctc aaaagttca
1321 tcatggaaac cttaaaagcc atcaagctgg atgggtgga tgtcatcggg tataccgcat
1381 ggtcctcat ggatggttc gagtggcaca gaggttacag catcaggcgt ggactcttct
1441 atgttgactt tctaagccag gacaagatgt tgttgccaaa gtcttcagcc ttgttctacc
1501 aaaagctgat agagaaaaat ggcttccctc ctttacctga aaatcagccc tagaaggga
1561 catttccctg tgactttgct tggggagttg ttgacaacta cattcaagta gataccactc
1621 tgtctcagtt taccgacctg aattgttacc tgtgggatgt ccaacacagt aaaaggctta
1681 ttaaagtgga tggggtgtg accaagaaga ggaaatccta ctgtgttgac tttgctgcca
1741 tccagcccca gatcgcttta ctccaggaaa tgcacgttac acattttgc ttctcctgg
1801 actgggcct gattctccct ctgggtaacc agtccaggt gaaccacacc atcctgcagt
1861 actatcgctg catggccagc gagcttgtcc gtgtcaacat cacccagtg gtggcctgt
1921 ggcagcctat ggccccgaac caaggactgc cgcgcctct ggccaggcag ggcgctggg
1981 agaaccccta cactgccctg cctttgcag agtatgccg actgtgcttt caagagctcg
2041 gccatcacgt caagctttgg ataacgatga atgagccgta taacaggaat atgcatacaa
2101 gtgctggcca caacctctgt aaggccatg cctggcttg catgtgtac aatgaaaagt
2161 ttaggcatgc tcagaatggg aaaatatcca tagccttgca ggctgattgg atagaacctg
2221 cctgccttt ctcccaaaag gacaaagagg tggcgagag agttttggaa tttgacattg
2281 gctggtggc tgagccatt ttcggctctg gagattatcc atgggtgatg agggactggc
2341 tgaaccaaag aaacaatttt cttcttcctt atttcactga agatgaaaaa agctaatcc
2401 agggtacctt tgacttttg gcttaagcc attataccac catccttgta gactcagaaa
2461 aagaagatcc aataaaatac aatgattacc tagaagtgca agaaatgacc gacatcacgt
2521 ggctcaactc ccccagtcag gtggcggtag tgccctgggg gttgcgcaaa gtgctgaact
2581 ggctgaagtt caagtacgga gacctcccca tgtacataat atccaacgga atcgatgacg
2641 ggctgcatgc tgaggacgac cagctgaggg tgtattatat gcagaattac ataaacgaag
2701 ctctcaaagc ccacatactg gatggtatca atctttgcgg atacttcgct tattcgttta
2761 acgacgcac agctccgagg tttggcctct atgttatgc tgcagatcag ttgagccca
2821 aggcatccat gaaacattaa aggaaaatta ttgacagcaa tggtttcccg ggccagaaa
2881 ctctggaaag attttgtcca gaagaattca ccgtgtgtac tgagtgcagt ttttttcaca
2941 cccgaaagtc tttactggct tcatagctt ttctatttt tgcttctatt atttctctct
3001 cccttatatt ttactactcg aagaaaggca gaagaagtta caaatagttc tgaacatttt
```

Figure 2 (continued)

```
3061 tctattcatt cattttgaaa taattatgca gacacatcag ctgttaacca tttgcacctc
3121 taagtgttgt gaaactgtaa attcataca tttgacttct agaaaacatt tttgtggctt
3181 atgacagagg ttttgaaatg ggcataggtg atcgtaaaat attgaataat gcgaatagtg
3241 cctgaatttg ttctctttt gggtgattaa aaaactgaca ggcactataa ttctgtaac
3301 acactaacaa aagcatgaaa ataggaacc acaccaatgc aacatttgtg cagaaatttg
3361 aatgacaaga ttaggaatat ttcttctgc acccacttct aaatttaatg ttttctgga
3421 agtagtaatt gcaagagttc gaatagaaag ttatgtacca agtaaccatt tctcagctgc
3481 cataataatg cctagtggct tccctctgt caaatctagt ttcctatgga aaagaagatg
3541 gcagatacag gagagacgac agagggtcct aggctggaat gttcctttcg aaagcaatgc
3601 ttctatcaaa tactagtatt aatttatgta tctggttaat gacatacttg gagagcaaat
3661 tatggaaatg tgtatttat atgattttg aggtcctgtc taaaccctgt gtcctgagg
3721 gatctgtctc actggcatct tgttgagggc cttgcacata ggaaactttt gataagtatc
3781 tgcggaaaaa caaacatgaa tcctctgata ttggctctt caggaagcat aaagcaattg
3841 tgaaatacag tataccgcag tggctctagg tggaggaaag gaggaaaaag tgcttattat
3901 gtgcaacatt atgattaatc tgattataca ccatttttga gcagatcttg gaatgaatga
3961 catgaccttt ccctagagaa taaggatgaa ataatcactc attctatgaa cagtgacact
4021 actttctatt ctttagctgt actgtaattt ctttgagttg atagtttac aaattcttaa
4081 taggttcaaa agcaatctgg tctgaataac actggatttg tttctgtgat ctctgaggtc
4141 tatttatgt ttttgctgct acttctgtg aagtagcttt gaactagttt tactttgaac
4201 tttcacgctg aaacatgcta gtgatatcta gaaagggcta attaggtctc atcctttaat
4261 gcccttaaa taagtcttgc tgattttcag acagggaagt ctctctatta cactggagct
4321 gttttataga taagtcaata ttgtatcagg caagataaac caatgtcata acaggcattg
4381 ccaacctcac tgacacaggg tcatagtgta taataatata ctgtactata taatatatca
4441 tctttagagg tatgatttt tcatgaaaga taagcttttg gtaatattca ttttaaagtg
4501 gacttattaa aattggatgc tagagaatca agtttatttt atgtatatat tttctgatt
4561 ataagagtaa tatatgttca ttgtaaaaat ttttaaaaca cagaaactat atgcaaagaa
4621 aaaataaaaa ttatctataa tctcagaacc cagaaatagc cactattaac atttcctacg
4681 tatttattt tacatagatc atattgtata tagttagtat cttattaat ttttattatg
4741 aaactttcct ttgtcattat tagtcttcaa aagcatgatt tttaatagtt gttgagtatt
4801 ccaccacagg aatgtatcac aacttaaccg ttcccgtttg ttagactagt ttcttattaa
4861 tgttgatgaa tgttgtttaa aaataatttt gttgctacat ttactttaat ttccttgact
4921 gtaaagagaa gtaattttgc tccttgataa agtattatat taataataaa tctgcctgca
4981 acttttgcc ttctttcata atc
```

Klotho amino acid sequence (NP_004786) (SEQ ID NO: 2)

```
  1 MPASAPPRRP RPPPPSLSLL LVLLGLGGRR LRAEPGDGAQ TWARFSRPPA PEAAGLFQGT
 61 FPDGFLWAVG SAAYQTEGGW QQHGKGASIW DTFTHHPLAP PGDSRNASLP LGAPSPLQPA
121 TGDVASDSYN NVFRDTEALR ELGVTHYRFS ISWARVLPNG SAGVPNREGL RYYRRLLERL
181 RELGVQPVVT LYHWDLPQRL QDAYGGWANR ALADHFRDYA ELCFRHFGGQ VKYWITIDNP
241 YVVAWHGYAT GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP DFTESEKKFI
361 KGTADFFALC FGPTLSFQLL DPHMKFRQLE SPNLRQLLSW IDLEFNHPQI FIVENGWFVS
421 GTTKRDDAKY MYYLKKFIME TLKAIKLDGV DVIGYTAWSL MDGFEWHRGY SIRRGLFYVD
481 FLSQDKMLLP KSSALFYQKL IEKNGFPPLP ENQPLEGTFP CDFAWGVVDN YIQVDTTLSQ
541 FTDLNVYLWD VHHSKRLIKV DGVVTKKRKS YCVDFAAIQP QIALLQEMHV THFRFSLDWA
601 LILPLGNQSQ VNHTILQYYR CMASELVRVN ITPVVALWQP MAPNQGLPRL LARQGAWENP
661 YTALAFAEYA RLCFQELGHH VKLWITMNEP YTRNMTYSAG HNLLKAHALA WHVYNEKFRH
721 AQNGKISIAL QADWIEPACP FSQKDKEVAE RVLEFDIGWL AEPIFGSGDY PWVMRDWLNQ
781 RNNFLLPYFT EDEKKLIQGT FDFLALSHYT TILVDSEKED PIKYNDYLEV QEMTDITWLN
841 SPSQVAVVPW GLRKVLNWLK FKYGDLPMYI ISNGIDDGLH AEDDQLRVYY MQNYINEALK
901 AHILDGINLC GYFAYSFNDR TAPRFGLYRY AADQFEPKAS MKHYRKIIDS NGFPGPETLE
961 RFCPEEFTVC TECSFFHTRK SLLAFIAFLF FASIISLSLI FYYSKKGRRS YK
```

Figure 2 (continued)

beta-Klotho nucleic acid sequence (NM_175737) (SEQ ID NO: 3)
Protein coding region: 98-3232

```
   1 atcctcagtc tcccagttca agctaatcat tgacagagct ttacaatcac aagcttttac
  61 tgaagctttg ataagacagt ccagcagttg gtggcaaatg aagccaggct gtgcggcagg
 121 atctccaggg aatgaatgga tttcttcag cactgatgaa ataaccacac gctataggaa
 181 tacaatgtcc aacggggat tgcaaagatc tgtcatcctg tcagcactta ttctgctacg
 241 agctgttact ggattctctg gagatggaag agctatatgg tctaaaaatc ctaattttac
 301 tccggtaaat gaaagtcagc tgtttctcta tgacactttc cctaaaaact ttttctgggg
 361 tattgggact ggagcattgc aagtggaagg gagttggaag aaggatggaa aaggacctto
 421 tatatgggat cattttcatcc acacacacct taaaaatgtc agcagcacga atggttccag
 481 tgacagttat atttttctgg aaaaagactt atcagccctg gatttatag gagtttcttt
 541 ttatcaattt tcaatttcct ggccaaggct tttcccgat ggaatagtaa cagttgccaa
 601 cgcaaaaggt ctgcagtact acagtactct tctggacgct ctagtgctta gaaacattga
 661 acctatagtt actttataccc actgggattt gctttggca ctacaagaaa atatgggggg
 721 gtggaaaaat gataccataa tagatatctt caatgactat gccacatact gttccagat
 781 gtttgggac cgtgtcaaat attggattac aattcacaac ccatatctag tggcttggca
 841 tggtatggg acaggtatgc atgcccctgg agagaaggga aatttagcag ctgtctacac
 901 tgtgggacac aactgatca aggctcactc gaaagtttgg catactaca acacacattt
 961 ccgcccacat cagaagggtt ggttatcgat cacgttggga tctcattgga tcgagccaaa
1021 ccggtcggaa aacacgatgg atatattcaa atgtcaacaa tccatggttt ctgtgcttgg
1081 atggtttgcc aaccctatcc atgggdatgc cgactatcca gaggggatga gaaagaagtt
1141 gttctccgtt ctacccattt tctctgaagc agagaagcat gagatgagag gcacagctga
1201 tttctttgcc ttttcttttg gacccaacaa cttcaagccc ctaaacacca tggctaaaat
1261 gggacaaaat gtttcactta atttaagaga agcgctgaac tggattaaac tggaataacaa
1321 caaccctcga atcttgattg ctgagaatgg ctggttcaca gacagtcgtg tgaaaacaga
1381 agacaccacg gccatctaca tgatgaagaa tttcctcagc caggtgcttc aagcaataag
1441 gttagatgaa atacgagtgt ttggttatac tgcctggtct ctcctggatg gctttgaatg
1501 gcaggatgct tacaccatcc gccgaggatt attttatgtg gatttttaaca gtaaacagaa
1561 agagcggaaa cctaagtctt cagcacacta ctacaaacag atcatacgag aaaatggttt
1621 ttcttaaaa gagtccacgc cagatgtgca gggccagttt ccctgtgact tctcctgggg
1681 tgtcactgaa tctgttctta agcccgagtc tgtggcttcg tcccacagt tcagcgatcc
1741 tcatctgtac gtgtggaacg ccactggcaa cagactgttg cacgagtgg aagggtgag
1801 gctgaaaaca cgaccgctc aatgcacaga ttttgtaaac atcaaaaaac aacttgagat
1861 gttggcaaga atgaaagtca cccactaccg gtttgctctg gattggcct cggtccttcc
1921 cactggcaac ctgtccgcgg tgaacgaca ggcctgagg tactacaggt gcgtggtcag
1981 tgaggggctg aagcttggca tctccgcgat ggtcacctg tattatccga cccacgccca
2041 cctaggccte cccgagcctc tgttgcatgc cgacgggcct ctgaaccaat cgacggccga
2101 ggcttccag gctacgctg ggctgtgctt ccaggagctg ggggactgg tgaagctctg
2161 gatcaccatc aacgagccta accggctaag tgacatctac aaccgctctg caacgacac
2221 ctacggggcg gcgcacaacc tgctggtggc ccacgcctg gcctggcgc tctacgaccg
2281 gcagttcagg cctcacagc gcgggcggt gtcgtcg ctgcacgcg actgggcgga
2341 accgcgcac ccctatgctg actgcactg gagggcggcc gagcgcttcc tgcagttcga
2401 gatcgctgg ttcgccgagc cgctcttcaa gaccgggac tacccccgg ccatgaggga
2461 atacattgcc tccagcaccc gacggggct ttccagctcg gccctgccgc gcctcaccga
2521 ggccgaaagg aggctgctca aggcacggt cgacttctgc gcgctcaacc acttcaccac
2581 taggttcgtg atgcacgagc agctggccgg cagcggctac gactcggaca gggacatccca
2641 gttttctgcag gacatcaccc gcctgagcte cccaagccgc ctgctgtga ttcctgggg
2701 ggtgcgcaag ctgctgcggt gggtccggag gaactacggc gacatggaca tttacatcac
2761 cgccagtggc atcgacgacc aggtctctga ggatgaccgg ctccggaagt actaccctag
2821 gaagtacctt caggaggtgc tgaaagcata cctgattgat aaagtcagaa tcaaggcta
2881 ttatgcattc aaactggctg aagagaaatc taaacccaga tttggattct tcacatctga
2941 ttttaaagct aaatcctcaa taacttttta caacaaagtg atcagcagca gggcttccc
3001 ttttgagac agtagttcta gatgcagtca gacccaagaa aatacagagt gcactgtctg
3061 cttattcctt gtgcagaaga accactgat attcctgggt gttgcttct tctccaccct
3121 ggttctactc ttatcaattg ccattttca aaggcagaag agaagaaagt ttggaaagc
```

Figure 2 (continued)

```
3181 aaaaaactta caacacatac cattaaagaa aggcaagaga gttgttagct aaactgatct
3241 gtctgcatga tagacagttt aaaaattcat cccagttcc
``` beta-Klotho amino acid sequence (NP_783864) (SEQ ID NO: 4)

```
   1 mkpgcaagsp gnewiffstd eittryrntm sngglqrsvi lsalillrav tgfsgdgrai
  61 wsknpnftpv nesqlflydt fpknffwgig tgalqvegsw kkdgkgpsiw dhfihthlkn
 121 vsstngssds yiflekdlsa ldfigvsfyq fsiswprlfp dgivtvanak glqyystlld
 181 alvlrniepi vtlyhwdlpl alqekyggwk ndtiidifnd yatycfqmfg drvkywitih
 241 npylvawhgy qtgmhapgek gnlaavytvg hnlikahskv whnynthfrp hqkgwlsitl
 301 gshwiepnrs entmdifkcq qsmvsvlgwf anpihgdgdy pegmrkklfs vlpifseaek
 361 hemrgtadff afsfgpnnfk plntmakmgq nvslnlreal nwikleynnp riliaengwf
 421 tdsrvktedt taiymmknfl sqvlqairld eirvfgytaw slldgfewqd aytirrglfy
 481 vdfnskqker kpkssahyyk qiirengfsl kestpdvqgq fpcdfswgvt esvlkpesva
 541 sspqfsdphl yvwnatgnrl lhrvegvrlk trpaqctdfv nikkqlemla rmkvthyrfa
 601 ldwasvlptg nlsavnrqal ryyrcvvseg lklgisamvt lyypthahlg lpepllhadg
 661 wlnpstaeaf qayaglcfqe lgdlvklwit inepnrlsdi ynrsgndtyg aahnllvaha
 721 lawrlydrqf rpsqrgavsl alhadwaepa npyadshwra aerflqfeia wfaeplfktg
 781 dypaamreyi askhrrglss salprlteae rrllkgtvdf calnhfttrf vmheqlagsr
 841 ydsdrdiqfl qditrlsspt rlavipwgvr kllrwvrrny gdmdiyitas giddqaledd
 901 rlrkyylgky lqevlkayli dkvrikgyya fklaeekskp rfgfftsdfk akssiqfynk
 961 vissrgfpfe nssrcsqtq entectvclf lvqkkplifl gccffstlvl llsiaifqrq
1021 krrkfwkakn lqhiplkkgk rvvs
```

Human Klotho domain 1 (KL-D1) amino acid sequence (SEQ ID NO: 5)

```
  58                                                                 qgt
  61 fpdgflwavg saayqteggw qqhgkgasiw dtfthhplap pgdsrnaslp lgapsplqpa
 121 tgdvasdsyn nvfrdtealr elgvthyrfs iswarvlpng sagvpnregl ryyrrllerl
 181 relgvqpvvt lyhwdlpqrl qdayggwanr aladhfrdya elcfrhfggq vkywitidnp
 241 yvvawhgyat grlapgirgs prlgylvahn lllahakvwh lyntsfrptq ggqvsialss
 301 hwinprrmtd hsikecqksl dfvlgwfakp vfldgdypes mknnlssilp dftesekkfi
 361 kgtadffalc fgptlsfqll dphmkfrqle spnlrqllsw idlefnhpqi fivengwfvs
 421 gttkrddaky myylkkfime tlkaikldgv dvigytawsl mdgfewhrgy sirrglfyvd
 481 flsqdkmllp kssalfyqkl iekngf
```

Human Klotho domain 2 (KL-D2) amino acid sequence (SEQ ID NO: 6)

```
 517                                  gt.fp cdfawgvvdn yiqvdttlsq
 541 ftdlnvylwd vhhskrlikv dgvvtkkrks ycvdfaaiqp qiallqemhv thfrfsldwa
 601 lillplgnqsq vnhtilqyyr cmaselvrvn itpvvalwqp mapnqgiprl larqgawenp
 661 ytalafaeya rlcfqelghh vklwitmnep ytrnmtysag hnllkahala whvynekfrh
 721 aqngkisial qadwiepacp fsqkdkevae rvlefdigwl aepifgsgdy pwvmrdwlnq
 781 rnnfllpyft edekkliqgt fdflalshyt tilvdseked pikyndylev qemtditwln
 841 spsqvavvpw glrkvlnwlk fkygdlpmyi isngiddglh aeddqlrvyy mqnyinealk
 901 ahildginlc gyfaysfndr taprfglyry aadqfepkas mkhyrkiids ngf
```

Klotho extracellular domain (without signal peptide) amino acid sequence (SEQ ID NO: 7)

```
  28                                     epgdgaq twarfsrppa peaaglfqgt
  61 fpdgflwavg saayqteggw qqhgkgasiw dtfthhplap pgdsrnaslp lgapsplqpa
 121 tgdvasdsyn nvfrdtealr elgvthyrfs iswarvlpng sagvpnregl ryyrrllerl
 181 relgvqpvvt lyhwdlpqrl qdayggwanr aladhfrdya elcfrhfggq vkywitidnp
```

Figure 2 (continued)

```
241 yvvawhgyat grlapgirgs prlgylvahn lllahakvwh lyntsfrptq ggqvsialss
301 hwinprrmtd hsikecqksl dfvlgwfakp vfidgdypes mknnlssilp dftesekkfi
361 kgtadffalc fgptlsfqll dphmkfrqle spnlrqllsw idlefnhpqi fivengwfvs
421 gttkrddaky myylkkfime tlkaikldgv dvigytawsl mdgfewhrgy sirrglfyvd
481 flsqdkmilp kssalfyqkl iekngfpplp enqplegtfp cdfawgvvdn yiqvdttlsq
541 ftdlnvylwd vhhskrlikv dgvvtkkrks ycvdfaaiqp qiallqemhv thfrfsldwa
601 lilplgnqsq vnhtilqyyr cmaselvrvn itpvvalwqp mapnqglprl larqgawenp
661 ytalafaeya rlcfqelghh vklwitmnep ytrnmtysaq hollkahala whvynekfrh
721 aqngkisial qadwiepacp fsqkdkevae rvlefdigwl aepifgsgdy pwvmrdwlnq
781 rnnfllpyft edekkliqgt fdflalshyt tilvdseked pikyndylev qemtditwln
841 spsqvavvpw glrkvlnwlk fkygdlpmyi isngiddglh aeddqlrvyy mqnyinealk
901 ahildginlc qyfaysfndr taprfglyry aadqfepkas mkhyrkiids ngfpgpetle
961 rfcpeeftvc tecsffhtrk sl
```

Klotho signal peptide amino acid sequence (SEQ ID NO: 8)

```
1 mpasapprrp rppppslsll lvllglggrr lra
```

IgG signal peptide amino acid sequence (SEQ ID NO: 9)

```
1 msvltqvlal lllwltgtrc rrlra
```

(Gly₄ Ser)₃ polypeptide linker nucleic acid sequence (SEQ ID NO: 10)

```
1 ggaggtggag gttcaggagg tggaggttca ggaggtggag gttca
```

(Gly₄ Ser)₃ polypeptide linker amino acid sequence (SEQ ID NO: 11)

```
1 GGGGSGGGGS GGGGS
```

(Gly₄ Ser) polypeptide linker amino acid sequence (SEQ ID NO: 12)

```
1 GGGGS
```

(Gly) polypeptide linker amino acid sequence (SEQ ID NO: 13)

```
1 G
```

(Gly Gly) polypeptide linker amino acid sequence (SEQ ID NO: 14)

```
1 GG
```

(Gly Ser) polypeptide linker amino acid sequence (SEQ ID NO: 15)

```
1 GS
```

(Gly₂ Ser) polypeptide linker amino acid sequence (SEQ ID NO: 16)

```
1 GGS
```

Figure 2 (continued)

(Ala) polypeptide linker amino acid sequence (SEQ ID NO: 17)

```
1 A
```

(Ala Ala) polypeptide linker amino acid sequence (SEQ ID NO: 18)

```
1 AA
```

Klotho signal peptide-Klotho extracellular domain-FGF23 (R179Q) amino acid sequence (SEQ ID NO: 19)

```
   1 MPASAPPRRP RPPPPSLSLL LVLLGLGGRR LRAEPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGTFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFTVC TECSFFHTRK SLGSGGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTRSAED DSERDPLNVL KPRARMTPAP ASCSQELPSA EDNSPMASDP
1201 LGVVRGGRVN THAGGTGPEG CRPFAKFI*
```

IgG signal peptide-Klotho extracellular domain-FGF23 (R179Q) amino acid sequence (SEQ ID NO: 20)

```
  1 MSVLTQVLAL LLLWLTGLGG RRLRAEPGDG AQTWARFSRP PAPEAAGLFQ
 51 GTFPDGFLWA VGSAAYQTEG GWQQHGKGAS IWDTFTHHPL APPGDSRNAS
101 LPLGAPSPLQ PATGDVASDS YNNVFRDTEA LRELGVTHYR FSISWARVLP
151 NGSAGVPNRE GLRYYRRLLE RLRELGVQPV VTLYHWDLPQ RLQDAYGGWA
201 NRALADHFRD YAELCFRHFG GQVKYWITID NPYVVAWHGY ATGRLAPGIR
251 GSPRLGYLVA HNLLLAHAKV WHLYNTSFRP TQGGQVSIAL SSHWINPRRM
301 TDHSIKECQK SLDFVLGWFA KPVFIDGDYP ESMKNNLSSI LPDFTESEKK
351 FIKGTADFFA LCFGPTLSFQ LLDPHMKFRQ LESPNLRQLL SWIDLEFNHP
401 QIFIVENGWF VSGTTKRDDA KYMYYLKKFI METLKAIKLD GVDVIGYTAW
451 SLMDGFEWHR GYSIRRGLFY VDFLSQDKML LPKSSALFYQ KLIEKNGFPP
501 LPENQPLEGT FPCDFAWGVV DNYIQVDTTL SQFTDLNVYL WDVHHSKRLI
551 KVDGVVTKKR KSYCVDFAAI QPQIALLQEM HVTHFRFSLD WALILPLGNQ
```

Figure 2 (continued)

```
 601 SQVNHTILQY YRCMASELVR VNITPVVALW QPMAPNQGLP RLLARQGAWE
 651 NPYTALAFAE YARLCFQELG HHVKLWITMN EPYTRNMTYS AGHNLLKAHA
 701 LAWHVYNEKF RHAQNGKISI ALQADWIEPA CPFSQKDKEV AERVLEFDIG
 751 WLAEPIFGSG DYPWVMRDWL NQRNNFLLPY FTEDEKKLIQ GTFDFLALSH
 801 YTTILVDSEK EDPIKYNDYL EVQEMTDITW LNSPSQVAVV PWGLRKVLNW
 851 LKFKYGDLPM YIISNGIDDG LHAEDDQLRV YYMQNYINEA LKAHILDGIN
 901 LCGYFAYSFN DRTAPRFGLY RYAADQFEPK ASMKHYRKII DSNGFPGPET
 951 LERFCPEEFT VCTECSFFHT RKSLGSGGGG SGGGGSGGGG SLKYPNASPL
1001 LGSSWGGLIH LYTATARNSY HLQIHKNGHV DGAPHQTIYS ALMIRSEDAG
1051 FVVITCVMSR RYLCMDFRGN IFCSHYFDPE NCRFQHQTLE NGYDVYHSPQ
1101 YHFLVSLGRA KRAFLPGMNP PPYSQFLSRR NEIPLIHFNT PIPRRHTQSA
1151 EDDSERDPLN VLKPRARMTP APASCSQELP SAEDNSPMAS DPLGVVRGGR
1201 VNTHAGGTGP EGCRPFAKFI *
```

KL-D1-FGF23 (R179Q) amino acid sequence (SEQ ID NO: 21)

```
   1 MPASAPPRRP RPPPPSLSLL LVLLGLGGRR LRAEPGDGAQ TWARFSRPPA
  51 PEAAGLFQGT FPDGFLWAVG SAAYQTEGGW QQHGKGASIW DTFTHHFLAP
 101 PGDSRNASLP LGAPSPLQPA TGDVASDSYN NVFRDTEALR ELGVTHYRFS
 151 ISWAPVLPNG SAGVPNREGL RYYRRLLERL RELGVQPVVT LYHWDLPQRL
 201 QDAYGGWANR ALADHFRDYA ELCFRHFGGV VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFHGY VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGSGG GGSGGGGSGG GGSLKYPNAS PLLGSSWGGL
 551 IHLYTATARN SYHLQIHKNG HVDGAPHQTI YSALMIRSED AGFVVITGVM
 601 SRRYLCMDFR GNIFGSHYFD PENCRFQHQT LENGYDVYHS PQYHFLVSLG
 651 RAKRAFLPGM NPPPYSQFLS RRNEIPLIHF NTPIPRRHTQ SAEDDSERDP
 701 LNVLKPRARM TPAPASCSQE LPSAEDNSPM ASDPLGVVRG GRVNTHAGGT
 751 GPEGCRPFAK FI*
```

KL-D2-FGF23 (R179Q) amino acid sequence (SEQ ID NO: 22)

```
   1 MPASAPPRRP RPPPPSLSLL LVLLGLGGRR LPLPENQPLE GTFPCDFAWG
  51 VVDNYIQVDT TLSQFTDLNV YLWDVHHSKR LIKVDGVVTK KRKSYCVDFA
 101 AIQPQIALLQ EMHVTHFRFS LDWALILPLG NQSQVNHTIL QYYRCMASEL
 151 VRVNITPVVA LWQPMAPNQG LPRLLARQGA WENPYTALAF AEYARLCFQE
 201 LGHHVKLWIT MNEPYTRNMT YSAGHNLLKA HALAWHVYNE KFRHAQNGKI
 251 SIALQADWIE PACPFSQKDK EVAERVLEFD IGWLAEPIFG SGDYPWVMRD
 301 WLNQRNNFLL PYFTEDEKKL IQGTFDFLAL SHYTTILVDS EKEDPIKYND
 351 YLEVQEMTDI TWLNSPSQVA VVPWGLRKVL NWLKFKYGDL PMYIISNGID
 401 DGLHAEDDQL RVYYMQNYIN EALKAHILDG INLCGYFAYS FNDRTAPRFG
 451 LYRYAADQFE PKASMKHYRK IIDSNGFPGP ETLERFCPEE FTVCTECSFF
 501 HTRKSLGSGG GGSGGGGSGG GGSLKYPNAS PLLGSSWGGL IHLYTATARN
 551 SYHLQIHKNG HVDGAPHQTI YSALMIRSED AGFVVITGVM SRRYLCMDFR
 601 GNIFGSHYFD PENCRFQHQT LENGYDVYHS PQYHFLVSLG RAKRAFLPGM
 651 NPPPYSQFLS RRNEIPLIHF NTPIPRRHTQ SAEDDSERDP LNVLKPRARM
 701 TPAPASCSQE LPSAEDNSPM ASDPLGVVRG GRVNTHAGGT GPEGCRPFAK
 751 FI*
```

(KL-D1)₂-FGF23 (R179Q) amino acid sequence (SEQ ID NO: 23)

```
   1 MPASAPPRRP RPPPPSLSLL LVLLGLGGRR LRAEPGDGAQ TWARFSRPPA
```

Figure 2 (continued)

```
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQKL
 501 IEKNGFPPLP ENQPLEGSGT FPDGFLWAVG SAAYQTEGGW QQHGKGASIW
 551 DTFTHHPLAP PGDSRNASLP LGAPSPLQPA TGDVASDSYN NVFRDTEALR
 601 ELGVTHYRFS ISWARVLPNG SAGVPNREGL RYYRRLLERL RELGVQPVVT
 651 LYHWDLPQRL QDAYGGWANR ALADHFRDYA ELCFRHFGGQ VKYWITIDNP
 701 YVVAWHGYAT GRLAPGIRGS PRLGYLVAHN LLLAHAKVWH LYNTSFRPTQ
 751 GGQVSIALSS HWINPRRMTD HSIKECQKSL DFVLGWFAKP VFIDGDYPES
 801 MKNNLSSILP DFTESEKKFI KGTADFFALC FGPTLSFQLL DPHMKFRQLE
 851 SPNLRQLLSW IDLEFNHPQI FIVENGWFVS GTTKRDDAKY MYYLKKFIME
 901 TLKAIKLDGV DVIGYTAWSL MDGFEWHRGY SIRRGLFYVD FLSQDKMLLP
 951 KSSALFYQKL IEKNGFPEFG SGGGGSGGGG SGGGGSLKYP NASPLLGSSW
1001 GGLIHLYTAT ARNSYHLQIH KNGHVDGAPH QTIYSALMIR SEDAGFVVIT
1051 GVMSRRYLCM DFRGNIFGSH YFDPENCRFQ HQTLENGYDV YHSPQYHFLV
1101 SLGRAKRAFL PGMNPPPYSQ FLSRRNEIPL IRFNTPIPRR HTQSAEDDSE
1151 RDPLNVLKPR ARMTPAPASC SQELPSAEDN SPMASDPLGV VRGGRVNTHA
1201 GGTGPEGCRP FAKFI*
```

(KL-D2)₂-FGF23 (R179Q) amino acid sequence (SEQ ID NO: 24)

```
   1 MPASAPPRRP RPFPPSLSLL LVLLGLGGRR LPLPENQPLE GTFPCDFAWG
  51 VVDNYIQVDT TLSQFTDLNV YLWDVHHSKR LIKVDGVVTK KRKSYCVDFA
 101 AIQPQIALLQ EMHVTHFRFS LDWALILPLG NQSQVNHTIL QYYRCMASEL
 151 VRVNITPVVA LWQPMAPNQG LPRLLARQGA WENPYTALAF AEYARLCFQE
 201 LGHHVKLWIT MNEPYTRNMT YSAGHNLLKA HALAWHVYNE KFRHAQNGKI
 251 SIALQADWIE PACPFSQKDK EVAERVLEFD IGWLAEPIFG SGDYPWVMRD
 301 WLNQRNNFLL PYFTEDEKKL IQGTFDFLAL SHYTTILVDS EKEDPIKYND
 351 YLEVQEMTDI TWLNSPSQVA VVPWGLRKVL NWLKFKYGDL PMYIISNGID
 401 DGLHAEDDQL RVYYMQNYIN EALKAHILDG INLCGYFAYS FNDRTAPRFG
 451 LYRYAADQFE PKASMKHYRK IIDSNGFPGP ETLERFCPEE FTVCTECSFF
 501 HTRKSLGTFP CDFAWGVVDN YIQVDTTLSQ FTDLNVYLWD VHHSKRLIKV
 551 DGVVTKKRKS YCVDFAAIQP QIALLQEMHV THFRFSLDWA LILPLGNQSQ
 601 VNHTILQYYR CMASELVRVN ITPVVALWQP MAPNQGLPRL LARQGAWENP
 651 YTALAFAEYA RLCFQELGHH VKLWITMNEP YTRNMTYSAG HNLLKAHALA
 701 WHVYNEKFRH AQNGKISIAL QADWIEPACP FSQKDKEVAE RVLEFDIGWL
 751 AEPIFGSGDY PWVMRDWLNQ RNNFLLPYFT EDEKKLIQGT FDFLALSHYT
 801 TILVDSEKED PIKYNDYLEV QEMTDITWLN SPSQVAVVPW GLRKVLNWLK
 851 FKYGDLPMYI ISNGIDDGLH AEDDQLRVYY MQNYINEALK AHILDGINLC
 901 GYFAYSFNDR TAPRFGLYRY AADQFEPKAS MKHYRKIIDS NGFPGPGGGS
 951 GGGGSGGGGS LKYPNASPLL GSSWGGLIHL YTATARNSYH LQIHKNGHVD
1001 GAPHQTIYSA LMIRSEDAGF VVITGVMSRR YLCMDFRGNI FGSHYFDPEN
1051 CRFQHQTLEN GYDVYHSPQY HFLVSLGRAK RAFLPGMNPP PYSQFLSRRN
1101 EIPLIHFNTP IPRRHTQSAE DDSERDPLNV LKPRARMTPA PASCSQELPS
1151 AEDNSPMASD PLGVVRGGRV NTHAGGTGPE GCRPFAKFI*
```

FGF23 (R179Q)-Klotho extracellular domain amino acid sequence (SEQ ID NO: 25)

```
   1 MLGARLRLWV CALCSVCSMS VLRAYPNASP LLGSSWGGLI HLYTATARNS
```

Figure 2 (continued)

```
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IGSGGGGSGG GGSGGGGSLK EPGDGAQTWA RFSRPPAPEA AGLFQGTFPD
 301 GFLWAVGSAA YQTEGGWQQH GKGASIWDTF THHPLAPPGD SRNASLPLGA
 351 PSPLQPATGD VASDSYNNVF RDTEALRELG VTHYRFSISW ARVLPNGSAG
 401 VPNREGLRYY RRLLERLREL GVQPVVTLYH WDLPQRLQDA YGGWANRALA
 451 DHFRDYAELC FRHFGGQVKY WITIDNPYVV AWHGYATGRL APGIRGSPRL
 501 GYLVAHNLLL AHAKVWHLYN TSFRPTQGGQ VSIALSSHWI NPRRMTDHSI
 551 KECQKSLDFV LGWFAKPVFI DGDYPESMKN NLSSILPDFT ESEKKFIKGT
 601 ADFFALCFGP TLSFQLLDPH MKFRQLESPN LRQLLSWIDL EFNHPQIFIV
 651 ENGWFVSGTT KRDDAKYMYY LKKFIMETLK AIKLDGVDVI GYTAWSLMDG
 701 FEWHRGYSIR RGLFYVDFLS QDKMLLPKSS ALFYQKLIEK NGFPPLPENQ
 751 PLEGTFPCDF AWGVVDNYIQ VDTTLSQFTD LNVYLWDVHH SKRLIKVDGV
 801 VTKKRKSYCV DFAAIQPQIA LLQEMHVTHF RFSLDWALIL PLGNQSQVNH
 851 TILQYYRCMA SELVRVNITP VVALWQPMAP NQGLPRLLAR QGAWENPYTA
 901 LAFAEYARLC FQELGHHVKL WITMNEPYTR NMTYSAGHNL LKAHALAWHV
 951 YNEKFRHAQN GKISIALQAD WIEPACPFSQ KDKEVAERVL EFDIGWLAEP
1001 IFGSGDYPWV MRDWLNQRNN FLLPYFTEDE KKLIQGTFDF LALSHYTTIL
1051 VDSEKEDPIK YNDYLEVQEM TDITWLNSPS QVAVVPWGLR KVLNWLKFKY
1101 GDLPMYIISN GIDDGLHAED DQLRVYYMQN YINEALKAHI LDGINLCGYF
1151 AYSFNDRTAP RFGLYRYAAD QFEPKASMKH YRKIIDSNGF PGPETLERFC
1201 PEEFTVCTEC SFFHTRKSL*
```

FGF23 (R179Q)-KL-D1 amino acid sequence (SEQ ID NO: 26)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IQGTFPDGFL WAVGSAAYQT EGGWQQHGKG ASIWDTFTHH PLAPPGDGRN
 301 ASLPLGAPSP LQPATGDVAS DSYNNVFRDT EALRELGVTH YRFSISWARV
 351 LPNGSAGVPN REGLRYYRRL LERLRELGVQ PVVTLYHWDL PQRLQDAYGG
 401 WANRALADHF RDYAELCFRH FGGQVKYWIT IDNPYVVAWH GYATGRLAPG
 451 IRGSPRLGYL VAHNLLAHA KVWHLYNTSF RPTQGGQVSI ALSSHWINPR
 501 RMTDHSIKEC QKSLDFVLGW FAKPVFIDGD YPESMKNNLS SILPDFTESE
 551 KKFIKGTADF FALCFGPTLS FQLLDPHMKF RQLESPNLRQ LLSWIDLEFN
 601 HPQIFIVENG WFVSGTTKRD DAKYMYYLKK FIMETLKAIK LDGVDVIGYT
 651 AWSLMDGFEW HRGYSIRRGL FYVDFLSQDK MLLPKSSALF YQKLIEKNGF
 652 *
```

FGF23 (R179Q)-KL-D2 amino acid sequence (SEQ ID NO: 27)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IGTFPCDFAW GVVDNYIQVD TTLSQFTDLN VYLWDVHHSK RLIKVDGVVT
 301 KKRKSYCVDF AAIQPQIALL QEMHVTHFRF SLDWALILPL GNQSQVNHTI
 351 LQYYRCMASE LVRVNITPVV ALWQPMAFNQ GLPRLLARQG AWENPYTALA
 401 FAEYARLCFQ ELGHHVKLWI TMNEPYTRNM TYSAGHNLLK AHALAWHVYN
 451 EKFRHAQNGK ISIALQADWI EPACPFSQKD KEVAERVLEF DIGWLAEPIF
```

Figure 2 (continued)

```
501 GSGDYPWVMR DWLNQRNNFL LPYFTEDEKK LIQGTFDFLA LSHYTTILVD
551 SEKEDPIKYN DYLEVQEMTD ITWLNSPSQV AVVPWGLRKV LNWLKFKYGD
601 LPMYIISNGI DDGLHAEDDQ LRVYYMQNYI NEALKAHILD GINLCGYFAY
651 SFNDRTAPRF GLYRYAADQF EPKASMKHYR KIIDSNGF*
```

FGF23 (R179Q) -(KL-D1)₂ amino acid sequence (SEQ ID NO: 28)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSFMA SDPLGVVRGG RVNTHAGGTG PEGCRPFAKF
 251 IQGTFPDGFL WAVGSAAYQT EGGWQQHGKG ASIWDTFTHH PLAPPGDSRN
 301 ASLPLGAPSP LQPATGDVAS DSYNNVFRDT EALRELGVTH YRFSISWARV
 351 LPNCSAGVPN RECLRYYRRL LERLRELCVQ PVVTLYHWDL PQRLQDAYGC
 401 WANRALADHF RDYAELCFRH FGGQVKYWIT IDNPYVVAWH GYATGRLAPG
 451 IRGSPRLGYL VAHNLLLAHA KVWHLYNTSF RPTQGGQVSI ALSSHWINPR
 501 RMTDHSIKEC QKSLDFVLGW FAKPVFIDGD YPESMKNNLS SILPDFTESE
 551 KKFIKGTADF FALCFGPTLS FQLLDPHMKF RQLESPNLRQ LLSWIDLEFN
 601 HPQIFIVENG WFVSGTTKRD DAKYMYYLKK FIMETLKAIK LDGVDVIGYT
 651 AWSLMDGFEW HRGYSIRRGL FYVDFLSQDK MLLPKSSALF YQKLIEKNGF
 701 QGTFPDGFLW AVGSAAYQTE GGWQQHGKGA SIWDTFTHHP LAPPGDSRNA
 751 SLPLGAPSPL QPATGDVASD SYNNVFRDTE ALRELGVTHY RFSISWARVL
 801 PNGSAGVPNR EGLRYYRRLL ERLRELGVQP VVTLYHWDLP QRLQDAYGGW
 851 ANRALADHFR DYAELCFRHF GGQVKYWITI DNPYVVAWHG YATGRLAPGI
 901 RGSPRLGYLV AHNLLLAHAK VWHLYNTSFR PTQGGQVSIA LSSHWINPRR
 951 MTDHSIKECQ KSLDFVLGWF AKPVFIDGDY PESMKNNLSS ILPDFTESEK
1001 KFIKGTADFF ALCFGPTLSF QLLDPHMKFR QLESPNLRQL LSWIDLEFNH
1051 PQIFIVENGW FVSGTTKRDD AKYMYYLKKF IMETLKAIKL DGVDVIGYTA
1101 WSLMDGFEWH RGYSIRRGLF YVDFLSQDKM LLPKSSALFY QKLIEKNGF*
```

FGF23 (R179Q) -(KL-D2)₂ amino acid sequence (SEQ ID NO: 29)

```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSFMA SDPLGVVRGG RVNTHAGGTG PEGCRPFAKF
 251 IGTFPCDFAW GVVDNYIQVD TTLSQFTDLN VYLWDVHHSK RLIKVDGVVT
 301 KKRKSYCVDF AAIQPQIALL QEMHVTHFRF SLDWALILPL GNQSQVNHTI
 351 LQYYRCMASE LVRVNITPVV ALWQPMAPNQ GLPRLLARQG AWENPYTALA
 401 FAEYARLCFQ ELGHHVKLWI TMNEPYTRNM TYSAGHNLLK AHALAWHVYN
 451 EKFRHAQNGK ISIALQADWI EPACPFSQKD KEVAERVLEF DIGWLAEPIF
 501 GSGDYPWVMR DWLNQRNNFL LPYFTEDEKK LIQGTFDFLA LSHYTTILVD
 551 SEKEDPIKYN DYLEVQEMTD ITWLNSPSQV AVVPWGLRKV LNWLKFKYGD
 601 LPMYIISNGI DDGLHAEDDQ LRVYYMQNYI NEALKAHILD GINLCGYFAY
 651 SFNDRTAPRF GLYRYAADQF EPKASMKHYR KIIDSNGFGT FPCDFAWGVV
 701 DNYIQVDTTL SQFTDLNVYL WDVHHSKRLI KVDGVVTKKR KSYCVDFAAI
 751 QPQIALLQEM HVTHFRFSLD WALILPLGNQ SQVNHTILQY YRCMASELVR
 801 VNITPVVALW QPMAPNQGLP RLLARQGAWE NPYTALAFAE YARLCFQELG
 851 HHVKLWITMN EPYTRNMTYS AGHNLLKAHA LAWHVYNEKF RHAQNGKISI
 901 ALQADWIEPA CPFSQKDKEV AERVLEFDIG WLAEPIFGSG DYPWVMRDWL
 951 NQRNNFLLPY FTEDEKKLIQ GTFDFLALSH YTTILVDSEK EDPIKYNDYL
1001 EVQEMTDITW LNSPSQVAVV PWGLRKVLNW LKFKYGDLPM YIISNGIDDG
1051 LHAEDDQLRV YYMQNYINEA LKAHILDGIN LCGYFAYSFN DRTAPRFGLY
1101 RYAADQFEPK ASMKHYRKII DSNGF*
```

Figure 2 (continued)

FGF19 nucleic acid sequence (NM_005117) (SEQ ID NO: 30)
Protein coding region (464-1114)

```
   1 gctcccagcc aagaacctcg gggccgctgc gcggtgggga ggagttcccc gaaacccggc
  61 cgctaagcga ggcctcctcc tcccgcagat ccgaacggcc tgggcggggt caccccggct
 121 gggacaagaa gccgccgcct gcctgcccgg gccgggggag ggggctgggg ctgggggccgg
 181 aggcggggtg tgagtggggtg tgtgcggggg gcggaggctt gatgcaatcc cgataagaaa
 241 tgctcggggtg tcttgggcac ctacccgtgg ggcccgtaag gcgctactat ataaggctgc
 301 cggccggag ccgccgcgcc gtcagagcag gagcgctgcg tccaggatct agggccacga
 361 ccatcccaac ccggcactca cagcccgca gcgcatcccg gtcgccgccc agcctcccgc
 421 accccatcg ccggagctgc gccgaagcc ccagggaggt gccatgcgga gcggtgtgt
 481 ggtggtccac gtatggatcc tggccggcct ctggctggcc gtggccgggc gccccctcgc
 541 cttctcggac gcggggcccc acgtgcacta cggctggggc gacccatcc gcctgcggca
 601 cctgtacacc tccggccccc acgggctctc cagctgcttc ctgcgcatcc gtgccgacgg
 661 cgtcgtggac tgcgcgcggg gccagagcgc gcacagtttg ctggagatca aggcagtcgc
 721 tctgcggacc gtggccatca aggcgtgca cagctgcgg tacctctgca tgggcgccga
 781 cggcaagatg caggggctgc ttcagtactc ggaggaagac tgtgctttcg aggaggagat
 841 ccgccccagat ggctacaatg tgtaccgatc cgagaagcac cgcctcccgg tctccctgag
 901 cagtgccaaa cagcggcagc tgtacaagaa cagaggcttt cttccactct ctcatttcct
 961 gccatgctg cccatggtcc cagaggagcc tgaggacctc aggggccact ggaatctga
1021 catgttctct tcgcctctgg agaccgacag catgacccca tttgggcttg tcacggact
1081 ggaggccgtg aggagtccca gctttgagaa gtaactgaga ccatgcccgg gcctcttcac
1141 tgctgccagg ggctgtggta cctgcagcgt gggggacgtg cttctacaag aacagtcctg
1201 agtccacgtt ctgtttaget ttaggaagaa acatctagaa gttgtacata ttcagagttt
1261 tccattggca gtgccagttt ctagccaata gacttgtctg atcataacat tgtaagcctg
1321 tagcttgccc agctgctgcc tgggccccca ttctgtccctc tcgaggttgc tggacaagct
1381 gctgcactgt ctcagttctg cttgaatacc tccatcgatg gggaactcac ttcctttgga
1441 aaaattctta tgtcaagctg aaattctcta atttttctc atcacttccc caggagcagc
1501 cagaagacag gcagtagttt taatttcagg aacaggtgat ccactctgta aaacagcagg
1561 taaatttcac tcaacccat gtgggaattg atctatatct ctacttccag ggaccatttg
1621 cccttccaaa atccctccag gccagaactg actggagcag gcatggccca ccagcttca
1681 ggagtagggg aagcctggag ccccactcca gccctgggac aacttgagaa ttccccctga
1741 ggccagttct gtcatggatg ctgtcctgag aataaccttgc tgtccggtg tcacctgctt
1801 ccatctccca gcccaccagc cctctgccca cctcacatgc ctccccatgg attggggcct
1861 cccaggcccc ccaccttatg tcaacctgca cttcttgttc aaaaatcagg aaaagaaaag
1921 atttgaagac cccaagtctt gtcaataact tgctgtgtgg aagcagcggg ggaagaccta
1981 gaaccctttc cccagcactt ggtttttccaa catgatattt atgagtaatt tattttgata
2041 tgtacatctc ttatttcttt acattattta tgcccccaaa ttatatttat gtatgtaagt
2101 gaggtttgtt ttgtatatta aaatggagtt tgtttgtaaa aaaaaaaaaa aaaaaaa
```

FGF19 amino acid sequence (NP_005108) (SEQ ID NO: 31)

```
   1 MRSGCVVVHV WILAGLWLAV AGRPLAFSDA GPHVHYGWGD PIRLRHLYTS GPHGLSSCFL
  61 RIRADGVVDC ARGQSAHSLL EIKAVALRTV AIKGVHSVRY LCMGADGKMQ GLLQYSEEDC
 121 AFEEEIRPDG YNVYRSEKHR LPVSLSSAKQ RQLYKNRGFL PLSHFLPMLP MVPEEPEDLR
 181 GHLESDMFSS PLETDSMDPF GLVTGLEAVR SPSFEK
```

FGF21 nucleic acid sequence (NM_019113 ) (SEQ ID NO: 32)
Protein coding region 151-780

```
   1 CTGTCAGCTG AGGATCCAGC CGAAAGAGGA GCCAGGCACT CAGGCCACCT GAGTCTACTC
  61 ACCTGGACAA CTGGAATCTG GCACCAATTC TAAACCACTC AGCTTCTCCG AGCTCACACC
 121 CCGGAGATCA CCTGAGGACC CGAGCCATTG ATGGACTCGG ACGAGACCGG GTTCCAGCAC
```

Figure 2 (continued)

```
 181 TCAGGACTGT GGGTTTCTGT GCTGGCTGGT CTTCTGCTGG GAGCCTGCCA GGCACACCCC
 241 ATCCCTGACT CCAGTCCTCT CCTGCAATTC GGGGGCCAAG TCCGGCAGCG GTACCTCTAC
 301 ACAGATGATG CCCAGCAGAC AGAAGCCCAC CTGGAGATCA GGGAGGATGG GACGGTGGGG
 361 GGCGCTGCTG ACCAGAGCCC CGAAAGTCTC CTGCAGCTGA AAGCCTTGAA GCCGGGAGTT
 421 ATTCAAATCT TGGGAGTCAA GACATCCAGG TTCCTGTGCC AGCGGCCAGA TGGGGCCCTG
 481 TATGGATCGC TCCACTTTGA CCCTGAGGCC TGCAGCTTCC GGGAGCTGCT TCTTGAGGAC
 541 GGATACAATG TTTACCAGTC CGAAGCCCAC GGCCTCCCGC TGCACCTGCC AGGGAACAAG
 601 TCCCCACACC GGGACCCTGC ACCCCGAGGA CCAGCTCGCT TCCTGCCACT ACCAGGCCTG
 661 CCCCCCGCAC TCCCGGAGCC ACCCGGAATC CTGGCCCCCC AGCCCCCCGA TGTGGGCTCC
 721 TCGGACCCTC TGAGCATGGT GGGACCTTCC CAGGGCCGAA GCCCCAGCTA CGCTTCCTGA
 781 AGCCAGAGGC TGTTTACTAT GACATCTCCT CTTTATTTAT TAGGTTATTT ATCTTATTTA
 841 TTTTTTTATT TTCTTACTT GAGATAATAA AGAGTTCCAG AGGAGAAAAA AAAAAAAAAA
 901 AAAAAAAAAA AAAAAAAAAA AAAAAAAAAA AAAAAAAAAA
```

FGF21 amino acid sequence (NP_061986) (SEQ ID NO: 33)

```
   1 MDSDETGFEH SGLWVSVLAG LLLGACQAHP IPDSSPLLQF GGQVRQRYLY TDDAQQTEAH
  61 LEIREDGTVG GAADQSPESL LQLKALKPGV IQILGVKTSR FLCQRPDGAL YGSLHFDPEA
 121 CSFRELLLED GYNVYQSEAH GLPLHLPGNK SPHRDPAPRG PARFLPLPGL PPALPEPPGI
 181 LAPQPPDVGS SDPLSMVGPS QGRSPSYAS
```

FGF23 nucleic acid sequence (NM_020638) (SEQ ID NO: 34)
Protein coding region 147-902

```
    1 cggcaaaaag gagggaatcc agtctaggat cctcacacca gctacttgca agggagaagg
   61 aaaaggccag taaggcctgg gccaggagag tccgacagg agtgtcaggt ttcaatctca
  121 gcaccagcca ctcagagcag ggcacgatgt tggggggcca cctcaggctc tgggtctgtg
  181 ccttgtgcag cgtctgcagc atgagcgtcc tcagagccta tccaatgcc tcccactgc
  241 tcggctccag ctggggtggc ctgatccacc tgtacacagc cacagccagg aacagctacc
  301 acctgcagat ccacaagaat ggccatgtgg atgggcacc ccatcagacc atctacagtg
  361 cctgatgat cagatcagga gatgctggct ttgtggtgta tacaggtgtg atgagcagaa
  421 gatacctctg catggatttc agaggcaaca ttttggatc acactattg gacccggaga
  481 actgcaggtt ccaacaccag acgctggaaa acgggtacga cgtctaccac tctcctcagt
  541 atcacttcct ggtcagtctg gcccgggcga agagagcctt cctgccaggc atgaacccac
  601 ccccgtactc ccagttcctg tccggagga acgagatccc cctaattcac ttcaacaccc
  661 ccataccacg gcggcaacac cggagcgcg aggacgccg ggagcatgta cccctgaacg
  721 tgctgaagcc ccgggccgg atgaccccgg ccccggcctc ctgttcacag gagctccga
  781 gcgccgagga caacagcccg atggccagtg accattaggg gtggtcagg ggcggtcgag
  841 tgaacacgca cgctggggga acgggccgg aaggctgccg cccttcgcc aagttcatct
  901 agggtcgctg gaagggcacc ctctttaacc catccctcag caaacgcagc tcttcccaag
  961 gaccaggtca cttgacgttc cgaggatggg aaaggtgaca gggcatgta tggaatttgc
 1021 tgcttctctg gggtcccttc cacaggaggt cctgtgaaaa ccaacctttg aggccaagt
 1081 catgggggttt cacgccttc ctcactccat atagaacacc tttcccaata ggaaaccca
 1141 acaggtaaac tagaaatttc cccttcatga aggtagagag aagggggtctc tcccaacata
 1201 tttctcttcc ttgtgcctct cctctttatc acttttaagc ataaaaaaaa aaaaaaaaaa
 1261 aaaaaaaaaa aaaagcagtg ggttcctgag ctcaagactt tgaaggtgta gggaagagga
 1321 aatcggagat cccagaagct tctccactgc cctatgcatt tatgttagat gccccgatcc
 1381 cactggcatt tgagtgtgca aaccttgaca ttaacagctg aatgggcaa gttgatgaaa
 1441 acactacttt caagccttcg ttcttccttg agcatctctg gggaagagct gtcaaagac
 1501 tggtggtagg ctggtgaaaa cttgacagct agacttgatg cttgctagga tgaggcagga
 1561 atcataatag aaaactcagc ctcccatacag ggtgagcagc ttctgtctcg ctgtctccct
 1621 ctgtcagcc acagccagag ggccagaat ggccccactc tgttccaag cagttcatga
 1681 tacagcctca cctttggcc ccatctctgg tttttgaaaa tttggtctaa ggaataaata
 1741 gcttttacac tggctcacga aaatctgccc tgctagaatt tgcttttcaa aatggaaata
 1801 aattccaact ctcctaagag gcatttaatt aaggctctac ttccaggttg agtaggaatc
```

Figure 2 (continued)

```
1861 cattctgaac aaactacaaa aatgtgactg ggaaggggc tttgagagac tgggactgct
1921 ctgggttagg ttttctgtgg actgaaaaat cgtgtcctt tctctaaatg aagtggcatc
1981 aaggactcag ggggaaagaa atcaggggac atgttataga agttatgaaa agacaaccac
2041 atggtcaggc tcttgtctgt ggtctctagg gctctgcagc agcagtggct cttcgattag
2101 ttaaaactct cctaggctga cacatctggg tctcaatccc cttggaaatt cttggtgcat
2161 taaatgaagc cttaccccat tactgcggtt cttctgtaa gggggctcca ttttcctccc
2221 tctctttaaa tgaccaccta aaggacagta tattaacaag caaagtcgat tcaacaacag
2281 cttcttccca gtcacttttt ttttctcac tgccatcaca tactaacctt atactttgat
2341 ctattctttt tggttatgag agaaatgttg ggcaactgtt tttacctgat ggttttaagc
2401 tgaacttgaa ggactggttc ctattctgaa acagtaaaac tatgtataat agtatatagc
2461 catgcatggc aaatatttta atatttctgt tttcatttcc tgttggaaat attatcctgc
2521 ataatagcta ttggaggctc ctcagtgaaa gatcccaaaa ggatttggt ggaaaactag
2581 ttgtaatctc acaaactcaa cactaccatc aggggttttc tttatggcaa agccaaaata
2641 gctcctacaa tttcttatat ccctcgtcat gtggcagtat ttatttattt atttggaagt
2701 ttgcctatcc ttctatattt atagatattt ataaaaatgt aacccctttt tcctttcttc
2761 tgtttaaaat aaaaataaaa tttatctcag cttctgttag cttatcctct ttgtagtact
2821 acttaaaagc atgtcggaat ataagaataa aaaggattat gggaggggaa cattagggaa
2881 atccagagaa ggcaaaattg aaaaaaagat tttagaattt taaaattttc aaagatttct
2941 tccattcata aggaagactca atgattttaa ttgatctaga cagaattatt taagttttat
3001 caatattgga tttctggt
```

FGF23 amino acid sequence (NP_065689) (SEQ ID NO: 35)

```
  1 MLGARLRLWV CALCSVCSMS VLRAYPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
121 ENGYDVYHSP QYHFLVSLGR AKRAFLPGMN PPPYSQFLSR RNEIPLIHFN TPIPRRHTRS
181 AEDDSERDPL NVLKPRARMT PAPASCSQEL PSAEDNSPMA SDPLGVVRGG RVNTHAGGTG
241 PEGCRPFAKF I
```

FGF23 (R179Q) amino acid sequence (SEQ ID NO: 36)

```
  1 MLGARLRLWV CALCSVCSMS VLRAYPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
121 ENGYDVYHSP QYHFLVSLGR AKRAFLPGMN PPPYSQFLSR RNEIPLIHFN TPIPRRHTQS
181 AEDDSERDPL NVLKPRARMT PAPASCSQEL PSAEDNSPMA SDPLGVVRGG RVNTHAGGTG
241 PEGCRPFAKF I
```

Human beta-Klotho domain 1 (b-KL-D1) amino acid sequence (SEQ ID NO: 37)

```
 77                     ydt fpknffwgig tgalqvegsw kkdgkgpsiw dhfihthlkn
121 vssatngssds yiflekdlsa ldfigvsfyq fsiswprlfp dgivtvanak glqyystlld
181 alvlrniepi vtlyhwdlpl alqekyggwk ndtiidifnd yatycfqmfg drvkywitih
241 npylvawhgy gtgmhapqek gnlaavytvg hnlikahskv whnynthfrp hqkgwlsitl
301 gshwiepnrs entmdifkcq qsmvsvlgwf anpihgdgdy pegmrkklfs vlpifseaek
361 hemrgtadff afsfgpnnfk plntmakmgq nvslnlreal nwikleynnp riiiaengwf
421 tdsrvktedt taiymmaknfl sqvlqairld eirvfgytaw slldgfewqd aytirrglfy
481 vdfnskqker kpkssahyyk qiirengf
```

Human beta-Klotho domain 2 (b-KL-D2) amino acid sequence (SEQ ID NO: 38)

```
571                           trpaqctdfv nikkqlemla rmkvthyrfa
601 ldwasvlptg nlsavnrqal ryyrcvvseg lklgisamvt lyypthahlg lpepllhadg
661 wlnpstaeaf qayaglcfqe lgdlvklwit inepnrlsdi ynrsgndtyg aahnllvaha
721 lawrlydrqf rpsqrgavsl slhadwaepa npyadshwra aerflqfeia wfaeplfktg
```

Figure 2 (continued)

```
781 dypaamreyi askhrrglss salprlteae rrllkgtvdf calnhfttrf vmheqlagsr
841 ydsdrdiqfl qditrlsspt rlavipwgvr kllrwvrrny gdmdiyitas giddqaledd
901 rlrkyylgky lqevlkayli dkvrikgyya fklaeekskp rfgfftsdfk akssiqfynk
961 vissrgf
```

Beta-Klotho extracellular domain (without signal peptide) amino acid sequence (SEQ ID NO: 39)

```
 52                                                              gfsqdgrai
 61 wsknpnftpv nesqlflydt fpknffwgig tgalqvegsw kkdgkgpsiw dhfihthlkn
121 vsstngssds yiflekdlsa ldfigvsfyq fsiswprlfp dgivtvanak glqyystlld
181 alvlrniepi vtlyhwdlpl alqekyggwk ndtiidifnd yatycfqmfg drvkywitih
241 npylvawhgy gtgmhapgek gnlaavytvg hnlikahskv whnynthfxp hqkgwlsitl
301 gshwiepnrs entmdifkcq qsmvsvlgwf anpihgdgdy pegmrkklfs vlpifseaek
361 hemrgtadff afsfgpnnfk plntmakmgq nvslnlreal nwikleynnp riliaengwf
421 tdsrvktedt taiymmknfl sqvlqairld eirvfgytaw slldgfewqd aytirrglfy
481 vdfnskqker kpkssahyyk qiirengfsl kestpdvqgq fpcdfswgvt esvlkpesva
541 sspqfsdphl yvwnatgnrl lhrvegvrlk trpaqctdfv nikkqlemla rmkvthyrfa
601 ldwasvlptg nisavnrqai ryyrcvvseg iklgisamvt iyypthahlg lpepllhadg
661 wlnpstaeaf qayaglcfqe lgdlvklwit inepnrlsdi ynrsgndtyg aahnlivaha
721 lawrlydrqf rpsqrgavsl slhadwaepa npyadshwra aerflqfeia wfaeplfktg
781 dypaamreyi askhrrglss salprlteae rrllkgtvdf calnhfttrf vmheqlagsr
841 ydsdrdiqfl qditrlsspt rlavipwgvr kllrwvrrny gdmdiyitas giddqaledd
901 rlrkyylgky lqevlkayli dkvrikgyya fklaeekskp rfgfftsdfk akssiqfynk
961 vissrgfpfe nsssrcsqtq entectvcif lvqkkpl
``` sKlotho without signal peptide – FGF23 amino acid sequence (without signal peptide) (SEQ ID NO: 40)

```
                              EPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQPA TGDVASDSYN NVFRDTEALR ELGVTHYRFS
 151 ISWARVLPNG SAGVPNREGL RYYRRLLERL RELGVQPVVT LYHWDLPQRL
 201 QDAYCGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDGV
 451 DVIGYTAWSL MDGFEWHRGY SIRRGLFYVD FLSQDKMLLP KSSALFYQRL
 501 IEKNGFPPLP ENQPLEGTFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDGLH AEDDQLRVYY MQNYINEALK
 901 AHILDGINLC GYFAYSFNDR TAPRFGLYRY AADQFEPKAS MKHYRKIIDS
 951 NGFPCPETLE RFCPEEFTVC TECSFFHTRK SLGSGGGQSG GGGSGGGGSL
1001 KYPNASPLLG SSWGGLIHLY TATARNSYHL QIHKNGHVDG APHQTGIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTRSAED DSERDPLNVL KPRARMTPAP ASCSQELPSA EDNSPMASDP
1201 LGVVRGCRVN THAGGTGPEG CRPFAKFI*
```

Figure 2 (continued)

sKlotho without signal peptide -FGF23 (R179Q) (without signal peptide) amino acid sequence (SEQ ID NO: 41)

```
                              EPGDGAQ TWARFSRPPA
  51 PEAAGLFQGT FPDGFLWAVG SAAYQTEGGW QQHGKGASIW DTFTHHPLAP
 101 PGDSRNASLP LGAPSPLQFA TGDVASDSYN NVFRDTEALR ELGVTHYRFS
 151 ISWARVLPNG SAGVPNREGL RYYRRLLERL RELGVQPVVT LYHWDLPQRL
 201 QDAYGGWANR ALADHFRDYA ELCFRHFGGQ VKYWITIDNP YVVAWHGYAT
 251 GRLAPGIRGS PRLGYLVAHN LLLAHAKVWH LYNTSFRPTQ GGQVSIALSS
 301 HWINPRRMTD HSIKECQKSL DFVLGWFAKP VFIDGDYPES MKNNLSSILP
 351 DFTESEKKFI KGTADFFALC FGPTLSFQLL DPHMKFRQLE SPNLRQLLSW
 401 IDLEFNHPQI FIVENGWFVS GTTKRDDAKY MYYLKKFIME TLKAIKLDCV
 451 DVIGYTAWSL MDGFEWHRGY SIRRGLFYVD FLSQDKMLLP KSSALFYQKL
 501 IEKNGFPPLP ENQPLEGTFP CDFAWGVVDN YIQVDTTLSQ FTDLNVYLWD
 551 VHHSKRLIKV DGVVTKKRKS YCVDFAAIQP QIALLQEMHV THFRFSLDWA
 601 LILPLGNQSQ VNHTILQYYR CMASELVRVN ITPVVALWQP MAPNQGLPRL
 651 LARQGAWENP YTALAFAEYA RLCFQELGHH VKLWITMNEP YTRNMTYSAG
 701 HNLLKAHALA WHVYNEKFRH AQNGKISIAL QADWIEPACP FSQKDKEVAE
 751 RVLEFDIGWL AEPIFGSGDY PWVMRDWLNQ RNNFLLPYFT EDEKKLIQGT
 801 FDFLALSHYT TILVDSEKED PIKYNDYLEV QEMTDITWLN SPSQVAVVPW
 851 GLRKVLNWLK FKYGDLPMYI ISNGIDDCLH AEDDQLRVYY MQNYINEALK
 901 AHILDGINLC GYFAYSFNDR TAPRFGLYRY AADQFEPKAS MKHYRKIIDS
 951 NGFPGPETLE RFCPEEFTVC TECSFFHTRK SLGSGGGGSG GGGSGGGGSL
1001 KYPNASPLLG SSWGGLIHLY TATARNSYHL QIHKNGHVDG APHQTIYSAL
1051 MLRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN THAGGTGPEG CRPFAKFI*
```

FGF23 without signal peptide (SEQ ID NO:42)

```
                              YPNASP LLGSSWGGLI HLYTATARNS YHLQIHKNGH
  61 VDGAPHQTIY SALMIRSEDA GFVVITGVMS RRYLCMDFRG NIFGSHYFDP ENCRFQHQTL
 121 ENGYDVYHSP QYHFLVSLGR AKRAFLPGMN PPPYSQFLSR RNEIPLIHFN TPIPRRHTRS
 181 AEDDSERDPL NVLKPRARMT PAPASCSQEL PSAEDNSPMA SDPLGVVRGG RVNTHAGGTG
 241 PEGCRPFAKF I
```

FGF23(R179Q) without signal peptide (SEQ ID NO:43)

```
                              YPNASP LLGSSWGGLI HLYTATARNS YHLQIHKNGH
  61 VDGAPHQTIY SALMIRSEDA GFVVITGVMS RRYLCMDFRG NIFGSHYFDP ENCRFQHQTL
 121 ENGYDVYHSP QYHFLVSLGR AKRAFLPGMN PPPYSQFLSR RNEIPLIHFN TPIPRRHTQS
 181 AEDDSERDPL NVLKPRARMT PAPASCSQEL PSAEDNSPMA SDPLGVVRGG RVNTHAGGTG
 241 PEGCRPFAKF I
```

Figured 2 (continued)

sKlotho with Klotho signal peptide (SEQ ID NO:44)

```
  1 MPASAPPRRP RPPPPSLSLL LVLLGLGGRR LRAEPGDGAQ TWARFSRPPA
 51 PEAAGLFQGT FPDGFLWAVG SAAYQTEGGW QQHGKGASIW DTFTHHPLAP
101 PGDSRNASLP LGAPSPLQPA TGDVASDSYN NVFRDTEALR ELGVTHYRFS
151 ISWARVLPNG SAGVPNREGL RYYRRLLERL RELGVQPVVT LYHWDLPQRL
201 QDAYGGWANR ALADHFRDYA ELCFRHFGSQ VKYWITIDNP YVVAWHGYAT
251 GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP
351 DFTESEKKFI KGTADFFALC FGPTLSFQLL DPHMKFRQLE SPNLRQLLSW
401 IDLEFNHPQI FIVENGWFVS GTTKRDDAKY MYYLKKFIME TLKAIKLDGV
451 DVIGYTAWSL MDGFEWHRGY SIRRGLFYVD FLSQDKMLLP KSSALFYQKL
501 IEKNGFPPLP ENQPLEGTFP CDFAWGVVDN YIQVDTTLSQ FTDLNVYLWD
551 VHHSKRLIKV DGVVTKKRKS YCVDFAAIQP QIALLQEMHV THFRFSLDWA
601 LILPLGNQSQ VNHTILQYYR CMASELVRVN ITPVVALWQP MAPNQGLPRL
651 LARQGAWENP YTALAFAEYA RLCFQELGHH VKLWITMNEP YTRNMTYSAG
701 HNLLKAHALA WHVYNEKFRH AQNGKISIAL QADWIEPACP FSQKDKEVAE
751 RVLEFDIGWL AEPIFGSGDY PWVMRDWLNQ RNNFLLPYFT EDEKKLIQGT
801 FDFLALSHYT TILVDSEKED PIKYNDYLEV QEMTDITWLN SPSQVAVVPW
851 GLRKVLNWLK FKYGDLPMYI ISNGIDDGLH AEDDQLRVYY MQNYINEALK
901 AHILDGINLC GYFAYSFNDR TAPRFGLYRY AADQFEPKAS MKHYRKIIDS
951 NGFPGPETLE RFCPEEFTVC TECSFFHTRK SL
``` sKlotho with IgG Signal peptide (SEQ ID NO:45)

```
  1 MSVLTQVLAL LLLWLTGLGG RRLRAEPGDG AQTWARFSRP PAPEAAGLFQ
 51 GTFPDGFLWA VGSAAYQTEG GWQQHGKGAS IWDTFTHHPL APPGDSRNAS
101 LPLGAPSPLQ PATGDVASDS YNNVFRDTEA LRELGVTHYR FSISWARVLP
151 NGSAGVPNRE GLRYYRRLLE RLRELGVQPV VTLYHWDLPQ RLQDAYGGWA
201 NRALADHFRD YAELCFRHFG GQVKYWITID NPYVVAWHGY ATGRLAPGIR
251 GSPRLGYLVA HNLLLAHAKV WHLYNTSFRP TQGGQVSIAL SSHWINPRRM
301 TDHSIKECQK SLDFVLGWFA KPVFIDGDYP ESMKNNLSSI LPDFTESEKK
351 FIKGTADFFA LCFGPTLSFQ LLDPHMKFRQ LESPNLRQLL SWIDLEFNHP
401 QIFIVENGWF VSGTTKRDDA KYMYYLKKFI METLKAIKLD GVDVIGYTAW
451 SLMDGFEWHR GYSIRRGLFY VDFLSQDKML LPKSSALFYQ KLIEKNGFPP
501 LPENQPLEGT FPCDFAWGVV DNYIQVDTTL SQFTDLNVYL WDVHHSKRLI
551 KVDGVVTKKR KSYCVDFAAI QPQIALLQEM HVTHFRFSLD WALILPLGNQ
601 SQVNHTILQY YRCMASELVR VNITPVVALW QPMAPNQGLP RLLARQGAWE
651 NPYTALAFAE YARLCFQELG HHVKLWITMN EPYTRNMTYS AGHNLLKAHA
701 LAWHVYNEKF RHAQNGKISI ALQADWIEPA CPFSQKDKEV AERVLEFDIG
751 WLAEPIFGSG DYPWVMRDWL NQRNNFLLPY FTEDEKKLIQ GTFDFLALSH
801 YTTILVDSEK EDPIKYNDYL EVQEMTDITW LNSPSQVAVV PWGLRKVLNW
851 LKFKYGDLPM YIISNGIDDG LHAEDDQLRV YYMQNYINEA LKAHILDGIN
901 LCGYFAYSFN DRTAPRFGLY RYAADQFEPK ASMKHYRKII DSNGFPGPET
951 LERFCPEEFT VCTECSFFHT RKSL*
``` lane 1, Ctrl; lane 2, FGF23; lane 3, sKlotho; lanes 4-6, sKlotho-FGF23 lane 1, Ctrl; lane 2, FGF23; lane 3, sKlotho; lanes 4-6, sKlotho-FGF23 lane 1, purified sKlotho-FGF23-6xHis;
lane 2, molecular weight marker

METHODS AND COMPOSITIONS USING FGF23 VARIANT POLYPEPTIDES WITH REDUCED AGGREGATION AND CLEAVAGE

This application is a divisional of U.S. application Ser. No. 13/015,159, filed Jan. 27, 2011, the contents of which are incorporated herein by reference in their entirety.

1. BACKGROUND

Fibroblast growth factors (FGFs) constitute a family of homologous polypeptide growth factors expressed in many organisms (Ornitz and Itoh, Genome Biol. 2: reviews, 3005.1-3005.12 (2001)). Among vertebrate species, FGFs are highly conserved in both gene structure and amino-acid sequence, having between 13-71% amino acid identity with one another. In humans, there are 22 known members of the FGF family (FGF15 is the mouse ortholog of human FGF19, hence there is no human FGF15). During early development, FGFs regulate cell proliferation, migration, and differentiation, but in the adult organism, FGFs maintain homeostasis, function in tissue repair, and respond to injury.

FGFs function as growth factors by binding and thereby activating cell-surface FGF receptors. FGF receptors (FGFRs) are tyrosine kinase receptors that activate signal transduction through autophosphorylation of FGFR, phosphorylation of FRS2 (FGF receptor substrate 2) and ERK1/2 (extracellular signal-regulated protein kinase 1/2), and activating Egr-1 (early growth response-1). FGFs also have a high affinity for heparin sulfate proteoglycans. When bound to FGFs, heparin sulfate enhances the activation of FGFRs.

The alpha-Klotho gene encodes a 130 kDa single pass type I transmembrane protein with an extracellular domain and a short cytoplasmic domain. The extracellular domain of alpha-Klotho protein comprises two subdomains termed, KL-D1 and KL-D2. These two subdomains share sequence homology to β-glucosidase of bacteria and plants. The extracellular domain of the alpha-Klotho protein may be bound to the cell surface by the transmembrane domain or may be cleaved and released into the extracellular milieu. Cleavage of the extracellular domain appears to be facilitated by local low extracellular $Ca^{2+}$ concentrations.

In addition to alpha-Klotho, a homolog of alpha-Klotho, beta-Klotho, has been identified (Ito et al., Mech. Dev. 98:115-9 (2000)). Beta-Klotho is also a single pass type I transmembrane protein with extracellular KL-D1 and KL-D2 subdomains.

Modulation of alpha-Klotho expression has been demonstrated to produce aging related characteristics in mammals. Mice homozygous for a loss of function mutation in the alpha-Klotho gene develop characteristics resembling human aging, including shortened lifespan, skin atrophy, muscle wasting, arteriosclerosis, pulmonary emphysema and osteoporosis (Kuro-o et al., Nature, 390:45-51 (1997)). In contrast, overexpression of the alpha-Klotho gene in mice extends lifespan and increases resistance to oxidative stress relative to wild-type mice (Kurosu et al., Science 309:1829-1833 (2005); Yamamoto et al., J. Biol. Chem. 280:38029-38034 (2005)).

Recent studies have demonstrated strikingly similar biological characteristics between FGF23-deficient mice and alpha-Klotho-deficient mice (Shimada et al., J. Clin. Invest. 113:561-568 (2004); Yoshida et al. Endocrinology 143:683-689 (2002)), indicating functional crosstalk between FGF23 and alpha-Klotho. These studies led to the identification of alpha-Klotho as an obligatory partner of FGF23, in terms of both binding and signaling through its cognate FGF receptors (Urakawa et al., Nature 22:1524-6 (2007)). The alpha-Klotho gene is mainly expressed in kidney, parathyroid gland and choroid plexus. It is hypothesized that the tissue-specific expression of alpha-Klotho restricts activation of FGF23 signaling to those tissues.

Similar to FGF23/alpha-Klotho, beta-Klotho is an obligatory partner of FGF19 and FGF21, both in binding and in signaling through their respective cognate FGF receptors (Ogawa et al., Proc. Natl. Acad. Sci. USA 104:7432-7 (2007); Lin et al., J. Biol Chem. 282:27227-84 (2007); and Wu et al., J. Biol. Chem. 282:29069-72 (2007)). Such studies have also demonstrated the involvement of beta-Klotho in regulating tissue-specific metabolic activity. Beta-Klotho was initially shown to act with FGF21 as a cofactor for regulating carbohydrate and lipid metabolism in adipose tissue. Beta-Klotho in conjunction with FGF19 regulates bile acid metabolism in liver, thus explaining elevated bile synthesis in beta-Klotho deficient mice (Ito et al., J Clin Invest. 2005 August;115(8): 2202-8).

U.S. Pat. No. 6,579,850 describes polypeptides and compositions comprising an alpha-Klotho polypeptide. Human and mouse alpha-Klotho polypeptides are disclosed. The patent also disclosed that compositions comprising the polypeptides are useful in treating a syndrome resembling premature aging, treating adult diseases, and suppressing aging.

U.S. Pat. No. 7,223,563 describes isolated nucleic acids encoding the FGF23 polypeptide sequence or recombinant cells comprising such an isolated nucleic acid. The patent further relates to methods of diagnosing and treating hypophosphatemic and hyperphosphatemic disorders, osteoporosis, dermatomyositis, and coronary artery disease.

U.S. Pat. No. 7,259,248 describes isolated nucleic acids encoding the FGF21 polypeptide sequence. The patent further relates to methods of diagnosing and treating liver disease, conditions related to thymic function, and methods of treating conditions of the testis.

2. SUMMARY OF THE INVENTION

The present disclosure is directed to methods, uses, kits and compositions for preventing or treating age-related conditions or metabolic disorders with fusion polypeptides or soluble polypeptides. The fusion polypeptides of the present disclosure are formed of a FGF (e.g., FGF23); and either a Klotho protein or an active fragment thereof (e.g., sKlotho) and/or a Fc fragment (e.g., FcLALA); and, optionally, a linker. In some embodiments, the FGF23 is mutated. In some embodiments, the present disclosure provides a Klotho fusion polypeptide comprising a Klotho protein or an active fragment thereof and a fibroblast growth factor or an active fragment thereof. In some embodiments, the fusion polypeptide comprises a Klotho polypeptide, a FGF (such as FGF23) and a modified Fc fragment. The Fc fragment can, for example, have decreased binding to Fc-gamma-receptor and increased serum half-life. Fusion proteins comprising sKlotho, FGF23 and FcLALA (a modified Fc fragment having decreased affinity for Fc-gamma-receptorand/or increased serum half-life) are described in SEQ ID NOs. 46, 47, 48, and 49. In some embodiments, the fusion polypeptide or protein comprises a FGF (e.g., FGF23), or a functionally active variant or derivative (e.g., a variant comprising at least one conservative amino acid substitution and/or one amino acid deletion) thereof; and a modified Fc fragment, or a functionally active variant or derivative (e.g., a variant comprising at least one conservative amino acid substitution and/or one amino acid deletion) thereof. Fusion proteins comprising FGF23 and FcLALA are described in SEQ ID NOs. 50, 51, 52 and 53. In some embodiments, the fusion polypeptide has one or more mutations in FGF23 which decrease aggregation and/or protease-mediated cleavage.

In a first aspect, the disclosure provides a fusion polypeptide having at least one extracellular subdomain of a Klotho protein and a fibroblast growth factor or an active fragment thereof. In some embodiments, the fusion further comprises a modified Fc fragment having decreased affinity (e.g., decreased Ka or increased Kd) for Fc-gamma-receptorand/or increased serum half-life. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs can be used in practicing the disclosure. The reader of the instant application may assume that each of every combination of alpha or beta extracellular domain with each human FGF protein or an active fragment thereof are individually and specifically contemplated.

According to the present disclosure, the extracellular domain of the Klotho protein can include one or both of the KL-D1 and KL-D2 domains of a Klotho protein, or a functionally active variant or derivative (e.g., a variant comprising at least one conservative amino acid substitution and/or one amino acid deletion) thereof. In some embodiments, the Klotho fusion polypeptide of the disclosure has at least two extracellular subdomains of a Klotho protein, or a functionally active variant or derivative (e.g., a variant comprising at least one conservative amino acid substitution and/or one amino acid deletion) thereof. For example, the at least two extracellular subdomains can be at least two KL-D1 domains in tandem repeats, at least two KL-D2 domains in tandem repeats, or at least one KL-D1 domain and at least one KL-D2 domain. In various embodiments, the fusion polypeptide of the disclosure comprises amino acids 28-292 of the full length alpha Klotho protein, or amino acids 28-982 (SEQ ID NO: 7). In another embodiment, the fusion polypeptide of the disclosure comprises amino acids 52-997 of the full length beta Klotho protein.

In one embodiment of the present disclosure, the components of a fusion polypeptide comprise: (a) a polypeptide comprising fibroblast growth factor 23 (FGF23), or a functionally active variant or derivative (e.g., a variant comprising at least one conservative amino acid substitution and/or one amino acid deletion) thereof, wherein FGF23 has a mutation at one or more of the positions Q156, C206 and C244; and (b) either a modified Fc fragment having decreased affinity for Fc-gamma-receptor and/or increased serum half-life, or a polypeptide comprising at least one extracellular subdomain of a Klotho protein, or a functionally active variant or derivative (e.g., a variant comprising at least one conservative amino acid substitution and/or one amino acid deletion) thereof and, optionally (c) a linker. The components can be, for example, chemically linked or fused in frame by a peptide bond. They may also linked via a linker. Non-limiting examples of polypeptide linker are SEQ ID NOs: 11, 12, 13, 14, 15, 16, 17, and 18. Such linkers may comprise at least one and up to about 30 repeats of SEQ ID NOs:11, 12, 13, 14, 15, 16, 17 and 18. In another non-limiting embodiment, the fusion comprises (2) a FGF or an active fragment thereof and (3) a modified Fc fragment. The various components of the fuion can be operatively linked in any order; the polypeptide (1) can be operatively linked to the N-terminus of the polypeptide for (2) or (3); the polypeptide for (2) can be operatively linked to the N-terminus of the polypeptide for (1) or (3); the polypeptide for (3) can be operatively linked to the N-terminus of the polypeptide for (1) or (2).

According to the present disclosure, the extracellular subdomain of a Klotho protein, the fibroblast growth factor and the (optional) modified Fc fragment having decreased affinity for Fc-gamma-receptorand/or increased serum half-life can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of an extracellular subdomain of the Klotho protein.

In one embodiment, the present disclosure provides a fusion polypeptide comprising a sKlotho of a Klotho protein and a linker. In another embodiment, the present disclosure provides a fusion polypeptide comprising a sKlotho of the alpha Klotho protein and a linker. In another embodiment, the present disclosure provides a fusion polypeptide comprising a sKlotho of the beta Klotho protein and a linker. In yet another embodiment, the present disclosure provides a human FGF protein or an active fragment thereof (e.g., without signal peptide) and a linker. In one embodiment the disclosure provides fusion proteins, nucleic acid molecules or pharmaceutical composition for use in therapy or as medicament for use in the treatment of a pathological disorder. Pharmaceutical compositions comprising the fusion proteins of the disclosure and their uses for treating or preventing age-related conditions or metabolic disorders are also encompassed by the present disclosure. In some embodiments, the fusion protein further comprises a modified Fc fragment having decreased affinity for Fc-gamma-receptorand/or increased serum half-life.

In one embodiment, the present disclosure provides a fusion polypeptide comprising a sKlotho of alpha Klotho protein with signal peptide fused (directly or indirectly via a linker) to FGF-23. In another embodiment, the present disclosure provides a fusion polypeptide comprising a sKlotho of alpha Klotho protein without signal peptide fused (directly or indirectly via a linker) to FGF-23. In another embodiment, the present disclosure provides sKlotho of alpha Klotho protein with signal peptide fused (directly or indirectly via a linker) to FGF-23 without signal peptide. In another embodiment, the present disclosure provides a fusion polypeptide comprising sKlotho of alpha Klotho protein without signal peptide fused (directly or indirectly via a linker) to FGF-23 without signal peptide. In some embodiments, the fusion protein further comprises a modified Fc fragment having decreased affinity for Fc-gamma-receptorand/or increased serum half-life.

In one embodiment, the present disclosure provides a fusion polypeptide comprising a sKlotho of alpha Klotho protein with signal peptide fused (directly or indirectly via a linker) to FGF-23 (R179Q) variant. In another embodiment, the present disclosure provides a fusion polypeptide comprising a sKlotho of alpha Klotho protein without signal peptide fused (directly or indirectly via a linker) to FGF-23 (R179Q) variant. In another embodiment, the present disclosure provides sKlotho of alpha Klotho protein with signal peptide fused (directly or indirectly via a linker) to FGF-23 (R179Q) variant without signal peptide. In another embodiment, the present disclosure provides a fusion polypeptide comprising sKlotho of alpha Klotho protein without signal peptide fused (directly or indirectly via a linker) to FGF-23 (R179Q) variant without signal peptide. In some embodiments, the fusion protein further comprises a modified Fc fragment having decreased affinity for Fc-gamma-receptorand/or increased serum half-life.

In one embodiment, the present disclosure provides a fusion polypeptide comprising: (a) a polypeptide comprising fibroblast growth factor 23 (FGF23), or a functionally active variant or derivative (e.g., a variant comprising at least one conservative amino acid substitution and/or one amino acid deletion) thereof, wherein FGF23 has a mutation at one or more of the positions Q156, C206 and C244; and (b) either a modified Fc fragment having decreased affinity for Fc-gamma-receptor and/or increased serum half-life, or a polypeptide comprising at least one extracellular subdomain of a Klotho protein, or a functionally active variant or derivative (e.g., a variant comprising at least one conservative amino acid substitution and/or one amino acid deletion) thereof; and, optionally (c) a linker. Such fusion polypeptides are disclosed in SEQ ID NOs: 54, 55, 56, 57, 58, 59, 60, 61, 62, 63, 64, 65, 66, 67, and 68.

In one embodiment, the present disclosure provides a fusion polypeptide comprising (1) sKlotho of alpha Klotho protein with signal peptide, or a functionally active variant or derivative (e.g., a variant comprising at least one conservative amino acid substitution and/or one amino acid deletion) thereof; (2) a linker; and (3) FGF-23 (R179Q) variant without signal peptide, or a functionally active variant or derivative (e.g., a variant comprising at least one conservative amino acid substitution and/or one amino acid deletion) thereof. In another embodiment, the present disclosure provides a fusion polypeptide comprising (1) sKlotho of alpha Klotho protein without signal peptide, or a functionally active variant or derivative (e.g., a variant comprising at least one conservative amino acid substitution and/or one amino acid deletion) thereof; (2) a linker; and (3) FGF-23 (R179Q) variant without signal peptide, or a functionally active variant or derivative (e.g., a variant comprising at least one conservative amino acid substitution and/or one amino acid deletion) thereof. In some embodiments, the fusion polypeptides of the disclosure are glycosylated. In some embodiments, the fusion protein further comprises a modified Fc fragment having decreased affinity for Fc-gamma-receptorand/or increased serum half-life.

In one embodiment, the present disclosure provides a fusion polypeptide comprising (1) sKlotho of alpha Klotho protein with signal peptide (SEQ ID NO: 44 or SEQ ID NO: 45), or a functionally active variant or derivative (e.g., a variant comprising at least one conservative amino acid substitution and/or one amino acid deletion) thereof (2) a linker comprising SEQ ID NO: 11; and (3) FGF-23 (R179Q) variant without signal peptide (SEQ ID NO: 43), or a functionally active variant or derivative (e.g., a variant comprising at least one conservative amino acid substitution and/or one amino acid deletion) thereof. In another embodiment, the present disclosure provides a fusion polypeptide comprising (1) sKlotho of alpha Klotho protein without signal peptide (SEQ ID NO: 7), or a functionally active variant or derivative (e.g., a variant comprising at least one conservative amino acid substitution and/or one amino acid deletion) thereof (2) a linker comprising SEQ ID NO: 11; and (3) FGF-23 (R179Q) variant without signal peptide (SEQ ID NO: 43), or a functionally active variant or derivative (e.g., a variant comprising at least one conservative amino acid substitution and/or one amino acid deletion) thereof. In one embodiment, the present disclosure provides a fusion polypeptide comprising the amino acid sequence of SEQ ID NO: 19, 20, 40, or 41. In some embodiments, the fusion polypeptides of the disclosure are glycosylated.

In one embodiment, the present disclosure provides a fusion polypeptide comprising sKlotho of alpha Klotho protein with signal peptide (SEQ ID NO: 44 or SEQ ID NO: 45), or a functionally active variant or derivative (e.g., a variant comprising at least one conservative amino acid substitution and/or one amino acid deletion) thereof; and a linker comprising SEQ ID NO: 11. In another embodiment, the present disclosure provides a fusion polypeptide comprising sKlotho of alpha Klotho protein without signal peptide (SEQ ID NO: 7); and a linker comprising SEQ ID NO: 11. In some embodiments, the fusion polypeptides of the disclosure are glycosylated. In some embodiments, the fusion protein further comprises a modified Fc fragment having decreased affinity for Fc-gamma-receptorand/or increased serum half-life.

In one embodiment, the present disclosure provides a fusion polypeptide comprising a human FGF protein or an active fragment thereof (e.g., without the signal peptide); and a linker comprising SEQ ID NO: 11. In some embodiments, the fusion polypeptides of the disclosure are glycosylated. In some embodiments, the fusion protein further comprises a modified Fc fragment having decreased affinity for Fc-gamma-receptorand/or increased serum half-life.

In one embodiment, the present disclosure provides a fusion polypeptide comprising a human FGF protein (e.g., FGF23) or an active fragment thereof (e.g., without the signal peptide); a linker (e.g., a linker comprising SEQ ID NO: 11); and sKlotho (with or without a signal peptide), or a functionally active variant or derivative (e.g., a variant comprising at least one conservative amino acid substitution and/or one amino acid deletion) thereof) or a Fc-gramma-receptor (e.g., FcLALA); wherein the FGF (e.g., FGF23) has one or more mutations at these residues: R179, Q156, C206, and/or C244. In various embodiments, the mutations are R179Q, Q156A, C206S, and/or C244S. Even though these mutations are conserved in the human, rhesus, bovine, mouse and rat FGF23, mutating them does not prevent FGF23 activity. Rather, mutating these amino acids unexpectedly enhances the qualities of the proteins, by reducing aggregation, reducing undesired protease-induced cleavage, and increasing protein production from cells. In various embodiments, the fusion protein comprising one or more FGF23 mutation is glycosylated.

In one embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) that comprises (1) FGF-23 (R179Q) variant without signal peptide (SEQ ID NO: 43), or a variant comprising additional mutations which reduce aggregation and/or protease-mediated cleavage, or a functionally active variant or derivative (e.g., a variant comprising at least one conservative amino acid substitution and/or one amino acid deletion) thereof (2) optionally, a linker comprising SEQ ID NO: 11; and (3) sKlotho of alpha Klotho protein with signal peptide (SEQ ID NO: 44 or SEQ ID NO: 45), or a functionally active variant or derivative (e.g., a variant comprising at least one conservative amino acid substitution and/or one amino acid deletion) thereof or a modified Fc fragment having decreased affinity for Fc-gamma-receptorand/or increased serum half-life; and uses of the pharmaceutical composition in therapy or as medicament for the treatment of a pathological disorder, for example treating and/or preventing age-related conditions, such as muscular atrophy. In another embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) that comprises (1) FGF-23 (R179Q) variant without signal peptide (SEQ ID NO: 43), or a variant comprising additional mutations which reduce aggregation and/or protease-mediated cleavage, or a functionally active variant or derivative (e.g., a variant comprising at least one conservative amino acid substitution and/or one amino acid deletion) thereof (2) a linker comprising SEQ ID NO: 11; and (3) sKlotho of alpha Klotho protein without signal peptide (SEQ ID NO: 7), or a functionally active variant or derivative (e.g., a variant comprising at least one conservative amino acid substitution and/or one amino acid deletion) thereof, or a modified Fc fragment having decreased affinity for Fc-gamma-receptorand/or increased serum half-life, or a functionally active variant or derivative (e.g., a variant comprising at least one conservative amino acid substitution and/or one amino acid deletion) thereof; and uses of the pharmaceutical composition in therapy or as medicament for the treatment of a pathological disorder, for example treating and/or preventing age-related conditions, such as muscular atrophy. In one embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) comprising the amino acid sequence of SEQ ID NO: 19, 20, 40, or 41; and uses of the pharmaceutical composition in therapy or as medicament for the treatment of a pathological disorder, for example treating and/or preventing age-related conditions, such as muscular atrophy.

In one embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) that comprises sKlotho of alpha Klotho protein with signal peptide (SEQ ID NO: 44 or SEQ ID NO: 45); and a linker comprising SEQ ID NO: 11; and uses of the pharmaceutical composition for treating and/or preventing age-related conditions, such as muscular atrophy. In another embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) comprising sKlotho of alpha Klotho protein without signal peptide (SEQ ID NO: 7); and a linker comprising SEQ ID NO: 11; and uses of the pharmaceutical composition in therapy or as medicament for the treatment of a pathological disorder, for example treating and/or preventing age-related conditions, such as muscular atrophy. In some embodiments, the fusion protein further comprises a modified Fc fragment.

In one embodiment, the present disclosure provides a pharmaceutical composition comprising (e.g., as a sole pharmaceutically active ingredient) a fusion polypeptide (e.g., glycosylated or non-glycosylated) that comprises a human FGF protein or an active fragment thereof (e.g., without the signal peptide); and a linker comprising SEQ ID NO: 11.

Pharmaceutical compositions comprising the fusion proteins of the disclosure and their uses in therapy or as medicament for the treatment of a pathological disorder therapy, for example treating or preventing age-related conditions (e.g., muscle atrophy) or metabolic disorders (e.g., diabete) are also encompassed by the present disclosure.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 19. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 20.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 40. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 41.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 46. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 47.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 48. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 49.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 50. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 51.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 52. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 53.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 54.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 55.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 56.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 57.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 58.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 59.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 60.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 61.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 62.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 63.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 64.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 65.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 66.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 67.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 68.

In one embodiment, the present disclosure provides a fusion polypeptide comprising a sKlotho of beta Klotho protein with signal peptide fused (directly or indirectly via a linker) to FGF-19 or an active fragment thereof. In some embodiments, the fusion further comprises a modified Fc fragment having decreased affinity for Fc-gamma-receptor and/or increased serum half-life. In another embodiment, the present disclosure provides a fusion polypeptide comprising a sKlotho of beta Klotho protein without signal peptide fused (directly or indirectly via a linker) to FGF-19 or an active fragment thereof. In another embodiment, the present disclosure provides a fusion polypeptide comprising a sKlotho of beta Klotho protein with signal peptide fused (directly or indirectly via a linker) to FGF-21 or an active fragment thereof. In another embodiment, the present disclosure provides a fusion polypeptide comprising a sKlotho of beta Klotho protein without signal peptide fused (directly or indirectly via a linker) to FGF-21 or an active fragment thereof.

The disclosure provides nucleic acid sequences encoding any of the Klotho fusion polypeptides described herein and host cells containing the nucleic acids. In some embodiments, the fusion further comprises a modified Fc fragment having decreased affinity for Fc-gamma-receptor and/or increased serum half-life.

The disclosure also provides composition having any of the Klotho fusion polypeptides contemplated herein. The compositions of the disclosure can further include heparin. In some embodiments, the fusion further comprises a modified Fc fragment having decreased affinity for Fc-gamma-receptor and/or increased serum half-life.

The disclosure also provides a method for treating or preventing an age-related condition in an individual. An individual (e.g., human) is administered a therapeutically effective dose of a pharmaceutical composition containing a Klotho fusion polypeptide, having at least one extracellular subdomain of a Klotho protein (e.g., alpha Klotho protein) and a fibroblast growth factor or an active fragment thereof so as to treat or prevent the age-related condition. In some embodiments, the fusion further comprises a modified Fc fragment having decreased affinity for Fc-gamma-receptor and/or increased serum half-life. In particular, the disclosure provides a method of treating or preventing muscle wasting comprising administering to an individual (e.g., human) an therapeutically effective amount of a fusion polypeptide having at least one extracellular subdomain of an alpha Klotho protein and a fibroblast growth factor (or an active fragment thereof).

Additionally, the disclosure provides a method for treating or preventing a metabolic disorder in an individual. An individual is administered a therapeutically effective dose of a pharmaceutical composition containing a fusion polypeptide of the disclosure, having at least one extracellular subdomain of a Klotho protein and a fibroblast growth factor (or an active fragment thereof) so as to treat the metabolic disorder. In some embodiments, the fusion further comprises a modified Fc fragment having decreased affinity for Fc-gamma-receptor and/or increased serum half-life. In particular, a fusion polypeptide of the disclosure having at least one extracellular subdomain of a beta-Klotho protein and a fibroblast growth factor 21 is useful for treating a metabolic disorder.

Klotho-FGF23 fusion polypeptides of the disclosure can be used for treating or preventing hyperphosphatemia or calcinosis in an individual. In some embodiments, the fusion further comprises a modified Fc fragment having decreased affinity for Fc-gamma-receptor and/or increased serum half-life. A pharmacologically effective dose of a pharmaceutical composition containing the Klotho fusion polypeptide of the disclosure, having at least one extracellular subdomain of a Klotho protein and a fibroblast growth factor, is administered to treat or prevent hyperphosphatemia or calcinosis. In particular, a Klotho fusion polypeptide of the disclosure having at least one extracellular subdomain of an alpha Klotho protein and a fibroblast growth factor 23 is useful for treating hyperphosphatemia or calcinosis.

Klotho-FGF23 fusion polypeptides of the disclosure can be used for treating or preventing chronic renal disease or chronic renal failure in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the disclosure, having at least one extracellular subdomain of a Klotho protein (e.g., alpha Klotho protein) and a fibroblast growth factor, is administered to treat or prevent chronic renal disease or chronic renal failure.

Klotho-FGF23 fusion polypeptides of the disclosure can be used for treating or preventing cancer (e.g., breast cancer) in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the disclosure, having at least one extracellular subdomain of a Klotho protein (e.g., alpha Klotho protein) and a fibroblast growth factor, is administered to treat or prevent cancer or breast cancer.

The present disclosure provides fusion polypeptides comprising at least one extracellular subdomain of Klotho protein and a FGF or an active fragment thereof for use in medicine. In some embodiments, the fusion further comprises a modified Fc fragment having decreased affinity for Fc-gamma-receptor and/or increased serum half-life. In one embodiment, the present disclosure provides fusion polypeptides comprising at least one extracellular subdomain of Klotho protein and a FGF or an active fragment thereof for use in treating or preventing muscle atrophy. The present disclosure also provides a method of treating or preventing an age related condition (e.g., muscle atrophy) comprising administering to an individual in need thereof a therapeutically effective dose of a pharmaceutical composition comprising a soluble Klotho protein.

The disclosure futhermore provides the above described peptides and fusion polypeptides or pharmaceutical compositions comprising said peptides for use in therapy, as a medicament or for use in the treatment of a pathological disorder, for example age-related condition, metabolic disorder, hyperphosphatemia or calcinosis, chronic renal disease or chronic renal failure or to prevent cancer or breast cancer, in an individual. Additonally, the disclosure further provides use of a polypeptide, nucleic acid or pharmaceutical composition of the invention in the manufacture of a medicament for the treatment of a pathological disorder, particularly for the treatment of the above mentioned disorders, preferably age related conditions like muscle atrophy.

The disclosure also includes kits for treating or preventing an age-related disorder or metabolic disorder in an individual. The kit includes instructions for use and a purified Klotho fusion polypeptide having at least one extracellular subdomain of a Klotho protein and a fibroblast growth factor. In some embodiments, the fusion further comprises a modified Fc fragment having decreased affinity for Fc-gamma-receptor and/or increased serum half-life.

The disclosure also provides a kit for producing a Klotho fusion polypeptide of the disclosure. The kit of the disclosure includes instructions for use and a nucleic acid encoding a Klotho fusion polypeptide, having at least one extracellular subdomain of Klotho protein and a fibroblast growth factor. In some embodiments, the fusion further comprises a modified Fc fragment having decreased affinity for Fc-gamma-receptor and/or increased serum half-life.

In one embodiment of the disclosure, the fusion polypeptide comprises: (a) a polypeptide comprising a fibroblast growth factor, or a functionally active variant or derivative (e.g., a variant comprising at least one conservative amino acid substitution and/or one amino acid deletion) thereof; and (b) a modified Fc fragment, or a functionally active variant or derivative (e.g., a variant comprising at least one conservative amino acid substitution and/or one amino acid deletion) thereof, having decreased affinity for Fc-gamma-receptor and/or increased serum half-life In one embodiment of the disclosure, the polypeptide of (a) and the polypeptide of (b) are connected by a polypeptide linker. The linker can be repeated 1 to 30 times, or more.

In one embodiment of the disclosure, the polypeptide linker comprises an amino acid sequence selected from the group consisting of: SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18.

In one embodiment of the disclosure, the polypeptide of (a) is connected by a peptide bond to the N-terminus of said polypeptide linker, and the polypeptide of (b) is connected by a peptide bond to the C-terminus of said polypeptide linker.

In one embodiment of the disclosure, the fusion polypeptide further comprises a signal peptide.

In one embodiment of the disclosure, the signal peptide is the IgG signal peptide.

In one embodiment of the disclosure, the fibroblast growth factor is fibroblast growth factor-23 or a fibroblast growth factor-23 variant (R179Q).

In one embodiment of the disclosure, the fibroblast growth factor is fibroblast growth factor-19 or fibroblast growth factor-21.

In one embodiment of the disclosure, fusion polypeptide comprises an amino acid sequence which is 95% or more identical to the amino acid sequence of SEQ ID NO: 51, or SEQ ID NO: 53.

In one embodiment of the disclosure, fusion polypeptide comprises the amino acid sequence of SEQ ID NO: 51, or SEQ ID NO: 53.

In one embodiment of the disclosure, fusion polypeptide comprises FcLALA.

3. BRIEF DESCRIPTION OF THE DRAWINGS

FIG. 1 illustrates several different embodiments of the Klotho fusion polypeptides of the disclosure. The represented fusion polypeptides include one or more Klotho extracellular subdomains operatively linked to a fibroblast growth factor. Polypeptides containing one or more Klotho extracellular subdomains include, for example, an extracellular domain of Klotho (e.g., aa 1 to 982 of human Klotho), or an active fragment of Klotho.

FIG. 2 illustrates the amino acid and nucleic acid sequences of several Klotho fusion polypeptides of the disclosure and components thereof (e.g., Klotho extracellular domain, FGF). Fusion proteins comprising sKlotho, FGF23 and FcLALA (a modified Fc fragment having decreased affinity for Fc-gamma-receptor and/or increased serum half-life) are described in SEQ ID NOs. 46, 47, 48, and 49. Fusion proteins comprising FGF23 and FcLALA are described in SEQ ID NOs. 50, 51, 52 and 53.

FIGS. 3A-3C depict protein expression of an sKlotho-FGF23 fusion protein. FIG. 3A shows that sKlotho-FGF23 fusion protein was detected in conditioned media by Western blotting with anti-FGF23 antibodies. FIG. 3B shows that sKlotho-FGF23 fusion protein was detected in conditioned media by SDS-PAGE and Coomassie blue staining FIG. 3C shows a highly purified sKlotho-FGF23-6×His fusion protein, analyzed by SDS-PAGE and Coomassie blue staining.

FIG. 4 illustrates the results of an Egr-1 luciferase assay comparing the activation level of Egr-1 in cells treated with conditioned media containing either a Klotho fusion polypeptide, a FGF 23 polypeptide only, a soluble Klotho (sKlotho) polypeptide only, and a soluble Klotho polypeptide in combination with a FGF 23 polypeptide in the absence or presence of heparin (20 μg/ml).

FIGS. 5A-5B depict the results of an Egr-1 luciferase assay comparing the activation level of Egr-1 in cells treated with purified Klotho fusion polypeptide, FGF 23 polypeptide, or soluble Klotho polypeptide in the absence or presence of heparin. FIG. 5A shows an the results of an experiment comparing the activation level of Egr-1 in cells treated with FGF 23 alone, sKlotho-His (10 nM or 20 nM) and a combination of FGF 23 and sKlotho-His (10 nM or 20 nM) in the absence or presence of heparin (20 μg/ml). FIG. 5B shows Egr-1 luciferase reporter activity in cells treated with sKlotho-FGF23-His fusion (0 nM, 0.6 nM, 1.21 nM, 2.41 nM, 4.83 nM, 9.65 nM, and 19.3 nM).

FIGS. 6A-6B illustrate the effect of treatment with a purified sKlotho fusion polypeptide on C2C12 muscle cells. FIG. 6A shows measurements of myotube diameter in C2C12 muscle cells treated with either IGF-1 (10 nM), FGF2 (20 ng/ml), or a purified Klotho fusion polypeptide (20 nM), in the absence or presence of dexamethasone (100 μM). FIG. 6B shows the phosphorylation of signaling pathway proteins in C2C12 muscle cells by IGF-1 (10 nM), FGF2 (20 ng/ml), or a purified Klotho fusion polypeptide (20 nM), in the absence or presence of rapamycin (40 nM).

Figure 11:
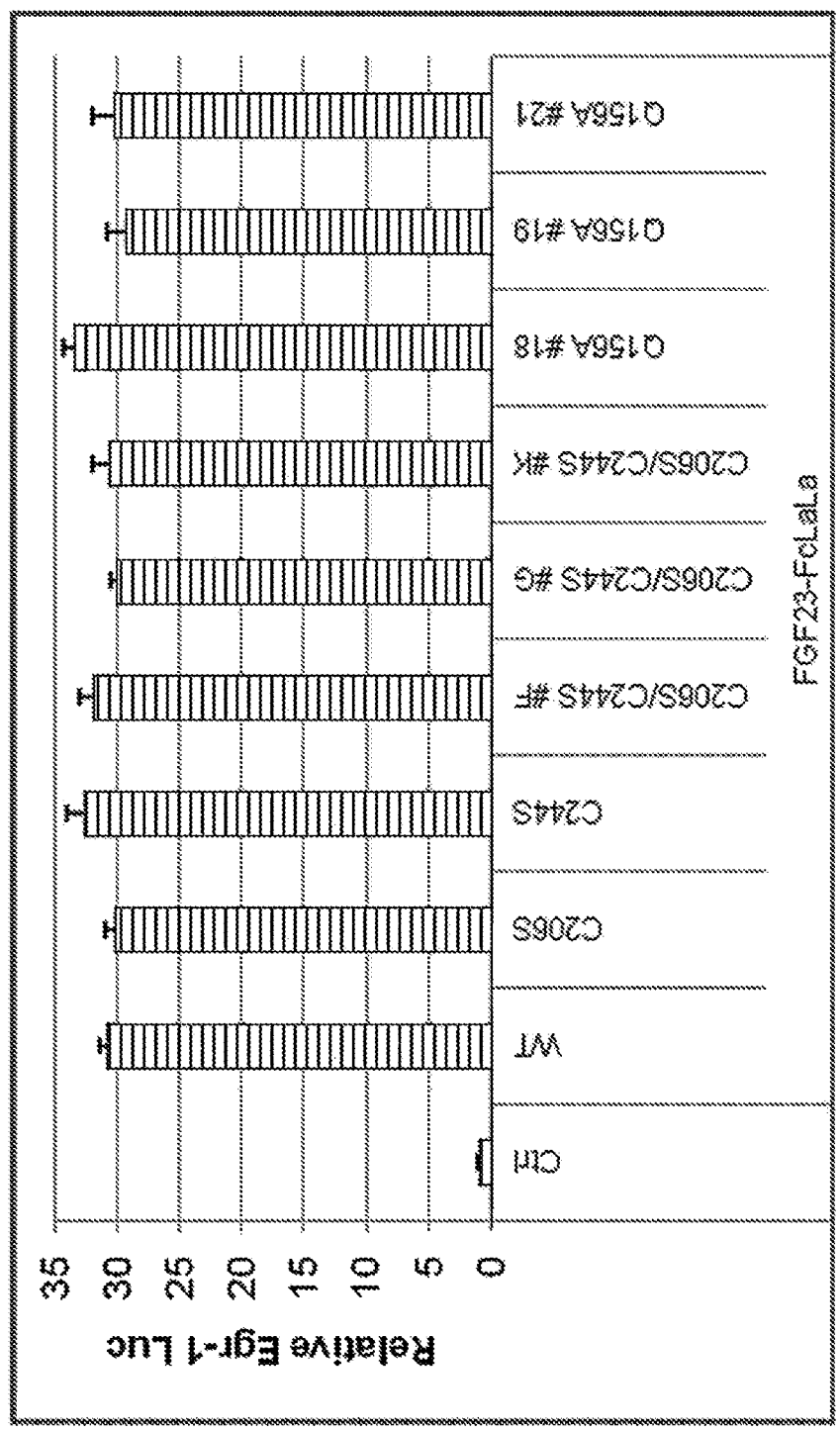

FIG. 11. This figure shows activation of EGR-1-luc reporter gene by FGF23(R179Q)-FcLALA and Q156A, C206S, C244S and C206S/C244S mutants.

Figure 12:
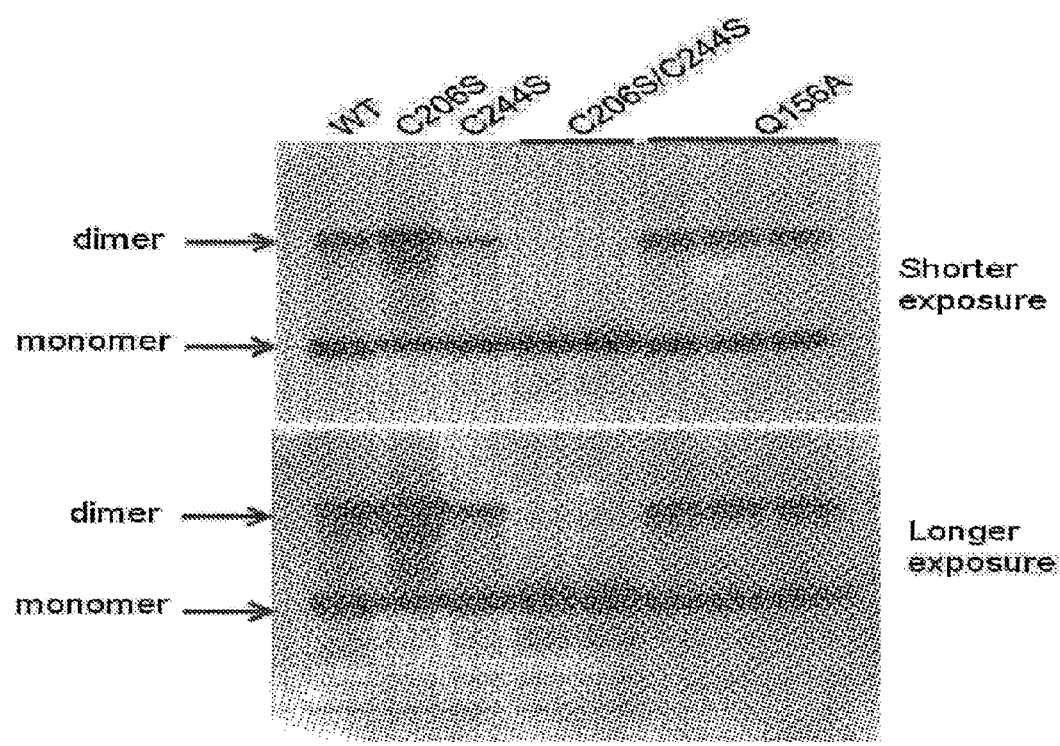

FIG. 12 shows protein qualities and dimerization of WT (wild-type), Q156A, C206S, C244S and C206S/C244S mutants of FGF23(R179Q)-FcLaLa.

4. DETAILED DESCRIPTION

The present disclosure is directed to methods, kits and compositions for preventing or treating age-related conditions and metabolic disorders; and to the use of said compositions in therapy, as a medicament or for use in the treatment of a pathological disorder. The fusion polypeptides of the disclosure include a Klotho protein or active fragment thereof. In some embodiments, the fusion polypeptides of the disclosure include a Klotho protein or an active fragment thereof operatively linked to a fibroblast growth factor polypeptide or active fragment thereof. In some embodiments, the fusion further comprises a modified Fc fragment with decreased ability to bind FcRn and/or increased stability in serum. In another embodiment, the fusion polypeptide comprises a FGF (e.g., FGF23) and a modified Fc fragment with decreased ability to bind FcRn and/or increased stability in serum.

The fusion proteins or sKlotho of the present disclosure are useful in the treatment and prevention of a variety of age-related conditions including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders including Type II Diabetes, Metabolic Syndrome, hyperglycemia, and obesity.

The present disclosure is based at least in part on the finding that despite the physical constraints (e.g., large size of both the Klotho and FGF polypeptides) the Klotho-FGF fusion polypeptides are highly effective in activating an FGF receptor. This finding is unexpected given that fusion of these two proteins would likely interfere with the heterodimerization and thus the activities of the proteins; e.g., the binding domains of the proteins may be perturbed by the fusion or the proteins may be mis-oriented spatially if put together in a "cis" formation.

The fusion polypeptides described herein are advantageous because they allow the administration of a single therapeutic protein that has enhanced activity compared to Klotho or FGF administered alone or together as separate polypeptides. The use of Klotho and FGF as a single fusion polypeptide rather than as two separate polypeptides (i.e., a Klotho polypeptide and a separate FGF polypeptide) is more effective at activating the FGF receptor.

Definitions

"Klotho polypeptide", "Klotho protein", or "Klotho" as used herein, includes active fragments, derivatives, mimetics, variants and chemically modified compounds or hybrids thereof of wild-type "Klotho". A Klotho active fragment has the ability to bind to an FGF polypeptide. Generally, a Klotho active polypeptide contains at least a Klotho subdomain (e.g., KL-D1 and KL-D2). Wild-type Klotho has the amino acid sequence as is found in nature. Example Klotho polypeptides suitable for use with the present disclosure include alpha-Klotho (SEQ ID NO: 2) and beta-Klotho (SEQ ID NO: 4). Nucleotide and amino acid sequences of the alpha-Klotho and beta-Klotho are found in the GenBank database at Accession No. NM_004795; NP_004786 and NM_175737; NP_783864, respectively. Klotho polypeptides include those described in U.S. Pat. No. 6,579,850, the content of which is herein incorporated by reference in its entirety. The Klotho polypeptides include those from other species besides humans, including alpha-Klotho from mouse (NP_038851), rat (NP_112626), rabbit (NP_001075692) and beta-Klotho from mouse (NP_112457). Species predicted to have alpha-Klotho include chimpanzee (XP_522655), macaque (XP_001101127), horse (XP_001495662), cow (XP_001252500), platypus (XP_001510981), and chicken (XP_417105). Species predicted to have beta-Klotho include chimpanzee (XP_526550), macaque (XP_001091413), horse (XP_001495248), dog (XP_536257), rat (XP_001078178), platypus (XP_001512722), and chicken (XP_423224). The Klotho polypeptides have an amino acid sequence that is substantially identical to the amino acid sequence of SEQ ID NO: 2 or SEQ ID NO: 4; i.e., at least 70%, 75%, 80%, 85%, 90%, 95%, 96%, 97%, 98%, 99% or more identical at the amino acid sequences of SEQ ID NO: 2 or SEQ ID NO: 4, or active fragment thereof.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond. As used herein a "Klotho fusion polypeptide" is a fusion polypeptide which includes an amino acid sequence from a Klotho polypeptide or active fragment thereof. A fusion polypeptide can comprise, as non-limiting examples, Klotho (e.g., sKlotho), FGF (e.g., FG23), and (optionally) a modified Fc fragment (e.g., a modified Fc fragment with decreased binding affinity to FC-gamma-receptor and/or increased serum half-life). Examples of this type of fusion polypeptide are presented in SEQ ID NOs. 46 to 49. In another embodiment, the fusion proteins comprise FGF (e.g., FGF23) and a modified Fc (e.g., FcLALA). Fusion proteins comprising FGF23 and FcLALA are described in SEQ ID NOs. 50, 51, 52 and 53. FcLALA is a Fc fragment with a LALA mutation (L234A, L235A), which triggers ADCC with lowered efficiency, and binds and activates human complement weakly. Hessell et al. 2007 Nature 449:101-104.

"Fibroblast growth factor" and "FGF" are used interchangeably herein and shall refer to polypeptides that regulate cell proliferation, migration, differentiation, homeostasis, tissue repair and response to injury in an animal, including a human subject. FGFs have the ability to bind to a fibroblast growth factor receptor and regulate its activity, including autophosphorylation of FGFR, phosphorylation of FRS2 (FGF receptor substrate 2) and ERK1/2 (extracellular signal-regulated protein kinase 1/2), and activating Egr-1 (early growth response-1). The term "FGF" includes active fragments, derivatives, mimetics, variants and chemically modified compounds or hybrids thereof of wild-type "FGF", e.g., as known in the art and as described in U.S. Pat. No. 7,223, 563 and U.S. Pat. No. 7,259,248, the contents of which are incorporated by reference in their entirety. Wild-type FGF has an amino acid sequence as is found in nature. Example fibroblast growth factors suitable for use with the present disclosure include fibroblast growth factor-19 (FGF19; SEQ ID NO: 31), fibroblast growth factor-21 (FGF21; SEQ ID NO: 33), and fibroblast growth factor-23 (FGF23; SEQ ID NO: 35). The FGF polypeptides include those from other species besides humans, including murine FGFs. Generally, FGF polypeptides have an amino acid sequence that is substantially identical to the amino acid sequence of SEQ ID NO: 31, SEQ ID NO: 33 or SEQ ID NO: 35; i.e., having an amino acid sequence is which is at least 70%, 75%, 80%, 85%, 90%, 95%, 96%, 97%, 98%, 99% or more or 100% identical to the amino acid sequences of SEQ ID NO: 31 SEQ ID NO: 33 or SEQ ID NO: 35, or active fragments thereof. Additional non-limiting examples of FGF, particularly FGF23, are provided at aa 1002-1228 of SEQ ID NO: 47; aa 1002-1228 of SEQ ID NO: 49; aa 1-251 of SEQ ID NO: 51, and aa 1-251 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

The term "FGF", includes active fragments of the full-length polypeptide. Active FGF fragments that are able to bind to their corresponding FGF receptors are known in the art and also contemplated for use in the present disclosure. One skilled in the art would appreciate, based on the sequences disclosed herein, that overlapping fragments of the FGFs can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF fragments could be tested by methods well known in the art and described herein, including binding to the FGF receptor. Similarly, cell culture models which possess the necessary FGF signal transduction machinery (i.e. FGF receptor) may be transfected with FGF fragments and subsequently tested for alterations in FGF signaling, relative to wild type FGF.

FGFs are grouped into seven subfamilies based on the homology of the FGF core homology domain (approximately 120 amino acids long), which is flanked by N- and C-terminal sequences that are highly variable in both length and primary sequence, particularly among different FGF subfamilies (Goetz et al., Molecular and Cellular Biology, 2007, Vol. 27, 3417-3428). An FGF active polypeptide generally contains at least an FGF core homology domain. In some embodiments, an FGF active polypeptide may contain, in addition to an FGF core homology domain, flanking sequences which may confer additional specificity in binding FGF receptors. FGF19, FGF21, and FGF23 are grouped in the FGF19 subfamily because the core region of these ligands share high sequence identity relative to other FGFs (FGF19 v. FGF21: 38% identity; FGF19 v. FGF23: 36% identity). FGF19 subfamily members act analogously to signaling molecules of the endocrine system and regulate diverse physiological processes uncommon to classical FGFs (e.g., FGF19: energy and bile acid homeostasis; FGF21: glucose and lipid metabolism; and FGF 23: phosphate and vitamin D homeostasis).

"Fibroblast growth factor receptor" and "FGFR" as used herein refer to any one of FGFRs 1-4 known in the art, or splice variants thereof (e.g., FGFR1c). Example fibroblast growth factor receptors suitable for use with the present disclosure include fibroblast growth factor receptor-19 (e.g., FGFR4-beta Klotho), fibroblast growth factor receptor-21 (e.g., FGFR1c-alpha Klotho), and fibroblast growth factor receptor-23 (e.g., FGFR1c-alpha Klotho, FGFR3-alpha Klotho, FGFR4-alpha Klotho).

"Extracellular domain", as used herein, refers to the fragment of a transmembrane protein existing outside of a cell (e.g., not including the intracellular or transmembrane region). The "extracellular domain of the Klotho protein", "soluble Klotho", or "sKlotho" (e.g., SEQ ID NO: 7; SEQ ID NO: 39), refers to an extracellular domain of the Klotho polypeptide that is capable of binding a fibroblast growth factor, and/or capable of enabling the binding of a fibroblast growth factor to a fibroblast growth factor receptor by binding to the fibroblast growth factor. The Klotho extracellular domain corresponds to amino acid residues 28-982 of the full length alpha Klotho sequence (SEQ ID NO: 2) and to amino acid residues 52-997 of the full length beta Klotho sequence (SEQ ID NO: 4).

"Extracellular subdomain of Klotho protein" and "extracellular subdomain of Klotho protein" are used interchangeably herein and shall refer to a region in the extracellular domain of the Klotho polypeptide that is capable of binding a fibroblast growth factor, and/or is capable of enabling the binding of a fibroblast growth factor to a fibroblast growth factor receptor by binding to the fibroblast growth factor. In various embodiments, the fusion comprises a polypeptide comprising at least one extracellular subdomain of a Klotho protein; a polypeptide comprising a fibroblast growth factor; and, optionally, a modified Fc fragment having decreased affinity for Fc-gamma-receptor and/or increased serum half-life. The Klotho extracellular domain has two homologous subdomains that are repeated, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and respectively to amino acid residues 77-508 and 571-967 of the full length beta Klotho polypeptide (SEQ ID NO: 4) and are suitable for use with the present disclosure. Generally, a polypeptide that contains at least one Klotho subdomain is a Klotho active polypeptide. The Klotho extracellular subdomain for use with the polypeptide of the disclosure may be an alpha Klotho or beta Klotho KL-D1 domain with an amino acid sequence that is substantially identical to the amino acid sequence of SEQ ID NO: 5 or SEQ ID NO: 37, respectively. Further, the Klotho KL-D1 domain may have an amino acid sequence that is at least 70%, 75%, 80%, 85%, 90%, 95%, 96%, 97%, 98%, 99% or more identical to the amino acid sequence of SEQ ID NO: 5 or SEQ ID NO: 37. The Klotho extracellular subdomain may also be an alpha or beta Klotho polypeptide KL-D2 domain that is substantially identical to the amino acid sequence of SEQ ID NO: 6 or SEQ ID NO: 38, respectively. In a further embodiment, the KL-D2 domain has an amino acid sequence that is at least at least 70%, 75%, 80%, 85%, 90%, 95%, 96%, 97%, 98%, 99% or more identical to the amino acid sequence of SEQ ID NO: 6 or SEQ ID NO: 38. In some embodiments, the fusion comprises at least two extracellular subdomains of the Klotho protein (e.g., KL-D1 and KL-D2; KL-D1 and KL-D1 in tandem repeats; KL-D2 and KL-D2 in tandem repeats, etc.).

"Modified Fc fragment", as used herein, shall mean an Fc fragment of an antibody comprising a modified sequence. The Fc fragment is a portion of an antibody comprising the CH2, CH3 and part of the hinge region. The modified Fc fragment can be derived from, for example, IgG1, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798. For example, in various modified Fc fragments: (a) amino acid residue 250 is glutamic acid and amino acid residue 428 is phenylalanine; or (b) amino acid residue 250 is glutamine and amino acid residue 428 is phenylalanine; or (c) amino acid residue 250 is glutamine and amino acid residue 428 is leucine. In some embodiments, amino acid residues 250 and 428 differ from the residues present in an unmodified Fc-fusion protein by amino acid residue 250 being glutamic acid or glutamine and amino acid residue 428 being leucine or phenylalanine, and wherein amino acid residues are numbered by the EU numbering system, as described in U.S. Pat. No. 7,217,798. In some embodiments, the modified Fc-fusion protein has a higher affinity for FcRn at pH 6.0 than at pH 8.0. Preferably, the modified Fc fragment has decreased affinity to FcRn and/or increased serum half-life. Non-limiting examples of modified Fc fragments include that at aa (amino acids) 1234-1459 of SEQ ID NO: 47; aa 1234 to 1450 of SEQ ID NO: 49; aa 257 to 482 of SEQ ID NO: 51; and aa 257 to 473 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

"Signal peptide", as used herein, shall mean a peptide chain (3-60 amino acids long) that directs the post-translational transport of a protein to the endoplasmic reticulum and may be cleaved off. Example signal peptides suitable for use with the present disclosure include the Klotho signal peptide (SEQ ID NO: 19) and the IgG signal peptide (SEQ ID NO: 20). Note that upon secretion and cleavage by the producer cell line, the signal peptide (e.g., of the peptides corresponding to SEQ ID NO: 19 and SEQ ID NO: 20) is cleaved off. Thus, after secretion and cleavage of the signal peptide by the producer cell lines, the peptide of SEQ ID NO: 19 would generate the peptide of SEQ ID NO: 41.

"Linker", as used herein, shall mean a functional group (e.g., chemical or polypeptide) that covalently attaches two or more polypeptides or nucleic acids so that they are connected with one another. As used herein, a "peptide linker" refers to one or more amino acids used to couple two proteins together (e.g., to couple the extracellular domain of Klotho and fibroblast growth factor-23). Peptide linkers suitable for use with the present disclosure include, but are not limited to, polypeptides with amino acid sequences represented by SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18. A polypeptide linker can comprise at least 1 and up to about 30 repeats of any of these amino acid sequences.

"Operatively linked", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

"Specifically binds", as used herein, shall refer to the ability of a first molecule to bind to a target molecule out of many, different types of molecules to which it may be exposed because of the ability of the first molecule to adopt a particular structure conducive to forming non-covalent interactions between itself and the other target molecule. The first molecule binds to the target forming a stable complex while there is substantially less recognition, contact, or complex formation of the first molecule with any other non-specific molecules.

"Polypeptide variant" or "protein variant", as used herein, refers to polypeptides in which one or more amino acids have been substituted by different amino acids from a reference sequence. It is well understood in the art that some amino acids may be substituted by others with broadly similar properties without changing the nature of the activity of the polypeptide (conservative substitutions) as described hereinafter. These terms also encompass polypeptides in which one or more amino acids have been added or deleted, or replaced with different amino acids, e.g., protein isoforms. An example variant of fibroblast growth factor-23 suitable for use with the present disclosure is the fibroblast growth factor-23 variant (R179Q).

"Pharmaceutical composition", as used herein, shall mean a composition containing a compound (e.g., a fusion polypeptide of the disclosure) that may be administered to treat or prevent a disease or disorder in an individual.

"Individual" or "subject", as used herein, shall refer to a mammal, including, but not limited to, a human or non-human mammal, such as a bovine, equine, canine, ovine, or feline.

"Treat", as used herein, shall mean decrease, suppress, attenuate, diminish, arrest, or stabilize the development or progression of a disease. In the context of the disclosure, the administration of the polypeptides of the disclosure may be used to treat age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity.

"Prevent", as used herein, shall refer to a decrease in the occurrence of a disorder or decrease in the risk of acquiring a disorder or its associated symptoms in a subject. In the context of the disclosure, the administration of the polypeptides of the disclosure may be used to prevent age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity. The prevention may be complete, e.g., the total absence of an age-related condition or metabolic disorder. The prevention may also be partial, such that the likelihood of the occurrence of the age-related condition or metabolic disorder in a subject is less likely to occur than had the subject not received the present disclosure.

"Disease", as used herein, shall mean any condition or disorder that damages or interferes with the normal function of a cell, tissue, or organ.

"Age-related condition", as used herein, shall mean any disease or disorder whose incidence in a population or severity in an individual correlates with the progression of age. In one embodiment, the age-related condition is a disease or disorder whose incidence is at least 1.5 fold higher among human individuals greater than 60 years of age relative to human individuals between the ages of 30-40 and in a selected population of greater than 100,000 individuals. Age-related conditions relevant to the present disclosure include, but are not limited to, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

"Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present disclosure include, but are not limited to, Type II Diabetes, Metabolic Syndrome, hyperglycemia, and obesity.

An "effective dose" or "effective amount" is an amount sufficient to effect a beneficial or desired clinical result. In the context of the disclosure, it is an amount of a Klotho fusion polypeptide or sKlotho effective to produce the intended pharmacological, therapeutic or preventive result. A therapeutically effective dose results in the prevention or amelioration of the disorder or one or more symptoms of the disorder, (e.g., an age-related condition or metabolic disorder). Therapeutically effective doses will vary depending upon the subject and disease condition being treated, the weight and age of the subject, the severity of the disease condition, the manner of administration and the like which can be readily be determined by one of ordinary skill in the art.

"Klotho nucleic acid molecule", as used herein is a gene encoding a Klotho protein. An example human Klotho gene is provided at GenBank Accession No. NM_004795 (SEQ ID NO: 1). Additional non-limiting examples of Klotho are provided at aa 1-982 of SEQ ID NO: 47 and aa 1-982 of SEQ ID NO: 49; and sequences which are at least 70%, 75%, 80%, 85%, 90%, 95%, 96%, 97%, 98%, 99% or more or 100% identical to these sequences.

"Fragment", as used herein, refers to a portion of a polypeptide or nucleic acid molecule. This portion contains, preferably, at least 10%, 20%, 30%, 40%, 50%, 60%, 70%, 80%, 90% or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or up to 3000 nucleotides or amino acids.

The term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, 70%, 75%, 80% or 85%, 90%, 91%, 92%, 93%, 94%, 95%, 96%, 97%, 98%, 99% or more identical at the amino acid level or nucleic acid to the sequence used for comparison.

The present disclosure is directed to methods, kits and compositions for preventing or treating age-related conditions and metabolic disorders; and to the use of said compositions in therapy, as a medicament or for use in the treatment of a pathological disorder. In some embodiments, the disclosure provides a fusion polypeptide having at least one extracellular subdomain of a Klotho protein. In some embodiments, the fusion polypeptides further comprise a fibroblast growth factor or an active fragment thereof. In some embodiments, the fusion further comprises a modified Fc fragment having decreased affinity for Fc-gamma-receptorand/or increased serum half-life. In other embodiments, the fusion comprises an FGF (e.g., FGF19, FGF21, FGF23 or FGF23 variant R179Q) fused to a modified Fc (e.g., FcLALA). FcLALA is a Fc fragment with a LALA mutation (L234A, L235A), which triggers ADCC with lowered efficiency, and binds and activates human complement weakly. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs or an active fragment thereof can be used in practicing the disclosure.

The extracellular domain of the Klotho protein can include one or both of the KL-D1 and KL-D2 domains of a Klotho protein. In some embodiments, the Klotho fusion polypeptide has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain.

The extracellular subdomain of a Klotho protein and the fibroblast growth factor (or an active fragment thereof) can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of the at least one extracellular subdomain of the Klotho protein.

The fusion polypeptide of the disclosure may include one or both of the Klotho extracellular domains, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and to amino acid residues 77-508 and 571-967 of the full length beta Klotho polypeptide (SEQ ID NO: 4) and are suitable for use with the present disclosure. The Klotho fusion polypeptide may have a KL-D1 domain of an alpha Klotho polypeptide having an amino acid sequence that is substantially identical to the amino acid sequence of SEQ ID NO: 5 or of a beta Klotho polypeptide having an amino acid sequence that is substantially identical to the amino acid sequence of SEQ ID NO: 37. Specifically, the Klotho fusion polypeptide may have an amino acid sequence that is at least at least 70%, 75%, 80%, 85%, 90%, 95%, 96%, 97%, 98%, 99% or more identical to SEQ ID NO: 5 or SEQ ID NO: 37. The Klotho fusion polypeptide may have a KL-D2 domain of an alpha Klotho polypeptide with an amino acid sequence that is substantially identical to the amino acid sequence of SEQ ID NO: 6 or of a beta Klotho polypeptide having an amino acid sequence that is substantially identical to the amino acid sequence of SEQ ID NO: 38. Specifically, the Klotho fusion polypeptide may have an amino acid sequence that is at least at least 70%, 75%, 80%, 85%, 90%, 95%, 96%, 97%, 98%, 99% or more identical to SEQ ID NO: 6 or SEQ ID NO: 38, respectively.

In some embodiments, the Klotho fusion polypeptide of the disclosure is soluble and is capable of binding to an FGF receptor.

The Klotho fusion polypeptides of the disclosure can contain a polypeptide linker which connects the polypeptide having at least one extracellular subdomain of a Klotho protein and the fibroblast growth factor and the (optional) modified Fc fragment. Suitable linkers are well known in the art and generally contain several Gly and several Ser residues, e.g., $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). In some embodiments, the linker will have at least 2 and up to about 30 repeats of an amino acid sequence represented by any one of SEQ ID NO: 12, SEQ ID NO: 13, SEQ ID NO: 14, SEQ ID NO: 15, SEQ ID NO: 16, SEQ ID NO: 17, or SEQ ID NO: 18.

When a polypeptide linker is present in the Klotho fusion polypeptide of the disclosure, the polypeptide having at least one extracellular subdomain of a Klotho protein may be connected by a peptide bond to the N-terminus of the linker polypeptide with the FGF connected by a peptide bond to the C-terminus of the polypeptide linker. Alternatively, the FGF may be connected by a peptide bond to the N-terminus of the linker polypeptide with the polypeptide having at least one extracellular subdomain of Klotho connected by a peptide bond to the C-terminus of the polypeptide linker. A chemical linker can also be used to link the two polypeptides.

The Klotho fusion polypeptide of the disclosure may include a signal peptide. Example signal peptides for use with the Klotho fusion polypeptide include, but are not limited to the Klotho signal peptide (SEQ ID NO: 8) and the IgG signal peptide (SEQ ID NO: 9).

In some embodiments, the disclosure provides a fusion between a FGF (e.g., FGF19, FGF21, FGF23, or FGF23 variant R179Q) and a modified Fc (e.g., FcLALA). The fusion can also optionally comprise linkers between the FGF and Fc portions. The fusion can also optionally comprise a signal peptide. In various embodiments, the disclosure encompasses nucleic acids encoding these fusion polypeptides, vectors comprising these nucleic acids, and host cells containing these nucleic acids.

4.1. Klotho and Fibroblast Growth Factor Polypeptides

The Klotho fusion polypeptides of the disclosure are expected to exhibit biological activities comparable to FGF in nature, such as binding to an FGF receptor and inducing the phosphorylation of an FGF receptor, FRS2 (FGF receptor substrate 2) and ERK1/2 (extracellular signal-regulated protein kinase 1/2) and activating Egr-1 (early growth response-1) gene. FGF is a secreted peptide growth factor that binds the FGF receptor. The amino acid and nucleic acid sequences of FGF are readily available to those of skill in the art. For example, example nucleotide sequences for FGF19, FGF21, and FGF23 can be found in the GenBank database at Accession numbers: NM_005117, NM_019113, and NM_020638, respectively, and herein as SEQ ID NOs: 30, 32, and 34, respectively. Example amino sequences for FGF19, FGF21, and FGF23 can be found in the GenBank database at Accession numbers: NP_005108, NP_061986, and NP_065689, respectively, and herein as SEQ ID NOs: 31, 35, and 35, respectively. Additionally, FGF may include one or more alterations which aid in the expression of the protein, e.g., the FGF23 (R179Q) variant (SEQ ID NO: 36).

The Klotho protein is a 130 kDa single pass type I transmembrane protein with an extracellular domain and a short cytoplasmic domain. The amino acid and nucleic acid sequences of Klotho are readily available to those of skill in the art. For example, example nucleotide sequences for alpha-Klotho and beta-Klotho can be found in the GenBank database at Accession numbers: NM_004795 and NM_175737, respectively, and herein as SEQ ID NOs: 7 and 8, respectively. Example amino acid sequences for alpha-Klotho and beta-Klotho can be found in the GenBank database at Accession numbers: NP_004786 and NP_783864, respectively, and herein as SEQ ID NOs: 2 and 4, respectively.

The Klotho fusion polypeptide of the disclosure can bind to a fibroblast growth factor receptor and has an alpha-Klotho or beta-Klotho extracellular domain operatively linked to either fibroblast growth factor-19 (SEQ ID NO: 31), fibroblast growth factor-21 (SEQ ID NO: 33), fibroblast growth factor-23 (SEQ ID NO: 35), or variants thereof (which include fibroblast growth factor-23 variant (R179Q) (SEQ ID NO: 36)).

Specifically, the Klotho fusion polypeptide of the disclosure may include an alpha-Klotho (SEQ ID NO: 2) which is operatively coupled to fibroblast growth factor-23 (SEQ ID NO: 35) or fibroblast growth factor-23 variant (R179Q) (SEQ ID NO: 36). Additionally, the Klotho fusion polypeptide of the disclosure may have beta-Klotho (SEQ ID NO: 4), which is operatively coupled to fibroblast growth factor-19 (SEQ ID NO: 31). The Klotho fusion polypeptide of the disclosure may include a beta-Klotho (SEQ ID NO: 4), which is operatively coupled to fibroblast growth factor-21 (SEQ ID NO: 33).

The disclosure includes homologs of the various Klotho and FGF genes and proteins encoded by those genes. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of Homologs of the genes described herein can be identified by percent identity between amino acid or nucleotide sequences for putative homologs and the sequences for the genes or proteins encoded by them (e.g., nucleotide sequences for genes encoding Klotho and FGF or their complementary strands). Percent identity may be determined, for example, by visual inspection or by using various computer programs known in the art or as described herein. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative amino acid substitutions typically include substitutions within the following groups:

glycine and alanine;
valine, isoleucine and leucine;
aspartic acid, glutamic acid, asparagine and glutamine;
serine and threonine;
lysine and arginine; and
phenylalanine and tyrosine.

Thus, mutating a glycine to alanine would be a conservative amino acid substititon, as would mutating an alanine to a glycine; mutating a valine to an isoleucine or leucine would be a conservative amino acid substation, as would replacing an isoleucine with valine or leucine, as would replacing leucine with valine or isoleucine, etc. The disclosure provides variants of all the amino acid sequences disclosed herein with at least one conservative amino acid substitution.

In an example approach to determining the degree of identity, a BLAST program may be used, with a probability score between $e^{-3}$ and $e^{-100}$ indicating a closely related sequence.

In one embodiment, the present disclosure provides a fusion polypeptide of SEQ ID NO: 19.

In another embodiment, the present disclosure provides a fusion polypeptide of SEQ ID NO: 20.

In one embodiment, the present disclosure provides a fusion polypeptide of SEQ ID NO: 40.

In another embodiment, the present disclosure provides a fusion polypeptide of SEQ ID NO: 41, or a variant thereof comprising at least one conservative amino acid substition.

In one embodiment, the present disclosure provides a fusion polypeptide of SEQ ID NO: 46.

In another embodiment, the present disclosure provides a fusion polypeptide of SEQ ID NO: 47, or a variant thereof comprising at least one conservative amino acid substition.

In another embodiment, the present disclosure provides a fusion polypeptide of SEQ ID NO: 48.

In another embodiment, the present disclosure provides a fusion polypeptide of SEQ ID NO: 49, or a variant thereof comprising at least one conservative amino acid substition.

In one embodiment, the present disclosure provides a fusion polypeptide of SEQ ID NO: 50.

In another embodiment, the present disclosure provides a fusion polypeptide of SEQ ID NO: 51, or a variant thereof comprising at least one conservative amino acid substition.

In one embodiment, the present disclosure provides a fusion polypeptide of SEQ ID NO: 52.

In another embodiment, the present disclosure provides a fusion polypeptide of SEQ ID NO: 53, or a variant thereof comprising at least one conservative amino acid substition.

In another embodiment, the present disclosure provides a fusion polypeptide of SEQ ID NO: 54, or a variant thereof comprising at least one conservative amino acid substition.

In another embodiment, the present disclosure provides a fusion polypeptide of SEQ ID NO: 55, or a variant thereof comprising at least one conservative amino acid substition.

In another embodiment, the present disclosure provides a fusion polypeptide of SEQ ID NO: 56, or a variant thereof comprising at least one conservative amino acid substition.

In another embodiment, the present disclosure provides a fusion polypeptide of SEQ ID NO: 57, or a variant thereof comprising at least one conservative amino acid substition.

In another embodiment, the present disclosure provides a fusion polypeptide of SEQ ID NO: 58, or a variant thereof comprising at least one conservative amino acid substition.

In another embodiment, the present disclosure provides a fusion polypeptide of SEQ ID NO: 59, or a variant thereof comprising at least one conservative amino acid substition.

In another embodiment, the present disclosure provides a fusion polypeptide of SEQ ID NO: 60, or a variant thereof comprising at least one conservative amino acid substition.

In another embodiment, the present disclosure provides a fusion polypeptide of SEQ ID NO: 61, or a variant thereof comprising at least one conservative amino acid substition.

In another embodiment, the present disclosure provides a fusion polypeptide of SEQ ID NO: 62, or a variant thereof comprising at least one conservative amino acid substition.

In another embodiment, the present disclosure provides a fusion polypeptide of SEQ ID NO: 63, or a variant thereof comprising at least one conservative amino acid substition.

In another embodiment, the present disclosure provides a fusion polypeptide of SEQ ID NO: 64, or a variant thereof comprising at least one conservative amino acid substition.

In another embodiment, the present disclosure provides a fusion polypeptide of SEQ ID NO: 65, or a variant thereof comprising at least one conservative amino acid substition.

In another embodiment, the present disclosure provides a fusion polypeptide of SEQ ID NO: 66, or a variant thereof comprising at least one conservative amino acid substition.

In another embodiment, the present disclosure provides a fusion polypeptide of SEQ ID NO: 67, or a variant thereof comprising at least one conservative amino acid substition.

In another embodiment, the present disclosure provides a fusion polypeptide of SEQ ID NO: 68, or a variant thereof comprising at least one conservative amino acid substition.

As used herein, the terms "homology" and "homologous" are not limited to designate proteins having a theoretical common genetic ancestor, but includes proteins which may be genetically unrelated that have, nonetheless, evolved to perform similar functions and/or have similar structures. Functional homology to the various proteins described herein also encompasses proteins that have an activity of the corresponding protein of which it is a homolog. For proteins to have functional homology, it is not required that they have significant identity in their amino acid sequences, but, rather, proteins having functional homology are so defined by having similar or identical activities. For example, with respect to a Klotho molecule, the polypeptide should have the functional characteristics of binding to an FGF polypeptide and enable the binding of the FGF to an FGFR. With respect to an FGF molecule, the polypeptide should have the functional characteristics of binding to an FGFR and causing the activation of FGFR (e.g., phosphorylation). Assays for assessing FGF binding to the FGF receptor and/or activation of the FGF signaling pathway are known in the art and described herein (See Example 2). Assays for assessing Klotho activity are also known in the art and described herein (e.g., binding to a FGF polypeptide). Proteins with structural homology are defined as having analogous tertiary (or quaternary) structure and do not necessarily require amino acid identity or nucleic acid identity for the genes encoding them. In certain circumstances, structural homologs may include proteins which maintain structural homology only at the active site or binding site of the protein.

In addition to structural and functional homology, the present disclosure further encompasses proteins having amino acid identity to the various Klotho and FGF amino acid sequences described herein. To determine the percent identity/homology of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

The amino acid sequences of molecules of the disclosure described herein have an amino acid sequence which is at least about 60%, 70%, 80%, 90%, 95%, 96%, 97%, 98%, 99% or more identical or homologous to an amino acid sequence described herein.

The nucleic acid sequences of molecules of the disclosure described herein have a nucleotide sequence which hybridizes to or is at least about 60%, 70%, 80%, 90%, 95%, 96%, 97%, 98%, 99% or more identical or homologous to a nucleotide sequence described herein.

Nucleic acid molecules appropriate for use in the fusion polypeptides of the disclosure may have a Klotho or FGF nucleotide sequence which hybridizes under stringent conditions to the complement of a nucleic acid molecule encoding Klotho or FGF, respectively. As used herein, the term "hybridizes under stringent conditions" is intended to describe conditions for hybridization and washing under which nucleotide sequences at least about 70%, 80%, 85%, 90% or more homologous to each other typically remain hybridized to each other. Such stringent conditions are known to those skilled in the art and can be found in Ausubel et al. *Current Protocols in Molecular Biology*, Wiley Interscience, New York (2001), 6.3.1-6.3.6. A specific, non-limiting example of stringent hybridization conditions are hybridization in 6× sodium chloride/sodium citrate (SSC) at about 45° C., followed by one or more washes in 0.2×SSC, 0.1% SDS at 50-65° C.

4.2. Klotho-FGF fusion polypeptides of the disclosure

In some embodiments of the disclosure, a Klotho fusion polypeptide has a polypeptide chain having a first polypeptide sequence of a Klotho polypeptide or an active fragment thereof and a second polypeptide sequence encoding FGF or an active fragment thereof. In some embodiments, the fusion further comprises a modified Fc fragment having decreased affinity for Fc-gamma-receptor and/or increased serum half-life.

The disclosure includes fusion polypeptides which are at least about 95% or more homologous to an amino acid sequence presented in SEQ ID NO: 19-28. The amino acid sequence of SEQ ID NO: 19 encodes a Klotho fusion polypeptide having a Klotho extracellular domain N-terminally linked to the FGF23 (R179Q) variant (SEQ ID NO: 36). The amino acid sequence of SEQ ID NO: 20 encodes a Klotho fusion polypeptide having an IgG signal peptide N-terminally linked to a Klotho extracellular domain lacking a signal peptide N-terminally linked to the FGF23 (R179Q) variant. The amino acid sequence of SEQ ID NO: 21 encodes a Klotho fusion polypeptide having a KL-D1 extracellular subdomain N-terminally linked to the FGF23 (R179Q) variant. The amino acid sequence of SEQ ID NO: 22 encodes a Klotho fusion polypeptide having a KL-D2 extracellular subdomain N-terminally linked to the FGF23 (R179Q) variant. The amino acid sequence of SEQ ID NO: 23 encodes a Klotho fusion polypeptide having two KL-D1 extracellular subdomains N-terminally linked to the FGF23 (R179Q) variant. The amino acid sequence of SEQ ID NO: 24 encodes a Klotho fusion polypeptide having two KL-D2 extracellular subdomains N-terminally linked to the FGF23 (R179Q) variant. The amino acid sequence of SEQ ID NO: 25 encodes a Klotho fusion polypeptide having the FGF23 (R179Q) variant N-terminally linked to a Klotho extracellular domain. The amino acid sequence of SEQ ID NO: 26 encodes a Klotho fusion polypeptide having the FGF23 (R179Q) variant N-terminally linked to a KL-D1 extracellular subdomain. The amino acid sequence of SEQ ID NO: 27 encodes a Klotho fusion polypeptide having the FGF23 (R179Q) variant N-terminally linked to a KL-D2 extracellular subdomain. The amino acid sequence of SEQ ID NO: 28 encodes a Klotho fusion polypeptide having the FGF23 (R179Q) variant N-terminally linked to two KL-D1 extracellular subdomains. The amino acid sequence of SEQ ID NO: 29 encodes a Klotho fusion polypeptide having the FGF23 (R179Q) variant N-terminally linked to two KL-D2 extracellular subdomains. In some embodiments, the fusion further comprises a modified Fc fragment having decreased affinity for Fc-gamma-receptor and/or increased serum half-life.

The Klotho fusion polypeptide of the disclosure may include an amino acid sequence which is at least about 95% identical to the amino acid sequence set forth in SEQ ID NO: 7. The amino acid sequence of SEQ ID NO: 7 encodes a Klotho extracellular domain lacking a signal peptide. In some embodiments, the fusion further comprises a modified Fc fragment having decreased affinity for Fc-gamma-receptor and/or increased serum half-life.

The subject fusion proteins are described herein and can be made using methods known in the art. For example, the fusion polypeptides of the disclosure may be constructed as described in U.S. Pat. No. 6,194,177. The use of Klotho polypeptides is described in U.S. Pat. No. 6,579,850. The use of FGF nucleic acid molecules is described in U.S. Pat. No. 7,223,563.

In some embodiments, a nucleic acid molecule encoding the Klotho is cloned by PCR and ligated, in frame, with a nucleic acid molecule encoding FGF. In some embodiments, the fusion further comprises a modified Fc fragment having decreased affinity for Fc-gamma-receptor and/or increased serum half-life. The nucleic acid encoding the fusion polypeptide is operatively linked to a promoter to allow for expression. The nucleic acid molecule encoding the fusion polypeptide is subsequently transfected into a host cell for expression. The sequence of the final construct can be confirmed by sequencing.

When preparing the fusion proteins of the present disclosure, a nucleic acid molecule encoding an extracellular subdomain of Klotho will be fused in frame to the nucleic acid molecule encoding FGF and the (optional) nucleic acid encoding the modified Fc fragment. Expression of the resulting nucleic acid molecule results in the extracellular subdomain of Klotho being fused N-terminal in relation to the FGF polypeptide. Fusions are also possible in which the extracellular subdomain of Klotho is fused C-terminal in relation to the FGF polypeptide. Methods for making fusion proteins are well known in the art.

The fusion polypeptides of the disclosure have at least two polypeptides that are covalently linked, in which one polypeptide comes from one protein sequence or domain, e.g., Klotho, and the other polypeptide comes from another protein sequence or domain, e.g., FGF. In some embodiments, the fusion further comprises a modified Fc fragment having decreased affinity for Fc-gamma-receptor and/or increased serum half-life. In another embodiment, the disclosure comprises a FGF fused to a modified Fc fragment. Klotho and/or FGF and/or the (optional) modified Fc fragment, of the fusion polypeptides of the disclosure, can be joined by methods well known to those of skill in the art. These methods include both chemical and recombinant means.

Nucleic acids encoding the domains to be incorporated into the fusion polypeptides of the disclosure can be obtained using routine techniques in the field of recombinant genetics. Basic texts disclosing the general methods of use in this disclosure include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). In nucleic acids encoding a Klotho fusion polypeptide of the disclosure, the nucleic acid sequence encoding alpha-Klotho or beta-Klotho, represented by SEQ ID NO: 1 and SEQ ID NO: 3, respectively, may be used. In nucleic acids encoding a Klotho fusion polypeptide, the nucleic acid sequence encoding FGF19, FGF21, or FGF23, represented by SEQ ID NO: 30, SEQ ID NO: 32 and SEQ ID NO: 34, respectively, may be used. Nucleic acid sequences of molecules of the disclosure described herein comprise a nucleotide sequence which hybridizes to or is at least about 60%, 70%, 80%, 90%, 95%, 96%, 97%, 98%, 99% or more identical or homologous to SEQ ID NO: 1, SEQ ID NO: 3, SEQ ID NO: 30, SEQ ID NO: 32, or SEQ ID NO: 34.

Nucleic acid sequences that encode the various components of the fusion [Klotho, and/or FGF peptide and/or the (optional) modified Fc fragment] can be obtained using any of a variety of methods. For example, the nucleic acid sequences encoding the polypeptides may be cloned from cDNA and genomic DNA libraries by hybridization with probes, or isolated using amplification techniques with oligonucleotide primers. More commonly, amplification techniques are used to amplify and isolate the Klotho and FGF sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding Klotho or FGF can also be isolated from expression libraries using antibodies as probes.

According to the present disclosure, the various components of the fusion [Klotho, and/or, FGF and/or the (optional) modified Fc fragment] can be linked either directly or via a covalent linker, including amino acid linkers, such as a polyglycine linker, or another type of chemical linker, including, carbohydrate linkers, lipid linkers, fatty acid linkers, polyether linkers, such as PEG, etc. (See for example, Hermanson, Bioconjugate techniques (1996)). The polypeptides forming the fusion/fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a fusion polypeptide of the disclosure. The polypeptides of the fusion protein can be in any order. The fusion polypeptides may be produced by covalently linking a chain of amino acids from one protein sequence, e.g., an extracellular subdomain of Klotho, to a chain of amino acids from another protein sequence, e.g., FGF, by preparing a recombinant polynucleotide contiguously encoding the fusion protein. The different chains of amino acids in a fusion protein may be directly spliced together or may be indirectly spliced together via a chemical linking group or an amino acid linking group. The amino acid linking group can be about 200 amino acids or more in length, or generally 1 to 100 amino acids. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

According to the present disclosure, the amino acid sequences of the fusion [an extracellular subdomain of Klotho and/or the FGF and/or the (optional) modified Fc fragment] may be linked via a peptide linker. Example peptide linkers are well known in the art and described herein. For example, peptide linkers generally include several Gly and several Ser residues, such as: $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). Specifically, a peptide linker for use in a fusion protein of the disclosure may act as a flexible hinge.

The signal sequence of Klotho or FGF may be excluded prior to incorporation of Klotho into a fusion protein of the disclosure. The signal sequence for Klotho or FGF of the fusion protein may be included, e.g., the polypeptide represented by SEQ ID NO: 19. However, such sequences may also be omitted and replaced with the signal sequence of a different protein, e.g., the IgG signal sequence (SEQ ID NO: 9). Generally, the pharmaceutical compositions of the disclosure will contain the mature form of Klotho and FGF.

Generally, introns are excluded from either one or both the Klotho or the FGF moieties prior to incorporation into a fusion polypeptide.

The fusion polypeptides of the disclosure may include one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, PEGylation of the fusion polypeptides of the disclosure is expected to provide such improved properties as increased half-life, solubility, and protease resistance. The fusion polypeptides of the disclosure may alternatively be modified by the covalent addition of polymers to free amino groups such as the lysine epsilon or the N-terminal amino group. Particular specific cysteines and lysines for covalent modification will be those not involved in receptor binding, heparin binding, or in proper protein folding. It will be apparent to one skilled in the art that the methods for assaying the biochemical and/or biological activity of the fusion polypeptides may be employed in order to determine if modification of a particular amino acid residue affects the activity of the protein as desired. Other similar suitable modifications are contemplated and known in the art.

The disclosure is also directed to the expression of a fusion polypeptide that is at least about 95% or more homologous to an amino acid sequence presented in SEQ ID NO: 19-28.

The present disclosure encompasses a fusion polypeptide comprising: (a) a polypeptide comprising at least one extracellular subdomain of a Klotho protein, or a functionally active variant or derivative thereof; (b) a polypeptide comprising a fibroblast growth factor, or a functionally active variant or derivative thereof; and (c) a modified Fc fragment having decreased affinity for Fc-gamma-receptor and/or increased serum half-life. By "a functionally active variant or derivative thereof" is meant a variant or derivative comprising a longer, shorter or altered amino acid sequence than the corresponding wild-type polypeptide, while retaining the biological activity. Thus "a functionally active variant or derivative" of an extracellular subdomain of a Klotho protein or a fibroblast growth factor comprises fewer, more, or an altered amino acid sequence than a wild-type extracellular subdomain of a Klotho protein or a fibroblast growth factor, but still retains at least one biological activity of the wild-type polypeptide sequence. A functionally active variant or derivative of a polypeptide disclosed herein can also comprise the same amino acid sequence of a polypeptide disclosed herein, but vary in post-translational modification (e.g., pegylation, methylation and/or glycosylation), or have additional moieties or elements added to it. In various embodiments, the variant or derivative of FGF23 comprises R179Q or does not.

In one embodiment, a functionally active variant or derivative polypeptide includes an amino acid sequence at least about 60% identical to a sequence disclosed herein (e.g., at least one extracellular domain of a Klotho protein or a fibroblast growth factor). Preferably, the polypeptide is at least 55%, 60%, 65%, 70%, 75%, 80%, 85%, 90%, 95%, 98%, 99% or more identical to a sequence disclosed herein.

As used herein, percent identity of two amino acid sequences (or of two nucleic acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

Identity or identical means amino acid sequence (or nucleic acid sequence) similarity and has an art recognized meaning. Sequences with identity share identical or similar amino acids (or nucleic acids). Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

Functionally active variants of a polypeptide disclosed herein retain substantially the same functional activity of the original polypeptide or fragment. Naturally occurring functionally active variants such as allelic variants and species variants and non-naturally occurring functionally active variants are included in the invention and can be produced by, for example, mutagenesis techniques or by direct synthesis.

A functionally active variant or derivative differs by about or at least, for example, 1, 2, 3, 4, 5, 6, 7, 8, 9, 10, 11, 12, 13, 14, 15, 16, 17, 18, 19, 20, 25, 30, 35, 40, 45, 50, 55, 60 or more amino acid residues from a polypeptide disclosed herein.

Where this comparison requires alignment the sequences are aligned for maximum homology. The site of variation can occur anywhere in the polypeptide, as long as activity substantially similar to a polypeptide disclosed herein.

Guidance concerning how to make variants and derivatives with phenotypically silent amino acid substitutions is provided in Bowie et al., Science, 247:1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. See e.g., FIG. 5. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific binding activity of the polypeptide.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., Science, 244:1081-1085 (1989)).

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Mutations can also be introduced using commercially available kits such as "QuikChange.™. Site-Directed Mutagenesis Kit" (Stratagene). The generation of a polypeptide functionally active variant or derivative to a polypeptide by replacing an amino acid that does not influence the function of a polypeptide can be accomplished by one skilled in the art.

A variant or derivative can have, for example, one or more conservative substitutions while still retaining at least one biological activity. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Particular example variants and derivatives include, without limitation, functionally active variants and derivatives of a polypeptide comprising at least one extracellular subdomain of a Klotho protein, e.g., a polypeptide comprising at least about 100, 150, 200, 250, 300, 350, 375, 400, or 425 contiguous amino acids of an extracellular domain of Klotho (e.g., SEQ ID NO: 5 or 6), with no more than about 1, 2, 3, 4, 5, 6, 7, 8, 9, 10, 11, 12, 13, 14, 15, 16, 17, 18, 19, 20, 25, 30, 35, 40, 45, 50, 55, 60 or more amino acid residue differences from the wild-type sequence (as disclosed in SEQ ID NO: 5 or 6), while retaining at least one biological activity of the wild-type polypeptide. For example, a functionally active variant or derivative of a polypeptide comprising at least one extracellular subdomain of a Klotho protein comprises a polypeptide comprising at least about 400 contiguous amino acids of SEQ ID NO: 5 or 6, with no more than about 100 amino acid residue differences. For example, a functionally active variant or derivative of a polypeptide comprising at least one extracellular subdomain of a Klotho protein comprises a polypeptide comprising at least about 400 contiguous amino acids of SEQ ID NO: 5 or 6, with no more than about 50 amino acid residue differences. For example, a functionally active variant or derivative of a polypeptide comprising at least one extracellular subdomain of a Klotho protein comprises a polypeptide comprising at least about 425 contiguous amino acids of SEQ ID NO: 5 or 6, with no more than about 25 amino acid residue differences. For example, a functionally active variant or derivative of a polypeptide comprising at least one extracellular subdomain of a Klotho protein comprises a polypeptide comprising at least about 425 contiguous amino acids of SEQ ID NO: 5 or 6, with no more than about 10 amino acid residue differences. In another example, a functionally active variant or derivative of a polypeptide comprising at least one extracellular subdomain of a Klotho protein comprises a polypeptide comprising at least about 100, 150, 200, 250, 300, 350, 400, 450, 500, 550, 600, 650, 700, 750, 800, 850, 900, 925, 950 or 982 contiguous amino acids of SEQ ID NO: 7, with no more than about 1, 2, 3, 4, 5, 6, 7, 8, 9, 10, 11, 12, 13, 14, 15, 16, 17, 18, 19, 20, 25, 30, 35, 40, 45, 50, 55, 60, 70, 75, 80, 85, 90, 95, 100, 110, 120, 140, 150, 160, 170, 180, 190, or 200 amino acid residue differences from the wild-type sequence. For example, a functionally active variant or derivative of a polypeptide comprising at least one extracellular subdomain of a Klotho protein comprises a polypeptide comprising at least about 500 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 600 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 700 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 800 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 900 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 900 contiguous amino acids of SEQ ID NO: 7, with no more than about 50 amino acid residue differences.

Particular example variants and derivatives include, without limitation, functionally active variants and derivatives of a polypeptide comprising a fibroblast growth factor, e.g., a polypeptide comprising at least about 100, 125, 150, 150, 175, 200, 225, or 250 contiguous amino acids of a fibroblast growth factor, e.g., FGF19 (SEQ ID NO: 31), FGF21 (SEQ ID NO: 33), or FGF23 (SEQ ID NO: 35), with no more than about 1, 2, 3, 4, 5, 6, 7, 8, 9, 10, 11, 12, 13, 14, 15, 16, 17, 18, 19, 20, 25, 30, 35, 40, 45, 50, 55, 60 or more amino acid residue differences from the wild-type sequence (as disclosed in SEQ ID NOs: 31, 33 or 35), while retaining at least one biological activity of the wild-type polypeptide. In various embodiments, the variant or derivative can comprise the R179Q variation or not. For example, a functionally active variant or derivative of a polypeptide comprising a fibroblast growth factor comprises a polypeptide comprising at least about 150 contiguous amino acids of SEQ ID NOs: 31, 33 or 35, with no more than about 25 amino acid residue differences. For example, a functionally active variant or derivative of a polypeptide comprising a fibroblast growth factor comprises a polypeptide comprising at least about 175 contiguous amino acids of SEQ ID NOs: 31, 33 or 35, with no more than about 25 amino acid residue differences. For example, a functionally active variant or derivative of a polypeptide comprising a fibroblast growth factor comprises a polypeptide comprising at least about 200 contiguous amino acids of SEQ ID NOs: 31, 33 or 35, with no more than about 25 amino acid residue differences. For example, a functionally active variant or derivative of a polypeptide comprising a fibroblast growth factor comprises a polypeptide comprising at least about 225 contiguous amino acids of SEQ ID NO: 35, with no more than about 50 amino acid residue differences. For example, a functionally active variant or derivative of a polypeptide comprising a fibroblast growth factor comprises a polypeptide comprising at least about 225 contiguous amino acids of SEQ ID NO: 35, with no more than about 25 amino acid residue differences.

4.3. Expression of Fusion Polypeptides of the Disclosure

In order to express the fusion protein of the disclosure, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the disclosure includes vectors (e.g., recombinant plasmids and bacteriophages) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a Klotho-FGF23 fusion operatively linked to regulatory sequences, e.g., promoter sequences, terminator sequences and/or artificial ribosome binding sites (RBSs), as defined herein. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast gal4 gene promoter, etc. Transcriptional initiation regulatory signals may be selected which allow for repression or activation, so that expression of the genes can be modulated.

In some of the molecules of the disclosure described herein, one or more DNA molecules having a nucleotide sequence encoding one or more polypeptide chains of a fusion polypeptide are operatively linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express fusion polypeptides of the disclosure. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particular method of high-yield production of the fusion polypeptides of the disclosure is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

4.4. Assays for Assessing Fusion Polypeptide Activity

Assays described herein (See Example 2) and those known in the art can be used for detecting Klotho or FGF activity of the fusion polypeptides of the disclosure. Suitable activity assays include receptor binding assays, cellular proliferation assays and cell signaling assays. For example, a binding assay which may be used for determining whether a fusion polypeptide has Klotho or FGF activity includes, assaying the binding of a fusion polypeptide to an FGF receptor. FGF receptor binding assays include, but are not limited to, both competitive and non-competitive assay. For example, FGF receptor binding can be detected by contacting cells expressing an FGF receptor with a labeled FGF (for example, radioactive label) and increasing concentrations of an unlabeled Klotho-FGF fusion polypeptide. The two ligands that compete for binding to the same receptor are added to a reaction mixture containing the cell. The cells are subsequently washed and labeled FGF is measured. A decrease in the amount of the labeled FGF to its receptor in the presence of the unlabeled fusion polypeptide is indicative of binding of the Klotho-FGF fusion polypeptide to the receptor. Alternatively, the Klotho-FGF fusion polypeptide may be labeled and direct binding of the fusion polypeptide to the cell is detected.

Klotho or FGF activity can also be measured by determining whether the fusion polypeptide induces a cellular response. For example, in some embodiments, an assay for detecting the biological activity of a Klotho-FGF fusion polypeptide involves contacting cells which express an FGF receptor with a fusion polypeptide, assaying a cellular response such as, for example, cell proliferation or Egr-1 activation, myotube diameter in C2C12 cells, and comparing the cellular response in the presence and absence of the fusion polypeptide. An increase in the cellular response in the presence of the fusion polypeptide complex relative to the absence indicates that the fusion polypeptide has biological activity. Also, an increase in a downstream signaling event from the receptor can also be measured as indicia of biological activity (e.g., phosphorylation of FGFR, FRS2, ERK1/2, p70S6K etc.).

4.5. Pharmaceutical Compositions and Methods of Treatment

The disclosure also pertains to pharmaceutical compositions containing one or more fusion polypeptides of the disclosure and a pharmaceutically acceptable diluent or carrier. The pharmaceutical compositions can further include a pharmaceutically effective dose of heparin. Such pharmaceutical compositions may be included in a kit or container. Such kit or container may be packaged with instructions pertaining to the extended in vivo half-life or the in vitro shelf life of the fusion polypeptides. Optionally associated with such kit or container(s) can be a notice in the form prescribed by a governmental agency regulating the manufacture, use or sale of pharmaceuticals or biological products, which notice reflects approval by the agency of manufacture, use or sale for human administration. Such compositions may be used in methods of treating, preventing, or ameliorating a disease or a disease symptom (e.g., age-related condition or metabolic disorder) in a patient, preferably a mammal and most preferably a human, by administering the pharmaceutical composition to the patient.

In general, a therapeutically effective amount of a pharmaceutical composition of the disclosure is from about 0.0001 mg/kg to 0.001 mg/kg; 0.001 mg/kg to about 10 mg/kg body weight or from about 0.02 mg/kg to about 5 mg/kg body weight. Commonly, a therapeutically effective amount of a fusion polypeptide is from about 0.001 mg to about 0.01 mg, about 0.01 mg to about 100 mg, or from about 100 mg to about 1000 mg, for example. Preferably, a therapeutically effective amount of a fusion polypeptide is from about 0.001 mg/kg to 2 mg/kg.

The optimal pharmaceutical formulations for a fusion polypeptide can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The fusion polypeptides of the disclosure may be administered as a pharmaceutical composition that may be in the form of a solid, liquid or gas (aerosol). Typical routes of administration may include, without limitation, oral, topical, parenteral, sublingual, rectal, vaginal, intradermal and intranasal. Parenteral administration includes subcutaneous injections, intravenous, intramuscular, intraperitoneal, intrapleural, intrasternal injection or infusion techniques. Preferably, the compositions are administered parenterally. More preferably, the compositions are administered intravenously. Pharmaceutical compositions of the disclosure can be formulated so as to allow a polypeptide of the disclosure to be bioavailable upon administration of the composition to a subject. Compositions can take the form of one or more dosage units, where, for example, a tablet can be a single dosage unit, and a container of a polypeptide of the disclosure in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of age-related condition or metabolic disorder the subject in need of treatment of, the use of the composition as part of a multi-drug regimen, the particular form of the polypeptide of the disclosure, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a polypeptide of the disclosure is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the polypeptides of the disclosure and pharmaceutically acceptable carriers are sterile. Water is a particular carrier when the polypeptide of the disclosure is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can contain one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the disclosure, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a particular specific adjuvant. An injectable composition is preferably sterile.

The pharmaceutical compositions contain an effective amount of a compound of the disclosure (e.g., fusion polypeptide) such that a suitable dosage will be obtained. The pharmaceutical compositions may contain the known effective amount of the compounds as currently prescribed for their respective disorders.

The route of administration of the polypeptide of the disclosure used in the prophylactic and/or therapeutic regimens which will be effective in the prevention, treatment, and/or management of a age-related condition or metabolic disorder can be based on the currently prescribed routes of administration for other therapeutics known in the art. The polypeptides of the disclosure can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a polypeptide of the disclosure. More than one polypeptides of the disclosure may be administered to a subject. Methods of administration may include, but are not limited to, oral administration and parenteral administration; parenteral administration including, but not limited to, intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin.

The polypeptides of the disclosure may be administered parenterally. Specifically, the polypeptides of the disclosure may be administered intravenously.

Pulmonary administration can also be employed, e.g., by use of an inhaler or nebulizer, and formulation with an aerosolizing agent, or via perfusion in a fluorocarbon or synthetic pulmonary surfactant. The polypeptides of the disclosure can also be formulated as a suppository, with traditional binders and carriers such as triglycerides.

The polypeptides of the disclosure can be delivered in a controlled release system. For example, a pump can be used (see Sefton, *CRC Crit. Ref Biomed. Eng.* 1987, 14, 201; Buchwald et al., Surgery 1980, 88: 507; Saudek et al., *N. Engl. J. Med.* 1989, 321: 574). Polymeric materials can also be used for controlled release of the polypeptides of the disclosure (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.*, 1989, 25, 351; Howard et al., *J. Neurosurg.*, 1989, 71, 105). Specifically, a controlled-release system can be placed in proximity of the target of the polypeptides of the disclosure, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (Science 1990, 249, 1527-1533) can be used.

Polymeric materials used to achieve controlled or sustained release of the polypeptides of the disclosure are disclosed, e.g., in U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Preferably, the polymer used in a sustained release formulation is inert, free of leachable impurities, stable on storage, sterile, and biodegradable.

In general, a therapeutically effective amount of a pharmaceutical composition of the disclosure is from about 0.0001 mg/kg to 0.001 mg/kg; 0.001 mg/kg to about 10 mg/kg body weight or from about 0.02 mg/kg to about 5 mg/kg body weight.

In other embodiments, the prophylactic and/or therapeutic regimen involves administering to a patient one or more doses of an effective amount of a polypeptide of the disclosure, wherein the dose of an effective amount achieves a plasma level of at least 0.01 µg/mL to at least 400 µg/mL of the polypeptide of the disclosure.

A prophylactic and/or therapeutic regimen may involve administering to a patient a plurality of doses of an effective amount of a polypeptide of the disclosure, wherein the plurality of doses maintains a plasma level of at least 0.01 µg/mL, to 400 µg/mL of the polypeptide of the disclosure. The prophylactic and/or therapeutic regimen may be administered for at least 1 day, 1 month, 2 months, 3 months, 4 months, 5 months, 6 months, 7 months, 8 months or 9 months.

The prophylactic and/or therapeutic regimen may involve administration of a polypeptide of the disclosure in combination with one or more additional therapeutics. The recommended dosages of the one or more therapeutics currently used for the prevention, treatment, and/or management of an age-related condition or metabolic disorder can be obtained from any reference in the art including, but not limited to, Hardman et al., eds., *Goodman & Gilman's The Pharmacological Basis Of Basis Of Therapeutics*, 10*th ed.*, McGraw-Hill, New York, 2001; *Physician's Desk Reference* (60$^{th}$ ed., 2006), which is incorporated herein by reference in its entirety.

The disclosure includes methods of treating disorders wherein agonistic activity of Klotho protein and FGF are desirable. The disclosure furthermore includes the use of the disclosed proteins, fusion proteins, nucleic acid molecules or pharmaceutical composition in therapy or as medicament for the treatment of a pathological disorder wherein agonistic activity of Klotho protein and FGF are desirable. Examples of such methods or uses of the disclosure include, but are not limited to age-related condition or metabolic disorders.

The disclosure includes methods for treating or preventing an age-related condition in an individual; and the use of the disclosed proteins, fusion proteins, nucleic acid molecules or pharmaceutical composition in therapy or as medicament for treating or preventing an age-related condition in an individual. An individual in need of treatment is administered a pharmacologically effective dose of a pharmaceutical composition containing a Klotho fusion polypeptide, having at least one extracellular subdomain of a Klotho protein and a fibroblast growth factor and an (optional) modified Fc fragment, so as to treat or prevent the age-related condition. In some embodiments, the Klotho fusion polypeptide is co-administered with a pharmacologically effective dose of heparin. Age-related conditions include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. In some embodiments, the Klotho fusion polypeptide contains at least one extracellular domain of an alpha Klotho protein. In a particular embodiment, a Klotho fusion protein containing at least one extracellular domain of alpha Klotho protein and fibroblast growth factor 23 is administered to an individual in need of treatment for muscle wasting.

The disclosure is also directed to a method for treating or preventing a metabolic disorder in an individual; and to the use of the disclosed proteins, fusion proteins, nucleic acid molecules or pharmaceutical composition in therapy or as medicament for treating or preventing metabolic disorder in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat the metabolic disorder, and an (optional) modified Fc fragment having decreased binding to FcRn and/or increased serum half-life and/or stability. In some embodiments, the Klotho fusion polypeptide is co-administered with a pharmacologically effective dose of heparin. The method may be used in the treatment or prevention of Type II Diabetes, Metabolic Syndrome, hyperglycemia, and obesity. In a particular embodiment, a Klotho fusion protein containing at least one extracellular domain of a beta-Klotho protein and fibroblast growth factor 21 is administered to an individual in need of treatment for a metabolic disorder.

The disclosure also provides methods for treating or preventing hyperphosphatemia or calcinosis in an individual; and the use of the disclosed proteins, fusion proteins, nucleic acid molecules or pharmaceutical composition in therapy or as medicament for treating or preventing hyperphosphatemia or calcinosis in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat hyperphosphatemia or calcinosis. In some embodiments, the Klotho fusion polypeptide is co-administered with a pharmacologically effective dose of heparin. In a particular embodiment, a Klotho fusion protein containing at least one extracellular domain of an alpha Klotho protein and fibroblast growth factor 23 and an (optional) modified Fc fragment is administered to an individual in need of treatment for a hyperphosphatemia or calcinosis.

The disclosure is also directed to a method for treating or preventing chronic renal disease or chronic renal failure in an individual; and to the use of the disclosed proteins, fusion proteins, nucleic acid molecules or pharmaceutical composition in therapy or as medicament for treating or preventing chronic renal disease or chronic renal failure in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat chronic renal disease or chronic renal failure. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for chronic renal disease or chronic renal failure.

The disclosure also includes methods for treating or preventing cancer in an individual; and the use of the disclosed proteins, fusion proteins, nucleic acid molecules or pharmaceutical composition in therapy or as medicament for treating or preventing cancer in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat cancer. The method may be used in the treatment or prevention of breast cancer. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for cancer.

In methods of treating disorders by administering a pharmaceutical composition containing a Klotho fusion polypeptide; or when using pharmaceutical composition containing a Klotho fusion polypeptide in therapy, the Klotho fusion polypeptide and an (optional) modified Fc fragment has at least one extracellular subdomain of a Klotho protein and a fibroblast growth factor. In a particular embodiment, the Klotho fusion protein contains at least one extracellular domain of a beta Klotho protein and fibroblast growth factor 21.

In another embodiment, the fusion comprises a FGF (e.g., FGF19, FGF21, FGF23 or FGF23 variant) and a modified Fc fragment with decreased binding to FcRn and/or increased serum stability. This type of fusion can be used in various diseases, as described above, or used to treat or prevent any FGF-related disease known in the art. The fusion can be administered to an individual in need thereof.

The fusion polypeptide compositions can be administered according to any method of administration known to those of skill in the art and described herein.

Particular specific methods of administration include subcutaneous or intravenous. Other effective modes of administration are described herein.

4.6. Methods of Treatment and Assays for Assessing Efficacy

Methods or uses of the disclosure which provide administering the fusion polypeptides described herein to an individual can be used to treat a variety of disorders including an age-related disorder or a metabolic disorder. Without being limited by any particular theory, fusion polypeptides may be used to treat disorders in which there is dysregulation of Klotho or FGF. Example disorders include metabolic disorders and age-related disorders. For example, both FGF23 or Klotho knock-out mice display a variety of similar phenotypes including, low physical activity, growth retardation, muscle wasting, skin atrophy, atherosclerosis, short life spans, etc. (See Razzaque and Lanske, *J. of Endrocrinology*, 194:1-10 (2007), which is herein incorporated by reference).

In particular, fusion polypeptides of the disclosure are particularly useful in the treatment of aging-related disorders, including muscle wasting. Without being bound to theory, the ability of Klotho and FGF23 to control mineral (e.g., phosphate and calcium) and vitamin D homeostasis may be the means by which these proteins modulate aging and muscle atrophy.

On the other hand, fusion polypeptides of the disclosure may be used for treating a metabolic disorder. For example, beta-Klotho and FGF19 have been shown to control bile acid homeostasis by regulating cholesterol 7-α-hydroxylase (CYP7A1). A non-limiting example of bile homeostasis disorder is cholestasis. The beta-Klotho and FGF21 have been shown to induce lipolysis in adipocytes and, therefore, reduced fat storage and increased glucose uptake. Non-limiting examples of lipolysis/fat storage disorders are obesity and associated metabolic and cardiovascular diseases.

Based at least in part on the finding that FGF23 is able to stimulate excretion of phosphate in the urine and thereby reduce phosphate levels in the serum, Klotho-FGF23 fusion polypeptides of the disclosure can be used for treating or preventing hyperphosphatemia or calcinosis in an individual. For example, it has been shown that a homozygous missense mutation in Klotho resulting in a deficiency in Klotho in a patient can cause severe tumoral calcinosis and artery calcification (Ichikawa et al., *J. Clin. Invest.* 117:2684-2691 (2007), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent hyperphosphatemia or calcinosis. In particular, a Klotho fusion polypeptide containing at least one extracellular domain of an alpha Klotho protein, a fibroblast growth factor and an (optional) modified Fc fragment is useful for treating hyperphosphatemia or calcinosis.

Klotho fusion polypeptides of the disclosure can also be used for treating or preventing chronic renal disease or chronic renal failure in an individual. For example, it has been shown that Klotho expression is reduced in kidney of patients with chronic renal failure, compared to that in unaffected kidneys (Koh et al., *Biochem. Biophys. Res. Comm.* 280: 1015-1020 (2001), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent chronic renal disease or chronic renal failure. In particular, a Klotho fusion polypeptide containing at least one extracellular domain of an alpha Klotho protein is useful for treating chronic renal disease or chronic renal failure.

Klotho fusion polypeptides of the disclosure can also be used for treating or preventing cancer in an individual. For example, it has been shown that Klotho expression is reduced in breast cancer tissue, compared to normal breast cancer tissue (Wolf et al., *Oncogene* (2008) advance online publication, which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent cancer or breast cancer. In particular, a Klotho fusion protein containing at least one extracellular domain of an alpha Klotho protein is useful for treating cancer or breast cancer.

Methods for evaluating the efficacy and/or determining the effective dose of a Klotho fusion polypeptide of the disclosure on an age-related disorder or metabolic disorder include organismal based assays, e.g., using a mammal (e.g., a mouse, rat, primate, or some other non-human), or other animal (e.g., *Xenopus*, zebrafish, or an invertebrate such as a fly or nematode). The Klotho fusion polypeptide can be administered to the organism once or as a regimen (regular or irregular). A parameter of the organism is then evaluated, e.g., an age-associated parameter. Klotho fusion polypeptides that are of interest result in a change in the parameter relative to a reference, e.g., a parameter of a control organism. Other parameters (e.g., related to toxicity, clearance, and pharmacokinetics) can also be evaluated.

The Klotho fusion polypeptide of the disclosure may be evaluated using an animal that has a particular disorder, e.g., a disorder described herein, e.g., an age-related disorder, a metabolic disorder. These disorders can also provide a sensitized system in which the test polypeptide's effects on physiology can be observed. Example disorders include: denervation, disuse atrophy; metabolic disorders (e.g., disorder of obese and/or diabetic animals such as db/db mouse and ob/ob mouse); cerebral, liver ischemia; cisplatin/taxol/vincristine models; various tissue (xenograph) transplants; transgenic bone models; pain syndromes (include inflammatory and neuropathic disorders); Paraquat, genotoxic, and oxidative stress models; and tumor I models.

For measuring an age-related disorder, the animal model can be an animal that has an altered phenotype when calorically restricted. For example, F344 rats provide a useful assay system for evaluating a Klotho fusion polypeptide. When calorically restricted, F344 rats have a 0 to 10% incidence of nephropathy. However, when fed ad libitum, they have a 60 to 100% incidence of nephropathy.

To evaluate a Klotho fusion polypeptide of the disclosure, it is administered to the animal (e.g., an F344 rat or other suitable animal) and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test polypeptide can be indicated as favorably altering lifespan regulation in the animal if the test polypeptide affects the parameter in the direction of the phenotype of a similar animal subject to caloric restriction. Such test polypeptides may cause at least some of the lifespan regulatory effects of caloric restriction, e.g., a subset of such effects, without having to deprive the organism of caloric intake.

The parameter to be tested may be an age-associated or disease associated parameter, e.g., a symptom of the disorder associated with the animal model. For example, the test polypeptide can be administered to a SH Rat, and blood pressure is monitored. A test polypeptide that is favorably indicated can cause an amelioration of the symptom relative to a similar reference animal not treated with the polypeptide. Other parameters relevant to a disorder or to aging can include: antioxidant levels (e.g. antioxidant enzyme levels or activity), stress resistance (e.g., paraquat resistance), core body temperature, glucose levels, insulin levels, thyroid-stimulating hormone levels, prolactin levels, and leutinizing hormone levels.

To measure the effectiveness of the polypeptides of the disclosure for treating an age-related disorder, an animal having decreased Klotho expression may be used, e.g., mouse with a mutant Klotho; See Kuroo, et al. Nature, 390; 45 (1997) and U.S. Pub. No. 2003/0119910, both of which are herein incorporated by reference in their entirety. For example, the test polypeptide is administered to the mutant mouse and age-related parameters are monitored. A test polypeptide that is favorably indicated can cause an amelioration of the symptom relative to a similar reference animal not treated with the polypeptide. A parameter relevant to a metabolic disorder or to aging can be assessed by measurement of body weight, examination on the acquisition of reproductive ability, measurement of blood sugar level, observation of life span, observation of skin, observation of motor functions such as walking, and the like. The assessment can also be made by measurement of thymus weight, observation of the size of calcified nodules formed on the inner surface of thoracic cavity, and the like. Further, quantitative determination of mRNA for the Klotho gene or Klotho protein is also useful for the assessment.

Still other in vivo models and organismal assays include evaluating an animal for a metabolic parameter, e.g., a parameter relevant to an insulin disorder, type II diabetes. Example metabolic parameters include: glucose concentration, insulin concentration, and insulin sensitivity.

Another example system features tumors, e.g., in an animal model. The tumors can be spontaneous or induced. For example, the tumors can be developed from cells that have a variety of genetic constitutions, e.g., they can be p53+ or p53−. It is also possible to use organisms that an autoimmune disorder, e.g., an NZB mouse, which is predisposed to SLE. To evaluate features of bone disease, it is possible, for example, to use an animal that has an ovariectomy as a model, e.g., for osteoporosis. Similarly, for joint disease, the model can be based on adjuvant arthritis (e.g., mice can be immunized with cartilage proteoglycans, high mobility group proteins, streptococcal cell wall material, or collagens); for kidney disease, kd/kd mice can be used. Animal models of cognition, particularly learning and memory are also available. Animal models of diabetes and its complications are also available, e.g., the streptozotocin model. Canine models can be used, for example, for evaluating stroke and ischemia.

In assessing whether a test polypeptide is capable of altering life span regulation, a number of age-associated parameters or biomarkers can be monitored or evaluated. Example age associated parameters include: (i) lifespan of the cell or the organism; (ii) presence or abundance of a gene transcript or gene product in the cell or organism that has a biological age dependent expression pattern; (iii) resistance of the cell or organism to stress; (iv) one so or more metabolic parameters of the cell or organism (example parameters include circulating insulin levels, blood glucose levels; fat content; core body temperature and so forth); (v) proliferative capacity of the cell or a set of cells present in the organism; and (vi) physical appearance or behavior of the cell or organism.

The term "average lifespan" refers to the average of the age of death of a cohort of organisms. In some cases, the "average lifespan" is assessed using a cohort of genetically identical organisms under controlled environmental conditions. Deaths due to mishap are discarded. Where average lifespan cannot be determined (e.g., for humans) under controlled environmental conditions, reliable statistical information (e.g., from actuarial tables) for a sufficiently large population can be used as the average lifespan.

Characterization of molecular differences between two such organisms, e.g., one reference organism and one organism treated with a Klotho fusion polypeptide can reveal a difference in the physiological state of the organisms. The reference organism and the treated organism are typically the same chronological age. The term "chronological age" as used herein refers to time elapsed since a preselected event, such as conception, a defined embryological or fetal stage, or, more preferably, birth. A variety of criteria can be used to determine whether organisms are of the "same" chronological age for the comparative analysis. Typically, the degree of accuracy required is a function of the average lifespan of a wildtype organism. For example, for the nematode C. elegans, for which the laboratory wildtype strain N2 lives an to average of about 16 days under some controlled conditions, organisms of the same age may have lived for the same number of days. For mice, organism of the same age may have lived for the same number of weeks or months; for primates or humans, the same number of years (or within 2, 3, or 5 years); and so forth. Generally, organisms of the same chronological age may have lived for an amount of time within 15, 10, 5, 3, 2 or 1% of the average lifespan of a wildtype organism of that species. Preferably, the organisms are adult organisms, e.g., the organisms have lived for at least an amount of time in which the average wildtype organism has matured to an age at which it is competent to reproduce.

The organismal screening assay can be performed before the organisms exhibit overt physical features of aging. For example, the organisms may be adults that have lived only 10, 20, 30, 40, 50, 60, or 70% of the average lifespan of a wildtype organism of the same species. Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein.

A marker associated with caloric restriction can also be evaluated in a subject organism of a screening assay (or a treated subject). Although these markers may not be age-associated, they may be indicative of a physiological state that is altered when the Klotho pathway is modulated. The marker can be an mRNA or protein whose abundance changes in calorically restricted animals. WO01/12851 and U.S. Pat. No. 6,406,853 describe example markers. Cellular models derived from cells of an animal described herein or analogous to an animal model described herein can be used for a cell-based assay.

Models for evaluating the effect of a test polypeptide on muscle atrophy include: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, *Shock* 7, 1-16 (1997)); and 5) skeletal muscle atrophy resulting from treatment with the glucocorticoid, dexamethasone (A. L. Goldberg, *J. Biol. Chem.* 244, 3223-9 (1969).)

Example animal models for AMD include: laser-induced mouse model simulating exudative (wet) macular degeneration Bora et al., *Proc. Natl. Acad. Sci. USA.*, 100:2679-84 (2003); a transgenic mouse expressing a mutated form of cathepsin D resulting in features associated with the "geographic atrophy" form of AMD (Rakoczy et al., *Am. J. Pathol.*, 161:1515-24 (2002)); and a transgenic mouse over expressing VEGF in the retinal pigment epithelium resulting in CNV. Schwesinger et al., *Am. J. Pathol.* 158:1161-72 (2001).

Example animal models of Parkinson's disease include primates rendered Parkinsonian by treatment with the dopaminergic neurotoxin 1-methyl-4 phenyl 1,2,3,6-tetrahydropyridine (MPTP) (see, e.g., U.S. Patent Publication No. 20030055231 and Wichmann et al., *Ann. N.Y. Acad. Sci.*, 991:199-213 (2003); 6-hydroxydopamine-lesioned rats (e.g., Lab. Anim. Sci., 49:363-71 (1999)); and transgenic invertebrate models (e.g., Lakso et al., *J. Neurochem.* 86:165-72 (2003) and Link, *Mech. Ageing Dev.*, 122:1639-49 (2001)).

Example molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., *Diabetes*, 50:1126-33 (2001); and a transgenic mouse with a dominant-negative IGF-I receptor (KR-IGF-IR) having Type 2 diabetes-like insulin resistance.

Example animal and cellular models for neuropathy include: vincristine induced sensory-motor neuropathy in mice (U.S. Pat. No. 5,420,112) or rabbits (Ogawa et al., *Neurotoxicology*, 21:501-11 (2000)); a streptozotocin (STZ)-diabetic rat for study of autonomic neuropathy (Schmidt et al., *Am. J. Pathol.*, 163:21-8 (2003)); and a progressive motor neuropathy (pmn) mouse (Martin et al., *Genomics*, 75:9-16 (2001)).

Example animal models of hyperphosphatemia or tumoral calcinosis include Klotho knockout mice and FGF23 knockout mice (Yoshida et al., *Endocrinology* 143:683-689 (2002)).

Example animal models of chronic renal disease or chronic renal failure include COL4A3±mice (Beirowski et al., *J. Am. Soc. Nephroi.* 17:1986-1994 (2006)).

Example animal models of cancer include the transplantation or implantation of cancer cells or tissue into nude mice, as is known in the art (Giovanella et al., *Adv. Cancer Res.* 44:69-120 (1985)). For example, animal models of breast cancer include nude mice transplanted or implanted with breast cancer cells or tissue (e.g., Yue et al., *Cancer Res.* 54:5092-5095 (1994); Glinsky et al., *Cancer Res.* 56:5319-5324 (1996); Visonneau *Am. J. Path.* 152:1299-1311 (1998)).

The compositions can be administered to a subject, e.g., an adult subject, particularly a healthy adult subject or a subject having an age-related disease. In the latter case, the method can include evaluating a subject, e.g., to characterize a symptom of an age-related disease or other disease marker, and thereby identifying a subject as having a neurodegenerative disease, e.g., Alzheimer's or an age-related disease or being pre-disposed to such a disease.

Skeletal Muscle Atrophy

Methods or uses of the disclosure which provide administering the Klotho fusion polypeptide to an individual can be used to treat skeletal muscle atrophy. Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al., *J. Biol. Chem.*, 265:8550-8557, 1990). The breakdown of these proteins can be followed, e.g., by measuring 3-methyl-histidine production, which is a specific constituent of actin, and in certain muscles of myosin (Goodman, Biochem. J. 241:121-12, 1987 and Lowell, et al., Metabolism, 35:1121-112, 1986; Stein and Schluter, *Am. J. Physiol. Endocrinol. Metab.* 272: E688-E696, 1997). Release of creatine kinase (a cell damage marker) (Jackson, et al., Neurology, 41: 101 104, 1991) can also be indicative.

Non-Insulin-Dependent Diabetes

Methods or uses of the disclosure which provide administering the Klotho fusion polypeptide to an individual can be used to treat Non-insulin-dependent Diabetes. Non-insulin-dependent Diabetes is also called "adult onset" diabetes and Type 2 diabetes. Type 2 diabetes also includes "non-obese type 2" and "obese type 2." Type II diabetes can be characterized by (1) reduced pancreatic-beta-islet-cell secretion of insulin such that less than necessary amounts of insulin are produced to keep blood glucose levels in balance and/or (2) "insulin resistance," wherein the body fails to respond normally to insulin. (U.S. Pat. No. 5,266,561 and U.S. Pat. No. 6,518,069). For example, glucose-stimulated insulin levels typically fail to rise above 4.0 nmol/L. (U.S. Pat. No. 5,266, 561). Example symptoms of Type II diabetes include: hyperglycemia while fasting (U.S. Pat. No. 5,266,561); fatigue; excessive thirst; frequent urination; blurred vision; and an increased rate of infections. Molecular indications of Type II diabetes include islet amyloid deposition in the pancreases.

Neuropathy

Neuropathy can include a central and/or peripheral nerve dysfunction caused by systemic disease, hereditary condition or toxic agent affecting motor, sensory, sensorimotor or autonomic nerves. (see, e.g., US Patent Application No. 20030013771). Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (U.S. Patent Application No. 20030013771) symptoms of autonomic neuropathy include constipation, cardiac irregularities and attenuation of the postural hypotensive reflex. (U.S. Patent Application No. 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Alzheimer's Disease

Methods or uses of the disclosure which provide administering the Klotho fusion polypeptide to an individual can be used to treat Alzheimer's Disease (AD). Alzheimer's Disease is a complex neurodegenerative disease that results in the irreversible loss of neurons. It provides merely one example of a neurodegenerative disease that is also an age-related condition. Clinical hallmarks of Alzheimer's Disease include progressive impairment in memory, judgment, orientation to physical surroundings, and language. Neuropathological hallmarks of AD include region-specific neuronal loss, amyloid plaques, and neurofibrillary tangles. Amyloid plaques are extracellular plaques containing the amyloid peptide (also known as Ap, or Ap42), which is a cleavage product of the, 8-amyloid precursor protein (also known as APP). Neurofibrillary tangles are insoluble intracellular aggregates composed of filaments of the abnormally hyperphosphorylated microtubule-associated protein, taut Amyloid plaques and neurofibrillary tangles may contribute to secondary events that lead to neuronal loss by apoptosis (Clark and Karlawish, *Ann. Intern. Med.* 138(5):400-410 (2003). For example, p-amyloid induces caspase-2-dependent apoptosis in cultured neurons (Troy et al. *J Neurosci.* 20(4):1386-1392). The deposition of plaques in viva may trigger apoptosis of proximal neurons in a similar manner.

A variety of criteria, including genetic, biochemical, physiological, and cognitive criteria, can be used to evaluate AD in a subject. Symptoms and diagnosis of AD are known to medical practitioners. Some example symptoms and markers of AD are presented below. Information about these indications and other indications known to be associated with AD can be used as an "AD-related parameter." An AD related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, *New Eng J. Med.* 348(14): 1356 35 1364 (2003)). Exclusion of other forms of dementia can assist in making a diagnosis of AD. Neuronal death leads to progressive cerebral atrophy in AD patients. Imaging techniques (e.g., magnetic resonance imaging, or computer assisted tomography) can be used to detect AD-associated lesions in the brain and/or brain atrophy.

AD patients may exhibit biochemical abnormalities that result from the pathology of the disease. For example, levels of tau protein in the cerebrospinal fluid is elevated in AD patients (Andreasen, N. et al. *Arch Neurol.* 58:349-350 (2001)).

Levels of amyloid beta 42 (A,B42) peptide can be reduced in CSF of AD patients. Levels of Ap42 can be increased in the plasma of AD patients (Ertekein-Taner, N., et al. *Science* 290:2303 2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3r Edition, Cold Spring Harbor Laboratory, N.Y. (2001), Ausubel et al., Current Protocols in Molecular Biology (Greene Publishing Associates and Wiley Interscience, N.Y. (1989), (Harrow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). *Nature Biotech.* 18, 989-994; Lucking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760 to 1763; and WO 99/5 1 773A1.

In one assay, a non-human animal model of AD (e.g., a mouse model) is used, e.g., to evaluate a polypeptide or a therapeutic regimen. For example, U.S. Pat. No. 6,509,515 describes one such model animal which is naturally able to be used with learning and memory tests. The animal expresses an amyloid precursor protein (APP) sequence at a level in brain tissues such that the animal develops a progressive necrologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant as foster female. The amyloid precursor protein genes are introduced into an animal embryo so as to be chromosomally incorporated in a state which results in super endogenous expression of the amyloid precursor protein and the development of a progressive necrologic disease in the cortico-limbic areas of the brain, areas of the brain which are prominently affected in progressive necrologic disease states such as AD. The gliosis and clinical manifestations in affected transgenic animals model necrologic disease. The progressive aspects of the neurologic disease are characterized by diminished exploratory and/or locomotor behavior and diminished deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6,187,992.

Parkinson's Disease

Methods or uses of the disclosure which provide administering the Klotho fusion polypeptide to an individual can be used to treat Parkinson's Disease. Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., *Nat. Rev. Neurosci.,* 3:932-42 (2002)). Example motor symptoms include: akinesia, stooped posture, gait difficulty, postural instability, catalepsy, muscle rigidity, and tremor. Example non-motor symptoms include: depression, lack of motivation, passivity, dementia and gastrointestinal dysfunction (see, e.g., Fahn, *Ann. N.Y. Acad. Sci.,* 991:1-14 (2003) and Pfeiffer, *Lancet Neurol.,* 2:107-16 (2003)) Parkinson's has been observed in 0.5 to 1 percent of persons 65 to 69 years of age and 1 to 3 percent among persons 80 years of age and older. (see, e.g., Nussbaum et al., *N Engl. J. Med.,* 348:1356-64 (2003)). Molecular markers of Parkinson's disease include reduction in aromatic L amino acid decarboxylase (AADC) (see, e.g., US App. No. 20020172664); and loss of dopamine content in the nigrostriatal neurons (see, e.g., Fahn, Ann. *N.Y. Acad. Sci.,* 991:1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:13 10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

Huntington's Disease

Methods or uses of the disclosure which provide administering the Klotho fusion polypeptide to an individual can be used to treat Huntington's Disease. Methods for evaluating the efficacy and/or determining the effective dose of a Klotho fusion polypeptide on Huntington's Disease include organismal based assays, e.g., using a mammal (e.g., a mouse, rat, primate, or some other non-human), or other animal (e.g., *Xenopus*, zebrafish, or an invertebrate such as a fly or nematode). A number of animal model system for Huntington's disease are available. See, e.g., Brouillet, Functional *Neurology* 15(4): 239-251 (2000); Ona et al. *Nature* 399: 263-267 (1999), Bates et al. *Hum Mol Genet.* 6(10):1633-7 (1997); Hansson et al. *J. of Neurochemistry* 78: 694-703;

and Rubinsztein, D. C., *Trends in Genetics, Vol.* 1S, No. 4, pp. 202-209 (a review on various animal and non-human models of HD).

An example of such an animal model is the transgenic mouse strain is the R6/2 line (Mangiarini et al. Cell 87: 493-506 (1996)). The R6/2 mice are transgenic Huntington's disease mice, which over-express exon 1 of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N terminal part of Huntingtin (encoded by HD exon 1), are observed in R6/2 mice, both 45 in the cytoplasm and nuclei of cells (Davies et al. *Cell* 90: 537-548 (1997)). For example, the human Huntingtin protein in the transgenic animal is encoded by a gene that includes at least 55 CAG repeats and more preferably about 150 CAG repeats. These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. *Cell* 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. *Cell* 87: 493-506 (1996), Davies et al. *Cell* 90: 537-548 (1997), Brouillet, Functional Neurology 15(4): 239-251 (2000) and Cha et al. *Proc. Natl. Acad. Sci. USA* 95: 6480-6485 (1998).

To test the effect of the test polypeptide or known polypeptide described in the application in an animal model, different concentrations of test polypeptide are administered to the transgenic animal, for example by injecting the test polypeptide into circulation of the animal. A Huntington's disease-like symptom may be evaluated in the animal. The progression of the Huntington's disease-like symptoms, e.g., as described above for the mouse model, is then monitored to determine whether treatment with the test polypeptide results in reduction or delay of symptoms. In another assay, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntington's antibody (e.g., the anti-Huntingtin antibody is mouse anti-human antibody and the secondary antibody is specific for human antibody) and visualizing the protein aggregates by fluorescent microscopy.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

Example motor evaluations include: ocular pursuit, saccade initiation, saccade velocity, dysarthria, tongue protrusion, finger tap ability, pronate/supinate, a lo fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An example treatment can cause a change in the Total Motor Score 4 (TMS-4), a subscale of the UHDRS, e.g., over a one-year period.

Cancer

Methods or uses of the disclosure which provide administering the Klotho fusion polypeptide to an individual can be used to treat cacner. Cancer includes any disease that is caused by or results in inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

All patents, patent applications, and published references cited herein are hereby incorporated by reference in their entirety. While this disclosure has been particularly shown and described with references to embodiments thereof, it will be understood by those skilled in the art that various changes in form and details may be made therein without departing from the scope of the disclosure encompassed by the appended claims.

5. EXAMPLES

Example 1

Expression and Purification of Klotho Fusion Polypeptides

Expression of the Klotho Fusion Polypeptide

Figure 1:
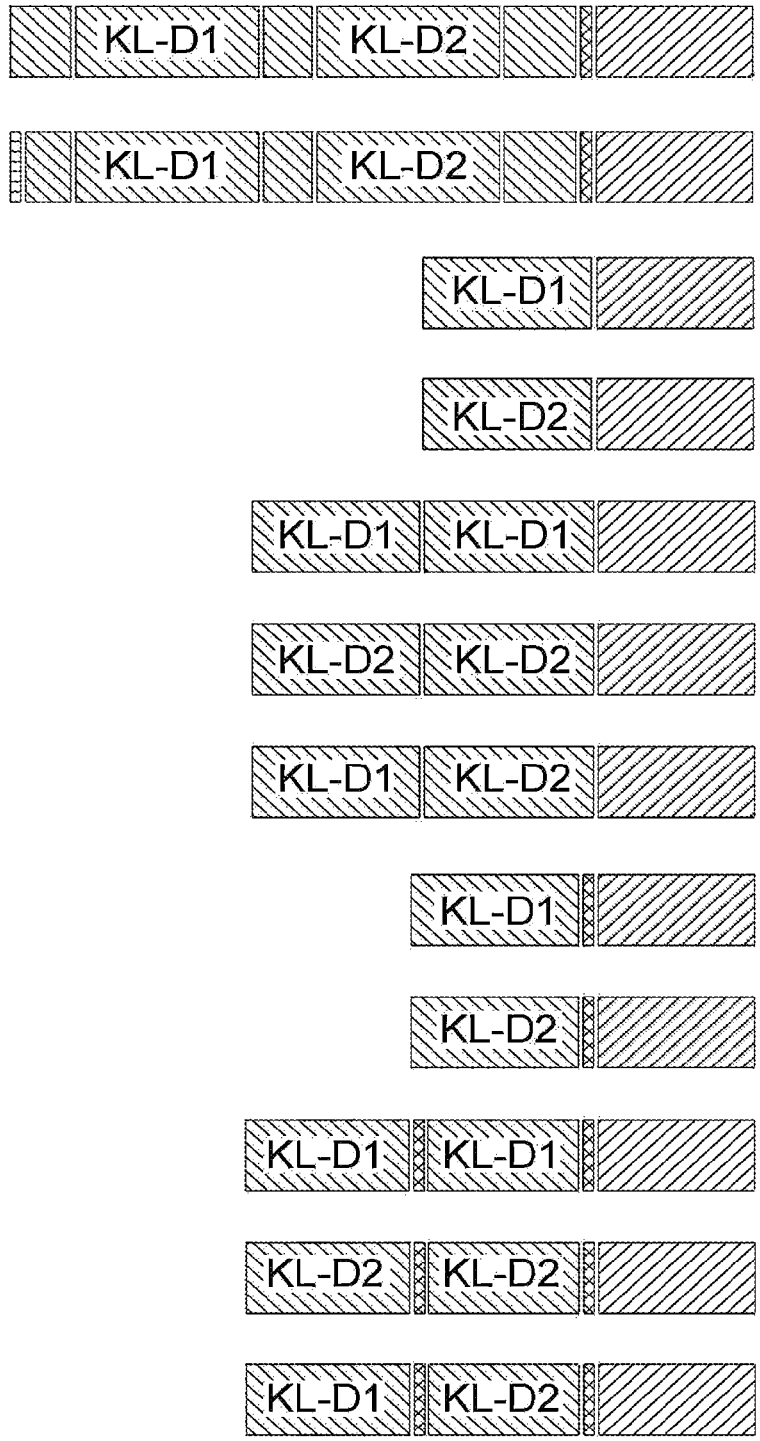
Figure 1:
Figure 3A:
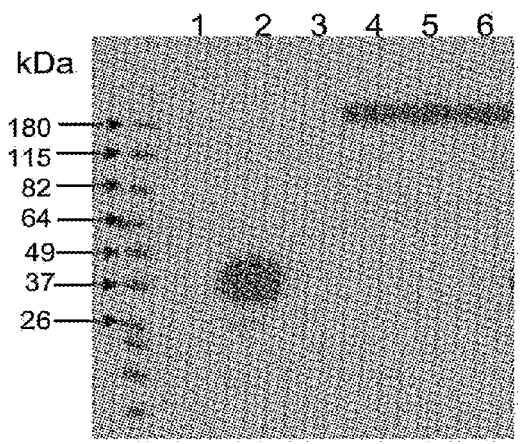
Figure 3B:
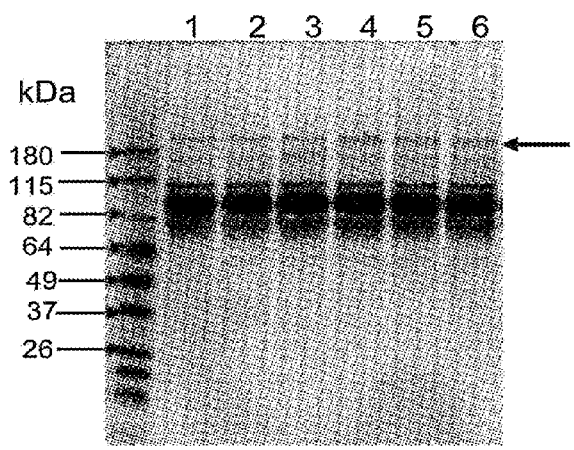

The polypeptides of the disclosure were made by transiently transfecting HEK293T cells with an expression vector encoding a Klotho fusion polypeptide having the extracellular domain of alpha Klotho and the FGF23 (R179Q) variant. Conditioned media containing expressed polypeptides were generated by transient transfection of the respective expression plasmids for Klotho, FGF23, and the Klotho-FGF23 (R179Q) fusion protein. The transfections were performed in 6-well plates using Lipofectamine 2000 (Invitrogen, Cat #11668-019). Five hours after transfection, the transfection mix was replaced with 3 ml DMEM plus 1% FBS. Conditioned media were collected 72 hours after the addition of 3 ml DMEM plus 1% FBS. Samples of conditioned medium from various transiently transfected HEK293T cells were separated by SDS-polyacrylamide gel electrophoresis (SDS-PAGE) and analyzed by Western blot (FIG. 3A) or stained with Coomassie blue (FIG. 3B).

SDS-polyacrylamide gel electrophoresis was performed on various samples (lane 1, Control; lane 2, FGF23; lane 3, sKlotho; lanes 4-6, sKlotho-FGF23). Coomassie blue staining revealed the expression of a high, >180 kDa band (FIG. 3B, indicated by arrow on the right) that was not present in lanes 1-3, which contained samples that had not been transfected with the vector encoding the Klotho fusion polypeptide. The quality of the Klotho fusion polypeptide secreted into the media was evaluated by Western blot (FIG. 3A). An anti-FGF23 rat monoclonal IgG2A (R&D Systems, Cat# MAB26291) was used as the primary antibody to detect the Klotho fusion polypeptides by Western blot. The Western blot confirmed that the additional bands observed in the Coomassie stained gels were Klotho fusion polypeptides. The Western blot confirmed that the Klotho fusion polypeptides had the expected molecular weight for the Klotho fusion polypeptide. This analysis shows the expression of the Klotho-FGF23(R179Q) fusion protein.

Purification of the Klotho Fusion Polypeptide

Figure 3C:
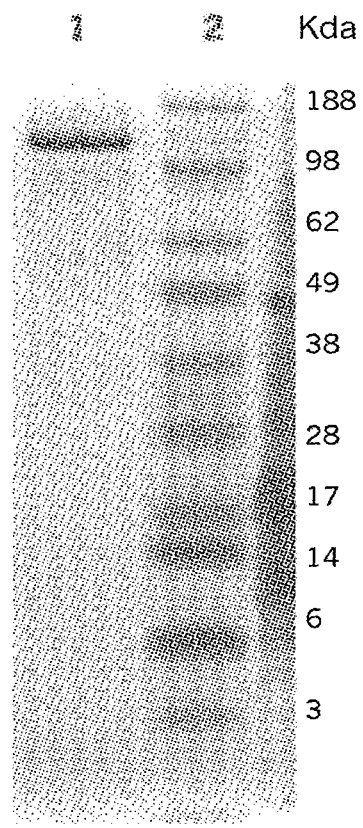

The polypeptides of the disclosure were purified from conditioned media from a culture of HEK293T cells transiently transfected with an expression vector encoding a Klotho fusion polypeptide having the extracellular domain of alpha Klotho and the FGF23 R179Q variant. To generate conditioned medium, an expression vector encoding sKlotho-FGF23-6×His was transfected (500 μg DNA in 18 ml of OptiMEM 1 (GIBCO, Cat #11058) mixed with 18 ml of 2 μg/ml polyethlinimine (PEI) into HEK293 cells grown in suspension in expression medium (464 ml of HEK293T cells at $10^6$ cells/ml in Freestype 293 expression medium (GIBCO, Cat #12338)). After transfection, the culture was allowed to grow (120 hours; 37° C. in a 5% $CO_2$ incubator; shaking at 125 rpm). At the end of incubation, conditioned medium was harvested by centrifugation (1000 rpm for five minutes). The conditioned medium was then applied to a nickel-agarose column. The sKlotho-FGF23-6×His bound tightly to the column and was eluted with 50 mM imidazole. The resulting purified material was then dialyzed in PBS to remove imidazole. A sample of the purified sKlotho-FGF23-6×His was separated by SDS-PAGE (lane 1, purified sKlotho-FGF23-6×His; lane 2, molecular weight marker) and analyzed by staining with Coomassie blue (FIG. 3C). The stained SDS-PAGE gel confirmed that the purified sKlotho-FGF23-6×His had the expected molecular weight. The inability to detect bands corresponding to proteins other than full-length sKlotho-FGF23-6×His in the lane loaded with the purified material also showed that the sKlotho-FGF23-6×His was purified.

Example 2

In Vitro Assay Assessing the Activity of the Klotho Fusion Polypeptide

Egr-1-Luciferase

Figure 4:
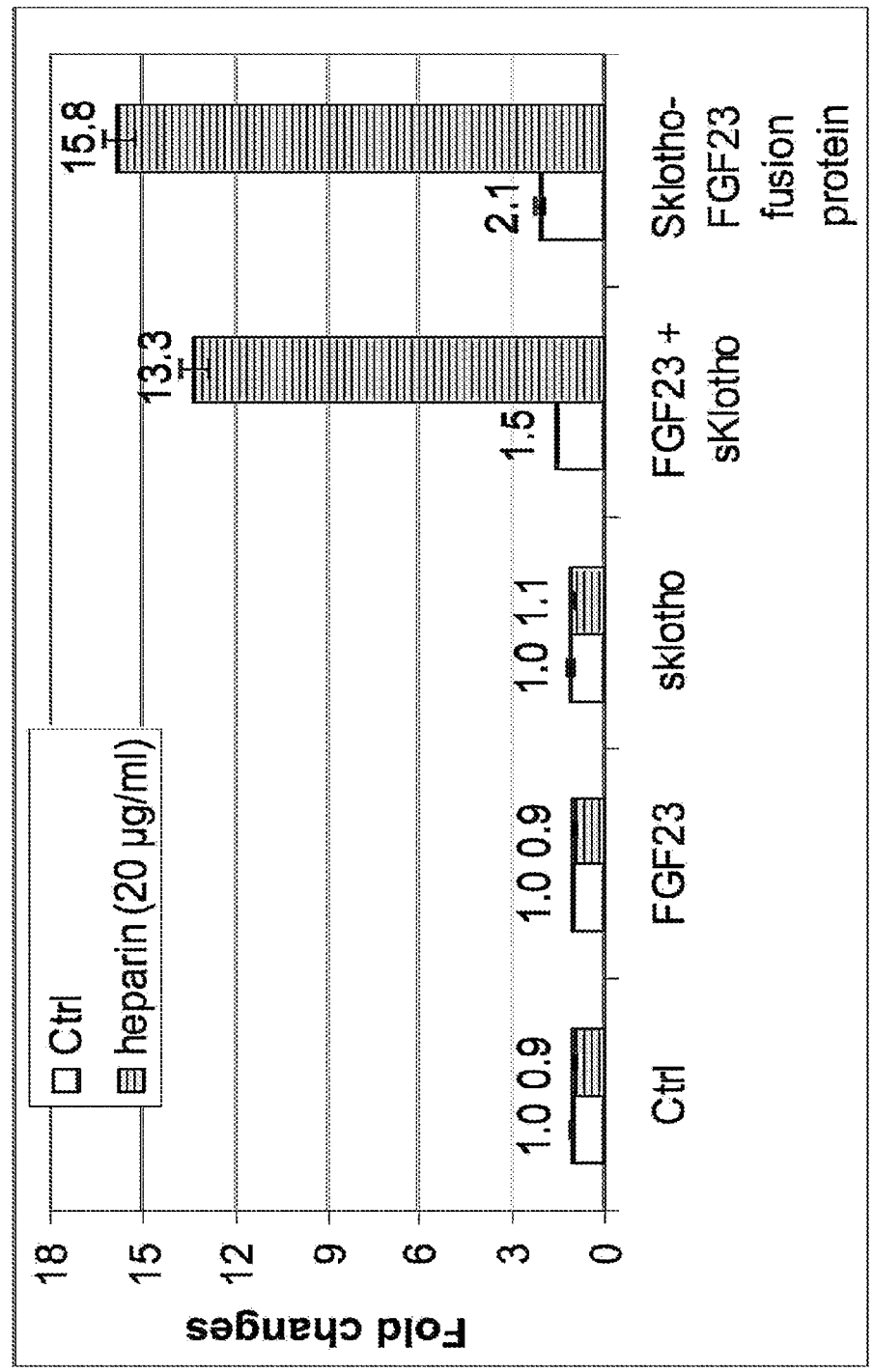
Figure 5A:
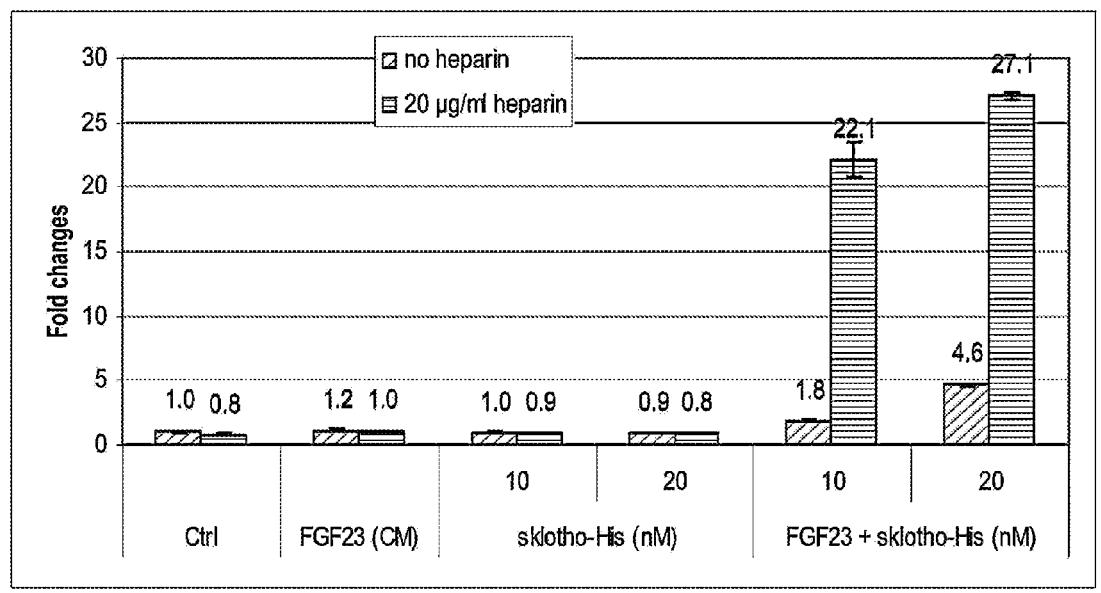
Figure 5B:
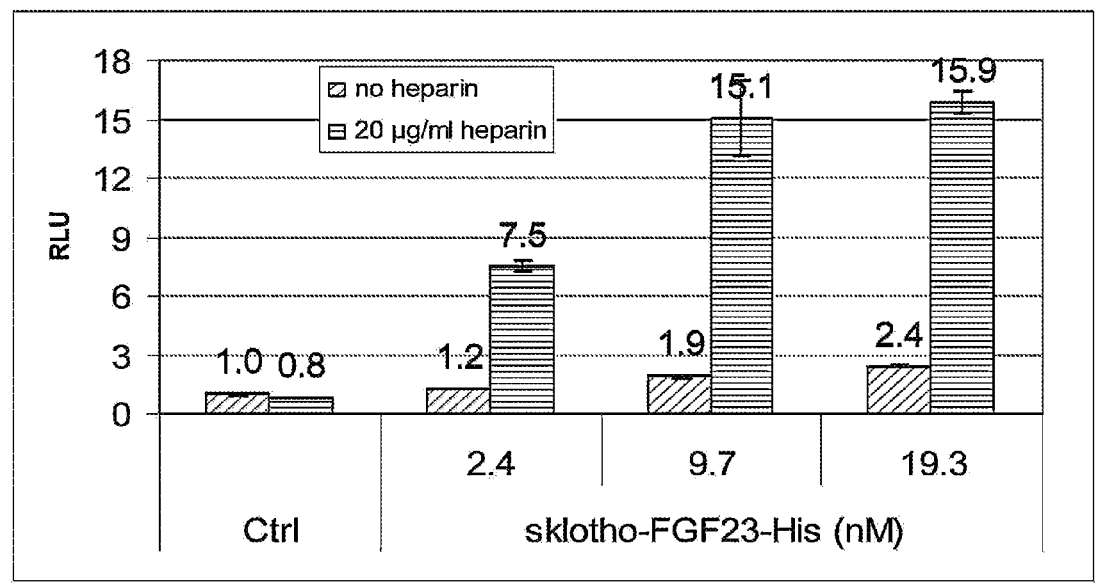
Figure 6A:
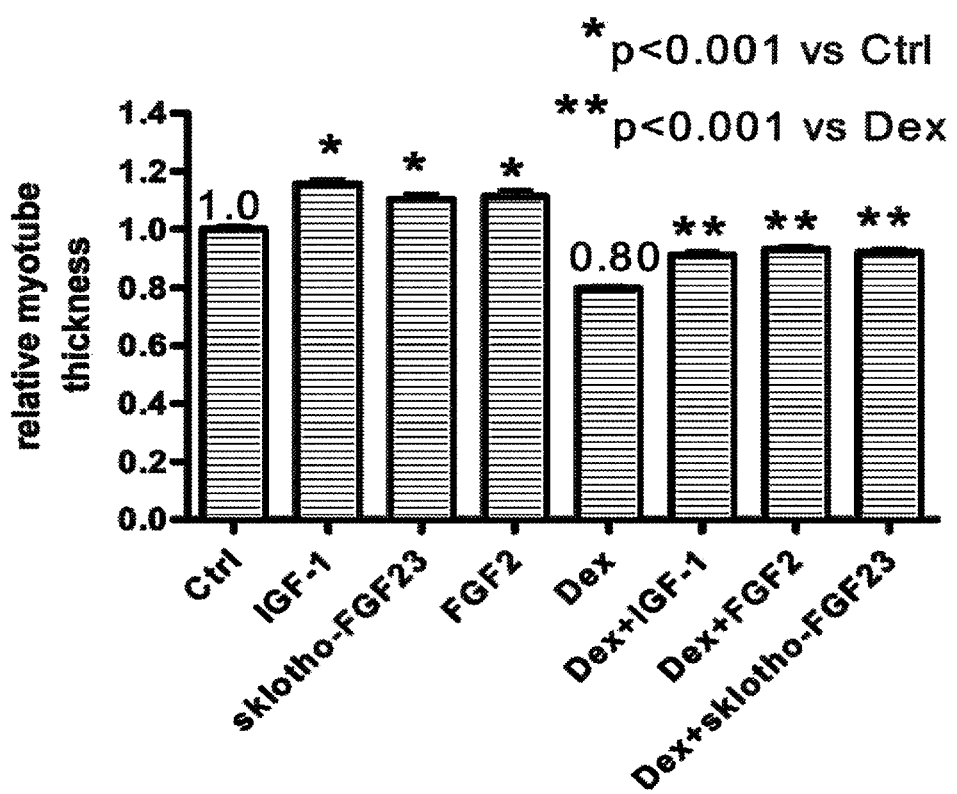
Figure 6B:
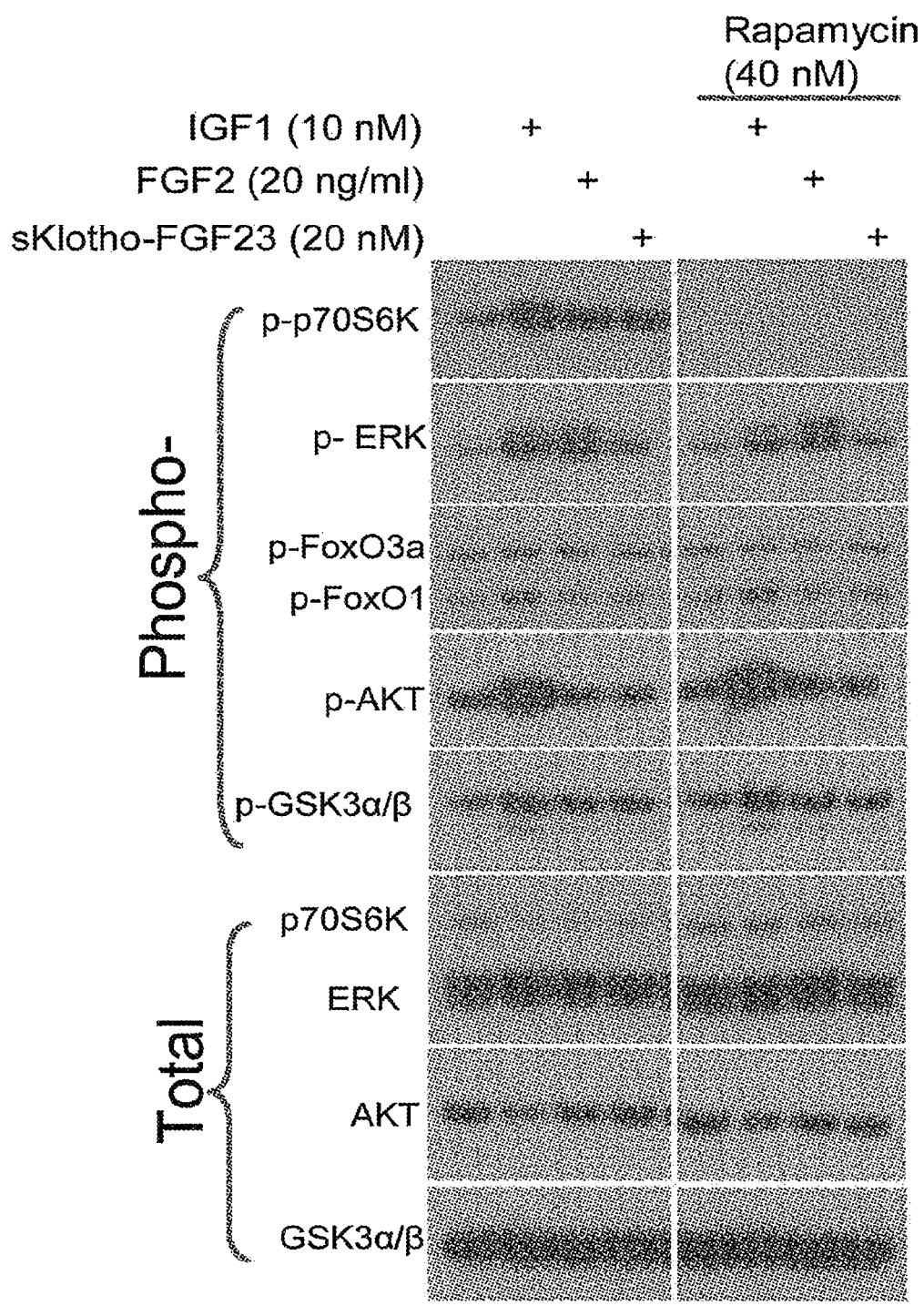

The biological activity of the expressed alpha Klotho fusion polypeptide was tested in Egr-1-luciferase reporter assays. Binding of the Klotho fusion polypeptide to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol 444, 770-774). HEK293T cells seeded in 48-well poly-D-lysine plate were transfected with the Egr-1-luciferase reporter gene together with a transfection normalization reporter gene (*Renilla luciferase*). Five hours after transfection of the Egr-1 luciferase reporter gene, the transfection mix was replaced with 3 ml DMEM plus 1% FBS. Conditioned media were collected 72 hours after the addition of 3 ml DMEM plus 1% FBS. Five hours later, the transfection mix was replaced with a sample to be tested for activity. In initial experiments, 50% conditioned medium (alone or containing Klotho, FGF23, Klotho and FGF23, and the Klotho-FGF23(R179Q) fusion protein) and 50% DMEM with 1% FBS in the presence or absence of 20 μg/ml heparin (Sigma, Cat#H8537; dissolved in DMEM as 2 mg/ml stock) were tested in the Egr-1-luciferase reporter assays (FIG. 4). Further experiments used defined quantities of the purified polypeptides (FIGS. 5A and 5B). Cells were lysed 20 hours later in passive lysis buffer (Promega, Cat #E194A) and luciferase activities were determined using Dual-Glo Luciferase Assay System (Promega, Cat #E2940).

In initial experiments, Klotho fusion polypeptide activity was demonstrated in unfractionated conditioned medium. Using the Egr-1-luciferase reporter gene (FIG. 4) these experiments quantified the fold changes in the expression of the luciferase reporter. Conditioned medium containing a combination of FGF23 and the extracellular domain of Klotho protein activated Egr-1-luciferase, but conditioned medium containing only FGF23 or conditioned medium containing only the extracellular domain of Klotho, did not activate Egr-1-luciferase. Conditioned medium containing the fusion protein sKlotho-FGF23(R179Q) activated the Egr-1-luciferase reporter gene in contrast to conditioned media containing either FGF23 or Klotho alone. In these experiments, conditioned medium containing the fusion protein sKlotho-FGF23(R179Q) activated the Egr-1-luciferase reporter gene significantly better than conditioned medium containing a combination of FGF23 and Klotho. In the presence of heparin, the inductions by conditioned medium containing the fusion protein sKlotho-FGF23(R179Q) and the conditioned medium containing a combination of FGF23 and Klotho were significantly enhanced. Table 1 lists the relative expression of various FGF-Klotho fusion polypeptides in conditioned medium and the relative activity of the unfractionated conditioned medium corresponding to the various FGF-Klotho fusion polypeptides in Egr-1-luciferase reporter assays.

TABLE 1

Expression and Activities of sKlotho-FGF23 fusion variants

| | sKlotho-FGF23 fusion constructs | Expression | Activity in Egr-1-luc reporter gene |
|---|---|---|---|
| 1 | sKlotho-FGF23 | good | yes |
| 2 | IgG sp-sKlotho-FGF23 | good | yes |
| 3 | sKL-D1-FGF23 | good | no |
| 4 | sKL-D2-FGF23 | no | n.a. |
| 5 | s(KL-D1)2-FGF23 | good | no |
| 6 | sKL-D1/D2-FGF23 | no | n.a. |
| 7 | ssKlotho(ΔN-26)-FGF23 | poor | no* |
| 8 | sKLD1-D2(Δ692 -965)-FGF23 | poor | no* |
| 9 | sKL-D1-D2(Δ507-798)-FGF23 | poor | no* |
| 10 | FGF23-sKlotho | poor | no* |

*lack of activity may be the result of low expression

Egr-1-luciferase reporter assays were also performed using defined quantities of proteins purified from the conditioned medium, using the purification procedure as described in Example 1. Consistent with previous results using unfractionated conditioned medium containing the expressed polypeptides, treatment with a combination of purified FGF23 and sKlotho resulted in luciferase reporter activity, but treatment with purified FGF23 alone did not (FIG. 5A). The luciferase reporter activity from the combination of purified FGF23 and sKlotho was further dependent on the dose of purified sKlotho, and the effect could be enhanced by the presence of heparin (20 μg/ml). An effect of the sKlotho-FGF23-6×His fusion polypeptide on luciferase activity could be detected at concentrations as low as about 1.21 nM (1.2 fold change) and at least up to about 19.3 nM (2.4 fold change) in Egr-1-luciferase reporter assays (FIG. 5B). The activity of the sKlotho-FGF23-6×His fusion polypeptide on luciferase activity was significantly enhanced in the presence of heparin (20 μg/ml). In the presence of heparin, the effect of the sKlotho-FGF23-6×His fusion polypeptide on luciferase activity could be detected at a concentration as low as about 0.6 nM (2.0 fold change). The result showed that purified sKlotho-FGF23-6×His dose-dependently induced the EGR-1-luc reporter gene, and that treatment with sKlotho-FGF23-6×His.

Example 3

In Vitro Assay Assessing the Effect of the Klotho Fusion Polypeptide on Muscle Cells The biological effect of the expressed Klotho fusion polypeptide was tested on C2C12 myoblasts. Treatment of C2C12 myoblasts with IGF-1, FGF2, or sKlotho-FGF23 resulted in myotube growth and phosphorylation of signaling proteins. C2C12 myoblasts were seeded at a density of 40,000 cells/well in 6-well poly-D-lysine and fibronectin coated plates in growth medium (3 parts DMEM and 1 part F12), 10% FBS, 1% Glut; 1% P/S; 1% Linolic acid; 0.1% ITS: [insulin (10 mg/ml), transferrin (5.5 mg/ml), and selenium (5 ng/ml)]. After myoblasts reached confluence (3 days), medium was changed into differentiation medium (DMED with 2% horse serum; 1% Glut; 1% P/S).

For the myotube diameter experiments, three days after confluent media was changed into differentiation medium, cells were treated with IGF-1 (10 nM), FGF2 (20 ng/ml) or sKlotho-FGF23 (20 nM) in the absence or presence of dexamethasone (100 µM) for 24 hours in differentiation medium. At the end of treatment, cells were fixed with glutaraldehyde (5% in PBS) and multiple fluorescent images were collected. Myotube diameter was measured using the Pipeline Pilot program to determine hypertrophy or atrophy.

For the signaling protein phosphorylation, experiments, three days after confluent media was changed into differentiation medium, cells were starved for four hours with DMEM without FBS and then treated with IGF-1 (10 nM), FGF2 (20 ng/ml) or sKlotho-FGF23 (20 nM) in the absence or presence of Rapamycin (40 nM) for 30 min. Cells were lysed in RIPA buffer in the presence of protease and phosphatase inhibitors. Western blot analysis was carried out and membranes were probed with different antibodies as indicated in the figure and developed on X-ray films, which were scanned.

The results of this study showed that sKlotho-FGF23 resulted in an increase in myotube diameter compared to the control and induced C2C12 myotube hypertrophy similar to results for IGF-1 and FGF2 (FIG. 5A). In addition, treatment with sKlotho-FGF23, IGF-1, and FGF2 could partially reverse myotube atrophy induced by dexamethasone, based on measurements of myotube diameter. No difference was observed between sKlotho-FGF23 and FGF2 on myotube morphology (measured by thickness of the myotubes) in the absence or presence of dexamethasone. The trophic effects of sKlotho-FGF23, IGF-1, and FGF2 were statistically significant.

Consistent with the effects on C2C12 myotubes, sKlotho-FGF23 fusion protein signaling led to the phosphorylation of p70S6K and ERK, but not AKT or FoxO, in C2C12 myotubes (FIG. 5B). The effect of sKlotho-FGF23 on signaling was similar to that of FGF2, but was distinct from that of IGF-1. The extent of ERK phosphorylation by sKlotho-FGF23 was observed to be less than that of IGF-1 or FGF2. The phosphorylation of p70S6K by sKlotho-FGF23 was rapamycin sensitive. In the experiments involving C2C12 cells, heparin was not required to activate signaling. These results show that a sKlotho-FGF23 fusion polypeptide activated signaling in C2C12 myotubes.

Example 4

Fusion Polypeptides Comprising sKlotho, FGF23 and FcLALA

Various fusion polypeptides are constructed using sKlotho, FGF23, and a modified Fc fragment of an antibody. These modified Fc molecules have altered (decreased) binding to FcRn and thus increased serum half-life. They also have modified bioavailability and alterered transport to mucosal surfaces and other targets in the body. In this example, the FGF23 and sKlotho are fused to FcLALA, which is described in U.S. Pat. No. 7,217,798 and Hessell et al. 2007 Nature 449:101-104, Intervening between the various components of these fusion polypeptides are linkers, as described in Lode et al. 1998 Proc. Natl. Acad. Sci. USA 95: 2475-2480. These fusions are inserted into constructs, e.g., pcDNA3.1

(Invitrogen, Carlsbad, Calif.), and expressed in HEK293 cells.

A. sKlotho-FGF23-FcLALA v1

A fusion is constructed which comprises: sKlotho, a linker, FGF23, another linker, and FcLALA. This embodiment, designated sKlotho-FGF23-FcLALA v1, is presented in SEQ ID NOs: 46 and 47, below.

The nucleotide sequence of sKlotho-FGF23-FcLALA v1 (wherein initiation ATG as 1) is presented as SEQ ID NO: 46.

The amino acid sequence of sKlotho-FGF23-FcLALA v1 is presented below as SEQ ID NO: 47.

In this sequence, the various components of the fusion are as follows:

sKlotho: 1-982; Linker1: 983-1001; FGF23: 1002-1228; Linker 2; 1229-1233; FcLALA: 1234-1459.

B. sKlotho-FGF23-FcLALA v2

A fusion is constructed which comprises: sKlotho, a linker, FGF23, another linker, and FcLALA. This embodiment is designated sKlotho-FGF23-FcLALA v2 and presented as SEQ ID NOs: 48 and 49, below.

The nucleotide sequence of sKlotho-FGF23-FcLALA v2 (wherein initiation ATG as 1) is presented as SEQ ID NO: 48.

The amino acid sequence of sKlotho-FGF23-FcLALA v2 is presented below as SEQ ID NO: 49.

In this sequence, the various components of the fusion are as follows:

sKlotho: (aa or amino acids) 1-982; Linker 1: 983-1001; FGF23: 1002-1228; Linker 2; 1229-1233; FcLALA: 1234-1450.

Other fusion polypeptides can be constructed by combining in various combinations the FGF, Klotho, modified Fc fragments, and (optionally) linker sequences, and variants and derivatives thereof, as described herein or known in the art.

Example 5

Fusion Polypeptides Comprising FGF23 and FcLALA

Various fusion polypeptides are constructed using FGF23, and a modified Fc fragment of an antibody, as described in U.S. Pat. No. 7,217,798. These modified Fc molecules have altered (decreased) binding to FcRn and thus increased serum half-life. They also have modified bioavailability and alterered transport to mucosal surfaces and other targets in the body. In this example, FGF23 is fused to FcLALA, Intervening between the various components of these fusion polypeptides are linkers, as described in Lode et al. 1998 Proc. Natl. Acad. Sci. USA 95: 2475-2480. These fusions are inserted constructs, e.g., pcDNA3.1 (Invitrogen, Carlsbad, Calif.), and expressed in HEK293 cells.

C. FGF23-FcLALA v1

A fusion is constructed which comprises: FGF23, a linker, and FcLALA. This construct is designated FGF23-FcLALA v1 and presented below as SEQ ID NOs: 50 and 51.

The nucleotide sequence of FGF23-FcLALA v1 (wherein initiation ATG as 1) is presented below as SEQ ID NO: 50.

The amino acid sequence of FGF23(R179Q)-FcLALAv1 is presented below as SEQ ID NO: 51.

In this sequence, the various components of the fusion are as follows:

FGF23: (aa) 1-251; Linker: 252-256; FcLALA: 257-482.

D. FGF23-FcLALA v2

A fusion is constructed which comprises: FGF23-FcLALA v2, which comprises FGF23 and FcLALA.

The nucleotide sequence of FGF23-FcLALA v2 (wherein initiation ATG as 1) is presented below as SEQ ID NO: 52.

The amino acid sequence of FGF23(R179Q)-FcLALAv2 is presented below as SEQ ID NO: 53.

In this sequence, the various components of the fusion are as follows:

FGF23: 1-251; Linker: 252-256; FcLALA: 257-473.

Other fusion polypeptides can be constructed by combining in various combinations the FGF sequences, modified Fc fragments, and (optionally) linkers, and variants and derivatives thereof, as described herein or known in the art.

E. Activation of Egr-1-luc reporter gene by sKlotho-FGF23(R179Q)-FcLALA fusion proteins; activation of Egr-1-luc reporter gene by FGF23(R179Q)-FcLALA proteins; and pharmacokinetic profile of FGF23(R179Q) vs FGF23(R179Q)-FcLaLay2 are determined.

Figure 7:
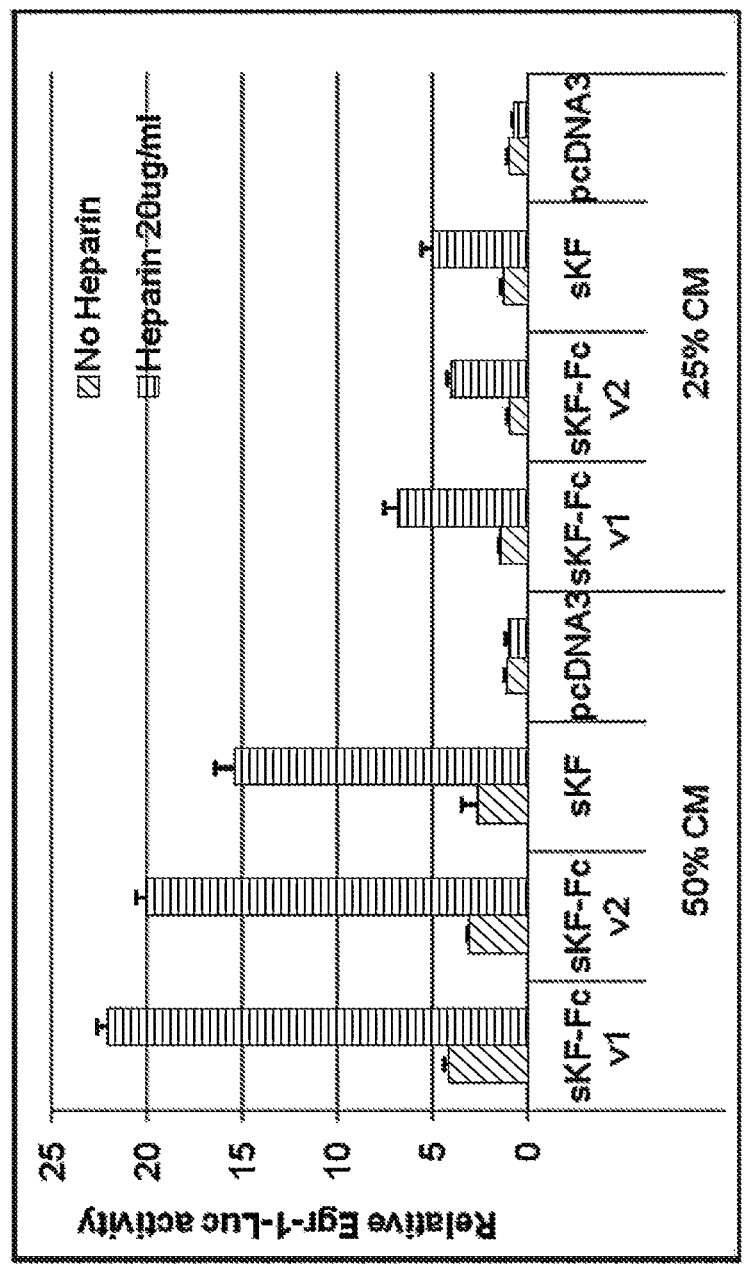
FIG. 7 shows activation of EGR-1-luc reporter gene by sKlotho-FGF23(R179Q)-FcLALA fusion proteins.

FIG. 7 shows the activation of Egr-1-luc reporter gene by sKlotho-FGF23(R179Q)-FcLALA fusion proteins. HEK293T cells are transiently transfected with the Egr-1-luc reporter gene and incubated with the indicated conditioned media in the absence or presence of 20 μg/ml heparin. Luciferase activities are then determined 18 hours later. The result shows that sklotho-FGF23-FcLALA fusion proteins induces the reporter gene activity. These inductions are significantly enhanced in the presence of heparin. sKF-Fcv1: sKlotho-FGF23-FcLALAy1; sKF-Fcv2: sKlotho-FGF23-FcLALAy2

Figure 8:
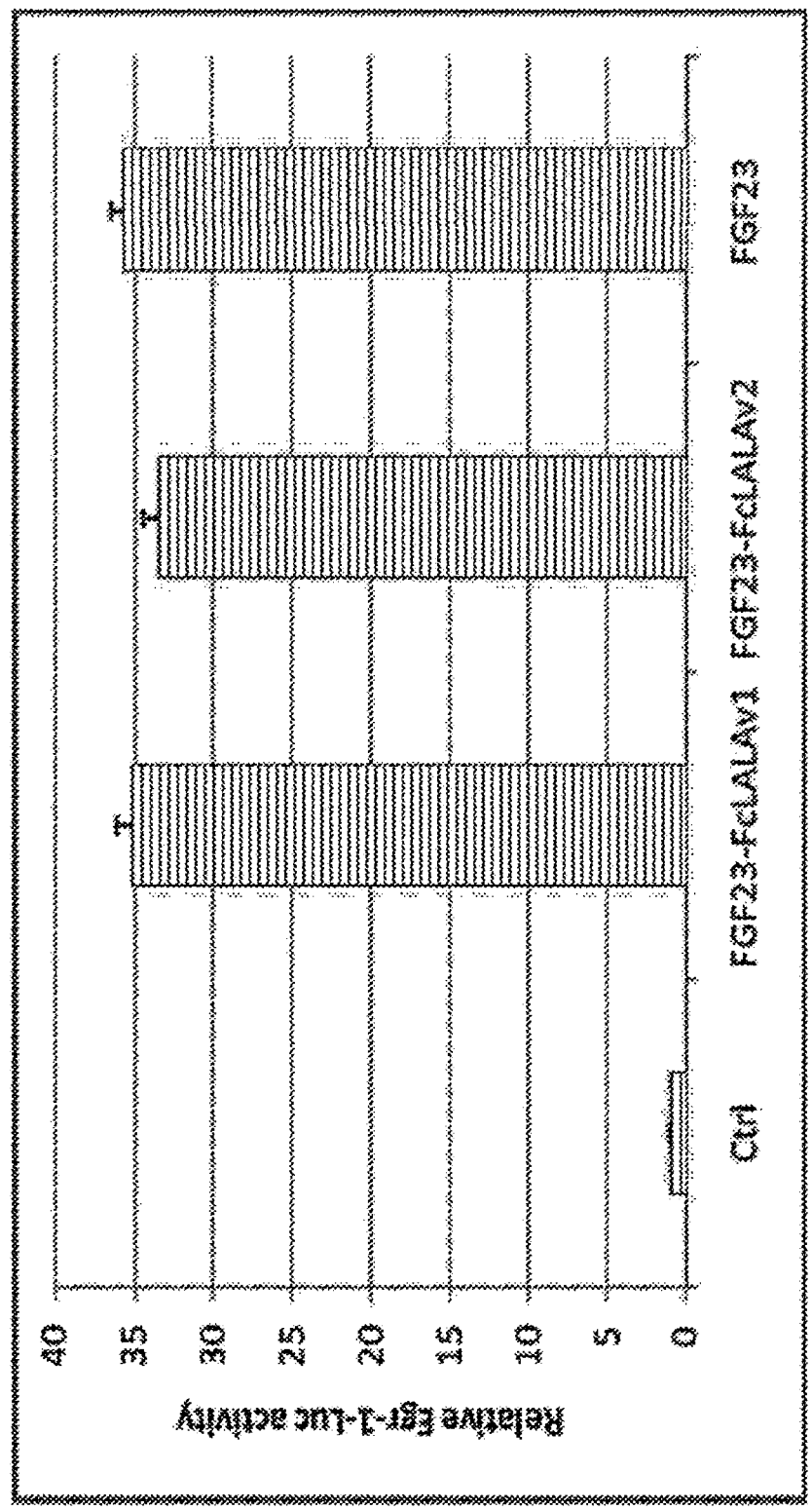
FIG. 8 shows the activation of EGR-1-luc reporter gene by FGF23(R179Q)-FcLALA proteins.

FIG. 8 shows the activation of Egr-1-luc reporter gene by FGF23(R179Q)-FcLALA proteins. HEK293T cells are transiently transfected with the Egr-1-luc reporter gene together with the full-length transmembrane form of Klotho and incubated with the indicated 30% conditioned media. Luciferase activities are then determined 18 hours later. The results show that FGF23-FcLALA fusion proteins induce the reporter gene activity in a similar manner as the FGF23.

Figure 9:
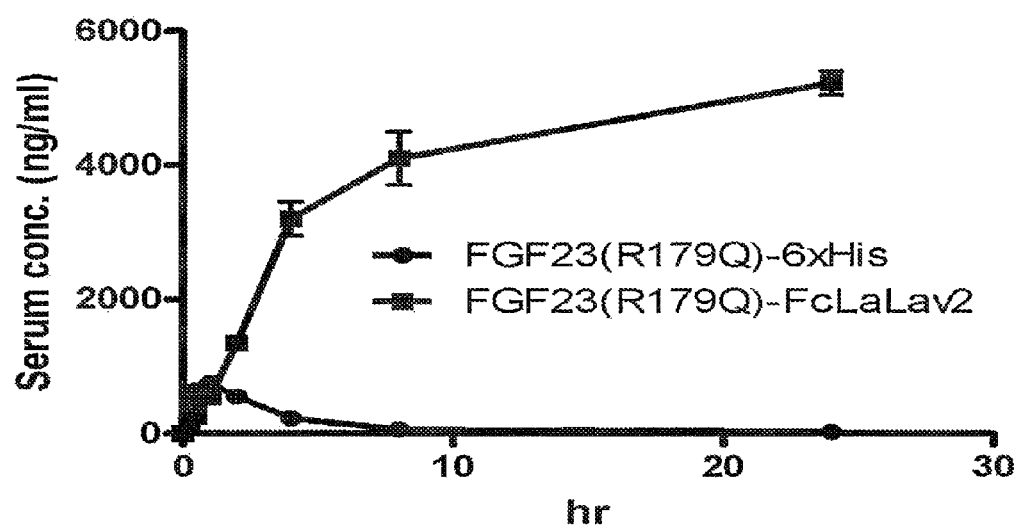
FIG. 9 shows the pharmacokinetic profile of FGF23 (R179Q) vs FGF23(R179Q)-FcLALAv2.

FIG. 9 shows the pharmacokinetic profile of FGF23(R179Q) vs FGF23(R179Q)-FcLALAy2. Four mice per group are injected subcutaneously with FGF23(R179Q)-6× His or FGF23(R179Q)-FcLALAv2 at 2 mg/kg. At the indicated times, serum samples are collected and analyzed for FGF23 by ELISA. FGF23(R179Q)-FcLALA concentration in serum remains elevated at the 24 hr time point, while FGF23(R179Q)-6×His is back to basal level. This results indicate that with the addition of FcLALA, the in vivo half-life of FGF23(R179Q) is significantly improved.

Example 6

In Vivo Efficacy of sKlotho-FGF23 Fusion in Enhancing Muscle Growth after Dexamethasone-Induced Muscle Atrophy Experimental data shows that intramuscular injection of sKlotho-FGF23 significantly enhanced growth of muscle mass after dexamethasone-induced muscle atrophy. In this experiment, the peptide corresponding to that of SEQ ID NO: 41 is used.

Figure 10:
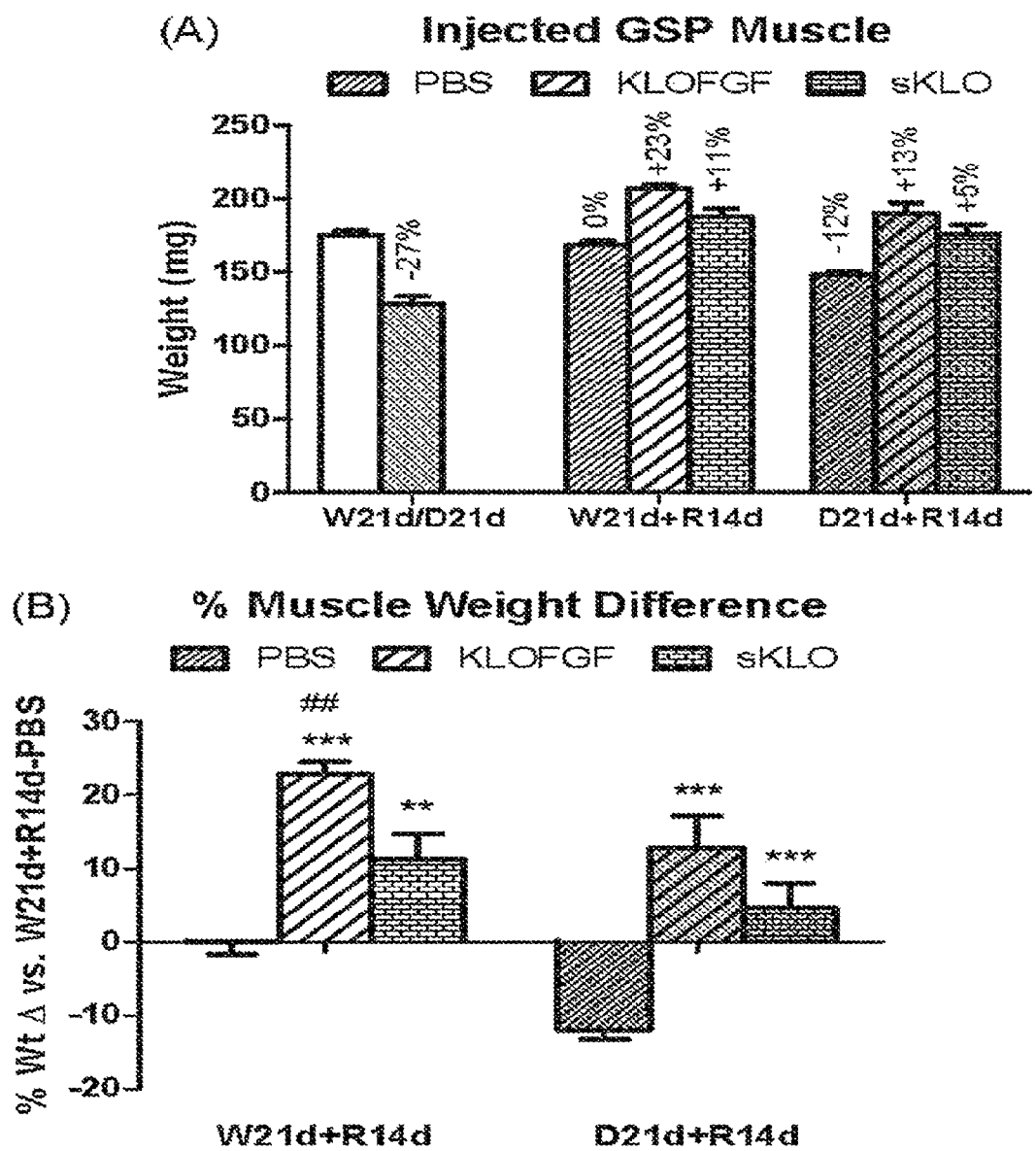
FIGS. 10A and 10B show the in vivo efficacy of sKlotho-FGF23 fusion in enhancing muscle growth after dexamethasone-induced muscle atrophy.

FIG. 10 shows absolute weights (A) and percent weight change (B) of the gastrocnemius-soleus-plantaris (GSP) muscles showing that intramuscular injection of sKlotho-FGF23 (KLOFGF) significantly enhanced regrowth of muscle mass after dexamethasone (DEX)-induced muscle atrophy compared with intramuscular injection of sKlotho (sKLO) or phosphate buffered saline (PBS).

Eighty male C57BL/6 mice, aged 15 weeks, are randomized by body weight into 8 groups each of 10 mice. Four groups receive water without DEX (W21d) while the other four receive DEX in drinking water at 2.4 mg/kg/day for three weeks (D21d). After the three weeks, DEX treatment is stopped and one W21d and one D21d group is immediately sacrificed to establish the degree of muscle atrophy induced by the DEX treatment. The remaining three groups of W21d or D21d mice are allowed to recover for another 14 days (R14d) during which period they receive an intramuscular injection of 2×50 μl of PBS, sKlotho-FGF23 (KLOFGF; 1.6 mg/ml), or sKlotho (sKLO; 1.6 mg/ml), respectively, every other day into the right gastrocnemius-soleus-plantaris muscle complex. The mice are sacrificed 24 h after the last intramuscular injection and the muscle weights determined and expressed as absolute weight (A) or percent change compared to the W21d+PBS group.

These data show the in vivo efficacy of sKlotho-FGF23 fusion in enhancing muscle growth after dexamethasone-induced muscle atrophy.

Example 7

Additional Mutations in the FGF23 Portion of Fusion Proteins which Reduce Aggregation, Reduce Undesired Protease-Induced Cleavage, and Increase Production Several mutations are investigated within the FGF23 portion of sKlotho-FGF23 and FGF23-FcLaLa fusion polypeptides. These include Q156, C206 and C244 (wherein the number is based on the FGF23 amino acid sequence). Example individual mutations include Q156A, C206S and C244S, and mutations at any of these sites can be combined with a mutation at R179 (e.g., R179Q). Example sequences are provided in SEQ ID NO: 54 to 68 of FIG. 2.

C206 and C244 are suspected to be involved in dimerization; and Q156 is a site identified by the inventors as a protease sensitive site. Mutating these amino acids to any other amino acid enhances the qualities of the proteins, by reducing aggregation, reducing undesired protease-induced cleavage, and increasing protein production from cells, without interfering with FGF23 activity. This is an unexpected result, as these three positions are conserved in the FGF23 proteins found in human, rhesus, bovine, mouse and rat. This conservation is shown below in the comparison between SEQ ID NOs: 69, 70, 71, 72 and 73, with the Q156, C206 and C244 in bold, underlined font.

```
hFGF23   MLGARLRLWVCALCSVCSMSVLRAYPNASPLLGSSWGGLIHLYTATARNSYHLQIHKNGH
rhesus   MLGARLRLWVCALCSVCSMSVIRAYPNASPLLGSSWGGLIHLYTATARNSYHLQIHKNGH
```

```
                              -continued
bovine     MLGARLGLWVCTLSCV-----VQAYPNSSPLLGSSWGGLTHLYTATARNSYHLQIHGDGH
mouse      MLGTCLRLLVGVLCIVCSLGTARAYPDTSPLLGSNWGSLTHLYTATARTSYHLQIHRDGH
rat        MLGACLRLLVGALCIVCSLGTARAYSDISPLLGSNWGSLTHLYTATARNSYHLQIHRDGH hFGF23     VDGAPHQTIYSALMIRSEDAGFVVITGVMSRRYLCMDFRGNIFGSHYFDPENCRFQHQTL
rhesus     VDGAPHQTIYSALMIRSEDAGFVVITGVMSRRYLCMDFRGNIFGSHYFNPENCRFRHWIL
bovine     VDGSPQQTVYSALMIRSEDAGFVVITGVMSRRYLCMDFIGNIFGSHHFSPESCRFRQRTL
mouse      VDGTPHQTIYSALMITSEDAGSVVITGAMTRRFLCMDLHGNIFGSLHFSPENCKFRQWIL
rat        VDGTPHQTIYSALMITSEDAGSVVIIGAMTRRFLCMDLRGNIFGSYHFSPENCRFRQWIL hFGF23     ENGYDVYHSPQYHFLVSLGRAKRAFLPGMNPPPYSQFLSRRNEIPLIHFNIPI-PRRHIR
rhesus     ENGYDVYHSPQHHFLVSLGRAKRAFLPGMNPPPYSQFLSRRNEIPLIHFNTPR-PRRHIR
bovine     ENGYDVYHSPQHRFLVSLGRAKRAFLPGINPPPYAQFLSRRNEIPLPHFAATARPRRHIR
mouse      ENGYDVYLSQKHHYLVSLGRAKRIFQPGINPPPFSQFLARRNEVPLLHFYIVR-PRRHIR
rat        ENGYDVYLSPKHHYLVSLGRSKRIFQPGINPPPFSQFLARRNEVPLLHFYTAR-PRRHIR hFGF23     SAEDDSERDPLNVLKPRARMTPAPASCSQELPSAEDNSPMASDPLGVVRGGRVNTHAGGT
rhesus     SAEDDSERDPLNVLKPRARMTPAPASCSQELPSAEDNSPVASDPLGVVRGGRVNTHAGGT
bovine     SAHDSG--DPLSVLKPRARATPVPAACSQELPSAEDSGPAASDPLGVLRGHRLDVRAGSA
mouse      SAEDPPERDPLNVLKPRPRATPVPVSCSRELPSAEEGGPAASDPLGVLRRGRGDARGGAG
rat        SAEDPPERDPLNVLKPRPRATPIPVSCSRELPSAEEGGPAASDPLGVLRRGRGDARRGAG hFGF23     GPEGCRPFAKFI    (SEQ ID NO: 69)
rhesus     GPEACRPFPKFI    (SEQ ID NO: 70)
bovine     GAERCRPFPGFA    (SEQ ID NO: 71)
mouse      GADRCRPFPRFV    (SEQ ID NO: 72)
rat        GTDRCRPFPRFV    (SEQ ID NO: 73)
```

The fact that these three mutations do not prevent FGF23 activity is shown in FIG. 11. This figure shows activation of Egr-1-luc reporter gene by FGF23(R179Q)-FcLALA and Q156A, C206S, C244S and C206S/C244S mutants.

HEK293T cells are transiently transfected with the EGR-1-luc reporter gene together with the full-length transmembrane form of Klotho and indicated FGF23-FcLaLa mutants. Luciferase activities are then determined 18 hours later. The results show that C206S, C244S, C206S/C244S (three independent clones) and Q156A (three independent clones) mutants are equally effective as FGF23-FcLALA fusion proteins in activating EGR-1-Luc reporter gene activity.

Data showing that mutating C244 and C206 alter dimerization and aggregation of FGF23 is shown in FIG. 12. This figure shows protein qualities of WT, Q156A, C206S, C244S and C206S/C244S mutants of FGF23(R179Q)-FcLaLa. Conditioned medium from HEK293T cells transient transfected with the indicated FGF23-FcLaLa expression vectors are analyzed by Western blot using an FGF23 antibody. The result shows that C206S/C244S mutation prevents protein dimerization and Q156A mutation has reduced proteolytic fragments.

Thus, surprisingly, even though these Q156, C206 and C244 residues are conserved across species, they can mutated without reducing FGF23 activity and can enhance the qualities of the protein by reducing aggregation and cleavage and by improving production.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the invention are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material or clone of interest is believed to be a matter of routine for a person of ordinary skill in the art with knowledge of the embodiments described herein. Other aspects, advantages, and modifications considered to be within the scope of the following claims. Redrafting of claim scope in later filed corresponding applications may be due to limitations by the patent laws of various countries and should not be interpreted as giving up subject matter of the claims.

What is claimed is:

1. A composition comprising a FGF23 variant polypeptide or a biologically active fragment thereof, in which the amino acids at positions 156, 206 and 244 of the polypeptide or fragment, with reference to the position numbering of the FGF23 sequence of SEQ ID NO: 35, have been mutated,
wherein the polypeptide or fragment is capable of activating Egr-1, and wherein the mutations at position 206 and 244 together reduce the dimerization of the polypeptide or fragment and the mutation at position 156 reduces proteolytic cleavage of the polypeptide or fragment.

2. A pharmaceutical composition comprising the composition of claim 1 and a pharmaceutically acceptable carrier.

3. The composition of claim 1, wherein the polypeptide or fragment further comprises a fusion partner.

4. The composition of claim 3, wherein the fusion partner is a Fc fragment or modified Fc fragment.

5. A pharmaceutical composition comprising the composition of claim 4 and a pharmaceutically acceptable carrier.

6. The composition of claim 1, wherein the polypeptide or fragment is conjugated to a polyethylene glycol.

7. A pharmaceutical composition comprising the composition of claim 4 and a pharmaceutically acceptable carrier.

8. The composition of claim 1, wherein the amino acid at position 179, with reference to the position numbering of the FGF23 sequence of SEQ ID NO: 35, has been mutated.

* * * * *

SEQUENCE LISTING

```
<160> NUMBER OF SEQ ID NOS: 73

<210> SEQ ID NO 1
<211> LENGTH: 5003
<212> TYPE: DNA
<213> ORGANISM: Homo Sapiens

<400> SEQUENCE: 1
cgcgcagcat gcccgccagc gcccgcgc  gccgccgcg  gccgccgccg  ccgtcgctgt      60
cgctgctgct ggtgctgctg ggcctgggcg gccgccgcct gcgtgcggag ccgggcgacg     120
```

-continued

```
gcgcgcagac ctgggcccgt ttctcgcggc ctcctgcccc cgaggccgcg ggcctcttcc    180
agggcaccct ccccgacggc ttcctctggg ccgtgggcag cgccgcctac cagaccgagg    240
gcggctggca gcagcacggc aagggtgcgt ccatctggga tacgttcacc caccaccccc    300
tggcaccccc gggagactcc cggaacgcca gtctgccgtt gggcgccccg tcgccgctgc    360
agcccgccac cggggacgta gccagcgaca gctacaacaa cgtcttccgc gacacggagg    420
cgctgcgcga gctcggggtc actcactacc gcttctccat ctcgtgggcg cgagtgctcc    480
ccaatggcag cgcgggcgtc cccaaccgcg agggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac cacttcaggg    660
attacgcgga gctctgcttc cgccacttcg gcggtcaggt caagtactgg atcaccatcg    720
acaaccccta cgtggtggcc tggcacggct acgccaccgg gcgcctggcc cccggcatcc    780
ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggtttg ccaaacccgt atttattgat ggtgactatc   1020
ccgagagcat gaagaataac cttcatcta ttctgcctga ttttactgaa tctgagaaaa   1080
agttcatcaa aggaactgct gactttttg ctctttgctt tggacccacc ttgagttttc   1140
aactttggga ccctcacatg aagttccgcc aattggaatc tcccaacctg aggcaactgc   1200
tttcctggat tgaccttgaa tttaaccatc tcaaatatt tattgtggaa aatggctggt   1260
ttgtctcagg gaccaccaag agagatgatg ccaaatatat gtattacctc aaaaagttca   1320
tcatggaaac cttaaaagcc atcaagctgg atggggtgga tgtcatcggg tataccgcat   1380
ggtccctcat ggatggtttc gagtggcaca gaggttacag catcaggcgt ggactcttct   1440
atgttgactt tctaagccag acaagatgt tgttgccaaa gtcttcagcc ttgttctacc   1500
aaaagctgat agagaaaaat ggcttccctc ctttacctga aaatcagccc ctagaaggga   1560
catttccctg tgacttttgct tggggagttg ttgacaacta cattcaagta gataccactc   1620
tgtctcagtt taccgacctg aatgtttacc tgtgggatgt ccaccacagt aaaaggctta   1680
ttaaagtgga tggggttgtg accaagaaga ggaaatccta ctgtgttgac tttgctgcca   1740
tccagcccca gatcgcttta ctccaggaaa tgcacgttac acattttcgc ttctccctgg   1800
actgggccct gattctccct ctgggtaacc agtcccaggt gaaccacacc atcctgcagt   1860
actatcgctg catggccagc gagcttgtcc gtgtcaacat caccccagtg gtggccctgt   1920
ggcagcctat ggccccgaac caaggactgc gcgcctcct ggccaggcag ggcgcctggg   1980
agaaccccta cactgccctg gcctttgcag agtatgcccg actgtgcttt caagagctcg   2040
gccatcacgt caagctttgg ataacgatga atgagccgta caaggaat atgcatacca   2100 gtgctggcca caaccttctg aaggcccatg ccctggcttg gcatgtgtac aatgaaaagt   2160
ttaggcatgc tcagaatggg aaaatatcca tagccttgca ggctgattgg ataagaacctg   2220 cctgcccttt ctcccaaaag gacaaagagg tggccgagag agttttggaa tttgacattg   2280
gctggctggc tgagcccatt ttcggctctg agattatcc atgggtgatg agggactggc   2340
tgaaccaaag aaacaatttt cttcttcctt atttcactga agatgaaaaa aagctaatcc   2400
agggtacctt tgacttttg gctttaagcc attataccac catccttgta gactcagaaa   2460
aagaagatcc aataaaatac aatgattacc tagaagtgca agaaatgacc gacatcacgt   2520
```

```
ggctcaactc ccccagtcag gtggcggtag tgccctgggg gttgcgcaaa gtgctgaact    2580
ggctgaagtt caagtacgga gacctcccca tgtacataat atccaacgga atcgatgacg    2640
ggctgcatgc tgaggacgac cagctgaggg tgtattatat gcagaattac ataaacgaag    2700
ctctcaaagc ccacatactg gatggtatca atctttgcgg atactttgct tattcgttta    2760
acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag attttgtcca gaagaattca ccgtgtgtac tgagtgcagt ttttttcaca    2940
cccgaaagtc tttactggct ttcatagctt ttctattttt tgcttctatt atttctctct    3000
cccttatatt ttactactcg aagaaaggca gaagaagtta caaatagttc tgaacatttt    3060
tctattcatt cattttgaaa taattatgca gacacatcag ctgttaacca tttgcacctc    3120
taagtgttgt gaaactgtaa atttcataca tttgacttct agaaaacatt tttgtggctt    3180
atgacagagg ttttgaaatg gcataggtg atcgtaaaat attgaataat gcgaatagtg    3240
cctgaatttg ttctcttttt gggtgattaa aaaactgaca ggcactataa tttctgtaac    3300
acactaacaa aagcatgaaa aataggaacc acaccaatgc aacatttgtg cagaaatttg    3360
aatgacaaga ttaggaatat tttcttctgc acccacttct aaatttaatg ttttttctgga   3420 agtagtaatt gcaagagttc gaatagaaag ttatgtacca agtaaccatt tctcagctgc    3480
cataataatg cctagtggct tcccctctgt caaatctagt ttcctatgga aagaagatg     3540 gcagatacag gagagacgac agagggtcct aggctggaat gttcctttcg aaagcaatgc    3600
ttctatcaaa tactagtatt aatttatgta tctggttaat gacatacttg gagagcaaat    3660
tatgaaaatg tgtattttat atgattttttg aggtcctgtc taaaccctgt gtccctgagg   3720
gatctgtctc actggcatct tgttgagggc cttgcacata ggaaactttt gataagtatc    3780
tgcggaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccattttttga gcagatcttg gaatgaatga   3960
catgaccttt ccctagagaa taaggatgaa ataatcactc attctatgaa cagtgacact    4020
actttctatt ctttagctgt actgtaattt ctttgagttg atagttttac aaattcttaa    4080
taggttcaaa agcaatctgg tctgaataac actggatttg tttctgtgat ctctgaggtc    4140
tattttatgt ttttgctgct acttctgtgg aagtagcttt gaactagttt tactttgaac    4200
tttcacgctg aaacatgcta gtgatatcta gaaagggcta attaggtctc atcctttaat    4260 gcccccttaaa taagtcttgc tgattttcag acagggaagt ctctctatta cactggagct    4320
gttttataga taagtcaata ttgtatcagg caagataaac caatgtcata acaggcattg    4380
ccaacctcac tgacacaggg tcatagtgta taataatata ctgtactata taatatatca    4440
tctttagagg tatgattttt tcatgaaaga taagcttttg gtaatattca ttttaaagtg    4500
gacttattaa aattggatgc tagagaatca agtttatttt atgtatatat ttttctgatt    4560
ataagagtaa tatatgttca ttgtaaaaat tttaaaaca cagaaactat atgcaaagaa    4620
aaaataaaaa ttatctataa tctcagaacc cagaaatagc cactattaac atttcctacg    4680
tatttatttt tacatagatc atattgtata tagttagtat ctttattaat ttttattatg    4740
aaactttcct ttgtcattat tagtcttcaa aagcatgatt tttaatagtt gttgagtatt    4800
ccaccacagg aatgtatcac aacttaaccg ttcccgtttg ttagactagt ttcttattaa    4860
```

```
tgttgatgaa tgttgtttaa aaataatttt gttgctacat ttactttaat ttccttgact    4920
gtaaagagaa gtaattttgc tccttgataa agtattatat taataataaa tctgcctgca    4980 acttttttgcc ttctttcata atc                                           5003
```

<210> SEQ ID NO 2
<211> LENGTH: 1012
<212> TYPE: PRT
<213> ORGANISM: Homo Sapiens

<400> SEQUENCE: 2

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350
```

```
Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
        530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765
```

```
Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile  Phe Tyr Tyr Ser Lys  Lys Gly Arg
        995                 1000                1005

Arg Ser  Tyr Lys
    1010

<210> SEQ ID NO 3
<211> LENGTH: 3279
<212> TYPE: DNA
<213> ORGANISM: Homo Sapiens

<400> SEQUENCE: 3
atcctcagtc tcccagttca agctaatcat tgacagagct ttacaatcac aagcttttac      60
tgaagctttg ataagacagt ccagcagttg gtggcaaatg aagccaggct gtgcggcagg     120
atctccaggg aatgaatgga ttttcttcag cactgatgaa ataaccacac gctataggaa     180
tacaatgtcc aacgggggat tgcaaagatc tgtcatcctg tcagcactta ttctgctacg     240
agctgttact ggattctctg gagatggaag agctatatgg tctaaaaatc ctaattttac     300
tccggtaaat gaaagtcagc tgtttctcta tgacactttc cctaaaaact ttttctgggg     360
tattgggact ggagcattgc aagtggaagg gagttggaag aaggatggaa aaggaccttc     420
tatatgggat catttcatcc acacacacct taaaaatgtc agcagcacga atggttccag     480
tgacagttat attttctgg aaaaagactt atcagccctg gatttatag gagtttcttt     540 ttatcaattt tcaatttcct ggccaaggct tttccccgat ggaatagtaa cagttgccaa     600
cgcaaaaggt ctgcagtact acagtactct tctggacgct ctagtgctta gaaacattga     660
acctatagtt actttatacc actgggattt gcctttggca ctacaagaaa aatatgggg     720
```

```
gtggaaaaat gataccataa tagatatctt caatgactat gccacatact gtttccagat    780
gtttggggac cgtgtcaaat attggattac aattcacaac ccatatctag tggcttggca    840
tgggtatggg acaggtatgc atgcccctgg agagaaggga aatttagcag ctgtctacac    900
tgtgggacac aacttgatca aggctcactc gaaagtttgg cataactaca acacacattt    960
ccgcccacat cagaagggtt ggttatcgat cacgttggga tctcattgga tcgagccaaa   1020
ccggtcggaa aacacgatgg atatattcaa atgtcaacaa tccatggttt ctgtgcttgg   1080
atggtttgcc aaccctatcc atggggatgg cgactatcca gaggggatga gaagaagtt    1140 gttctccgtt ctacccattt tctctgaagc agagaagcat gagatgagag cacagctga    1200 tttctttgcc ttttcttttg gacccaacaa cttcaagccc ctaaacacca tggctaaaat   1260
gggacaaaat gtttcactta atttaagaga agcgctgaac tggattaaac tggaatacaa   1320
caaccctcga atcttgattg ctgagaatgg ctggttcaca gacagtcgtg tgaaaacaga   1380
agacaccacg gccatctaca tgatgaagaa tttcctcagc caggtgcttc aagcaataag   1440
gttagatgaa atacgagtgt ttggttatac tgcctggtct ctcctggatg gctttgaatg   1500
gcaggatgct tacaccatcc gccgaggatt attttatgtg gattttaaca gtaaacagaa   1560
agagcggaaa cctaagtctt cagcacacta ctacaaacag atcatacgag aaaatggttt   1620
ttctttaaaa gagtccacgc cagatgtgca gggccagttt ccctgtgact ctcctgggg    1680 tgtcactgaa tctgttctta agcccgagtc tgtggcttcg tccccacagt tcagcgatcc   1740
tcatctgtac gtgtggaacg ccactggcaa cagactgttg caccgagtgg aagggggtgag  1800 gctgaaaaca cgaccgctc aatgcacaga ttttgtaaac atcaaaaaac aacttgagat   1860
gttggcaaga atgaaagtca cccactaccg gtttgctctg gattgggcct cggtccttcc   1920
cactggcaac ctgtccgcgg tgaaccgaca ggccctgagg tactacaggt gcgtggtcag   1980
tgaggggctg aagcttggca tctccgcgat ggtcaccctg tattatccga cccacgccca   2040
cctaggcctc cccgagcctc tgttgcatgc cgacgggtgg ctgaacccat cgacggccga   2100
ggccttccag gcctacgctg ggctgtgctt ccaggagctg ggggacctgg tgaagctctg   2160
gatcaccatc aacgagccta accggctaag tgacatctac aaccgctctg caacgacac    2220 ctacggggcg cgcacaaacc tgctggtggc ccacgccctg gcctggcgcc tctacgaccg   2280
gcagttcagg ccctcacagc gcggggccgt gtcgctgtcg ctgcacgcgg actgggcgga   2340
acccgccaac ccctatgctg actcgcactg gagggcggcc gagcgcttcc tgcagttcga   2400
gatcgcctgg ttcgccgagc cgctcttcaa gaccggggac taccccgcgg ccatgaggga   2460
atacattgcc tccaagcacc gacgggggct ttccagctcg cccctgccgc gcctcaccga   2520
ggccgaaagg aggctgctca agggcacggt cgacttctgc gcgctcaacc acttcaccac   2580
taggttcgtg atgcacgagc agctggccgg cagccgctac gactcggaca gggacatcca   2640
gtttctgcag gacatcaccc gcctgagctc ccccacgcgc ctggctgtga ttccctgggg   2700
ggtgcgcaag ctgctgcggt gggtccggag gaactacggc gacatggaca tttacatcac   2760
cgccagtggc atcgacgacc aggctctgga ggatgaccgg ctccggaagt actacctagg   2820
gaagtacctt caggaggtgc tgaaagcata cctgattgat aaagtcagaa tcaaaggcta   2880
ttatgcattc aaaactggctg aagagaaatc taaacccaga tttggattct tcacatctga   2940
ttttaaagct aaatcctcaa tacaatttta caacaaagtg atcagcagca ggggcttccc   3000
ttttgagaac agtagttcta gatgcagtca gacccaagaa aatacagagt gcactgtctg   3060
```

-continued

```
cttattcctt gtgcagaaga aaccactgat attcctgggt tgttgcttct tctccaccct   3120
ggttctactc ttatcaattg ccattttca aaggcagaag agaagaaagt tttggaaagc    3180
aaaaaactta caacacatac cattaaagaa aggcaagaga gttgttagct aaactgatct   3240
gtctgcatga tagacagttt aaaaattcat cccagttcc                          3279
```

<210> SEQ ID NO 4
<211> LENGTH: 1044
<212> TYPE: PRT
<213> ORGANISM: Homo Sapiens

<400> SEQUENCE: 4

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335
```

-continued

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
            435                 440                 445

Leu Asp Glu Ile Arg Val Phe Gly Tyr Thr Ala Trp Ser Leu Leu Asp
            450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
            515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
            690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu

```
                755                 760                 765
Ile Ala Trp Phe Ala Glu Pro Leu Phe Lys Thr Gly Asp Tyr Pro Ala
770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Leu Leu Lys Gly
                805                 810                 815

Thr Val Asp Phe Cys Ala Leu Asn His Phe Thr Thr Arg Phe Val Met
                820                 825                 830

His Glu Gln Leu Ala Gly Ser Arg Tyr Asp Ser Asp Arg Asp Ile Gln
                835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
                900                 905                 910

Glu Val Leu Lys Ala Tyr Leu Ile Asp Lys Val Arg Ile Lys Gly Tyr
                915                 920                 925

Tyr Ala Phe Lys Leu Ala Glu Glu Lys Ser Lys Pro Arg Phe Gly Phe
930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
                980                 985                 990

Gln Lys Lys Pro Leu Ile Phe Leu Gly Cys Cys Phe Phe Ser Thr Leu
                995                 1000                1005

Val Leu Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 5
<211> LENGTH: 449
<212> TYPE: PRT
<213> ORGANISM: Homo Sapiens

<400> SEQUENCE: 5

Gln Gly Thr Phe Pro Asp Gly Phe Leu Trp Ala Val Gly Ser Ala Ala
1               5                   10                  15

Tyr Gln Thr Glu Gly Gly Trp Gln Gln His Gly Lys Gly Ala Ser Ile
                20                  25                  30

Trp Asp Thr Phe Thr His His Pro Leu Ala Pro Pro Gly Asp Ser Arg
            35                  40                  45

Asn Ala Ser Leu Pro Leu Gly Ala Pro Ser Pro Leu Gln Pro Ala Thr
        50                  55                  60

Gly Asp Val Ala Ser Asp Ser Tyr Asn Asn Val Phe Arg Asp Thr Glu
65                  70                  75                  80
```

```
Ala Leu Arg Glu Leu Gly Val Thr His Tyr Arg Phe Ser Ile Ser Trp
                85                  90                  95

Ala Arg Val Leu Pro Asn Gly Ser Ala Gly Val Pro Asn Arg Glu Gly
            100                 105                 110

Leu Arg Tyr Tyr Arg Arg Leu Leu Glu Arg Leu Arg Glu Leu Gly Val
        115                 120                 125

Gln Pro Val Val Thr Leu Tyr His Trp Asp Leu Pro Gln Arg Leu Gln
130                 135                 140

Asp Ala Tyr Gly Gly Trp Ala Asn Arg Ala Leu Ala Asp His Phe Arg
145                 150                 155                 160

Asp Tyr Ala Glu Leu Cys Phe Arg His Phe Gly Gly Gln Val Lys Tyr
                165                 170                 175

Trp Ile Thr Ile Asp Asn Pro Tyr Val Val Ala Trp His Gly Tyr Ala
            180                 185                 190

Thr Gly Arg Leu Ala Pro Gly Ile Arg Gly Ser Pro Arg Leu Gly Tyr
        195                 200                 205

Leu Val Ala His Asn Leu Leu Leu Ala His Ala Lys Val Trp His Leu
    210                 215                 220

Tyr Asn Thr Ser Phe Arg Pro Thr Gln Gly Gly Gln Val Ser Ile Ala
225                 230                 235                 240

Leu Ser Ser His Trp Ile Asn Pro Arg Arg Met Thr Asp His Ser Ile
                245                 250                 255

Lys Glu Cys Gln Lys Ser Leu Asp Phe Val Leu Gly Trp Phe Ala Lys
            260                 265                 270

Pro Val Phe Ile Asp Gly Asp Tyr Pro Glu Ser Met Lys Asn Asn Leu
        275                 280                 285

Ser Ser Ile Leu Pro Asp Phe Thr Glu Ser Glu Lys Lys Phe Ile Lys
290                 295                 300

Gly Thr Ala Asp Phe Phe Ala Leu Cys Phe Gly Pro Thr Leu Ser Phe
305                 310                 315                 320

Gln Leu Leu Asp Pro His Met Lys Phe Arg Gln Leu Glu Ser Pro Asn
                325                 330                 335

Leu Arg Gln Leu Leu Ser Trp Ile Asp Leu Glu Phe Asn His Pro Gln
            340                 345                 350

Ile Phe Ile Val Glu Asn Gly Trp Phe Val Ser Gly Thr Thr Lys Arg
        355                 360                 365

Asp Asp Ala Lys Tyr Met Tyr Tyr Leu Lys Lys Phe Ile Met Glu Thr
370                 375                 380

Leu Lys Ala Ile Lys Leu Asp Gly Val Asp Val Ile Gly Tyr Thr Ala
385                 390                 395                 400

Trp Ser Leu Met Asp Gly Phe Glu Trp His Arg Gly Tyr Ser Ile Arg
                405                 410                 415

Arg Gly Leu Phe Tyr Val Asp Phe Leu Ser Gln Asp Lys Met Leu Leu
            420                 425                 430

Pro Lys Ser Ser Ala Leu Phe Tyr Gln Lys Leu Ile Glu Lys Asn Gly
        435                 440                 445

Phe

<210> SEQ ID NO 6
<211> LENGTH: 437
<212> TYPE: PRT
<213> ORGANISM: Homo Sapiens

<400> SEQUENCE: 6
```

```
Gly Thr Phe Pro Cys Asp Phe Ala Trp Gly Val Val Asp Asn Tyr Ile
 1               5                  10                  15

Gln Val Asp Thr Thr Leu Ser Gln Phe Thr Asp Leu Asn Val Tyr Leu
             20                  25                  30

Trp Asp Val His His Ser Lys Arg Leu Ile Lys Val Asp Gly Val Val
             35                  40                  45

Thr Lys Lys Arg Lys Ser Tyr Cys Val Asp Phe Ala Ile Gln Pro
 50                  55                  60

Gln Ile Ala Leu Leu Gln Glu Met His Val Thr His Phe Arg Phe Ser
 65                  70                  75                  80

Leu Asp Trp Ala Leu Ile Leu Pro Leu Gly Asn Gln Ser Gln Val Asn
             85                  90                  95

His Thr Ile Leu Gln Tyr Tyr Arg Cys Met Ala Ser Glu Leu Val Arg
             100                 105                 110

Val Asn Ile Thr Pro Val Val Ala Leu Trp Gln Pro Met Ala Pro Asn
             115                 120                 125

Gln Gly Leu Pro Arg Leu Leu Ala Arg Gln Gly Ala Trp Glu Asn Pro
             130                 135                 140

Tyr Thr Ala Leu Ala Phe Ala Glu Tyr Ala Arg Leu Cys Phe Gln Glu
145                 150                 155                 160

Leu Gly His His Val Lys Leu Trp Ile Thr Met Asn Glu Pro Tyr Thr
             165                 170                 175

Arg Asn Met Thr Tyr Ser Ala Gly His Asn Leu Leu Lys Ala His Ala
             180                 185                 190

Leu Ala Trp His Val Tyr Asn Glu Lys Phe Arg His Ala Gln Asn Gly
             195                 200                 205

Lys Ile Ser Ile Ala Leu Gln Ala Asp Trp Ile Glu Pro Ala Cys Pro
 210                 215                 220

Phe Ser Gln Lys Asp Lys Glu Val Ala Glu Arg Val Leu Glu Phe Asp
225                 230                 235                 240

Ile Gly Trp Leu Ala Glu Pro Ile Phe Gly Ser Gly Asp Tyr Pro Trp
             245                 250                 255

Val Met Arg Asp Trp Leu Asn Gln Arg Asn Asn Phe Leu Leu Pro Tyr
             260                 265                 270

Phe Thr Glu Asp Glu Lys Lys Leu Ile Gln Gly Thr Phe Asp Phe Leu
             275                 280                 285

Ala Leu Ser His Tyr Thr Thr Ile Leu Val Asp Ser Glu Lys Glu Asp
             290                 295                 300

Pro Ile Lys Tyr Asn Asp Tyr Leu Glu Val Gln Glu Met Thr Asp Ile
305                 310                 315                 320

Thr Trp Leu Asn Ser Pro Ser Gln Val Ala Val Val Pro Trp Gly Leu
             325                 330                 335

Arg Lys Val Leu Asn Trp Leu Lys Phe Lys Tyr Gly Asp Leu Pro Met
             340                 345                 350

Tyr Ile Ile Ser Asn Gly Ile Asp Asp Gly Leu His Ala Glu Asp Asp
             355                 360                 365

Gln Leu Arg Val Tyr Tyr Met Gln Asn Tyr Ile Asn Glu Ala Leu Lys
             370                 375                 380

Ala His Ile Leu Asp Gly Ile Asn Leu Cys Gly Tyr Phe Ala Tyr Ser
385                 390                 395                 400

Phe Asn Asp Arg Thr Ala Pro Arg Phe Gly Leu Tyr Arg Tyr Ala Ala
             405                 410                 415

Asp Gln Phe Glu Pro Lys Ala Ser Met Lys His Tyr Arg Lys Ile Ile
```

```
                    420                 425                 430
Asp Ser Asn Gly Phe
        435

<210> SEQ ID NO 7
<211> LENGTH: 949
<212> TYPE: PRT
<213> ORGANISM: Homo Sapiens

<400> SEQUENCE: 7

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350
```

```
Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
        515                 520                 525

Gly Val Val Thr Lys Lys Arg Lys Ser Tyr Cys Val Asp Phe Ala Ala
            530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
```

```
                770                 775                 780
Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
            805                 810                 815

Trp Gly Leu Arg Lys Val Leu Asn Trp Leu Lys Phe Lys Tyr Gly Asp
                820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gly Asn Tyr Ile Asn Glu
        850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
930                 935                 940

Thr Arg Lys Ser Leu
945

<210> SEQ ID NO 8
<211> LENGTH: 33
<212> TYPE: PRT
<213> ORGANISM: Homo Sapiens

<400> SEQUENCE: 8

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Arg Arg Leu Arg
            20                  25                  30

Ala

<210> SEQ ID NO 9
<211> LENGTH: 25
<212> TYPE: PRT
<213> ORGANISM: Homo Sapiens

<400> SEQUENCE: 9

Met Ser Val Leu Thr Gln Val Leu Ala Leu Leu Leu Leu Trp Leu Thr
1               5                   10                  15

Gly Thr Arg Cys Arg Arg Leu Arg Ala
            20                  25

<210> SEQ ID NO 10
<211> LENGTH: 45
<212> TYPE: DNA
<213> ORGANISM: Homo Sapiens

<400> SEQUENCE: 10
ggaggtggag gttcaggagg tggaggttca ggaggtggag gttca          45

<210> SEQ ID NO 11
<211> LENGTH: 15
<212> TYPE: PRT
```

```
<213> ORGANISM: Homo Sapiens

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 5
<212> TYPE: PRT
<213> ORGANISM: Homo Sapiens

<400> SEQUENCE: 12

Gly Gly Gly Gly Ser
1               5

<210> SEQ ID NO 13
<211> LENGTH: 1
<212> TYPE: PRT
<213> ORGANISM: Homo Sapiens

<400> SEQUENCE: 13

Gly
1

<210> SEQ ID NO 14
<211> LENGTH: 2
<212> TYPE: PRT
<213> ORGANISM: Homo Sapiens

<400> SEQUENCE: 14

Gly Gly
1

<210> SEQ ID NO 15
<211> LENGTH: 2
<212> TYPE: PRT
<213> ORGANISM: Homo Sapiens

<400> SEQUENCE: 15

Gly Ser
1

<210> SEQ ID NO 16
<211> LENGTH: 3
<212> TYPE: PRT
<213> ORGANISM: Homo Sapiens

<400> SEQUENCE: 16

Gly Gly Ser
1

<210> SEQ ID NO 17
<211> LENGTH: 1
<212> TYPE: PRT
<213> ORGANISM: Homo Sapiens

<400> SEQUENCE: 17

Ala
1

<210> SEQ ID NO 18
<211> LENGTH: 2
<212> TYPE: PRT
<213> ORGANISM: Homo Sapiens
```

<400> SEQUENCE: 18

Ala Ala
1

<210> SEQ ID NO 19
<211> LENGTH: 1228
<212> TYPE: PRT
<213> ORGANISM: Homo Sapiens

<400> SEQUENCE: 19

```
Met Pro Ala Ser Ala Pro Pro Arg Arg Pro Arg Pro Pro Pro Ser
1               5                  10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
            50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350
```

```
Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
    515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
```

-continued

```
            770             775             780
Leu Leu Pro Tyr Phe Thr Glu Asp Glu Lys Lys Leu Ile Gln Gly Thr
785             790             795             800

Phe Asp Phe Leu Ala Leu Ser His Tyr Thr Thr Ile Leu Val Asp Ser
            805             810             815

Glu Lys Glu Asp Pro Ile Lys Tyr Asn Asp Tyr Leu Glu Val Gln Glu
            820             825             830

Met Thr Asp Ile Thr Trp Leu Asn Ser Pro Ser Gln Val Ala Val Val
            835             840             845

Pro Trp Gly Leu Arg Lys Val Leu Asn Trp Leu Lys Phe Lys Tyr Gly
850             855             860

Asp Leu Pro Met Tyr Ile Ile Ser Asn Gly Ile Asp Asp Gly Leu His
865             870             875             880

Ala Glu Asp Asp Gln Leu Arg Val Tyr Tyr Met Gln Asn Tyr Ile Asn
            885             890             895

Glu Ala Leu Lys Ala His Ile Leu Asp Gly Ile Asn Leu Cys Gly Tyr
            900             905             910

Phe Ala Tyr Ser Phe Asn Asp Arg Thr Ala Pro Arg Phe Gly Leu Tyr
            915             920             925

Arg Tyr Ala Ala Asp Gln Phe Glu Pro Lys Ala Ser Met Lys His Tyr
            930             935             940

Arg Lys Ile Ile Asp Ser Asn Gly Phe Pro Gly Pro Glu Thr Leu Glu
945             950             955             960

Arg Phe Cys Pro Glu Glu Phe Thr Val Cys Thr Glu Cys Ser Phe Phe
            965             970             975

His Thr Arg Lys Ser Leu Gly Ser Gly Gly Gly Ser Gly Gly Gly
            980             985             990

Gly Ser Gly Gly Gly Ser Leu Lys Tyr Pro Asn Ala Ser Pro Leu
            995             1000            1005

Leu Gly Ser Ser Trp Gly Gly Leu Ile His Leu Tyr Thr Ala Thr
1010            1015            1020

Ala Arg Asn Ser Tyr His Leu Gln Ile His Lys Asn Gly His Val
1025            1030            1035

Asp Gly Ala Pro His Gln Thr Ile Tyr Ser Ala Leu Met Ile Arg
1040            1045            1050

Ser Glu Asp Ala Gly Phe Val Val Ile Thr Gly Val Met Ser Arg
1055            1060            1065

Arg Tyr Leu Cys Met Asp Phe Arg Gly Asn Ile Phe Gly Ser His
1070            1075            1080

Tyr Phe Asp Pro Glu Asn Cys Arg Phe Gln His Gln Thr Leu Glu
1085            1090            1095

Asn Gly Tyr Asp Val Tyr His Ser Pro Gln Tyr His Phe Leu Val
1100            1105            1110

Ser Leu Gly Arg Ala Lys Arg Ala Phe Leu Pro Gly Met Asn Pro
1115            1120            1125

Pro Pro Tyr Ser Gln Phe Leu Ser Arg Arg Asn Glu Ile Pro Leu
1130            1135            1140

Ile His Phe Asn Thr Pro Ile Pro Arg Arg His Thr Gln Ser Ala
1145            1150            1155

Glu Asp Asp Ser Glu Arg Asp Pro Leu Asn Val Leu Lys Pro Arg
1160            1165            1170

Ala Arg Met Thr Pro Ala Pro Ala Ser Cys Ser Gln Glu Leu Pro
1175            1180            1185
```

```
Ser Ala Glu Asp Asn Ser Pro Met Ala Ser Asp Pro Leu Gly Val
    1190            1195            1200

Val Arg Gly Gly Arg Val Asn Thr His Ala Gly Gly Thr Gly Pro
    1205            1210            1215

Glu Gly Cys Arg Pro Phe Ala Lys Phe Ile
    1220            1225

<210> SEQ ID NO 20
<211> LENGTH: 1220
<212> TYPE: PRT
<213> ORGANISM: Homo Sapiens

<400> SEQUENCE: 20

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Pro Ala Pro Glu Ala Ala Gly Leu
        35                  40                  45

Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65              70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110

Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
            180                 185                 190

Gln Asp Ala Tyr Gly Gly Trp Ala Asn Arg Ala Leu Ala Asp His Phe
        195                 200                 205

Arg Asp Tyr Ala Glu Leu Cys Phe Arg His Phe Gly Gly Gln Val Lys
    210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
            260                 265                 270

Leu Tyr Asn Thr Ser Phe Arg Pro Thr Gln Gly Gly Gln Val Ser Ile
        275                 280                 285

Ala Leu Ser Ser His Trp Ile Asn Pro Arg Arg Met Thr Asp His Ser
    290                 295                 300

Ile Lys Glu Cys Gln Lys Ser Leu Asp Phe Val Leu Gly Trp Phe Ala
305                 310                 315                 320

Lys Pro Val Phe Ile Asp Gly Asp Tyr Pro Glu Ser Met Lys Asn Asn
```

-continued

```
                325                 330                 335
Leu Ser Ser Ile Leu Pro Asp Phe Thr Glu Ser Glu Lys Lys Phe Ile
            340                 345                 350
Lys Gly Thr Ala Asp Phe Phe Ala Leu Cys Phe Gly Pro Thr Leu Ser
            355                 360                 365
Phe Gln Leu Leu Asp Pro His Met Lys Phe Arg Gln Leu Glu Ser Pro
            370                 375                 380
Asn Leu Arg Gln Leu Leu Ser Trp Ile Asp Leu Glu Phe Asn His Pro
385                 390                 395                 400
Gln Ile Phe Ile Val Glu Asn Gly Trp Phe Val Ser Gly Thr Thr Lys
            405                 410                 415
Arg Asp Asp Ala Lys Tyr Met Tyr Tyr Leu Lys Lys Phe Ile Met Glu
            420                 425                 430
Thr Leu Lys Ala Ile Lys Leu Asp Gly Val Asp Val Ile Gly Tyr Thr
            435                 440                 445
Ala Trp Ser Leu Met Asp Gly Phe Glu Trp His Arg Gly Tyr Ser Ile
            450                 455                 460
Arg Arg Gly Leu Phe Tyr Val Asp Phe Leu Ser Gln Asp Lys Met Leu
465                 470                 475                 480
Leu Pro Lys Ser Ser Ala Leu Phe Tyr Gln Lys Leu Ile Glu Lys Asn
            485                 490                 495
Gly Phe Pro Pro Leu Pro Glu Asn Gln Pro Leu Glu Gly Thr Phe Pro
            500                 505                 510
Cys Asp Phe Ala Trp Gly Val Val Asp Asn Tyr Ile Gln Val Asp Thr
            515                 520                 525
Thr Leu Ser Gln Phe Thr Asp Leu Asn Val Tyr Leu Trp Asp Val His
            530                 535                 540
His Ser Lys Arg Leu Ile Lys Val Asp Gly Val Val Thr Lys Lys Arg
545                 550                 555                 560
Lys Ser Tyr Cys Val Asp Phe Ala Ala Ile Gln Pro Gln Ile Ala Leu
            565                 570                 575
Leu Gln Glu Met His Val Thr His Phe Arg Phe Ser Leu Asp Trp Ala
            580                 585                 590
Leu Ile Leu Pro Leu Gly Asn Gln Ser Gln Val Asn His Thr Ile Leu
            595                 600                 605
Gln Tyr Tyr Arg Cys Met Ala Ser Glu Leu Val Arg Val Asn Ile Thr
            610                 615                 620
Pro Val Val Ala Leu Trp Gln Pro Met Ala Pro Asn Gln Gly Leu Pro
625                 630                 635                 640
Arg Leu Leu Ala Arg Gln Gly Ala Trp Glu Asn Pro Tyr Thr Ala Leu
            645                 650                 655
Ala Phe Ala Glu Tyr Ala Arg Leu Cys Phe Gln Glu Leu Gly His His
            660                 665                 670
Val Lys Leu Trp Ile Thr Met Asn Glu Pro Tyr Thr Arg Asn Met Thr
            675                 680                 685
Tyr Ser Ala Gly His Asn Leu Leu Lys Ala His Ala Leu Ala Trp His
            690                 695                 700
Val Tyr Asn Glu Lys Phe Arg His Ala Gln Asn Gly Lys Ile Ser Ile
705                 710                 715                 720
Ala Leu Gln Ala Asp Trp Ile Glu Pro Ala Cys Pro Phe Ser Gln Lys
            725                 730                 735
Asp Lys Glu Val Ala Glu Arg Val Leu Glu Phe Asp Ile Gly Trp Leu
            740                 745                 750
```

```
Ala Glu Pro Ile Phe Gly Ser Gly Asp Tyr Pro Trp Val Met Arg Asp
            755                 760                 765

Trp Leu Asn Gln Arg Asn Asn Phe Leu Leu Pro Tyr Phe Thr Glu Asp
    770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
                805                 810                 815

Asn Asp Tyr Leu Glu Val Gln Glu Met Thr Asp Ile Thr Trp Leu Asn
                820                 825                 830

Ser Pro Ser Gln Val Ala Val Val Pro Trp Gly Leu Arg Lys Val Leu
            835                 840                 845

Asn Trp Leu Lys Phe Lys Tyr Gly Asp Leu Pro Met Tyr Ile Ile Ser
    850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
                885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
    915                 920                 925

Pro Lys Ala Ser Met Lys His Tyr Arg Lys Ile Ile Asp Ser Asn Gly
    930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu Gly Ser
                965                 970                 975

Gly Gly Gly Gly Ser Gly Gly Gly Ser Gly Gly Gly Gly Ser Leu
            980                 985                 990

Lys Tyr Pro Asn Ala Ser Pro Leu Leu Gly Ser Ser Trp Gly Gly Leu
    995                 1000                1005

Ile His Leu Tyr Thr Ala Thr Ala Arg Asn Ser Tyr His Leu Gln
    1010                1015                1020

Ile His Lys Asn Gly His Val Asp Gly Ala Pro His Gln Thr Ile
    1025                1030                1035

Tyr Ser Ala Leu Met Ile Arg Ser Glu Asp Ala Gly Phe Val Val
    1040                1045                1050

Ile Thr Gly Val Met Ser Arg Arg Tyr Leu Cys Met Asp Phe Arg
    1055                1060                1065

Gly Asn Ile Phe Gly Ser His Tyr Phe Asp Pro Glu Asn Cys Arg
    1070                1075                1080

Phe Gln His Gln Thr Leu Glu Asn Gly Tyr Asp Val Tyr His Ser
    1085                1090                1095

Pro Gln Tyr His Phe Leu Val Ser Leu Gly Arg Ala Lys Arg Ala
    1100                1105                1110

Phe Leu Pro Gly Met Asn Pro Pro Tyr Ser Gln Phe Leu Ser
    1115                1120                1125

Arg Arg Asn Glu Ile Pro Leu Ile His Phe Asn Thr Pro Ile Pro
    1130                1135                1140

Arg Arg His Thr Gln Ser Ala Glu Asp Asp Ser Glu Arg Asp Pro
    1145                1150                1155
```

```
Leu Asn Val Leu Lys Pro Arg Ala Arg Met Thr Pro Ala Pro Ala
    1160            1165            1170

Ser Cys Ser Gln Glu Leu Pro Ser Ala Glu Asp Asn Ser Pro Met
    1175            1180            1185

Ala Ser Asp Pro Leu Gly Val Val Arg Gly Gly Arg Val Asn Thr
    1190            1195            1200

His Ala Gly Gly Thr Gly Pro Glu Gly Cys Arg Pro Phe Ala Lys
    1205            1210            1215

Phe Ile
    1220

<210> SEQ ID NO 21
<211> LENGTH: 762
<212> TYPE: PRT
<213> ORGANISM: Homo Sapiens

<400> SEQUENCE: 21

Met Pro Ala Ser Ala Pro Pro Arg Arg Pro Arg Pro Pro Pro Ser
1               5               10              15

Leu Ser Leu Leu Leu Val Leu Leu Gly Leu Gly Gly Arg Leu Arg
                20              25              30

Ala Glu Pro Gly Asp Gly Ala Gln Thr Trp Ala Arg Phe Ser Arg
            35              40              45

Pro Ala Pro Glu Ala Ala Gly Leu Phe Gln Gly Thr Phe Pro Asp Gly
    50              55              60

Phe Leu Trp Ala Val Gly Ser Ala Ala Tyr Gln Thr Glu Gly Gly Trp
65              70              75              80

Gln Gln His Gly Lys Gly Ala Ser Ile Trp Asp Thr Phe Thr His His
                85              90              95

Pro Leu Ala Pro Pro Gly Asp Ser Arg Asn Ala Ser Leu Pro Leu Gly
                100             105             110

Ala Pro Ser Pro Leu Gln Pro Ala Thr Gly Asp Val Ala Ser Asp Ser
            115             120             125

Tyr Asn Asn Val Phe Arg Asp Thr Glu Ala Leu Arg Glu Leu Gly Val
    130             135             140

Thr His Tyr Arg Phe Ser Ile Ser Trp Ala Arg Val Leu Pro Asn Gly
145             150             155             160

Ser Ala Gly Val Pro Asn Arg Glu Gly Leu Arg Tyr Tyr Arg Arg Leu
                165             170             175

Leu Glu Arg Leu Arg Glu Leu Gly Val Gln Pro Val Val Thr Leu Tyr
                180             185             190

His Trp Asp Leu Pro Gln Arg Leu Gln Asp Ala Tyr Gly Gly Trp Ala
            195             200             205

Asn Arg Ala Leu Ala Asp His Phe Arg Asp Tyr Ala Glu Leu Cys Phe
    210             215             220

Arg His Phe Gly Gly Gln Val Lys Tyr Trp Ile Thr Ile Asp Asn Pro
225             230             235             240

Tyr Val Val Ala Trp His Gly Tyr Ala Thr Gly Arg Leu Ala Pro Gly
                245             250             255

Ile Arg Gly Ser Pro Arg Leu Gly Tyr Leu Val Ala His Asn Leu Leu
                260             265             270

Leu Ala His Ala Lys Val Trp His Leu Tyr Asn Thr Ser Phe Arg Pro
            275             280             285

Thr Gln Gly Gly Gln Val Ser Ile Ala Leu Ser Ser His Trp Ile Asn
    290             295             300
```

```
Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Gly Gly Ser Gly Gly Gly Gly Ser
        515                 520                 525

Gly Gly Gly Gly Ser Leu Lys Tyr Pro Asn Ala Ser Pro Leu Leu Gly
530                 535                 540

Ser Ser Trp Gly Gly Leu Ile His Leu Tyr Thr Ala Thr Ala Arg Asn
545                 550                 555                 560

Ser Tyr His Leu Gln Ile His Lys Asn Gly His Val Asp Gly Ala Pro
                565                 570                 575

His Gln Thr Ile Tyr Ser Ala Leu Met Ile Arg Ser Glu Asp Ala Gly
            580                 585                 590

Phe Val Val Ile Thr Gly Val Met Ser Arg Arg Tyr Leu Cys Met Asp
        595                 600                 605

Phe Arg Gly Asn Ile Phe Gly Ser His Tyr Phe Asp Pro Glu Asn Cys
610                 615                 620

Arg Phe Gln His Gln Thr Leu Glu Asn Gly Tyr Asp Val Tyr His Ser
625                 630                 635                 640

Pro Gln Tyr His Phe Leu Val Ser Leu Gly Arg Ala Lys Arg Ala Phe
                645                 650                 655

Leu Pro Gly Met Asn Pro Pro Tyr Ser Gln Phe Leu Ser Arg Arg
            660                 665                 670

Asn Glu Ile Pro Leu Ile His Phe Asn Thr Pro Ile Pro Arg Arg His
        675                 680                 685

Thr Gln Ser Ala Glu Asp Asp Ser Glu Arg Asp Pro Leu Asn Val Leu
690                 695                 700

Lys Pro Arg Ala Arg Met Thr Pro Ala Pro Ala Ser Cys Ser Gln Glu
705                 710                 715                 720
```

```
Leu Pro Ser Ala Glu Asp Asn Ser Pro Met Ala Ser Asp Pro Leu Gly
                725                 730                 735

Val Val Arg Gly Gly Arg Val Asn Thr His Ala Gly Gly Thr Gly Pro
            740                 745                 750

Glu Gly Cys Arg Pro Phe Ala Lys Phe Ile
        755                 760
```

<210> SEQ ID NO 22
<211> LENGTH: 752
<212> TYPE: PRT
<213> ORGANISM: Homo Sapiens

<400> SEQUENCE: 22

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Pro
                20                  25                  30

Leu Pro Glu Asn Gln Pro Leu Glu Gly Thr Phe Pro Cys Asp Phe Ala
            35                  40                  45

Trp Gly Val Val Asp Asn Tyr Ile Gln Val Asp Thr Thr Leu Ser Gln
        50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
        275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335
```

-continued

```
Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
            355                 360                 365

Val Ala Val Pro Trp Gly Leu Arg Lys Val Leu Asn Trp Leu Lys
370                 375                 380

Phe Lys Tyr Gly Asp Leu Pro Met Tyr Ile Ile Ser Asn Gly Ile Asp
385                 390                 395                 400

Asp Gly Leu His Ala Glu Asp Gln Leu Arg Val Tyr Tyr Met Gln
            405                 410                 415

Asn Tyr Ile Asn Glu Ala Leu Lys Ala His Ile Leu Asp Gly Ile Asn
            420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
            450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
            485                 490                 495

Cys Ser Phe Phe His Thr Arg Lys Ser Leu Gly Ser Gly Gly Gly Gly
            500                 505                 510

Ser Gly Gly Gly Gly Ser Gly Gly Gly Gly Ser Leu Lys Tyr Pro Asn
            515                 520                 525

Ala Ser Pro Leu Leu Gly Ser Ser Trp Gly Gly Leu Ile His Leu Tyr
            530                 535                 540

Thr Ala Thr Ala Arg Asn Ser Tyr His Leu Gln Ile His Lys Asn Gly
545                 550                 555                 560

His Val Asp Gly Ala Pro His Gln Thr Ile Tyr Ser Ala Leu Met Ile
            565                 570                 575

Arg Ser Glu Asp Ala Gly Phe Val Val Ile Thr Gly Val Met Ser Arg
            580                 585                 590

Arg Tyr Leu Cys Met Asp Phe Arg Gly Asn Ile Phe Gly Ser His Tyr
            595                 600                 605

Phe Asp Pro Glu Asn Cys Arg Phe Gln His Gln Thr Leu Glu Asn Gly
610                 615                 620

Tyr Asp Val Tyr His Ser Pro Gln Tyr His Phe Leu Val Ser Leu Gly
625                 630                 635                 640

Arg Ala Lys Arg Ala Phe Leu Pro Gly Met Asn Pro Pro Tyr Ser
            645                 650                 655

Gln Phe Leu Ser Arg Arg Asn Glu Ile Pro Leu Ile His Phe Asn Thr
            660                 665                 670

Pro Ile Pro Arg Arg His Thr Gln Ser Ala Glu Asp Asp Ser Glu Arg
            675                 680                 685

Asp Pro Leu Asn Val Leu Lys Pro Arg Ala Arg Met Thr Pro Ala Pro
            690                 695                 700

Ala Ser Cys Ser Gln Glu Leu Pro Ser Ala Glu Asp Asn Ser Pro Met
705                 710                 715                 720

Ala Ser Asp Pro Leu Gly Val Val Arg Gly Gly Arg Val Asn Thr His
            725                 730                 735

Ala Gly Gly Thr Gly Pro Glu Gly Cys Arg Pro Phe Ala Lys Phe Ile
            740                 745                 750
```

```
<210> SEQ ID NO 23
<211> LENGTH: 1215
<212> TYPE: PRT
<213> ORGANISM: Homo Sapiens

<400> SEQUENCE: 23

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380
```

-continued

```
Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
            405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Thr Phe Pro Asp Gly Phe Leu Trp Ala
        515                 520                 525

Val Gly Ser Ala Ala Tyr Gln Thr Glu Gly Gly Trp Gln Gln His Gly
530                 535                 540

Lys Gly Ala Ser Ile Trp Asp Thr Phe Thr His His Pro Leu Ala Pro
545                 550                 555                 560

Pro Gly Asp Ser Arg Asn Ala Ser Leu Pro Leu Gly Ala Pro Ser Pro
                565                 570                 575

Leu Gln Pro Ala Thr Gly Asp Val Ala Ser Asp Ser Tyr Asn Asn Val
            580                 585                 590

Phe Arg Asp Thr Glu Ala Leu Arg Glu Leu Gly Val Thr His Tyr Arg
        595                 600                 605

Phe Ser Ile Ser Trp Ala Arg Val Leu Pro Asn Gly Ser Ala Gly Val
        610                 615                 620

Pro Asn Arg Glu Gly Leu Arg Tyr Tyr Arg Arg Leu Leu Glu Arg Leu
625                 630                 635                 640

Arg Glu Leu Gly Val Gln Pro Val Val Thr Leu Tyr His Trp Asp Leu
                645                 650                 655

Pro Gln Arg Leu Gln Asp Ala Tyr Gly Gly Trp Ala Asn Arg Ala Leu
            660                 665                 670

Ala Asp His Phe Arg Asp Tyr Ala Glu Leu Cys Phe Arg His Phe Gly
        675                 680                 685

Gly Gln Val Lys Tyr Trp Ile Thr Ile Asp Asn Pro Tyr Val Val Ala
        690                 695                 700

Trp His Gly Tyr Ala Thr Gly Arg Leu Ala Pro Gly Ile Arg Gly Ser
705                 710                 715                 720

Pro Arg Leu Gly Tyr Leu Val Ala His Asn Leu Leu Leu Ala His Ala
                725                 730                 735

Lys Val Trp His Leu Tyr Asn Thr Ser Phe Arg Pro Thr Gln Gly Gly
            740                 745                 750

Gln Val Ser Ile Ala Leu Ser Ser His Trp Ile Asn Pro Arg Arg Met
        755                 760                 765

Thr Asp His Ser Ile Lys Glu Cys Gln Lys Ser Leu Asp Phe Val Leu
        770                 775                 780

Gly Trp Phe Ala Lys Pro Val Phe Ile Asp Gly Asp Tyr Pro Glu Ser
785                 790                 795                 800
```

-continued

```
Met Lys Asn Asn Leu Ser Ser Ile Leu Pro Asp Phe Thr Glu Ser Glu
                805                 810                 815
Lys Lys Phe Ile Lys Gly Thr Ala Asp Phe Ala Leu Cys Phe Gly
        820                 825                 830
Pro Thr Leu Ser Phe Gln Leu Leu Asp Pro His Met Lys Phe Arg Gln
            835                 840                 845
Leu Glu Ser Pro Asn Leu Arg Gln Leu Leu Ser Trp Ile Asp Leu Glu
850                 855                 860
Phe Asn His Pro Gln Ile Phe Ile Val Glu Asn Gly Trp Phe Val Ser
865                 870                 875                 880
Gly Thr Thr Lys Arg Asp Asp Ala Lys Tyr Met Tyr Tyr Leu Lys Lys
                885                 890                 895
Phe Ile Met Glu Thr Leu Lys Ala Ile Lys Leu Asp Gly Val Asp Val
                900                 905                 910
Ile Gly Tyr Thr Ala Trp Ser Leu Met Asp Gly Phe Glu Trp His Arg
        915                 920                 925
Gly Tyr Ser Ile Arg Arg Gly Leu Phe Tyr Val Asp Phe Leu Ser Gln
    930                 935                 940
Asp Lys Met Leu Leu Pro Lys Ser Ser Ala Leu Phe Tyr Gln Lys Leu
945                 950                 955                 960
Ile Glu Lys Asn Gly Phe Pro Glu Phe Gly Ser Gly Gly Gly Ser
                965                 970                 975
Gly Gly Gly Gly Ser Gly Gly Gly Ser Leu Lys Tyr Pro Asn Ala
                980                 985                 990
Ser Pro Leu Leu Gly Ser Ser Trp Gly Gly Leu Ile His Leu Tyr Thr
            995                 1000                1005
Ala Thr Ala Arg Asn Ser Tyr His Leu Gln Ile His Lys Asn Gly
    1010                1015                1020
His Val Asp Gly Ala Pro His Gln Thr Ile Tyr Ser Ala Leu Met
    1025                1030                1035
Ile Arg Ser Glu Asp Ala Gly Phe Val Val Ile Thr Gly Val Met
    1040                1045                1050
Ser Arg Arg Tyr Leu Cys Met Asp Phe Arg Gly Asn Ile Phe Gly
    1055                1060                1065
Ser His Tyr Phe Asp Pro Glu Asn Cys Arg Phe Gln His Gln Thr
    1070                1075                1080
Leu Glu Asn Gly Tyr Asp Val Tyr His Ser Pro Gln Tyr His Phe
    1085                1090                1095
Leu Val Ser Leu Gly Arg Ala Lys Arg Ala Phe Leu Pro Gly Met
    1100                1105                1110
Asn Pro Pro Pro Tyr Ser Gln Phe Leu Ser Arg Arg Asn Glu Ile
    1115                1120                1125
Pro Leu Ile His Phe Asn Thr Pro Ile Pro Arg Arg His Thr Gln
    1130                1135                1140
Ser Ala Glu Asp Asp Ser Glu Arg Asp Pro Leu Asn Val Leu Lys
    1145                1150                1155
Pro Arg Ala Arg Met Thr Pro Ala Pro Ala Ser Cys Ser Gln Glu
    1160                1165                1170
Leu Pro Ser Ala Glu Asp Asn Ser Pro Met Ala Ser Asp Pro Leu
    1175                1180                1185
Gly Val Val Arg Gly Gly Arg Val Asn Thr His Ala Gly Gly Thr
    1190                1195                1200
Gly Pro Glu Gly Cys Arg Pro Phe Ala Lys Phe Ile
```

<210> SEQ ID NO 24
<211> LENGTH: 1189
<212> TYPE: PRT
<213> ORGANISM: Homo Sapiens

<400> SEQUENCE: 24

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
    50                  55                  60

Phe Thr Asp Leu Asn Val Tyr Leu Trp Asp Val His His Ser Lys Arg
65                  70                  75                  80

Leu Ile Lys Val Asp Gly Val Val Thr Lys Lys Arg Lys Ser Tyr Cys
                85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
        115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
            180                 185                 190

Tyr Ala Arg Leu Cys Phe Gln Glu Leu Gly His His Val Lys Leu Trp
        195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
        275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
        355                 360                 365

Val Ala Val Val Pro Trp Gly Leu Arg Lys Val Leu Asn Trp Leu Lys
370                 375                 380

Phe Lys Tyr Gly Asp Leu Pro Met Tyr Ile Ile Ser Asn Gly Ile Asp
385                 390                 395                 400

Asp Gly Leu His Ala Glu Asp Gln Leu Arg Val Tyr Tyr Met Gln
            405                 410                 415

Asn Tyr Ile Asn Glu Ala Leu Lys Ala His Ile Leu Asp Gly Ile Asn
                420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
                485                 490                 495

Cys Ser Phe Phe His Thr Arg Lys Ser Leu Gly Thr Phe Pro Cys Asp
            500                 505                 510

Phe Ala Trp Gly Val Val Asp Asn Tyr Ile Gln Val Asp Thr Thr Leu
515                 520                 525

Ser Gln Phe Thr Asp Leu Asn Val Tyr Leu Trp Asp Val His His Ser
530                 535                 540

Lys Arg Leu Ile Lys Val Asp Gly Val Val Thr Lys Lys Arg Lys Ser
545                 550                 555                 560

Tyr Cys Val Asp Phe Ala Ala Ile Gln Pro Gln Ile Ala Leu Leu Gln
                565                 570                 575

Glu Met His Val Thr His Phe Arg Phe Ser Leu Asp Trp Ala Leu Ile
            580                 585                 590

Leu Pro Leu Gly Asn Gln Ser Gln Val Asn His Thr Ile Leu Gln Tyr
            595                 600                 605

Tyr Arg Cys Met Ala Ser Glu Leu Val Arg Val Asn Ile Thr Pro Val
610                 615                 620

Val Ala Leu Trp Gln Pro Met Ala Pro Asn Gln Gly Leu Pro Arg Leu
625                 630                 635                 640

Leu Ala Arg Gln Gly Ala Trp Glu Asn Pro Tyr Thr Ala Leu Ala Phe
                645                 650                 655

Ala Glu Tyr Ala Arg Leu Cys Phe Gln Glu Leu Gly His His Val Lys
            660                 665                 670

Leu Trp Ile Thr Met Asn Glu Pro Tyr Thr Arg Asn Met Thr Tyr Ser
            675                 680                 685

Ala Gly His Asn Leu Leu Lys Ala His Ala Leu Ala Trp His Val Tyr
690                 695                 700

Asn Glu Lys Phe Arg His Ala Gln Asn Gly Lys Ile Ser Ile Ala Leu
705                 710                 715                 720

Gln Ala Asp Trp Ile Glu Pro Ala Cys Pro Phe Ser Gln Lys Asp Lys
                725                 730                 735

Glu Val Ala Glu Arg Val Leu Glu Phe Asp Ile Gly Trp Leu Ala Glu
            740                 745                 750

Pro Ile Phe Gly Ser Gly Asp Tyr Pro Trp Val Met Arg Asp Trp Leu
            755                 760                 765

Asn Gln Arg Asn Asn Phe Leu Leu Pro Tyr Phe Thr Glu Asp Glu Lys
770                 775                 780

Lys Leu Ile Gln Gly Thr Phe Asp Phe Leu Ala Leu Ser His Tyr Thr

```
                785                 790                 795                 800
            Thr Ile Leu Val Asp Ser Glu Lys Glu Asp Pro Ile Lys Tyr Asn Asp
                            805                 810                 815
            Tyr Leu Glu Val Gln Glu Met Thr Asp Ile Thr Trp Leu Asn Ser Pro
                            820                 825                 830
            Ser Gln Val Ala Val Pro Trp Gly Leu Arg Lys Val Leu Asn Trp
                            835                 840                 845
            Leu Lys Phe Lys Tyr Gly Asp Leu Pro Met Tyr Ile Ile Ser Asn Gly
                850                 855                 860
            Ile Asp Asp Gly Leu His Ala Glu Asp Gln Leu Arg Val Tyr Tyr
            865                 870                 875                 880
            Met Gln Asn Tyr Ile Asn Glu Ala Leu Lys Ala His Ile Leu Asp Gly
                            885                 890                 895
            Ile Asn Leu Cys Gly Tyr Phe Ala Tyr Ser Phe Asn Asp Arg Thr Ala
                            900                 905                 910
            Pro Arg Phe Gly Leu Tyr Arg Tyr Ala Ala Asp Gln Phe Glu Pro Lys
                            915                 920                 925
            Ala Ser Met Lys His Tyr Arg Lys Ile Ile Asp Ser Asn Gly Phe Gly
                930                 935                 940
            Ser Gly Gly Gly Gly Ser Gly Gly Gly Gly Ser Gly Gly Gly Gly Ser
            945                 950                 955                 960
            Leu Lys Tyr Pro Asn Ala Ser Pro Leu Leu Gly Ser Ser Trp Gly Gly
                            965                 970                 975
            Leu Ile His Leu Tyr Thr Ala Thr Ala Arg Asn Ser Tyr His Leu Gln
                            980                 985                 990
            Ile His Lys Asn Gly His Val Asp  Gly Ala Pro His Gln  Thr Ile Tyr
                            995                 1000                1005
            Ser Ala  Leu Met Ile Arg Ser  Glu Asp Ala Gly Phe  Val Val Ile
                    1010                1015                1020
            Thr Gly  Val Met Ser Arg Arg  Tyr Leu Cys Met Asp  Phe Arg Gly
                    1025                1030                1035
            Asn Ile  Phe Gly Ser His Tyr  Phe Asp Pro Glu Asn  Cys Arg Phe
                    1040                1045                1050
            Gln His  Gln Thr Leu Glu Asn  Gly Tyr Asp Val Tyr  His Ser Pro
                    1055                1060                1065
            Gln Tyr  His Phe Leu Val Ser  Leu Gly Arg Ala Lys  Arg Ala Phe
                    1070                1075                1080
            Leu Pro  Gly Met Asn Pro Pro  Pro Tyr Ser Gln Phe  Leu Ser Arg
                    1085                1090                1095
            Arg Asn  Glu Ile Pro Leu Ile  His Phe Asn Thr Pro  Ile Pro Arg
                    1100                1105                1110
            Arg His  Thr Gln Ser Ala Glu  Asp Asp Ser Glu Arg  Asp Pro Leu
                    1115                1120                1125
            Asn Val  Leu Lys Pro Arg Ala  Arg Met Thr Pro Ala  Pro Ala Ser
                    1130                1135                1140
            Cys Ser  Gln Glu Leu Pro Ser  Ala Glu Asp Asn Ser  Pro Met Ala
                    1145                1150                1155
            Ser Asp  Pro Leu Gly Val Val  Arg Gly Gly Arg Val  Asn Thr His
                    1160                1165                1170
            Ala Gly  Gly Thr Gly Pro Glu  Gly Cys Arg Pro Phe  Ala Lys Phe
                    1175                1180                1185
            Ile
```

-continued

```
<210> SEQ ID NO 25
<211> LENGTH: 1219
<212> TYPE: PRT
<213> ORGANISM: Homo Sapiens

<400> SEQUENCE: 25

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Ser Gly Gly Gly
                245                 250                 255

Gly Ser Gly Gly Gly Gly Ser Gly Gly Gly Gly Ser Leu Lys Glu Pro
            260                 265                 270

Gly Asp Gly Ala Gln Thr Trp Ala Arg Phe Ser Arg Pro Pro Ala Pro
        275                 280                 285

Glu Ala Ala Gly Leu Phe Gln Gly Thr Phe Pro Asp Gly Phe Leu Trp
    290                 295                 300

Ala Val Gly Ser Ala Ala Tyr Gln Thr Glu Gly Gly Trp Gln Gln His
305                 310                 315                 320

Gly Lys Gly Ala Ser Ile Trp Asp Thr Phe Thr His His Pro Leu Ala
                325                 330                 335

Pro Pro Gly Asp Ser Arg Asn Ala Ser Leu Pro Leu Gly Ala Pro Ser
            340                 345                 350

Pro Leu Gln Pro Ala Thr Gly Asp Val Ala Ser Asp Ser Tyr Asn Asn
        355                 360                 365

Val Phe Arg Asp Thr Glu Ala Leu Arg Glu Leu Gly Val Thr His Tyr
    370                 375                 380
```

```
Arg Phe Ser Ile Ser Trp Ala Arg Val Leu Pro Asn Gly Ser Ala Gly
385                 390                 395                 400

Val Pro Asn Arg Glu Gly Leu Arg Tyr Tyr Arg Arg Leu Leu Glu Arg
            405                 410                 415

Leu Arg Glu Leu Gly Val Gln Pro Val Val Thr Leu Tyr His Trp Asp
        420                 425                 430

Leu Pro Gln Arg Leu Gln Asp Ala Tyr Gly Gly Trp Ala Asn Arg Ala
        435                 440                 445

Leu Ala Asp His Phe Arg Asp Tyr Ala Glu Leu Cys Phe Arg His Phe
450                 455                 460

Gly Gly Gln Val Lys Tyr Trp Ile Thr Ile Asp Asn Pro Tyr Val Val
465                 470                 475                 480

Ala Trp His Gly Tyr Ala Thr Gly Arg Leu Ala Pro Gly Ile Arg Gly
            485                 490                 495

Ser Pro Arg Leu Gly Tyr Leu Val Ala His Asn Leu Leu Ala His
            500                 505                 510

Ala Lys Val Trp His Leu Tyr Asn Thr Ser Phe Arg Pro Thr Gln Gly
        515                 520                 525

Gly Gln Val Ser Ile Ala Leu Ser Ser His Trp Ile Asn Pro Arg Arg
        530                 535                 540

Met Thr Asp His Ser Ile Lys Glu Cys Gln Lys Ser Leu Asp Phe Val
545                 550                 555                 560

Leu Gly Trp Phe Ala Lys Pro Val Phe Ile Asp Gly Asp Tyr Pro Glu
            565                 570                 575

Ser Met Lys Asn Asn Leu Ser Ser Ile Leu Pro Asp Phe Thr Glu Ser
            580                 585                 590

Glu Lys Lys Phe Ile Lys Gly Thr Ala Asp Phe Phe Ala Leu Cys Phe
            595                 600                 605

Gly Pro Thr Leu Ser Phe Gln Leu Leu Asp Pro His Met Lys Phe Arg
            610                 615                 620

Gln Leu Glu Ser Pro Asn Leu Arg Gln Leu Leu Ser Trp Ile Asp Leu
625                 630                 635                 640

Glu Phe Asn His Pro Gln Ile Phe Ile Val Glu Asn Gly Trp Phe Val
            645                 650                 655

Ser Gly Thr Thr Lys Arg Asp Asp Ala Lys Tyr Met Tyr Tyr Leu Lys
            660                 665                 670

Lys Phe Ile Met Glu Thr Leu Lys Ala Ile Lys Leu Asp Gly Val Asp
            675                 680                 685

Val Ile Gly Tyr Thr Ala Trp Ser Leu Met Asp Gly Phe Glu Trp His
            690                 695                 700

Arg Gly Tyr Ser Ile Arg Arg Gly Leu Phe Tyr Val Asp Phe Leu Ser
705                 710                 715                 720

Gln Asp Lys Met Leu Leu Pro Lys Ser Ser Ala Leu Phe Tyr Gln Lys
            725                 730                 735

Leu Ile Glu Lys Asn Gly Phe Pro Pro Leu Pro Glu Asn Gln Pro Leu
            740                 745                 750

Glu Gly Thr Phe Pro Cys Asp Phe Ala Trp Gly Val Val Asp Asn Tyr
            755                 760                 765

Ile Gln Val Asp Thr Thr Leu Ser Gln Phe Thr Asp Leu Asn Val Tyr
            770                 775                 780

Leu Trp Asp Val His His Ser Lys Arg Leu Ile Lys Val Asp Gly Val
785                 790                 795                 800
```

```
Val Thr Lys Lys Arg Lys Ser Tyr Cys Val Asp Phe Ala Ala Ile Gln
            805                 810                 815

Pro Gln Ile Ala Leu Leu Gln Glu Met His Val Thr His Phe Arg Phe
        820                 825                 830

Ser Leu Asp Trp Ala Leu Ile Leu Pro Leu Gly Asn Gln Ser Gln Val
        835                 840                 845

Asn His Thr Ile Leu Gln Tyr Tyr Arg Cys Met Ala Ser Glu Leu Val
    850                 855                 860

Arg Val Asn Ile Thr Pro Val Val Ala Leu Trp Gln Pro Met Ala Pro
865                 870                 875                 880

Asn Gln Gly Leu Pro Arg Leu Leu Ala Arg Gln Gly Ala Trp Glu Asn
            885                 890                 895

Pro Tyr Thr Ala Leu Ala Phe Ala Glu Tyr Ala Arg Leu Cys Phe Gln
        900                 905                 910

Glu Leu Gly His His Val Lys Leu Trp Ile Thr Met Asn Glu Pro Tyr
        915                 920                 925

Thr Arg Asn Met Thr Tyr Ser Ala Gly His Asn Leu Leu Lys Ala His
    930                 935                 940

Ala Leu Ala Trp His Val Tyr Asn Glu Lys Phe Arg His Ala Gln Asn
945                 950                 955                 960

Gly Lys Ile Ser Ile Ala Leu Gln Ala Asp Trp Ile Glu Pro Ala Cys
            965                 970                 975

Pro Phe Ser Gln Lys Asp Lys Glu Val Ala Glu Arg Val Leu Glu Phe
        980                 985                 990

Asp Ile Gly Trp Leu Ala Glu Pro Ile Phe Gly Ser Gly Asp Tyr Pro
        995                 1000                1005

Trp Val Met Arg Asp Trp Leu Asn Gln Arg Asn Asn Phe Leu Leu
        1010                1015                1020

Pro Tyr Phe Thr Glu Asp Glu Lys Lys Leu Ile Gln Gly Thr Phe
        1025                1030                1035

Asp Phe Leu Ala Leu Ser His Tyr Thr Thr Ile Leu Val Asp Ser
        1040                1045                1050

Glu Lys Glu Asp Pro Ile Lys Tyr Asn Asp Tyr Leu Glu Val Gln
        1055                1060                1065

Glu Met Thr Asp Ile Thr Trp Leu Asn Ser Pro Ser Gln Val Ala
        1070                1075                1080

Val Val Pro Trp Gly Leu Arg Lys Val Leu Asn Trp Leu Lys Phe
        1085                1090                1095

Lys Tyr Gly Asp Leu Pro Met Tyr Ile Ile Ser Asn Gly Ile Asp
        1100                1105                1110

Asp Gly Leu His Ala Glu Asp Asp Gln Leu Arg Val Tyr Tyr Met
        1115                1120                1125

Gln Asn Tyr Ile Asn Glu Ala Leu Lys Ala His Ile Leu Asp Gly
        1130                1135                1140

Ile Asn Leu Cys Gly Tyr Phe Ala Tyr Ser Phe Asn Asp Arg Thr
        1145                1150                1155

Ala Pro Arg Phe Gly Leu Tyr Arg Tyr Ala Ala Asp Gln Phe Glu
        1160                1165                1170

Pro Lys Ala Ser Met Lys His Tyr Arg Lys Ile Ile Asp Ser Asn
        1175                1180                1185

Gly Phe Pro Gly Pro Glu Thr Leu Glu Arg Phe Cys Pro Glu Glu
        1190                1195                1200

Phe Thr Val Cys Thr Glu Cys Ser Phe Phe His Thr Arg Lys Ser
```

Leu

<210> SEQ ID NO 26
<211> LENGTH: 700
<212> TYPE: PRT
<213> ORGANISM: Homo Sapiens

<400> SEQUENCE: 26

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
```

```
                355                 360                 365
Arg Leu Leu Glu Arg Leu Arg Glu Leu Gly Val Gln Pro Val Val Thr
370                 375                 380
Leu Tyr His Trp Asp Leu Pro Gln Arg Leu Gln Asp Ala Tyr Gly Gly
385                 390                 395                 400
Trp Ala Asn Arg Ala Leu Ala Asp His Phe Arg Asp Tyr Ala Glu Leu
                405                 410                 415
Cys Phe Arg His Phe Gly Gly Gln Val Lys Tyr Trp Ile Thr Ile Asp
                420                 425                 430
Asn Pro Tyr Val Val Ala Trp His Gly Tyr Ala Thr Gly Arg Leu Ala
                435                 440                 445
Pro Gly Ile Arg Gly Ser Pro Arg Leu Gly Tyr Leu Val Ala His Asn
                450                 455                 460
Leu Leu Leu Ala His Ala Lys Val Trp His Leu Tyr Asn Thr Ser Phe
465                 470                 475                 480
Arg Pro Thr Gln Gly Gly Gln Val Ser Ile Ala Leu Ser Ser His Trp
                485                 490                 495
Ile Asn Pro Arg Arg Met Thr Asp His Ser Ile Lys Glu Cys Gln Lys
                500                 505                 510
Ser Leu Asp Phe Val Leu Gly Trp Phe Ala Lys Pro Val Phe Ile Asp
                515                 520                 525
Gly Asp Tyr Pro Glu Ser Met Lys Asn Asn Leu Ser Ser Ile Leu Pro
530                 535                 540
Asp Phe Thr Glu Ser Glu Lys Lys Phe Ile Lys Gly Thr Ala Asp Phe
545                 550                 555                 560
Phe Ala Leu Cys Phe Gly Pro Thr Leu Ser Phe Gln Leu Leu Asp Pro
                565                 570                 575
His Met Lys Phe Arg Gln Leu Glu Ser Pro Asn Leu Arg Gln Leu Leu
                580                 585                 590
Ser Trp Ile Asp Leu Glu Phe Asn His Pro Gln Ile Phe Ile Val Glu
                595                 600                 605
Asn Gly Trp Phe Val Ser Gly Thr Thr Lys Arg Asp Asp Ala Lys Tyr
                610                 615                 620
Met Tyr Tyr Leu Lys Lys Phe Ile Met Glu Thr Leu Lys Ala Ile Lys
625                 630                 635                 640
Leu Asp Gly Val Asp Val Ile Gly Tyr Thr Ala Trp Ser Leu Met Asp
                645                 650                 655
Gly Phe Glu Trp His Arg Gly Tyr Ser Ile Arg Arg Gly Leu Phe Tyr
                660                 665                 670
Val Asp Phe Leu Ser Gln Asp Lys Met Leu Leu Pro Lys Ser Ser Ala
                675                 680                 685
Leu Phe Tyr Gln Lys Leu Ile Glu Lys Asn Gly Phe
                690                 695                 700

<210> SEQ ID NO 27
<211> LENGTH: 688
<212> TYPE: PRT
<213> ORGANISM: Homo Sapiens

<400> SEQUENCE: 27

Met Leu Gly Ala Arg Leu Arg Leu Trp Val Cys Ala Leu Cys Ser Val
1               5                   10                  15
Cys Ser Met Ser Val Leu Arg Ala Tyr Pro Asn Ala Ser Pro Leu Leu
                20                  25                  30
```

-continued

```
Gly Ser Ser Trp Gly Gly Leu Ile His Leu Tyr Thr Ala Thr Ala Arg
         35                  40                  45

Asn Ser Tyr His Leu Gln Ile His Lys Asn Gly His Val Asp Gly Ala
 50                  55                  60

Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                 85                  90                  95

Asp Phe Arg Gly Asn Ile Phe Gly Ser His Tyr Phe Asp Pro Glu Asn
             100                 105                 110

Cys Arg Phe Gln His Gln Thr Leu Glu Asn Gly Tyr Asp Val Tyr His
         115                 120                 125

Ser Pro Gln Tyr His Phe Leu Val Ser Leu Gly Arg Ala Lys Arg Ala
130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                 165                 170                 175

His Thr Gln Ser Ala Glu Asp Ser Glu Arg Asp Pro Leu Asn Val
             180                 185                 190

Leu Lys Pro Arg Ala Arg Met Thr Pro Ala Pro Ala Ser Cys Ser Gln
         195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                 245                 250                 255

Asp Phe Ala Trp Gly Val Val Asp Asn Tyr Ile Gln Val Asp Thr Thr
             260                 265                 270

Leu Ser Gln Phe Thr Asp Leu Asn Val Tyr Leu Trp Asp Val His His
         275                 280                 285

Ser Lys Arg Leu Ile Lys Val Asp Gly Val Val Thr Lys Lys Arg Lys
290                 295                 300

Ser Tyr Cys Val Asp Phe Ala Ala Ile Gln Pro Gln Ile Ala Leu Leu
305                 310                 315                 320

Gln Glu Met His Val Thr His Phe Arg Phe Ser Leu Asp Trp Ala Leu
                 325                 330                 335

Ile Leu Pro Leu Gly Asn Gln Ser Gln Val Asn His Thr Ile Leu Gln
             340                 345                 350

Tyr Tyr Arg Cys Met Ala Ser Glu Leu Val Arg Val Asn Ile Thr Pro
         355                 360                 365

Val Val Ala Leu Trp Gln Pro Met Ala Pro Asn Gln Gly Leu Pro Arg
370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                 405                 410                 415

Lys Leu Trp Ile Thr Met Asn Glu Pro Tyr Thr Arg Asn Met Thr Tyr
             420                 425                 430

Ser Ala Gly His Asn Leu Leu Lys Ala His Ala Leu Ala Trp His Val
         435                 440                 445

Tyr Asn Glu Lys Phe Arg His Ala Gln Asn Gly Lys Ile Ser Ile Ala
```

```
                   450                 455                 460
Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                    485                 490                 495

Glu Pro Ile Phe Gly Ser Gly Asp Tyr Pro Trp Val Met Arg Asp Trp
                500                 505                 510

Leu Asn Gln Arg Asn Asn Phe Leu Leu Pro Tyr Phe Thr Glu Asp Glu
                515                 520                 525

Lys Lys Leu Ile Gln Gly Thr Phe Asp Phe Leu Ala Leu Ser His Tyr
            530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                    565                 570                 575

Pro Ser Gln Val Ala Val Pro Trp Gly Leu Arg Lys Val Leu Asn
                580                 585                 590

Trp Leu Lys Phe Lys Tyr Gly Asp Leu Pro Met Tyr Ile Ile Ser Asn
                595                 600                 605

Gly Ile Asp Asp Gly Leu His Ala Glu Asp Asp Gln Leu Arg Val Tyr
        610                 615                 620

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                    645                 650                 655

Ala Pro Arg Phe Gly Leu Tyr Arg Tyr Ala Ala Asp Gln Phe Glu Pro
                660                 665                 670

Lys Ala Ser Met Lys His Tyr Arg Lys Ile Ile Asp Ser Asn Gly Phe
            675                 680                 685

<210> SEQ ID NO 28
<211> LENGTH: 1149
<212> TYPE: PRT
<213> ORGANISM: Homo Sapiens

<400> SEQUENCE: 28

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                    85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140
```

```
Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
            165                 170                 175

His Thr Gln Ser Ala Glu Asp Ser Glu Arg Asp Pro Leu Asn Val
        180                 185                 190

Leu Lys Pro Arg Ala Arg Met Thr Pro Ala Pro Ala Ser Cys Ser Gln
    195                 200                 205

Glu Leu Pro Ser Ala Glu Asp Asn Ser Pro Met Ala Ser Asp Pro Leu
    210                 215                 220

Gly Val Arg Gly Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
            355                 360                 365

Arg Leu Leu Glu Arg Leu Arg Glu Leu Gly Val Gln Pro Val Val Thr
    370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
            420                 425                 430

Asn Pro Tyr Val Val Ala Trp His Gly Tyr Ala Thr Gly Arg Leu Ala
            435                 440                 445

Pro Gly Ile Arg Gly Ser Pro Arg Leu Gly Tyr Leu Val Ala His Asn
    450                 455                 460

Leu Leu Leu Ala His Ala Lys Val Trp His Leu Tyr Asn Thr Ser Phe
465                 470                 475                 480

Arg Pro Thr Gln Gly Gly Gln Val Ser Ile Ala Leu Ser Ser His Trp
                485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
        515                 520                 525

Gly Asp Tyr Pro Glu Ser Met Lys Asn Asn Leu Ser Ser Ile Leu Pro
    530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
```

```
                565                 570                 575
His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
            595                 600                 605

Asn Gly Trp Phe Val Ser Gly Thr Thr Lys Arg Asp Asp Ala Lys Tyr
    610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
            675                 680                 685

Leu Phe Tyr Gln Lys Leu Ile Glu Lys Asn Gly Phe Gln Gly Thr Phe
        690                 695                 700

Pro Asp Gly Phe Leu Trp Ala Val Gly Ser Ala Ala Tyr Gln Thr Glu
705                 710                 715                 720

Gly Gly Trp Gln Gln His Gly Lys Gly Ala Ser Ile Trp Asp Thr Phe
                725                 730                 735

Thr His His Pro Leu Ala Pro Pro Gly Asp Ser Arg Asn Ala Ser Leu
            740                 745                 750

Pro Leu Gly Ala Pro Ser Pro Leu Gln Pro Ala Thr Gly Asp Val Ala
            755                 760                 765

Ser Asp Ser Tyr Asn Asn Val Phe Arg Asp Thr Glu Ala Leu Arg Glu
    770                 775                 780

Leu Gly Val Thr His Tyr Arg Phe Ser Ile Ser Trp Ala Arg Val Leu
785                 790                 795                 800

Pro Asn Gly Ser Ala Gly Val Pro Asn Arg Glu Gly Leu Arg Tyr Tyr
                805                 810                 815

Arg Arg Leu Leu Glu Arg Leu Arg Glu Leu Gly Val Gln Pro Val Val
            820                 825                 830

Thr Leu Tyr His Trp Asp Leu Pro Gln Arg Leu Gln Asp Ala Tyr Gly
        835                 840                 845

Gly Trp Ala Asn Arg Ala Leu Ala Asp His Phe Arg Asp Tyr Ala Glu
    850                 855                 860

Leu Cys Phe Arg His Phe Gly Gly Gln Val Lys Tyr Trp Ile Thr Ile
865                 870                 875                 880

Asp Asn Pro Tyr Val Val Ala Trp His Gly Tyr Ala Thr Gly Arg Leu
                885                 890                 895

Ala Pro Gly Ile Arg Gly Ser Pro Arg Leu Gly Tyr Leu Val Ala His
            900                 905                 910

Asn Leu Leu Leu Ala His Ala Lys Val Trp His Leu Tyr Asn Thr Ser
            915                 920                 925

Phe Arg Pro Thr Gln Gly Gly Gln Val Ser Ile Ala Leu Ser Ser His
        930                 935                 940

Trp Ile Asn Pro Arg Arg Met Thr Asp His Ser Ile Lys Glu Cys Gln
945                 950                 955                 960

Lys Ser Leu Asp Phe Val Leu Gly Trp Phe Ala Lys Pro Val Phe Ile
                965                 970                 975

Asp Gly Asp Tyr Pro Glu Ser Met Lys Asn Asn Leu Ser Ser Ile Leu
            980                 985                 990
```

```
Pro Asp Phe Thr Glu Ser Glu Lys Lys Phe Ile Lys Gly Thr Ala Asp
    995                 1000                1005

Phe Phe Ala Leu Cys Phe Gly Pro Thr Leu Ser Phe Gln Leu Leu
    1010                1015                1020

Asp Pro His Met Lys Phe Arg Gln Leu Glu Ser Pro Asn Leu Arg
    1025                1030                1035

Gln Leu Leu Ser Trp Ile Asp Leu Glu Phe Asn His Pro Gln Ile
    1040                1045                1050

Phe Ile Val Glu Asn Gly Trp Phe Val Ser Gly Thr Thr Lys Arg
    1055                1060                1065

Asp Asp Ala Lys Tyr Met Tyr Tyr Leu Lys Lys Phe Ile Met Glu
    1070                1075                1080

Thr Leu Lys Ala Ile Lys Leu Asp Gly Val Asp Val Ile Gly Tyr
    1085                1090                1095

Thr Ala Trp Ser Leu Met Asp Gly Phe Glu Trp His Arg Gly Tyr
    1100                1105                1110

Ser Ile Arg Arg Gly Leu Phe Tyr Val Asp Phe Leu Ser Gln Asp
    1115                1120                1125

Lys Met Leu Leu Pro Lys Ser Ser Ala Leu Phe Tyr Gln Lys Leu
    1130                1135                1140

Ile Glu Lys Asn Gly Phe
    1145

<210> SEQ ID NO 29
<211> LENGTH: 1125
<212> TYPE: PRT
<213> ORGANISM: Homo Sapiens

<400> SEQUENCE: 29

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
```

-continued

```
            195                 200                 205
Glu Leu Pro Ser Ala Glu Asp Asn Ser Pro Met Ala Ser Asp Pro Leu
210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gly Thr Phe Pro Cys
                    245                 250                 255

Asp Phe Ala Trp Gly Val Val Asp Asn Tyr Ile Gln Val Asp Thr Thr
                260                 265                 270

Leu Ser Gln Phe Thr Asp Leu Asn Val Tyr Leu Trp Asp Val His His
                275                 280                 285

Ser Lys Arg Leu Ile Lys Val Asp Gly Val Val Thr Lys Lys Arg Lys
290                 295                 300

Ser Tyr Cys Val Asp Phe Ala Ile Gln Pro Gln Ile Ala Leu Leu
305                 310                 315                 320

Gln Glu Met His Val Thr His Phe Arg Phe Ser Leu Asp Trp Ala Leu
                    325                 330                 335

Ile Leu Pro Leu Gly Asn Gln Ser Gln Val Asn His Thr Ile Leu Gln
                340                 345                 350

Tyr Tyr Arg Cys Met Ala Ser Glu Leu Val Arg Val Asn Ile Thr Pro
                355                 360                 365

Val Val Ala Leu Trp Gln Pro Met Ala Pro Asn Gln Gly Leu Pro Arg
370                 375                 380

Leu Leu Ala Arg Gln Gly Ala Trp Glu Asn Pro Tyr Thr Ala Leu Ala
385                 390                 395                 400

Phe Ala Glu Tyr Ala Arg Leu Cys Phe Gln Glu Leu Gly His His Val
                    405                 410                 415

Lys Leu Trp Ile Thr Met Asn Glu Pro Tyr Thr Arg Asn Met Thr Tyr
                420                 425                 430

Ser Ala Gly His Asn Leu Leu Lys Ala His Ala Leu Ala Trp His Val
                435                 440                 445

Tyr Asn Glu Lys Phe Arg His Ala Gln Asn Gly Lys Ile Ser Ile Ala
450                 455                 460

Leu Gln Ala Asp Trp Ile Glu Pro Ala Cys Pro Phe Ser Gln Lys Asp
465                 470                 475                 480

Lys Glu Val Ala Glu Arg Val Leu Glu Phe Asp Ile Gly Trp Leu Ala
                    485                 490                 495

Glu Pro Ile Phe Gly Ser Gly Asp Tyr Pro Trp Val Met Arg Asp Trp
                500                 505                 510

Leu Asn Gln Arg Asn Asn Phe Leu Leu Pro Tyr Phe Thr Glu Asp Glu
                515                 520                 525

Lys Lys Leu Ile Gln Gly Thr Phe Asp Phe Leu Ala Leu Ser His Tyr
530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Pro Trp Gly Leu Arg Lys Val Leu Asn
                580                 585                 590

Trp Leu Lys Phe Lys Tyr Gly Asp Leu Pro Met Tyr Ile Ile Ser Asn
                595                 600                 605

Gly Ile Asp Asp Gly Leu His Ala Glu Asp Gln Leu Arg Val Tyr
610                 615                 620
```

-continued

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
            645                 650                 655

Ala Pro Arg Phe Gly Leu Tyr Arg Tyr Ala Ala Asp Gln Phe Glu Pro
        660                 665                 670

Lys Ala Ser Met Lys His Tyr Arg Lys Ile Ile Asp Ser Asn Gly Phe
        675                 680                 685

Gly Thr Phe Pro Cys Asp Phe Ala Trp Gly Val Val Asp Asn Tyr Ile
    690                 695                 700

Gln Val Asp Thr Thr Leu Ser Gln Phe Thr Asp Leu Asn Val Tyr Leu
705                 710                 715                 720

Trp Asp Val His His Ser Lys Arg Leu Ile Lys Val Asp Gly Val Val
            725                 730                 735

Thr Lys Lys Arg Lys Ser Tyr Cys Val Asp Phe Ala Ala Ile Gln Pro
        740                 745                 750

Gln Ile Ala Leu Leu Gln Glu Met His Val Thr His Phe Arg Phe Ser
        755                 760                 765

Leu Asp Trp Ala Leu Ile Leu Pro Leu Gly Asn Gln Ser Gln Val Asn
    770                 775                 780

His Thr Ile Leu Gln Tyr Tyr Arg Cys Met Ala Ser Glu Leu Val Arg
785                 790                 795                 800

Val Asn Ile Thr Pro Val Val Ala Leu Trp Gln Pro Met Ala Pro Asn
            805                 810                 815

Gln Gly Leu Pro Arg Leu Leu Ala Arg Gln Gly Ala Trp Glu Asn Pro
        820                 825                 830

Tyr Thr Ala Leu Ala Phe Ala Glu Tyr Ala Arg Leu Cys Phe Gln Glu
        835                 840                 845

Leu Gly His His Val Lys Leu Trp Ile Thr Met Asn Glu Pro Tyr Thr
    850                 855                 860

Arg Asn Met Thr Tyr Ser Ala Gly His Asn Leu Leu Lys Ala His Ala
865                 870                 875                 880

Leu Ala Trp His Val Tyr Asn Glu Lys Phe Arg His Ala Gln Asn Gly
            885                 890                 895

Lys Ile Ser Ile Ala Leu Gln Ala Asp Trp Ile Glu Pro Ala Cys Pro
        900                 905                 910

Phe Ser Gln Lys Asp Lys Glu Val Ala Glu Arg Val Leu Glu Phe Asp
        915                 920                 925

Ile Gly Trp Leu Ala Glu Pro Ile Phe Gly Ser Gly Asp Tyr Pro Trp
    930                 935                 940

Val Met Arg Asp Trp Leu Asn Gln Arg Asn Asn Phe Leu Leu Pro Tyr
945                 950                 955                 960

Phe Thr Glu Asp Glu Lys Lys Leu Ile Gln Gly Thr Phe Asp Phe Leu
            965                 970                 975

Ala Leu Ser His Tyr Thr Thr Ile Leu Val Asp Ser Glu Lys Glu Asp
        980                 985                 990

Pro Ile Lys Tyr Asn Asp Tyr Leu Glu Val Gln Glu Met Thr Asp Ile
        995                 1000                1005

Thr Trp Leu Asn Ser Pro Ser Gln Val Ala Val Val Pro Trp Gly
    1010                1015                1020

Leu Arg Lys Val Leu Asn Trp Leu Lys Phe Lys Tyr Gly Asp Leu
    1025                1030                1035

```
Pro Met Tyr Ile Ile Ser Asn Gly Ile Asp Asp Gly Leu His Ala
    1040                1045                1050

Glu Asp Asp Gln Leu Arg Val Tyr Tyr Met Gln Asn Tyr Ile Asn
    1055                1060                1065

Glu Ala Leu Lys Ala His Ile Leu Asp Gly Ile Asn Leu Cys Gly
    1070                1075                1080

Tyr Phe Ala Tyr Ser Phe Asn Asp Arg Thr Ala Pro Arg Phe Gly
    1085                1090                1095

Leu Tyr Arg Tyr Ala Ala Asp Gln Phe Glu Pro Lys Ala Ser Met
    1100                1105                1110

Lys His Tyr Arg Lys Ile Ile Asp Ser Asn Gly Phe
    1115                1120                1125

<210> SEQ ID NO 30
<211> LENGTH: 2157
<212> TYPE: DNA
<213> ORGANISM: Homo Sapiens

<400> SEQUENCE: 30
gctcccagcc aagaacctcg gggccgctgc gcggtgggga ggagttcccc gaaacccggc      60
cgctaagcga ggcctcctcc tcccgcagat ccgaacggcc tgggcggggt caccccggct     120
gggacaagaa gccgccgcct gcctgcccgg gcccggggag ggggctgggg ctggggccgg     180
aggcggggtg tgagtgggtg tgtgcggggg gcggaggctt gatgcaatcc cgataagaaa     240
tgctcgggtg tcttgggcac ctacccgtgg ggcccgtaag gcgctactat ataaggctgc     300
cggcccggag ccgccgcgcc gtcagagcag gagcgctgcg tccaggatct agggccacga     360
ccatcccaac ccggcactca cagccccgca gcgcatcccg gtcgccgccc agcctcccgc     420 accccccatcg ccggagctgc gccgagagcc cagggaggt gccatgcgga gcgggtgtgt     480
ggtggtccac gtatggatcc tggccggcct ctggctggcc gtggccgggc gcccctcgc     540 cttctcggac gcggggcccc acgtgcacta cggctgggc gacccccatcc gcctgcggca     600 cctgtacacc tccggccccc acgggctctc cagctgcttc ctgcgcatcc gtgccgacgg     660
cgtcgtggac tgcgcgcggg gccagagcgc gcacagtttg ctggagatca aggcagtcgc     720
tctgcggacc gtggccatca agggcgtgca cagcgtgcgg tacctctgca tgggcgccga     780
cggcaagatg caggggctgc ttcagtactc ggaggaagac tgtgctttcg aggaggagat     840
ccgcccagat ggctacaatg tgtaccgatc cgagaagcac cgcctcccgg tctccctgag     900
cagtgccaaa cagcggcagc tgtacaagaa cagaggcttt cttccactct ctcatttcct     960
gcccatgctg cccatggtcc cagaggagcc tgaggacctc aggggccact ggaatctga    1020 catgttctct tcgcccctgg agaccgacag catggaccca tttgggcttg tcaccggact    1080
ggaggccgtg aggagtccca gctttgagaa gtaactgaga ccatgcccgg gcctcttcac    1140
tgctgccagg ggctgtggta cctgcagcgt ggggacgtg cttctacaag aacagtcctg    1200
agtccacgtt ctgtttagct ttaggaagaa acatctagaa gttgtacata ttcagagttt    1260
tccattggca gtgccagttt ctagccaata gacttgtctg atcataacat tgtaagcctg    1320
tagcttgccc agctgctgcc tgggccccca ttctgctccc tcgaggttgc tggacaagct    1380
gctgcactgt ctcagttctg cttgaatacc tccatcgatg gggaactcac ttcctttgga    1440
aaaattctta tgtcaagctg aaattctcta attttttctc atcacttccc caggagcagc    1500
cagaagacag gcagtagttt taatttcagg aacaggtgat ccactctgta aaacagcagg    1560
taaatttcac tcaaccccat gtgggaattg atctatatct ctacttccag ggaccatttg    1620
```

-continued

```
ccccttcccaa atccctccag gccagaactg actggagcag gcatggccca ccaggcttca    1680
ggagtagggg aagcctggag ccccactcca gccctgggac aacttgagaa ttccccctga    1740
ggccagttct gtcatggatg ctgtcctgag aataacttgc tgtcccggtg tcacctgctt    1800
ccatctccca gcccaccagc cctctgccca cctcacatgc ctccccatgg attggggcct    1860
cccaggcccc ccaccttatg tcaacctgca cttcttgttc aaaaatcagg aaaagaaaag    1920
atttgaagac cccaagtctt gtcaataact tgctgtgtgg aagcagcggg ggaagaccta    1980 gaacccttc cccagcactt ggttttccaa catgatattt atgagtaatt tattttgata     2040
tgtacatctc ttatttcctt acattattta tgcccccaaa ttatatttat gtatgtaagt    2100
gaggtttgtt ttgtatatta aaatggagtt tgtttgtaaa aaaaaaaaa aaaaaaa        2157
```

<210> SEQ ID NO 31
<211> LENGTH: 216
<212> TYPE: PRT
<213> ORGANISM: Homo Sapiens

<400> SEQUENCE: 31

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 32
<211> LENGTH: 940
<212> TYPE: PRT
<213> ORGANISM: Homo Sapiens

<400> SEQUENCE: 32

```
Cys Thr Gly Thr Cys Ala Gly Cys Thr Gly Ala Gly Gly Ala Thr Cys
1               5                   10                  15
```

```
Cys Ala Gly Cys Cys Gly Ala Ala Ala Gly Ala Gly Gly Ala Gly Cys
            20                  25                  30

Cys Ala Gly Gly Cys Ala Cys Thr Cys Ala Gly Gly Cys Cys Ala Cys
        35                  40                  45

Cys Thr Gly Ala Gly Thr Cys Thr Ala Cys Thr Cys Ala Cys Cys Thr
    50                  55                  60

Gly Gly Ala Cys Ala Ala Cys Thr Gly Gly Ala Ala Thr Cys Thr Gly
65                  70                  75                  80

Gly Cys Ala Cys Cys Ala Ala Thr Thr Cys Thr Ala Ala Ala Cys Cys
                85                  90                  95

Ala Cys Thr Cys Ala Gly Cys Thr Thr Cys Thr Cys Cys Gly Ala Gly
            100                 105                 110

Cys Thr Cys Ala Cys Ala Cys Cys Cys Cys Gly Gly Ala Gly Ala Thr
        115                 120                 125

Cys Ala Cys Cys Thr Gly Ala Gly Gly Ala Cys Cys Cys Gly Ala Gly
    130                 135                 140

Cys Cys Ala Thr Thr Gly Ala Thr Gly Gly Ala Cys Thr Cys Gly Gly
145                 150                 155                 160

Ala Cys Gly Ala Gly Ala Cys Cys Gly Gly Gly Thr Thr Cys Gly Ala
                165                 170                 175

Gly Cys Ala Cys Thr Cys Ala Gly Gly Ala Cys Thr Gly Thr Gly Gly
            180                 185                 190

Gly Thr Thr Thr Cys Thr Gly Thr Gly Cys Thr Gly Gly Cys Thr Gly
        195                 200                 205

Gly Thr Cys Thr Thr Cys Thr Gly Cys Thr Gly Gly Gly Ala Gly Cys
    210                 215                 220

Cys Thr Gly Cys Cys Ala Gly Gly Cys Ala Cys Ala Cys Cys Cys Cys
225                 230                 235                 240

Ala Thr Cys Cys Cys Thr Gly Ala Cys Thr Cys Cys Ala Gly Thr Cys
                245                 250                 255

Cys Thr Cys Thr Cys Cys Thr Gly Cys Ala Ala Thr Thr Cys Gly Gly
            260                 265                 270

Gly Gly Gly Cys Cys Ala Ala Gly Thr Cys Cys Gly Gly Cys Ala Gly
        275                 280                 285

Cys Gly Gly Thr Ala Cys Cys Thr Cys Thr Ala Cys Ala Cys Ala Gly
    290                 295                 300

Ala Thr Gly Ala Thr Gly Cys Cys Cys Ala Gly Cys Ala Gly Ala Cys
305                 310                 315                 320

Ala Gly Ala Ala Gly Cys Cys Cys Ala Cys Cys Thr Gly Gly Ala Gly
                325                 330                 335

Ala Thr Cys Ala Gly Gly Gly Ala Gly Gly Ala Thr Gly Gly Gly Ala
            340                 345                 350

Cys Gly Gly Thr Gly Gly Gly Gly Gly Gly Cys Gly Cys Thr Gly Cys
        355                 360                 365

Thr Gly Ala Cys Cys Ala Gly Ala Gly Cys Cys Cys Cys Gly Ala Ala
    370                 375                 380

Ala Gly Thr Cys Thr Cys Cys Thr Gly Cys Ala Gly Cys Thr Gly Ala
385                 390                 395                 400

Ala Ala Gly Cys Cys Thr Thr Gly Ala Ala Gly Cys Cys Gly Gly Gly
                405                 410                 415

Ala Gly Thr Thr Ala Thr Thr Cys Ala Ala Ala Thr Cys Thr Thr Gly
            420                 425                 430
```

-continued

```
Gly Gly Ala Gly Thr Cys Ala Gly Ala Cys Ala Thr Cys Cys Ala
            435                 440                 445
Gly Gly Thr Thr Cys Cys Thr Gly Thr Gly Cys Cys Ala Gly Cys Gly
450                 455                 460
Gly Cys Ala Gly Ala Thr Gly Gly Gly Cys Cys Cys Thr Gly
465                 470                 475                 480
Thr Ala Thr Gly Gly Ala Thr Cys Gly Cys Thr Cys Ala Cys Thr
                485                 490                 495
Thr Thr Gly Ala Cys Cys Cys Thr Gly Ala Gly Gly Cys Cys Thr Gly
            500                 505                 510
Cys Ala Gly Cys Thr Thr Cys Cys Gly Gly Gly Ala Gly Cys Thr Gly
            515                 520                 525
Cys Thr Thr Cys Thr Thr Gly Ala Gly Gly Ala Cys Gly Gly Ala Thr
            530                 535                 540
Ala Cys Ala Ala Thr Gly Thr Thr Thr Ala Cys Cys Ala Gly Thr Cys
545                 550                 555                 560
Cys Gly Ala Ala Gly Cys Cys Ala Cys Gly Gly Cys Cys Thr Cys
                565                 570                 575
Cys Cys Gly Cys Thr Gly Cys Ala Cys Cys Thr Gly Cys Cys Ala Gly
            580                 585                 590
Gly Gly Ala Ala Cys Ala Ala Gly Thr Cys Cys Cys Ala Cys Ala
                595                 600                 605
Cys Cys Gly Gly Gly Ala Cys Cys Cys Thr Gly Cys Ala Cys Cys Cys
            610                 615                 620
Cys Gly Ala Gly Ala Cys Ala Gly Cys Thr Cys Gly Cys Thr
625                 630                 635                 640
Thr Cys Cys Thr Gly Cys Cys Ala Cys Thr Ala Cys Ala Gly Gly
                645                 650                 655
Cys Cys Thr Gly Cys Cys Cys Cys Cys Gly Cys Ala Cys Thr Cys
            660                 665                 670
Cys Cys Gly Gly Ala Gly Cys Cys Ala Cys Cys Gly Gly Ala Ala
            675                 680                 685
Thr Cys Cys Thr Gly Gly Cys Cys Cys Cys Cys Ala Gly Cys Cys
            690                 695                 700
Cys Cys Cys Cys Gly Ala Thr Gly Thr Gly Gly Gly Cys Thr Cys Cys
705                 710                 715                 720
Thr Cys Gly Gly Ala Cys Cys Cys Thr Cys Thr Gly Ala Gly Cys Ala
                725                 730                 735
Thr Gly Gly Thr Gly Gly Gly Ala Cys Cys Thr Thr Cys Cys Cys Ala
            740                 745                 750
Gly Gly Gly Cys Cys Gly Ala Ala Gly Cys Cys Cys Ala Gly Cys
                755                 760                 765
Thr Ala Cys Gly Cys Thr Thr Cys Cys Thr Gly Ala Ala Gly Cys Cys
770                 775                 780
Ala Gly Ala Gly Gly Cys Thr Gly Thr Thr Thr Ala Cys Thr Ala Thr
785                 790                 795                 800
Gly Ala Cys Ala Thr Cys Thr Cys Cys Thr Cys Thr Thr Ala Thr
                805                 810                 815
Thr Thr Ala Thr Thr Ala Gly Gly Thr Thr Thr Ala Thr Thr Ala Thr
            820                 825                 830
Cys Thr Thr Ala Thr Thr Ala Thr Thr Thr Thr Thr Thr Ala
            835                 840                 845
Thr Thr Thr Thr Thr Cys Thr Thr Ala Cys Thr Thr Gly Ala Gly Ala
```

```
                    850                 855                 860
Thr Ala Ala Thr Ala Ala Ala Gly Ala Gly Thr Thr Cys Cys Ala Gly
865                 870                 875                 880

Ala Gly Gly Ala Gly Ala Ala Ala Ala Ala Ala Ala Ala Ala
                    885                 890                 895

Ala Ala Ala Ala Ala Ala Ala Ala Ala Ala Ala Ala Ala Ala
                    900                 905                 910

Ala Ala Ala Ala Ala Ala Ala Ala Ala Ala Ala Ala
            915                 920                 925

Ala Ala Ala Ala Ala Ala Ala Ala Ala Ala
            930                 935             940

<210> SEQ ID NO 33
<211> LENGTH: 209
<212> TYPE: PRT
<213> ORGANISM: Homo Sapiens

<400> SEQUENCE: 33

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 34
<211> LENGTH: 3018
<212> TYPE: DNA
<213> ORGANISM: Homo Sapiens

<400> SEQUENCE: 34
cggcaaaaag agggaatcc agtctaggat cctcacacca gctacttgca agggagaagg      60
aaaaggccag taaggcctgg ccaggagag tcccgacagg agtgtcaggt ttcaatctca     120
gcaccagcca ctcagagcag ggcacgatgt tgggggcccg cctcaggctc tgggtctgtg    180
```

| | |
|---|---|
| ccttgtgcag cgtctgcagc atgagcgtcc tcagagccta tcccaatgcc tccccactgc | 240 |
| tcggctccag ctggggtggc ctgatccacc tgtacacagc cacagccagg aacagctacc | 300 |
| acctgcagat ccacaagaat ggccatgtgg atggcgcacc ccatcagacc atctacagtg | 360 |
| ccctgatgat cagatcagag gatgctggct tgtggtgat acaggtgtg atgagcagaa | 420 |
| gatacctctg catggatttc agaggcaaca ttttggatc acactatttc gacccggaga | 480 |
| actgcaggtt ccaacaccag acgctggaaa acgggtacga cgtctaccac tctcctcagt | 540 |
| atcacttcct ggtcagtctg ggccgggcga agagagcctt cctgccaggc atgaacccac | 600 |
| ccccgtactc ccagttcctg tcccggagga acgagatccc cctaattcac ttcaacaccc | 660 |
| ccataccacg gcggcacacc cggagcgccg aggacgactc ggagcgggac cccctgaacg | 720 |
| tgctgaagcc ccgggcccgg atgacccggg ccccggcctc ctgttcacag gagctcccga | 780 |
| gcgccgagga caacagcccg atggccagtg acccattagg ggtggtcagg ggcggtcgag | 840 |
| tgaacacgca cgctggggga acgggcccgg aaggctgccg ccccttcgcc aagttcatct | 900 |
| agggtcgctg gaagggcacc ctctttaacc catccctcag caaacgcagc tcttcccaag | 960 |
| gaccaggtcc cttgacgttc cgaggatggg aaaggtgaca ggggcatgta tggaatttgc | 1020 |
| tgcttctctg gggtcccttc cacaggaggt cctgtgagaa ccaacctttg aggcccaagt | 1080 |
| catgggggttt caccgccttc ctcactccat atagaacacc tttcccaata ggaaacccca | 1140 |
| acaggtaaac tagaaatttc cccttcatga aggtagagag aagggggtctc tcccaacata | 1200 |
| tttctcttcc ttgtgcctct cctctttatc acttttaagc ataaaaaaaa aaaaaaaaa | 1260 |
| aaaaaaaaa aaaagcagtg ggttcctgag ctcaagactt tgaaggtgta gggaagagga | 1320 |
| aatcggagat cccagaagct tctccactgc cctatgcatt tatgttagat gccccgatcc | 1380 |
| cactggcatt tgagtgtgca aaccttgaca ttaacagctg aatggggcaa gttgatgaaa | 1440 |
| acactacttt caagccttcg ttcttccttg agcatctctg gggaagagct gtcaaaagac | 1500 |
| tggtggtagg ctggtgaaaa cttgacagct agacttgatg cttgctgaaa tgaggcagga | 1560 |
| atcataatag aaaactcagc ctccctacag ggtgagcacc ttctgtctcg ctgtctccct | 1620 |
| ctgtgcagcc acagccagag ggcccagaat ggccccactc tgttcccaag cagttcatga | 1680 |
| tacagcctca ccttttggcc ccatctctgg ttttgaaaa tttggtctaa ggaataaata | 1740 |
| gcttttacac tggctcacga aaatctgccc tgctagaatt tgcttttcaa aatgaaaata | 1800 |
| aattccaact ctcctaagag gcatttaatt aaggctctac ttccaggttg agtaggaatc | 1860 |
| cattctgaac aaaactacaaa aatgtgactg gaaggggggc tttgagagac tgggactgct | 1920 |
| ctgggttagg ttttctgtgg actgaaaaat cgtgtccttt tctctaaatg aagtggcatc | 1980 |
| aaggactcag ggggaaagaa atcagggggac atgttataga agttatgaaa agacaaccac | 2040 |
| atggtcaggc tcttgtctgt ggtctctagg gctctgcagc agcagtggct cttcgattag | 2100 |
| ttaaaactct cctaggctga cacatctggg tctcaatccc cttggaaatt cttggtgcat | 2160 |
| taaatgaagc cttaccccat tactgcggtt cttcctgtaa gggggctcca ttttcctccc | 2220 |
| tctctttaaa tgaccaccta aaggacagta tattaacaag caaagtcgat tcaacaacag | 2280 |
| cttcttccca gtcactttt ttttctcac tgccatcaca tactaacctt atactttgat | 2340 |
| ctattctttt tggttatgag agaaatgttg ggcaactgtt tttacctgat ggttttaagc | 2400 |
| tgaacttgaa ggactggttc ctattctgaa acagtaaaac tatgtataat agtatatagc | 2460 |
| catgcatggc aaatatttta atatttctgt tttcatttcc tgttggaaat attatcctgc | 2520 |

```
ataatagcta ttggaggctc ctcagtgaaa gatcccaaaa ggattttggt ggaaaactag    2580
ttgtaatctc acaaactcaa cactaccatc aggggttttc tttatggcaa agccaaaata    2640
gctcctacaa tttcttatat ccctcgtcat gtggcagtat ttatttattt atttggaagt    2700
ttgcctatcc ttctatattt atagatattt ataaaaatgt aaccccttt tcctttcttc     2760 tgtttaaaat aaaaataaaa tttatctcag cttctgttag cttatcctct ttgtagtact    2820
acttaaaagc atgtcggaat ataagaataa aaggattat gggaggggaa cattagggaa     2880
atccagagaa ggcaaaattg aaaaaaagat tttagaattt taaaattttc aaagatttct    2940
tccattcata aggagactca atgattttaa ttgatctaga cagaattatt taagttttat    3000
caatattgga tttctggt                                                  3018
```

<210> SEQ ID NO 35
<211> LENGTH: 251
<212> TYPE: PRT
<213> ORGANISM: Homo Sapiens

<400> SEQUENCE: 35

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 36
<211> LENGTH: 251
<212> TYPE: PRT
<213> ORGANISM: Homo Sapiens

<400> SEQUENCE: 36

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 37
<211> LENGTH: 431
<212> TYPE: PRT
<213> ORGANISM: Homo Sapiens

<400> SEQUENCE: 37

Tyr Asp Thr Phe Pro Lys Asn Phe Phe Trp Gly Ile Gly Thr Gly Ala
1               5                   10                  15

Leu Gln Val Glu Gly Ser Trp Lys Lys Asp Gly Lys Gly Pro Ser Ile
            20                  25                  30

Trp Asp His Phe Ile His Thr His Leu Lys Asn Val Ser Ser Thr Asn
        35                  40                  45

Gly Ser Ser Asp Ser Tyr Ile Phe Leu Glu Lys Asp Leu Ser Ala Leu
    50                  55                  60

Asp Phe Ile Gly Val Ser Phe Tyr Gln Phe Ser Ile Ser Trp Pro Arg
65                  70                  75                  80

Leu Phe Pro Asp Gly Ile Val Thr Val Ala Asn Ala Lys Gly Leu Gln
                85                  90                  95

Tyr Tyr Ser Thr Leu Leu Asp Ala Leu Val Leu Arg Asn Ile Glu Pro
            100                 105                 110

```
Ile Val Thr Leu Tyr His Trp Asp Leu Pro Leu Ala Leu Gln Glu Lys
            115                 120                 125

Tyr Gly Gly Trp Lys Asn Asp Thr Ile Ile Asp Ile Phe Asn Asp Tyr
130                 135                 140

Ala Thr Tyr Cys Phe Gln Met Phe Gly Asp Arg Val Lys Tyr Trp Ile
145                 150                 155                 160

Thr Ile His Asn Pro Tyr Leu Val Ala Trp His Gly Tyr Gly Thr Gly
                165                 170                 175

Met His Ala Pro Gly Glu Lys Gly Asn Leu Ala Ala Val Tyr Thr Val
            180                 185                 190

Gly His Asn Leu Ile Lys Ala His Ser Lys Val Trp His Asn Tyr Asn
            195                 200                 205

Thr His Phe Arg Pro His Gln Lys Gly Trp Leu Ser Ile Thr Leu Gly
        210                 215                 220

Ser His Trp Ile Glu Pro Asn Arg Ser Glu Asn Thr Met Asp Ile Phe
225                 230                 235                 240

Lys Cys Gln Gln Ser Met Val Ser Val Leu Gly Trp Phe Ala Asn Pro
                245                 250                 255

Ile His Gly Asp Gly Asp Tyr Pro Glu Gly Met Arg Lys Lys Leu Phe
            260                 265                 270

Ser Val Leu Pro Ile Phe Ser Glu Ala Glu Lys His Glu Met Arg Gly
        275                 280                 285

Thr Ala Asp Phe Phe Ala Phe Ser Phe Gly Pro Asn Asn Phe Lys Pro
    290                 295                 300

Leu Asn Thr Met Ala Lys Met Gly Gln Asn Val Ser Leu Asn Leu Arg
305                 310                 315                 320

Glu Ala Leu Asn Trp Ile Lys Leu Glu Tyr Asn Asn Pro Arg Ile Leu
                325                 330                 335

Ile Ala Glu Asn Gly Trp Phe Thr Asp Ser Arg Val Lys Thr Glu Asp
            340                 345                 350

Thr Thr Ala Ile Tyr Met Met Lys Asn Phe Leu Ser Gln Val Leu Gln
        355                 360                 365

Ala Ile Arg Leu Asp Glu Ile Arg Val Phe Gly Tyr Thr Ala Trp Ser
    370                 375                 380

Leu Leu Asp Gly Phe Glu Trp Gln Asp Ala Tyr Thr Ile Arg Arg Gly
385                 390                 395                 400

Leu Phe Tyr Val Asp Phe Asn Ser Lys Gln Lys Glu Arg Lys Pro Lys
                405                 410                 415

Ser Ser Ala His Tyr Tyr Lys Gln Ile Ile Arg Glu Asn Gly Phe
            420                 425                 430

<210> SEQ ID NO 38
<211> LENGTH: 397
<212> TYPE: PRT
<213> ORGANISM: Homo Sapiens

<400> SEQUENCE: 38

Thr Arg Pro Ala Gln Cys Thr Asp Phe Val Asn Ile Lys Lys Gln Leu
1               5                   10                  15

Glu Met Leu Ala Arg Met Lys Val Thr His Tyr Arg Phe Ala Leu Asp
                20                  25                  30

Trp Ala Ser Val Leu Pro Thr Gly Asn Leu Ser Ala Val Asn Arg Gln
            35                  40                  45

Ala Leu Arg Tyr Tyr Arg Cys Val Val Ser Glu Gly Leu Lys Leu Gly
```

```
            50                  55                  60
Ile Ser Ala Met Val Thr Leu Tyr Tyr Pro Thr His Ala His Leu Gly
 65                  70                  75                  80

Leu Pro Glu Pro Leu Leu His Ala Asp Gly Trp Leu Asn Pro Ser Thr
                 85                  90                  95

Ala Glu Ala Phe Gln Ala Tyr Ala Gly Leu Cys Phe Gln Glu Leu Gly
            100                 105                 110

Asp Leu Val Lys Leu Trp Ile Thr Ile Asn Glu Pro Asn Arg Leu Ser
        115                 120                 125

Asp Ile Tyr Asn Arg Ser Gly Asn Asp Thr Tyr Gly Ala Ala His Asn
    130                 135                 140

Leu Leu Val Ala His Ala Leu Ala Trp Arg Leu Tyr Asp Arg Gln Phe
145                 150                 155                 160

Arg Pro Ser Gln Arg Gly Ala Val Ser Leu Ser Leu His Ala Asp Trp
                165                 170                 175

Ala Glu Pro Ala Asn Pro Tyr Ala Asp Ser His Trp Arg Ala Ala Glu
            180                 185                 190

Arg Phe Leu Gln Phe Glu Ile Ala Trp Phe Ala Glu Pro Leu Phe Lys
        195                 200                 205

Thr Gly Asp Tyr Pro Ala Ala Met Arg Glu Tyr Ile Ala Ser Lys His
    210                 215                 220

Arg Arg Gly Leu Ser Ser Ala Leu Pro Arg Leu Thr Glu Ala Glu
225                 230                 235                 240

Arg Arg Leu Leu Lys Gly Thr Val Asp Phe Cys Ala Leu Asn His Phe
                245                 250                 255

Thr Thr Arg Phe Val Met His Glu Gln Leu Ala Gly Ser Arg Tyr Asp
            260                 265                 270

Ser Asp Arg Asp Ile Gln Phe Leu Gln Asp Ile Thr Arg Leu Ser Ser
        275                 280                 285

Pro Thr Arg Leu Ala Val Ile Pro Trp Gly Val Arg Lys Leu Leu Arg
    290                 295                 300

Trp Val Arg Arg Asn Tyr Gly Asp Met Asp Ile Tyr Ile Thr Ala Ser
305                 310                 315                 320

Gly Ile Asp Asp Gln Ala Leu Glu Asp Asp Arg Leu Arg Lys Tyr Tyr
                325                 330                 335

Leu Gly Lys Tyr Leu Gln Glu Val Leu Lys Ala Tyr Leu Ile Asp Lys
            340                 345                 350

Val Arg Ile Lys Gly Tyr Tyr Ala Phe Lys Leu Ala Glu Glu Lys Ser
        355                 360                 365

Lys Pro Arg Phe Gly Phe Phe Thr Ser Asp Phe Lys Ala Lys Ser Ser
    370                 375                 380

Ile Gln Phe Tyr Asn Lys Val Ile Ser Ser Arg Gly Phe
385                 390                 395

<210> SEQ ID NO 39
<211> LENGTH: 946
<212> TYPE: PRT
<213> ORGANISM: Homo Sapiens

<400> SEQUENCE: 39

Gly Phe Ser Gly Asp Gly Arg Ala Ile Trp Ser Lys Asn Pro Asn Phe
 1               5                  10                  15

Thr Pro Val Asn Glu Ser Gln Leu Phe Leu Tyr Asp Thr Phe Pro Lys
                20                  25                  30
```

Asn Phe Phe Trp Gly Ile Gly Thr Gly Ala Leu Gln Val Glu Gly Ser
         35                  40                  45

Trp Lys Lys Asp Gly Lys Gly Pro Ser Ile Trp Asp His Phe Ile His
 50                  55                  60

Thr His Leu Lys Asn Val Ser Ser Thr Asn Gly Ser Ser Asp Ser Tyr
 65                  70                  75                  80

Ile Phe Leu Glu Lys Asp Leu Ser Ala Leu Asp Phe Ile Gly Val Ser
                 85                  90                  95

Phe Tyr Gln Phe Ser Ile Ser Trp Pro Arg Leu Phe Pro Asp Gly Ile
            100                 105                 110

Val Thr Val Ala Asn Ala Lys Gly Leu Gln Tyr Tyr Ser Thr Leu Leu
        115                 120                 125

Asp Ala Leu Val Leu Arg Asn Ile Glu Pro Ile Val Thr Leu Tyr His
    130                 135                 140

Trp Asp Leu Pro Leu Ala Leu Gln Glu Lys Tyr Gly Gly Trp Lys Asn
145                 150                 155                 160

Asp Thr Ile Ile Asp Ile Phe Asn Asp Tyr Ala Thr Tyr Cys Phe Gln
                165                 170                 175

Met Phe Gly Asp Arg Val Lys Tyr Trp Ile Thr Ile His Asn Pro Tyr
            180                 185                 190

Leu Val Ala Trp His Gly Tyr Gly Thr Gly Met His Ala Pro Gly Glu
        195                 200                 205

Lys Gly Asn Leu Ala Ala Val Tyr Thr Val Gly His Asn Leu Ile Lys
    210                 215                 220

Ala His Ser Lys Val Trp His Asn Tyr Asn Thr His Phe Arg Pro His
225                 230                 235                 240

Gln Lys Gly Trp Leu Ser Ile Thr Leu Gly Ser His Trp Ile Glu Pro
                245                 250                 255

Asn Arg Ser Glu Asn Thr Met Asp Ile Phe Lys Cys Gln Gln Ser Met
            260                 265                 270

Val Ser Val Leu Gly Trp Phe Ala Asn Pro Ile His Gly Asp Gly Asp
        275                 280                 285

Tyr Pro Glu Gly Met Arg Lys Lys Leu Phe Ser Val Leu Pro Ile Phe
    290                 295                 300

Ser Glu Ala Glu Lys His Glu Met Arg Gly Thr Ala Asp Phe Phe Ala
305                 310                 315                 320

Phe Ser Phe Gly Pro Asn Asn Phe Lys Pro Leu Asn Thr Met Ala Lys
                325                 330                 335

Met Gly Gln Asn Val Ser Leu Asn Leu Arg Glu Ala Leu Asn Trp Ile
            340                 345                 350

Lys Leu Glu Tyr Asn Asn Pro Arg Ile Leu Ile Ala Glu Asn Gly Trp
        355                 360                 365

Phe Thr Asp Ser Arg Val Lys Thr Glu Asp Thr Thr Ala Ile Tyr Met
    370                 375                 380

Met Lys Asn Phe Leu Ser Gln Val Leu Gln Ala Ile Arg Leu Asp Glu
385                 390                 395                 400

Ile Arg Val Phe Gly Tyr Thr Ala Trp Ser Leu Leu Asp Gly Phe Glu
                405                 410                 415

Trp Gln Asp Ala Tyr Thr Ile Arg Arg Gly Leu Phe Tyr Val Asp Phe
            420                 425                 430

Asn Ser Lys Gln Lys Glu Arg Lys Pro Lys Ser Ser Ala His Tyr Tyr
        435                 440                 445

Lys Gln Ile Ile Arg Glu Asn Gly Phe Ser Leu Lys Glu Ser Thr Pro

```
            450                 455                 460
Asp Val Gln Gly Gln Phe Pro Cys Asp Phe Ser Trp Gly Val Thr Glu
465                 470                 475                 480

Ser Val Leu Lys Pro Glu Ser Val Ala Ser Ser Pro Gln Phe Ser Asp
                485                 490                 495

Pro His Leu Tyr Val Trp Asn Ala Thr Gly Asn Arg Leu Leu His Arg
                    500                 505                 510

Val Glu Gly Val Arg Leu Lys Thr Arg Pro Ala Gln Cys Thr Asp Phe
                515                 520                 525

Val Asn Ile Lys Lys Gln Leu Glu Met Leu Ala Arg Met Lys Val Thr
                530                 535                 540

His Tyr Arg Phe Ala Leu Asp Trp Ala Ser Val Leu Pro Thr Gly Asn
545                 550                 555                 560

Leu Ser Ala Val Asn Arg Gln Ala Leu Arg Tyr Tyr Arg Cys Val Val
                565                 570                 575

Ser Glu Gly Leu Lys Leu Gly Ile Ser Ala Met Val Thr Leu Tyr Tyr
                580                 585                 590

Pro Thr His Ala His Leu Gly Leu Pro Glu Pro Leu Leu His Ala Asp
                595                 600                 605

Gly Trp Leu Asn Pro Ser Thr Ala Glu Ala Phe Gln Ala Tyr Ala Gly
610                 615                 620

Leu Cys Phe Gln Glu Leu Gly Asp Leu Val Lys Leu Trp Ile Thr Ile
625                 630                 635                 640

Asn Glu Pro Asn Arg Leu Ser Asp Ile Tyr Asn Arg Ser Gly Asn Asp
                    645                 650                 655

Thr Tyr Gly Ala Ala His Asn Leu Leu Val Ala His Ala Leu Ala Trp
                660                 665                 670

Arg Leu Tyr Asp Arg Gln Phe Arg Pro Ser Gln Arg Gly Ala Val Ser
                675                 680                 685

Leu Ser Leu His Ala Asp Trp Ala Glu Pro Ala Asn Pro Tyr Ala Asp
                690                 695                 700

Ser His Trp Arg Ala Ala Glu Arg Phe Leu Gln Phe Glu Ile Ala Trp
705                 710                 715                 720

Phe Ala Glu Pro Leu Phe Lys Thr Gly Asp Tyr Pro Ala Ala Met Arg
                725                 730                 735

Glu Tyr Ile Ala Ser Lys His Arg Arg Gly Leu Ser Ser Ser Ala Leu
                740                 745                 750

Pro Arg Leu Thr Glu Ala Glu Arg Arg Leu Leu Lys Gly Thr Val Asp
                755                 760                 765

Phe Cys Ala Leu Asn His Phe Thr Thr Arg Phe Val Met His Glu Gln
770                 775                 780

Leu Ala Gly Ser Arg Tyr Asp Ser Asp Arg Asp Ile Gln Phe Leu Gln
785                 790                 795                 800

Asp Ile Thr Arg Leu Ser Ser Pro Thr Arg Leu Ala Val Ile Pro Trp
                805                 810                 815

Gly Val Arg Lys Leu Leu Arg Trp Val Arg Arg Asn Tyr Gly Asp Met
                820                 825                 830

Asp Ile Tyr Ile Thr Ala Ser Gly Ile Asp Asp Gln Ala Leu Glu Asp
                835                 840                 845

Asp Arg Leu Arg Lys Tyr Tyr Leu Gly Lys Tyr Leu Gln Glu Val Leu
                850                 855                 860

Lys Ala Tyr Leu Ile Asp Lys Val Arg Ile Lys Gly Tyr Tyr Ala Phe
865                 870                 875                 880
```

```
Lys Leu Ala Glu Glu Lys Ser Lys Pro Arg Phe Gly Phe Phe Thr Ser
                885                 890                 895

Asp Phe Lys Ala Lys Ser Ser Ile Gln Phe Tyr Asn Lys Val Ile Ser
            900                 905                 910

Ser Arg Gly Phe Pro Phe Glu Asn Ser Ser Arg Cys Ser Gln Thr
        915                 920                 925

Gln Glu Asn Thr Glu Cys Thr Val Cys Leu Phe Leu Val Gln Lys Lys
        930                 935                 940

Pro Leu
945

<210> SEQ ID NO 40
<211> LENGTH: 1195
<212> TYPE: PRT
<213> ORGANISM: Homo Sapiens

<400> SEQUENCE: 40

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
```

```
              290                 295                 300
Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
                340                 345                 350

Phe Arg Gln Leu Glu Ser Pro Asn Leu Arg Gln Leu Leu Ser Trp Ile
                355                 360                 365

Asp Leu Glu Phe Asn His Pro Gln Ile Phe Ile Val Glu Asn Gly Trp
            370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
        435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp Asp Val His His Ser Lys Arg Leu Ile Lys Val Asp
            515                 520                 525

Gly Val Val Thr Lys Lys Arg Lys Ser Tyr Cys Val Asp Phe Ala Ala
        530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
        595                 600                 605

Ala Pro Asn Gln Gly Leu Pro Arg Leu Leu Ala Arg Gln Gly Ala Trp
610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
690                 695                 700

Ala Cys Pro Phe Ser Gln Lys Asp Lys Glu Val Ala Glu Arg Val Leu
705                 710                 715                 720
```

-continued

```
Glu Phe Asp Ile Gly Trp Leu Ala Glu Pro Ile Phe Gly Ser Gly Asp
            725                 730                 735
Tyr Pro Trp Val Met Arg Asp Trp Leu Asn Gln Arg Asn Asn Phe Leu
            740                 745                 750
Leu Pro Tyr Phe Thr Glu Asp Glu Lys Lys Leu Ile Gln Gly Thr Phe
            755                 760                 765
Asp Phe Leu Ala Leu Ser His Tyr Thr Thr Ile Leu Val Asp Ser Glu
            770                 775                 780
Lys Glu Asp Pro Ile Lys Tyr Asn Asp Tyr Leu Glu Val Gln Glu Met
785                 790                 795                 800
Thr Asp Ile Thr Trp Leu Asn Ser Pro Ser Gln Val Ala Val Val Pro
            805                 810                 815
Trp Gly Leu Arg Lys Val Leu Asn Trp Leu Lys Phe Lys Tyr Gly Asp
            820                 825                 830
Leu Pro Met Tyr Ile Ile Ser Asn Gly Ile Asp Asp Gly Leu His Ala
            835                 840                 845
Glu Asp Asp Gln Leu Arg Val Tyr Tyr Met Gln Asn Tyr Ile Asn Glu
            850                 855                 860
Ala Leu Lys Ala His Ile Leu Asp Gly Ile Asn Leu Cys Gly Tyr Phe
865                 870                 875                 880
Ala Tyr Ser Phe Asn Asp Arg Thr Ala Pro Arg Phe Gly Leu Tyr Arg
            885                 890                 895
Tyr Ala Ala Asp Gln Phe Glu Pro Lys Ala Ser Met Lys His Tyr Arg
            900                 905                 910
Lys Ile Ile Asp Ser Asn Gly Phe Pro Gly Pro Glu Thr Leu Glu Arg
            915                 920                 925
Phe Cys Pro Glu Glu Phe Thr Val Cys Thr Glu Cys Ser Phe Phe His
            930                 935                 940
Thr Arg Lys Ser Leu Gly Ser Gly Gly Gly Ser Gly Gly Gly Gly
945                 950                 955                 960
Ser Gly Gly Gly Gly Ser Leu Lys Tyr Pro Asn Ala Ser Pro Leu Leu
            965                 970                 975
Gly Ser Ser Trp Gly Gly Leu Ile His Leu Tyr Thr Thr Ala Arg
            980                 985                 990
Asn Ser Tyr His Leu Gln Ile His Lys Asn Gly His Val Asp Gly Ala
            995                 1000                1005
Pro His Gln Thr Ile Tyr Ser Ala Leu Met Ile Arg Ser Glu Asp
            1010                1015                1020
Ala Gly Phe Val Val Ile Thr Gly Val Met Ser Arg Arg Tyr Leu
            1025                1030                1035
Cys Met Asp Phe Arg Gly Asn Ile Phe Gly Ser His Tyr Phe Asp
            1040                1045                1050
Pro Glu Asn Cys Arg Phe Gln His Gln Thr Leu Glu Asn Gly Tyr
            1055                1060                1065
Asp Val Tyr His Ser Pro Gln Tyr His Phe Leu Val Ser Leu Gly
            1070                1075                1080
Arg Ala Lys Arg Ala Phe Leu Pro Gly Met Asn Pro Pro Pro Tyr
            1085                1090                1095
Ser Gln Phe Leu Ser Arg Arg Asn Glu Ile Pro Leu Ile His Phe
            1100                1105                1110
Asn Thr Pro Ile Pro Arg Arg His Thr Arg Ser Ala Glu Asp Asp
            1115                1120                1125
```

```
Ser Glu Arg Asp Pro Leu Asn Val Leu Lys Pro Arg Ala Arg Met
    1130                1135                1140

Thr Pro Ala Pro Ala Ser Cys Ser Gln Glu Leu Pro Ser Ala Glu
    1145                1150                1155

Asp Asn Ser Pro Met Ala Ser Asp Pro Leu Gly Val Val Arg Gly
    1160                1165                1170

Gly Arg Val Asn Thr His Ala Gly Gly Thr Gly Pro Glu Gly Cys
    1175                1180                1185

Arg Pro Phe Ala Lys Phe Ile
    1190                1195

<210> SEQ ID NO 41
<211> LENGTH: 1195
<212> TYPE: PRT
<213> ORGANISM: Homo Sapiens

<400> SEQUENCE: 41

Glu Pro Gly Asp Gly Ala Gln Thr Trp Ala Arg Phe Ser Arg Pro
1               5                   10                  15

Ala Pro Glu Ala Ala Gly Leu Phe Gln Gly Thr Phe Pro Asp Gly Phe
                20                  25                  30

Leu Trp Ala Val Gly Ser Ala Ala Tyr Gln Thr Glu Gly Gly Trp Gln
                35                  40                  45

Gln His Gly Lys Gly Ala Ser Ile Trp Asp Thr Phe Thr His His Pro
        50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
                115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
                180                 185                 190

His Phe Gly Gly Gln Val Lys Tyr Trp Ile Thr Ile Asp Asn Pro Tyr
                195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
                260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
290                 295                 300
```

-continued

```
Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
            325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
            355                 360                 365

Asp Leu Glu Phe Asn His Pro Gln Ile Phe Ile Val Glu Asn Gly Trp
            370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
            450                 455                 460

Gln Lys Leu Ile Glu Lys Asn Gly Phe Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp Asp Val His His Ser Lys Arg Leu Ile Lys Val Asp
            515                 520                 525

Gly Val Val Thr Lys Lys Arg Lys Ser Tyr Cys Val Asp Phe Ala Ala
            530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
            595                 600                 605

Ala Pro Asn Gln Gly Leu Pro Arg Leu Leu Ala Arg Gln Gly Ala Trp
            610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
                660                 665                 670

Ala His Ala Leu Ala Trp His Val Tyr Asn Glu Lys Phe Arg His Ala
            675                 680                 685

Gln Asn Gly Lys Ile Ser Ile Ala Leu Gln Ala Asp Trp Ile Glu Pro
            690                 695                 700

Ala Cys Pro Phe Ser Gln Lys Asp Lys Glu Val Ala Glu Arg Val Leu
705                 710                 715                 720
```

-continued

```
Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu Gly Ser Gly Gly Gly Ser Gly Gly Gly Gly
945                 950                 955                 960

Ser Gly Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
        995                 1000                1005

Pro His  Gln Thr Ile Tyr Ser  Ala Leu Met Ile Arg  Ser Glu Asp
    1010                1015                1020

Ala Gly  Phe Val Val Ile Thr  Gly Val Met Ser Arg  Arg Tyr Leu
    1025                1030                1035

Cys Met  Asp Phe Arg Gly Asn  Ile Phe Gly Ser His  Tyr Phe Asp
    1040                1045                1050

Pro Glu  Asn Cys Arg Phe Gln  His Gln Thr Leu Glu  Asn Gly Tyr
    1055                1060                1065

Asp Val  Tyr His Ser Pro Gln  Tyr His Phe Leu Val  Ser Leu Gly
    1070                1075                1080

Arg Ala  Lys Arg Ala Phe Leu  Pro Gly Met Asn Pro  Pro Pro Tyr
    1085                1090                1095

Ser Gln  Phe Leu Ser Arg Arg  Asn Glu Ile Pro Leu  Ile His Phe
    1100                1105                1110

Asn Thr  Pro Ile Pro Arg Arg  His Thr Gln Ser Ala  Glu Asp Asp
    1115                1120                1125

Ser Glu  Arg Asp Pro Leu Asn  Val Leu Lys Pro Arg  Ala Arg Met
```

```
              1130                1135                1140

Thr Pro Ala Pro Ala Ser Cys Ser Gln Glu Leu Pro Ser Ala Glu
        1145                1150                1155

Asp Asn Ser Pro Met Ala Ser Asp Pro Leu Gly Val Val Arg Gly
        1160                1165                1170

Gly Arg Val Asn Thr His Ala Gly Gly Thr Gly Pro Glu Gly Cys
        1175                1180                1185

Arg Pro Phe Ala Lys Phe Ile
        1190                1195
```

<210> SEQ ID NO 42
<211> LENGTH: 227
<212> TYPE: PRT
<213> ORGANISM: Homo Sapiens

<400> SEQUENCE: 42

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225
```

<210> SEQ ID NO 43
<211> LENGTH: 227
<212> TYPE: PRT
<213> ORGANISM: Homo Sapiens

<400> SEQUENCE: 43

```
Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
```

-continued

```
                20                  25                  30
Lys Asn Gly His Val Asp Gly Ala Pro His Gln Thr Ile Tyr Ser Ala
            35                  40                  45
Leu Met Ile Arg Ser Glu Asp Ala Gly Phe Val Ile Thr Gly Val
        50                  55                  60
Met Ser Arg Arg Tyr Leu Cys Met Asp Phe Arg Gly Asn Ile Phe Gly
65                  70                  75                  80
Ser His Tyr Phe Asp Pro Glu Asn Cys Arg Phe Gln His Gln Thr Leu
                85                  90                  95
Glu Asn Gly Tyr Asp Val Tyr His Ser Pro Gln Tyr His Phe Leu Val
            100                 105                 110
Ser Leu Gly Arg Ala Lys Arg Ala Phe Leu Pro Gly Met Asn Pro Pro
        115                 120                 125
Pro Tyr Ser Gln Phe Leu Ser Arg Arg Asn Glu Ile Pro Leu Ile His
    130                 135                 140
Phe Asn Thr Pro Ile Pro Arg Arg His Thr Gln Ser Ala Glu Asp Asp
145                 150                 155                 160
Ser Glu Arg Asp Pro Leu Asn Val Leu Lys Pro Arg Ala Arg Met Thr
                165                 170                 175
Pro Ala Pro Ala Ser Cys Ser Gln Glu Leu Pro Ser Ala Glu Asp Asn
            180                 185                 190
Ser Pro Met Ala Ser Asp Pro Leu Gly Val Val Arg Gly Gly Arg Val
        195                 200                 205
Asn Thr His Ala Gly Gly Thr Gly Pro Glu Gly Cys Arg Pro Phe Ala
    210                 215                 220
Lys Phe Ile
225

<210> SEQ ID NO 44
<211> LENGTH: 982
<212> TYPE: PRT
<213> ORGANISM: Homo Sapiens

<400> SEQUENCE: 44

Met Pro Ala Ser Ala Pro Pro Arg Arg Pro Arg Pro Pro Pro Ser
1               5                   10                  15
Leu Ser Leu Leu Leu Val Leu Leu Gly Leu Gly Gly Arg Arg Leu Arg
                20                  25                  30
Ala Glu Pro Gly Asp Gly Ala Gln Thr Trp Ala Arg Phe Ser Arg Pro
            35                  40                  45
Pro Ala Pro Glu Ala Ala Gly Leu Phe Gln Gly Thr Phe Pro Asp Gly
        50                  55                  60
Phe Leu Trp Ala Val Gly Ser Ala Ala Tyr Gln Thr Glu Gly Gly Trp
65                  70                  75                  80
Gln Gln His Gly Lys Gly Ala Ser Ile Trp Asp Thr Phe Thr His His
                85                  90                  95
Pro Leu Ala Pro Pro Gly Asp Ser Arg Asn Ala Ser Leu Pro Leu Gly
            100                 105                 110
Ala Pro Ser Pro Leu Gln Pro Ala Thr Gly Asp Val Ala Ser Asp Ser
        115                 120                 125
Tyr Asn Asn Val Phe Arg Asp Thr Glu Ala Leu Arg Glu Leu Gly Val
    130                 135                 140
Thr His Tyr Arg Phe Ser Ile Ser Trp Ala Arg Val Leu Pro Asn Gly
145                 150                 155                 160
```

```
Ser Ala Gly Val Pro Asn Arg Glu Gly Leu Arg Tyr Tyr Arg Arg Leu
            165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Ala Trp His Gly Tyr Ala Thr Gly Arg Leu Ala Pro Gly
            245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
        290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
```

```
                580              585              590
Phe Arg Phe Ser Leu Asp Trp Ala Leu Ile Leu Pro Leu Gly Asn Gln
            595              600              605
Ser Gln Val Asn His Thr Ile Leu Gln Tyr Tyr Arg Cys Met Ala Ser
610              615              620
Glu Leu Val Arg Val Asn Ile Thr Pro Val Val Ala Leu Trp Gln Pro
625              630              635              640
Met Ala Pro Asn Gln Gly Leu Pro Arg Leu Leu Ala Arg Gln Gly Ala
            645              650              655
Trp Glu Asn Pro Tyr Thr Ala Leu Ala Phe Ala Glu Tyr Ala Arg Leu
            660              665              670
Cys Phe Gln Glu Leu Gly His His Val Lys Leu Trp Ile Thr Met Asn
            675              680              685
Glu Pro Tyr Thr Arg Asn Met Thr Tyr Ser Ala Gly His Asn Leu Leu
            690              695              700
Lys Ala His Ala Leu Ala Trp His Val Tyr Asn Glu Lys Phe Arg His
705              710              715              720
Ala Gln Asn Gly Lys Ile Ser Ile Ala Leu Gln Ala Asp Trp Ile Glu
            725              730              735
Pro Ala Cys Pro Phe Ser Gln Lys Asp Lys Glu Val Ala Glu Arg Val
            740              745              750
Leu Glu Phe Asp Ile Gly Trp Leu Ala Glu Pro Ile Phe Gly Ser Gly
            755              760              765
Asp Tyr Pro Trp Val Met Arg Asp Trp Leu Asn Gln Arg Asn Asn Phe
            770              775              780
Leu Leu Pro Tyr Phe Thr Glu Asp Glu Lys Lys Leu Ile Gln Gly Thr
785              790              795              800
Phe Asp Phe Leu Ala Leu Ser His Tyr Thr Thr Ile Leu Val Asp Ser
            805              810              815
Glu Lys Glu Asp Pro Ile Lys Tyr Asn Asp Tyr Leu Glu Val Gln Glu
            820              825              830
Met Thr Asp Ile Thr Trp Leu Asn Ser Pro Ser Gln Val Ala Val Val
            835              840              845
Pro Trp Gly Leu Arg Lys Val Leu Asn Trp Leu Lys Phe Lys Tyr Gly
            850              855              860
Asp Leu Pro Met Tyr Ile Ile Ser Asn Gly Ile Asp Asp Gly Leu His
865              870              875              880
Ala Glu Asp Asp Gln Leu Arg Val Tyr Tyr Met Gln Asn Tyr Ile Asn
            885              890              895
Glu Ala Leu Lys Ala His Ile Leu Asp Gly Ile Asn Leu Cys Gly Tyr
            900              905              910
Phe Ala Tyr Ser Phe Asn Asp Arg Thr Ala Pro Arg Phe Gly Leu Tyr
            915              920              925
Arg Tyr Ala Ala Asp Gln Phe Glu Pro Lys Ala Ser Met Lys His Tyr
            930              935              940
Arg Lys Ile Ile Asp Ser Asn Gly Phe Pro Gly Pro Glu Thr Leu Glu
945              950              955              960
Arg Phe Cys Pro Glu Glu Phe Thr Val Cys Thr Glu Cys Ser Phe Phe
            965              970              975
His Thr Arg Lys Ser Leu
            980

<210> SEQ ID NO 45
```

```
<211> LENGTH: 974
<212> TYPE: PRT
<213> ORGANISM: Homo Sapiens

<400> SEQUENCE: 45
```

| | | | | | | | | | | | | | | |
|---|---|---|---|---|---|---|---|---|---|---|---|---|---|---|
|Met|Ser|Val|Leu|Thr|Gln|Val|Leu|Ala|Leu|Leu|Leu|Trp|Leu|Thr|
|1| | | |5| | | | |10| | | | |15|
|Gly|Leu|Gly|Gly|Arg|Arg|Leu|Arg|Ala|Glu|Pro|Gly|Asp|Gly|Ala|Gln|
| | | | |20| | | | |25| | | | |30|
|Thr|Trp|Ala|Arg|Phe|Ser|Arg|Pro|Pro|Ala|Pro|Glu|Ala|Ala|Gly|Leu|
| | |35| | | | |40| | | | |45| | |
|Phe|Gln|Gly|Thr|Phe|Pro|Asp|Gly|Phe|Leu|Trp|Ala|Val|Gly|Ser|Ala|
| |50| | | | |55| | | | |60| | | | |
|Ala|Tyr|Gln|Thr|Glu|Gly|Gly|Trp|Gln|Gln|His|Gly|Lys|Gly|Ala|Ser|
|65| | | | |70| | | | |75| | | | |80|
|Ile|Trp|Asp|Thr|Phe|Thr|His|His|Pro|Leu|Ala|Pro|Pro|Gly|Asp|Ser|
| | | | |85| | | | |90| | | | |95| |
|Arg|Asn|Ala|Ser|Leu|Pro|Leu|Gly|Ala|Pro|Ser|Pro|Leu|Gln|Pro|Ala|
| | | |100| | | | |105| | | | |110| | |
|Thr|Gly|Asp|Val|Ala|Ser|Asp|Ser|Tyr|Asn|Asn|Val|Phe|Arg|Asp|Thr|
| | |115| | | | |120| | | | |125| | | |
|Glu|Ala|Leu|Arg|Glu|Leu|Gly|Val|Thr|His|Tyr|Arg|Phe|Ser|Ile|Ser|
|130| | | | |135| | | | |140| | | | | |
|Trp|Ala|Arg|Val|Leu|Pro|Asn|Gly|Ser|Ala|Gly|Val|Pro|Asn|Arg|Glu|
|145| | | | |150| | | | |155| | | | |160|
|Gly|Leu|Arg|Tyr|Tyr|Arg|Arg|Leu|Leu|Glu|Arg|Leu|Arg|Glu|Leu|Gly|
| | | | |165| | | | |170| | | | |175| |
|Val|Gln|Pro|Val|Val|Thr|Leu|Tyr|His|Trp|Asp|Leu|Pro|Gln|Arg|Leu|
| | | |180| | | | |185| | | | |190| | |
|Gln|Asp|Ala|Tyr|Gly|Gly|Trp|Ala|Asn|Arg|Ala|Leu|Ala|Asp|His|Phe|
| | |195| | | | |200| | | | |205| | | |
|Arg|Asp|Tyr|Ala|Glu|Leu|Cys|Phe|Arg|His|Phe|Gly|Gly|Gln|Val|Lys|
|210| | | | |215| | | | |220| | | | | |
|Tyr|Trp|Ile|Thr|Ile|Asp|Asn|Pro|Tyr|Val|Val|Ala|Trp|His|Gly|Tyr|
|225| | | | |230| | | | |235| | | | |240|
|Ala|Thr|Gly|Arg|Leu|Ala|Pro|Gly|Ile|Arg|Gly|Ser|Pro|Arg|Leu|Gly|
| | | | |245| | | | |250| | | | |255| |
|Tyr|Leu|Val|Ala|His|Asn|Leu|Leu|Ala|His|Ala|Lys|Val|Trp|His|
| | | | |260| | | | |265| | | | |270| |
|Leu|Tyr|Asn|Thr|Ser|Phe|Arg|Pro|Thr|Gln|Gly|Gly|Gln|Val|Ser|Ile|
| | | |275| | | | |280| | | | |285| | |
|Ala|Leu|Ser|Ser|His|Trp|Ile|Asn|Pro|Arg|Arg|Met|Thr|Asp|His|Ser|
| |290| | | | |295| | | | |300| | | | |
|Ile|Lys|Glu|Cys|Gln|Lys|Ser|Leu|Asp|Phe|Val|Leu|Gly|Trp|Phe|Ala|
|305| | | | |310| | | | |315| | | | |320|
|Lys|Pro|Val|Phe|Ile|Asp|Gly|Asp|Tyr|Pro|Glu|Ser|Met|Lys|Asn|Asn|
| | | |325| | | | |330| | | | |335| | |
|Leu|Ser|Ser|Ile|Leu|Pro|Asp|Phe|Thr|Glu|Ser|Glu|Lys|Lys|Phe|Ile|
| | | |340| | | | |345| | | | |350| | |
|Lys|Gly|Thr|Ala|Asp|Phe|Phe|Ala|Leu|Cys|Phe|Gly|Pro|Thr|Leu|Ser|
| | |355| | | | |360| | | | |365| | | |
|Phe|Gln|Leu|Leu|Asp|Pro|His|Met|Lys|Phe|Arg|Gln|Leu|Glu|Ser|Pro|
|370| | | | |375| | | | |380| | | | | |
|Asn|Leu|Arg|Gln|Leu|Leu|Ser|Trp|Ile|Asp|Leu|Glu|Phe|Asn|His|Pro|

```
            385                 390                 395                 400
        Gln Ile Phe Ile Val Glu Asn Gly Trp Phe Val Ser Gly Thr Thr Lys
                        405                 410                 415

Arg Asp Asp Ala Lys Tyr Met Tyr Tyr Leu Lys Lys Phe Ile Met Glu
                        420                 425                 430

Thr Leu Lys Ala Ile Lys Leu Asp Gly Val Asp Val Ile Gly Tyr Thr
                        435                 440                 445

Ala Trp Ser Leu Met Asp Gly Phe Glu Trp His Arg Gly Tyr Ser Ile
                        450                 455                 460

Arg Arg Gly Leu Phe Tyr Val Asp Phe Leu Ser Gln Asp Lys Met Leu
        465                 470                 475                 480

Leu Pro Lys Ser Ser Ala Leu Phe Tyr Gln Lys Leu Ile Glu Lys Asn
                        485                 490                 495

Gly Phe Pro Pro Leu Pro Glu Asn Gln Pro Leu Glu Gly Thr Phe Pro
                        500                 505                 510

Cys Asp Phe Ala Trp Gly Val Val Asp Asn Tyr Ile Gln Val Asp Thr
                        515                 520                 525

Thr Leu Ser Gln Phe Thr Asp Leu Asn Val Tyr Leu Trp Asp Val His
                        530                 535                 540

His Ser Lys Arg Leu Ile Lys Val Asp Gly Val Val Thr Lys Lys Arg
        545                 550                 555                 560

Lys Ser Tyr Cys Val Asp Phe Ala Ala Ile Gln Pro Gln Ile Ala Leu
                        565                 570                 575

Leu Gln Glu Met His Val Thr His Phe Arg Phe Ser Leu Asp Trp Ala
                        580                 585                 590

Leu Ile Leu Pro Leu Gly Asn Gln Ser Gln Val Asn His Thr Ile Leu
                        595                 600                 605

Gln Tyr Tyr Arg Cys Met Ala Ser Glu Leu Val Arg Val Asn Ile Thr
                        610                 615                 620

Pro Val Val Ala Leu Trp Gln Pro Met Ala Pro Asn Gln Gly Leu Pro
        625                 630                 635                 640

Arg Leu Leu Ala Arg Gln Gly Ala Trp Glu Asn Pro Tyr Thr Ala Leu
                        645                 650                 655

Ala Phe Ala Glu Tyr Ala Arg Leu Cys Phe Gln Glu Leu Gly His His
                        660                 665                 670

Val Lys Leu Trp Ile Thr Met Asn Glu Pro Tyr Thr Arg Asn Met Thr
                        675                 680                 685

Tyr Ser Ala Gly His Asn Leu Leu Lys Ala His Ala Leu Ala Trp His
                        690                 695                 700

Val Tyr Asn Glu Lys Phe Arg His Ala Gln Asn Gly Lys Ile Ser Ile
        705                 710                 715                 720

Ala Leu Gln Ala Asp Trp Ile Glu Pro Ala Cys Pro Phe Ser Gln Lys
                        725                 730                 735

Asp Lys Glu Val Ala Glu Arg Val Leu Glu Phe Asp Ile Gly Trp Leu
                        740                 745                 750

Ala Glu Pro Ile Phe Gly Ser Gly Asp Tyr Pro Trp Val Met Arg Asp
                        755                 760                 765

Trp Leu Asn Gln Arg Asn Asn Phe Leu Leu Pro Tyr Phe Thr Glu Asp
                        770                 775                 780

Glu Lys Lys Leu Ile Gln Gly Thr Phe Asp Phe Leu Ala Leu Ser His
        785                 790                 795                 800

Tyr Thr Thr Ile Leu Val Asp Ser Glu Lys Glu Asp Pro Ile Lys Tyr
                        805                 810                 815
```

```
Asn Asp Tyr Leu Glu Val Gln Glu Met Thr Asp Ile Thr Trp Leu Asn
            820                 825                 830
Ser Pro Ser Gln Val Ala Val Pro Trp Gly Leu Arg Lys Val Leu
        835                 840                 845
Asn Trp Leu Lys Phe Lys Tyr Gly Asp Leu Pro Met Tyr Ile Ile Ser
850                 855                 860
Asn Gly Ile Asp Asp Gly Leu His Ala Glu Asp Gln Leu Arg Val
865                 870                 875                 880
Tyr Tyr Met Gln Asn Tyr Ile Asn Glu Ala Leu Lys Ala His Ile Leu
                885                 890                 895
Asp Gly Ile Asn Leu Cys Gly Tyr Phe Ala Tyr Ser Phe Asn Asp Arg
            900                 905                 910
Thr Ala Pro Arg Phe Gly Leu Tyr Arg Tyr Ala Ala Asp Gln Phe Glu
            915                 920                 925
Pro Lys Ala Ser Met Lys His Tyr Arg Lys Ile Ile Asp Ser Asn Gly
        930                 935                 940
Phe Pro Gly Pro Glu Thr Leu Glu Arg Phe Cys Pro Glu Glu Phe Thr
945                 950                 955                 960
Val Cys Thr Glu Cys Ser Phe Phe His Thr Arg Lys Ser Leu
                965                 970

<210> SEQ ID NO 46
<211> LENGTH: 4380
<212> TYPE: DNA
<213> ORGANISM: Homo Sapiens

<400> SEQUENCE: 46
atgcccgcca gcgccccgcc gcgccgcccg cggccgccgc cgccgtcgct gtcgctgctg      60
ctggtgctgc tgggcctggg cggccgccgc ctgcgtgcgg agccgggcga cggcgcgcag     120
acctgggccc gtttctcgcg gcctcctgcc cccgaggccg cgggcctctt ccagggcacc     180
ttccccgacg gcttcctctg ggccgtgggc agcgccgcct accagaccga gggcggctgg     240
cagcagcacg gcaagggtgc gtccatctgg gatacgttca cccaccaccc cctggcaccc     300
ccgggagact cccggaacgc cagtctgccg ttgggcgccc cgtcgccgct gcagcccgcc     360
accggggacg tagccagcga cagctacaac aacgtcttcc gcgacacgga ggcgctgcgc     420
gagctcgggg tcactcacta ccgcttctcc atctcgtggg cgcgagtgct ccccaatggc     480
agcgcgggcg tccccaaccg cgaggggctg cgctactacc ggcgcctgct ggagcggctg     540
cgggagctgg gcgtgcagcc cgtggtcacc ctgtaccact gggacctgcc ccagcgcctg     600
caggacgcct acggcggctg ggccaaccgc gccctggccg accacttcag ggattacgcg     660
gagctctgct ccgccactt cggcggtcag gtcaagtact ggatcaccat cgacaacccc     720
tacgtggtgg cctggcacgg ctacgccacc gggcgcctgg ccccggcat ccggggcagc     780 ccgcggctcg gtacctggt ggcgcacaac ctcctcctgg ctcatgccaa agtctggcat     840
ctctacaata cttctttccg tcccactcag ggaggtcagg tgtccattgc cctaagctct     900
cactggatca atcctcgaag aatgaccgac acacagcatca aagaatgtca aaaatctctg     960
gactttgtac taggttggtt tgccaaaccc gtatttattg atggtgacta tcccgagagc    1020
atgaagaata accttttcatc tattctgcct gattttactg aatctgagaa aagttcatc    1080 aaaggaactg ctgactttt tgctctttgc tttggaccca ccttgagttt tcaacttttg    1140
gaccctcaca tgaagttccg ccaattggaa tctcccaacc tgaggcaact gcttccctgg    1200
```

```
attgaccttg aatttaacca tcctcaaata tttattgtgg aaaatggctg gtttgtctca    1260
gggaccacca agagagatga tgccaaatat atgtattacc tcaaaaagtt catcatggaa    1320
accttaaaag ccatcaagct ggatggggtg gatgtcatcg ggtataccgc atggtccctc    1380
atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tcctttacct gaaaatcagc ccctagaagg gacatttccc    1560
tgtgactttg cttggggagt tgttgacaac tacattcaag tagataccac tctgtctcag    1620
tttaccgacc tgaatgttta cctgtgggat gtccaccaca gtaaaaggct tattaaagtg    1680
gatggggttg tgaccaagaa gaggaaatcc tactgtgttg actttgctgc catccagccc    1740
cagatcgctt tactccagga aatgcacgtt acacattttc gcttctccct ggactgggcc    1800
ctgattctcc ctctgggtaa ccagtcccag gtgaaccaca ccatcctgca gtactatcgc    1860
tgcatggcca gcgagcttgt ccgtgtcaac atcaccccag tggtggccct gtggcagcct    1920
atggccccga accaaggact gccgcgcctc ctggccaggc agggcgcctg ggagaacccc    1980
tacactgccc tggcctttgc agagtatgcc cgactgtgct ttcaagagct cggccatcac    2040
gtcaagcttt ggataacgat gaatgagccg tatacaagga atatgacata cagtgctggc    2100
cacaaccttc tgaaggccca tgccctggct tggcatgtgt acaatgaaaa gtttaggcat    2160
gctcagaatg ggaaaatatc catagccttg caggctgatt ggatagaacc tgcctgccct    2220
ttctcccaaa aggacaaaga ggtggccgag agagttttgg aatttgacat tggctggctg    2280
gctgagccca tttcggctc tggagattat ccatgggtga tgagggactg gctgaaccaa    2340
agaaacaatt ttcttcttcc ttatttcact gaagatgaaa aaaagctaat ccagggtacc    2400
tttgactttt tggctttaag ccattatacc accatccttg tagactcaga aaagaagat     2460
ccaataaaat acaatgatta cctagaagtg caagaaatga ccgacatcac gtggctcaac    2520
tcccccagtc aggtggcggt agtgccctgg gggttgcgca agtgctgaa ctggctgaag      2580
ttcaagtacg agagacctccc catgtacata atatccaacg gaatcgatga cgggctgcat    2640
gctgaggacg accagctgag ggtgtattat atgcagaatt acataaacga agctctcaaa    2700
gcccacatac tggatggtat caatctttgc ggatactttg cttattcgtt taacgaccgc    2760
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttttca cacccgaaag    2940
tctttaggat ccggaggtgg aggttcagga ggtggaggtt caggaggtgg aggttcactt    3000
aagtatccca tgcctccccc actgctcggc tccagctggg gtggcctgat ccacctgtac    3060
acagccacag ccaggaacag ctaccacctg cagatccaca agaatggcca tgtggatggc    3120
gcacccatc agaccatcta cagtgccctg atgatcagat cagaggatgc tggctttgtg    3180
gtgattacag gtgtgatgag cagaagatac ctctgcatgg atttcagagg caacattttt    3240
ggatcacact atttcgaccc ggagaactgc aggttccaac accagacgct ggaaaacggg    3300
tacgacgtct accactctcc tcagtatcac ttcctggtca gtctgggccg ggcgaagaga    3360
gccttcctgc caggcatgaa cccaccccccg tactcccagt tcctgtcccg gaggaacgag    3420
atccccctaa ttcacttcaa cacccccata ccacggcggc acaccagag cgccgaggac    3480
gactcggagc gggacccccct gaacgtgctg aagcccggg cccggatgac cccggccccg    3540
gcctcctgtt cacaggagct cccgagcgcc gaggacaaca gcccgatggc cagtgaccca    3600
```

-continued

```
ttaggggtgg tcaggggcgg tcgagtgaac acgcacgctg ggggaacggg cccggaaggc    3660
tgccgcccct tcgccaagtt catcggaggt ggaggttcaa aaacccacac gtgtcctcct    3720
tgtcctgccc cagaagcagc aggtggtcca tcagtttttc ttttccctcc caaacccaag    3780
gatacgctga tgatctctcg cacgcctgag gtgacatgcg tcgtagtaga cgtgagccac    3840
gaagatcccg aggtgaagtt caattggtat gtggacggag tagaagtgca taacgcgaaa    3900
actaagccgc gcgaggaaca atataacagt acttacaggg tggtatccgt gctcacagtc    3960
ctgcaccagg actggctgaa cggtaaggaa tacaagtgca aagtaagcaa caaggcactt    4020
cccgcgccta ttgagaaaac aatctccaag gcgaagggac aaccaagaga acctcaggtt    4080
tacactctcc cgccttccag ggaagagatg accaaaaatc aagtttccct gacttgcctc    4140
gtcaaaggat tctacccttc cgacattgct gttgaatggg aaagcaatgg acaaccagag    4200
aacaactaca agacaacacc cccggtgctg gatagtgacg gatctttctt tctctactca    4260
aagctgaccg tggataagtc caggtggcag cagggaaacg tgttttcctg ctctgtcatg    4320
catgaagcgc tgcataatca ctatacccag aagtctctga gcttgagccc aggcaagtaa    4380
```

<210> SEQ ID NO 47
<211> LENGTH: 1459
<212> TYPE: PRT
<213> ORGANISM: Homo Sapiens

<400> SEQUENCE: 47

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240
```

-continued

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
                290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
                370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
                450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
                610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

```
Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
            690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
            770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
            965                 970                 975

His Thr Arg Lys Ser Leu Gly Ser Gly Gly Gly Ser Gly Gly Gly
            980                 985                 990

Gly Ser Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
        1010                1015                1020

Ala Arg Asn Ser Tyr His Leu Gln Ile His Lys Asn Gly His Val
        1025                1030                1035

Asp Gly Ala Pro His Gln Thr Ile Tyr Ser Ala Leu Met Ile Arg
        1040                1045                1050

Ser Glu Asp Ala Gly Phe Val Val Ile Thr Gly Val Met Ser Arg
        1055                1060                1065

Arg Tyr Leu Cys Met Asp Phe Arg Gly Asn Ile Phe Gly Ser His
```

```
              1070                1075                1080
Tyr Phe Asp Pro Glu Asn Cys Arg Phe Gln His Gln Thr Leu Glu
         1085                1090                1095
Asn Gly Tyr Asp Val Tyr His Ser Pro Gln Tyr His Phe Leu Val
         1100                1105                1110
Ser Leu Gly Arg Ala Lys Arg Ala Phe Leu Pro Gly Met Asn Pro
         1115                1120                1125
Pro Pro Tyr Ser Gln Phe Leu Ser Arg Arg Asn Glu Ile Pro Leu
         1130                1135                1140
Ile His Phe Asn Thr Pro Ile Pro Arg Arg His Thr Gln Ser Ala
         1145                1150                1155
Glu Asp Asp Ser Glu Arg Asp Pro Leu Asn Val Leu Lys Pro Arg
         1160                1165                1170
Ala Arg Met Thr Pro Ala Pro Ala Ser Cys Ser Gln Glu Leu Pro
         1175                1180                1185
Ser Ala Glu Asp Asn Ser Pro Met Ala Ser Asp Pro Leu Gly Val
         1190                1195                1200
Val Arg Gly Gly Arg Val Asn Thr His Ala Gly Gly Thr Gly Pro
         1205                1210                1215
Glu Gly Cys Arg Pro Phe Ala Lys Phe Ile Gly Gly Gly Gly Ser
         1220                1225                1230
Lys Thr His Thr Cys Pro Pro Cys Pro Ala Pro Glu Ala Ala Gly
         1235                1240                1245
Gly Pro Ser Val Phe Leu Phe Pro Pro Lys Pro Lys Asp Thr Leu
         1250                1255                1260
Met Ile Ser Arg Thr Pro Glu Val Thr Cys Val Val Val Asp Val
         1265                1270                1275
Ser His Glu Asp Pro Glu Val Lys Phe Asn Trp Tyr Val Asp Gly
         1280                1285                1290
Val Glu Val His Asn Ala Lys Thr Lys Pro Arg Glu Glu Gln Tyr
         1295                1300                1305
Asn Ser Thr Tyr Arg Val Val Ser Val Leu Thr Val Leu His Gln
         1310                1315                1320
Asp Trp Leu Asn Gly Lys Glu Tyr Lys Cys Lys Val Ser Asn Lys
         1325                1330                1335
Ala Leu Pro Ala Pro Ile Glu Lys Thr Ile Ser Lys Ala Lys Gly
         1340                1345                1350
Gln Pro Arg Glu Pro Gln Val Tyr Thr Leu Pro Pro Ser Arg Glu
         1355                1360                1365
Glu Met Thr Lys Asn Gln Val Ser Leu Thr Cys Leu Val Lys Gly
         1370                1375                1380
Phe Tyr Pro Ser Asp Ile Ala Val Glu Trp Glu Ser Asn Gly Gln
         1385                1390                1395
Pro Glu Asn Asn Tyr Lys Thr Thr Pro Pro Val Leu Asp Ser Asp
         1400                1405                1410
Gly Ser Phe Phe Leu Tyr Ser Lys Leu Thr Val Asp Lys Ser Arg
         1415                1420                1425
Trp Gln Gln Gly Asn Val Phe Ser Cys Ser Val Met His Glu Ala
         1430                1435                1440
Leu His Asn His Tyr Thr Gln Lys Ser Leu Ser Leu Ser Pro Gly
         1445                1450                1455
Lys
```

<210> SEQ ID NO 48
<211> LENGTH: 4353
<212> TYPE: DNA
<213> ORGANISM: Homo Sapiens

<400> SEQUENCE: 48

| | |
|---|---|
| atgcccgcca gcgccccgcc gcgccgcccg cggccgccgc cgccgtcgct gtcgctgctg | 60 |
| ctggtgctgc tgggcctggg cggccgccgc ctgcgtgcgg agccgggcga cggcgcgcag | 120 |
| acctgggccc gtttctcgcg gcctcctgcc cccgaggccg cgggcctctt ccagggcacc | 180 |
| ttccccgacg gcttcctctg ggccgtgggc agcgccgcct accagaccga gggcggctgg | 240 |
| cagcagcacg gcaagggtgc gtccatctgg gatacgttca cccaccaccc cctggcaccc | 300 |
| ccgggagact cccggaacgc cagtctgccg ttgggcgccc gtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggcg tccccaaccg cgaggggctg cgctactacc ggcgcctgct ggagcggctg | 540 |
| cgggagctgg gcgtgcagcc cgtggtcacc ctgtaccact gggacctgcc ccagcgcctg | 600 |
| caggacgcct acggcggctg gccaaccgc gccctggccg accacttcag ggattacgcg | 660 |
| gagctctgct ccgccactt cggcggtcag gtcaagtact ggatcaccat cgacaacccc | 720 |
| tacgtggtgg cctggcacgg ctacgccacc gggcgcctgg ccccggcat ccggggcagc | 780 |
| ccgcggctcg ggtacctggt ggcgcacaac ctcctcctgg ctcatgccaa agtctggcat | 840 |
| ctctacaata cttctttccg tcccactcag ggaggtcagg tgtccattgc cctaagctct | 900 |
| cactggatca atcctcgaag aatgaccgac cacagcatca agaatgtca aaaatctctg | 960 |
| gactttgtac taggttggtt tgccaaaccc gtatttattg atggtgacta tcccgagagc | 1020 |
| atgaagaata acctttcatc tattctgcct gattttactg aatctgagaa aagttcatc | 1080 |
| aaaggaactg ctgactttt tgctctttgc tttggaccca ccttgagttt caacttttg | 1140 |
| gaccctcaca tgaagttccg ccaattggaa tctcccaacc tgaggcaact gcttttcctgg | 1200 |
| attgaccttt aatttaacca tcctcaaata tttattgtgg aaaatggctg gtttgtctca | 1260 |
| gggaccacca agagagatga tgccaaatat atgtattacc tcaaaaagtt catcatggaa | 1320 |
| accttaaaag ccatcaagct ggatggggtg gatgtcatcg gtataccgc atggtccctc | 1380 |
| atggatggtt tcgagtggca cagaggttac agcatcaggc gtggactctt ctatgttgac | 1440 |
| tttctaagcc aggacaagat gttgttgcca aagtcttcag ccttgttcta ccaaaagctg | 1500 |
| atagagaaaa atggcttccc tccttacct gaaaatcagc cctagaagg gacatttccc | 1560 |
| tgtgactttg cttggggagt tgttgacaac tacattcaag tagataccac tctgtctcag | 1620 |
| tttaccgacc tgaatgttta cctgtgggat gtccaccaca gtaaaaggct tattaaagtg | 1680 |
| gatgggggttg tgaccaagaa gaggaaatcc tactgtgttg actttgctgc catccagccc | 1740 |
| cagatcgctt tactccagga aatgcacgtt acacattttc gcttctcccct ggactgggcc | 1800 |
| ctgattctcc ctctgggtaa ccagtcccag gtgaaccaca ccatcctgca gtactatcgc | 1860 |
| tgcatggcca gcgagcttgt ccgtgtcaac atcacccag tggtggccct gtggcagcct | 1920 |
| atggccccga accaaggact gccgcgcctc ctggccaggc agggcgcctg ggagaacccc | 1980 |
| tacactgccc tggcctttgc agagtatgcc cgactgtgct tcaagagct cggccatcac | 2040 |
| gtcaagcttt ggataacgat gaatgagccg tatacaagga atatgacata cagtgctggc | 2100 |
| cacaaccttc tgaaggccca tgccctggct tggcatgtgt acaatgaaaa gtttaggcat | 2160 |

```
gctcagaatg ggaaaatatc catagccttg caggctgatt ggatagaacc tgcctgccct    2220
ttctcccaaa aggacaaaga ggtggccgag agagttttgg aatttgacat ggctggctg     2280
gctgagccca ttttcggctc tggagattat ccatgggtga tgagggactg gctgaaccaa   2340
agaaacaatt ttcttcttcc ttatttcact gaagatgaaa aaaagctaat ccagggtacc   2400
tttgactttt tggctttaag ccattatacc accatccttg tagactcaga aaaagaagat   2460
ccaataaaat acaatgatta cctagaagtg caagaaatga ccgacatcac gtggctcaac   2520
tcccccagtc aggtggcggt agtgccctgg ggttgcgca aagtgctgaa ctggctgaag    2580
ttcaagtacg agacctccc catgtacata atatccaacg gaatcgatga cgggctgcat    2640
gctgaggacg accagctgag ggtgtattat atgcagaatt acataaacga agctctcaaa   2700
gcccacatac tggatggtat caatctttgc ggatactttg cttattcgtt taacgaccgc   2760
acagctccga ggtttggcct ctatcgttat gctgcagatc agtttgagcc caaggcatcc   2820
atgaaacatt acaggaaaat tattgacagc aatggtttcc cgggcccaga aactctggaa   2880
agattttgtc cagaagaatt caccgtgtgt actgagtgca gttttttttca cacccgaaag   2940
tctttaggat ccggaggtgg aggttcagga ggtggaggtt caggaggtgg aggttcactt   3000
aagtatccca atgcctcccc actgctcggc tccagctggg gtggcctgat ccacctgtac   3060
acagccacag ccaggaacag ctaccacctg cagatccaca agaatggcca tgtggatggc   3120
gcaccccatc agaccatcta cagtgccctg atgatcagat cagaggatgc tggctttgtg   3180
gtgattacag gtgtgatgag cagaagatac ctctgcatgg atttcagagg caacattttt   3240
ggatcacact atttcgaccc ggagaactgc aggttccaac accagacgct ggaaaacggg   3300
tacgacgtct accactctcc tcagtatcac ttcctggtca gtctgggccg gcgaagagaa   3360
gccttcctgc caggcatgaa cccaccccg tactcccagt tcctgtcccg gaggaacgag   3420
atcccctaa ttcacttcaa cacccccata ccacggcggc acacccagag cgccgaggac   3480
gactcggagc gggacccct gaacgtgctg aagccccggg cccggatgac cccggccccg   3540
gcctcctgtt cacaggagct cccgagcgcc gaggacaaca gcccgatggc cagtgaccca   3600
ttaggggtgg tcagggcgg tcgagtgaac acgcacgctg ggggaacggg cccggaaggc   3660
tgccgcccct tcgccaagtt catcggaggt ggaggttcag ccccagaagc agcaggtggt   3720
ccatcagttt ttcttttccc tcccaaaccc aaggatacgc tgatgatctc tcgcacgcct   3780
gaggtgacat gcgtcgtagt agacgtgagc cacgaagatc ccgaggtgaa gttcaattgg   3840
tatgtggacg gagtagaagt gcataacgcg aaaactaagc cgcgcgagga acaatataac   3900
agtacttaca gggtggtatc cgtgctcaca gtcctgcacc aggactggct gaacggtaag   3960
gaatacaagt gcaaagtaag caacaaggca cttcccgcgc ctattgagaa aacaatctcc   4020
aaggcgaagg gacaaccaag agaacctcag gtttacactc tcccgccttc cagggaagag   4080
atgaccaaaa atcaagtttc cctgacttgc ctcgtcaaag gattctaccc ttccgacatt   4140
gctgttgaat gggaaagcaa tggacaacca gagaacaact caagacaac accccggtg    4200
ctggatagtg acggatcttt ctttctctac tcaaagctga ccgtggataa gtccaggtgg   4260
cagcagggaa acgtgttttc ctgctctgtc atgcatgaag cgctgcataa tcactatacc   4320
cagaagtctc tgagcttgag cccaggcaag taa                                 4353
```

<210> SEQ ID NO 49
<211> LENGTH: 1450
<212> TYPE: PRT

-continued

<213> ORGANISM: Homo Sapiens

<400> SEQUENCE: 49

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400
```

-continued

```
Ile Asp Leu Glu Phe Asn His Pro Gln Ile Phe Ile Val Glu Asn Gly
                405                 410                 415
Trp Phe Val Ser Gly Thr Thr Lys Arg Asp Asp Ala Lys Tyr Met Tyr
            420                 425                 430
Tyr Leu Lys Lys Phe Ile Met Glu Thr Leu Lys Ala Ile Lys Leu Asp
        435                 440                 445
Gly Val Asp Val Ile Gly Tyr Thr Ala Trp Ser Leu Met Asp Gly Phe
    450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
            500                 505                 510
Gln Pro Leu Glu Gly Thr Phe Pro Cys Asp Phe Ala Trp Gly Val Val
        515                 520                 525
Asp Asn Tyr Ile Gln Val Asp Thr Thr Leu Ser Gln Phe Thr Asp Leu
    530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
        595                 600                 605
Ser Gln Val Asn His Thr Ile Leu Gln Tyr Tyr Arg Cys Met Ala Ser
    610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
            660                 665                 670
Cys Phe Gln Glu Leu Gly His His Val Lys Leu Trp Ile Thr Met Asn
        675                 680                 685
Glu Pro Tyr Thr Arg Asn Met Thr Tyr Ser Ala Gly His Asn Leu Leu
    690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
        755                 760                 765
Asp Tyr Pro Trp Val Met Arg Asp Trp Leu Asn Gln Arg Asn Asn Phe
    770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
```

```
                    820             825             830
Met Thr Asp Ile Thr Trp Leu Asn Ser Pro Ser Gln Val Ala Val
            835             840             845
Pro Trp Gly Leu Arg Lys Val Leu Asn Trp Leu Lys Phe Lys Tyr Gly
        850             855             860
Asp Leu Pro Met Tyr Ile Ile Ser Asn Gly Ile Asp Asp Gly Leu His
865             870             875             880
Ala Glu Asp Asp Gln Leu Arg Val Tyr Tyr Met Gln Asn Tyr Ile Asn
                885             890             895
Glu Ala Leu Lys Ala His Ile Leu Asp Gly Ile Asn Leu Cys Gly Tyr
            900             905             910
Phe Ala Tyr Ser Phe Asn Asp Arg Thr Ala Pro Arg Phe Gly Leu Tyr
        915             920             925
Arg Tyr Ala Ala Asp Gln Phe Glu Pro Lys Ala Ser Met Lys His Tyr
    930             935             940
Arg Lys Ile Ile Asp Ser Asn Gly Phe Pro Gly Pro Glu Thr Leu Glu
945             950             955             960
Arg Phe Cys Pro Glu Glu Phe Thr Val Cys Thr Glu Cys Ser Phe Phe
                965             970             975
His Thr Arg Lys Ser Leu Gly Ser Gly Gly Gly Ser Gly Gly Gly
            980             985             990
Gly Ser Gly Gly Gly Ser Leu Lys Tyr Pro Asn Ala Ser Pro Leu
        995             1000            1005
Leu Gly Ser Ser Trp Gly Gly Leu Ile His Leu Tyr Thr Ala Thr
    1010            1015            1020
Ala Arg Asn Ser Tyr His Leu Gln Ile His Lys Asn Gly His Val
    1025            1030            1035
Asp Gly Ala Pro His Gln Thr Ile Tyr Ser Ala Leu Met Ile Arg
    1040            1045            1050
Ser Glu Asp Ala Gly Phe Val Val Ile Thr Gly Val Met Ser Arg
    1055            1060            1065
Arg Tyr Leu Cys Met Asp Phe Arg Gly Asn Ile Phe Gly Ser His
    1070            1075            1080
Tyr Phe Asp Pro Glu Asn Cys Arg Phe Gln His Gln Thr Leu Glu
    1085            1090            1095
Asn Gly Tyr Asp Val Tyr His Ser Pro Gln Tyr His Phe Leu Val
    1100            1105            1110
Ser Leu Gly Arg Ala Lys Arg Ala Phe Leu Pro Gly Met Asn Pro
    1115            1120            1125
Pro Pro Tyr Ser Gln Phe Leu Ser Arg Arg Asn Glu Ile Pro Leu
    1130            1135            1140
Ile His Phe Asn Thr Pro Ile Pro Arg Arg His Thr Gln Ser Ala
    1145            1150            1155
Glu Asp Asp Ser Glu Arg Asp Pro Leu Asn Val Leu Lys Pro Arg
    1160            1165            1170
Ala Arg Met Thr Pro Ala Pro Ala Ser Cys Ser Gln Glu Leu Pro
    1175            1180            1185
Ser Ala Glu Asp Asn Ser Pro Met Ala Ser Asp Pro Leu Gly Val
    1190            1195            1200
Val Arg Gly Gly Arg Val Asn Thr His Ala Gly Gly Thr Gly Pro
    1205            1210            1215
Glu Gly Cys Arg Pro Phe Ala Lys Phe Ile Gly Gly Gly Gly Ser
    1220            1225            1230
```

```
Ala Pro Glu Ala Ala Gly Gly Pro Ser Val Phe Leu Phe Pro Pro
    1235                1240                1245

Lys Pro Lys Asp Thr Leu Met Ile Ser Arg Thr Pro Glu Val Thr
    1250                1255                1260

Cys Val Val Val Asp Val Ser His Glu Asp Pro Glu Val Lys Phe
    1265                1270                1275

Asn Trp Tyr Val Asp Gly Val Glu Val His Asn Ala Lys Thr Lys
    1280                1285                1290

Pro Arg Glu Glu Gln Tyr Asn Ser Thr Tyr Arg Val Val Ser Val
    1295                1300                1305

Leu Thr Val Leu His Gln Asp Trp Leu Asn Gly Lys Glu Tyr Lys
    1310                1315                1320

Cys Lys Val Ser Asn Lys Ala Leu Pro Ala Pro Ile Glu Lys Thr
    1325                1330                1335

Ile Ser Lys Ala Lys Gly Gln Pro Arg Glu Pro Gln Val Tyr Thr
    1340                1345                1350

Leu Pro Pro Ser Arg Glu Glu Met Thr Lys Asn Gln Val Ser Leu
    1355                1360                1365

Thr Cys Leu Val Lys Gly Phe Tyr Pro Ser Asp Ile Ala Val Glu
    1370                1375                1380

Trp Glu Ser Asn Gly Gln Pro Glu Asn Asn Tyr Lys Thr Thr Pro
    1385                1390                1395

Pro Val Leu Asp Ser Asp Gly Ser Phe Phe Leu Tyr Ser Lys Leu
    1400                1405                1410

Thr Val Asp Lys Ser Arg Trp Gln Gln Gly Asn Val Phe Ser Cys
    1415                1420                1425

Ser Val Met His Glu Ala Leu His Asn His Tyr Thr Gln Lys Ser
    1430                1435                1440

Leu Ser Leu Ser Pro Gly Lys
    1445            1450

<210> SEQ ID NO 50
<211> LENGTH: 1449
<212> TYPE: DNA
<213> ORGANISM: Homo Sapiens

<400> SEQUENCE: 50
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
gtggatggcg cacccatca gaccatctac agtgccctga tgatcagatc agaggatgct     240
ggctttgtgg tgattacagg tgtgatgagc agaagatacc tctgcatgga tttcagaggc     300 aacattttg gatcacacta tttcgacccg gagaactgca ggttccaaca ccagacgctg     360
gaaaacgggt acgacgtcta ccactctcct cagtatcact cctggtcag tgggcgg      420 gcgaagagag cttcctgcc aggcatgaac ccacccccgt actcccagtt cctgtcccgg     480
aggaacgaga tccccctaat tcacttcaac accccatac cacggcggca cacccagagc     540
gccgaggacg actcggagcg ggaccccctg aacgtgctga gccccgggc ccggatgacc     600 ccggccccgg cctcctgttc acaggagctc ccgagcgccg aggacaacag cccgatggcc     660
agtgacccat tagggggtggt caggggcggt cgagtgaaca cgcacgctgg ggaacgggc     720 ccggaaggct gccgcccctt cgccaagttc atcggaggtg gaggttcaaa acccacacg     780
```

-continued

```
tgtcctcctt gtcctgcccc agaagcagca ggtggtccat cagttttct tttccctccc    840
aaacccaagg atacgctgat gatctctcgc acgcctgagg tgacatgcgt cgtagtagac    900
gtgagccacg aagatcccga ggtgaagttc aattggtatg tggacggagt agaagtgcat    960
aacgcgaaaa ctaagccgcg cgaggaacaa tataacagta cttacagggt ggtatccgtg   1020
ctcacagtcc tgcaccagga ctggctgaac ggtaaggaat acaagtgcaa agtaagcaac   1080
aaggcacttc ccgcgcctat tgagaaaaca atctccaagg cgaagggaca accaagagaa   1140
cctcaggttt acactctccc gccttccagg gaagagatga ccaaaaatca gtttccctg    1200
acttgcctcg tcaaaggatt ctaccttcc gacattgctg ttgaatggga aagcaatgga   1260
caaccagaga caactacaa gacaacaccc ccggtgctgg atagtgacgg atctttcttt   1320
ctctactcaa agctgaccgt ggataagtcc aggtggcagc agggaaacgt gttttcctgc   1380
tctgtcatgc atgaagcgct gcataatcac tatacccaga agtctctgag cttgagccca   1440
ggcaagtaa                                                            1449
```

<210> SEQ ID NO 51
<211> LENGTH: 482
<212> TYPE: PRT
<213> ORGANISM: Homo Sapiens

<400> SEQUENCE: 51

```
Met Leu Gly Ala Arg Leu Arg Leu Trp Val Cys Ala Leu Cys Ser Val
 1               5                  10                  15
Cys Ser Met Ser Val Leu Arg Ala Tyr Pro Asn Ala Ser Pro Leu Leu
            20                  25                  30
Gly Ser Ser Trp Gly Gly Leu Ile His Leu Tyr Thr Ala Thr Ala Arg
        35                  40                  45
Asn Ser Tyr His Leu Gln Ile His Lys Asn Gly His Val Asp Gly Ala
    50                  55                  60
Pro His Gln Thr Ile Tyr Ser Ala Leu Met Ile Arg Ser Glu Asp Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asp Pro Glu Asn
            100                 105                 110
Cys Arg Phe Gln His Gln Thr Leu Glu Asn Gly Tyr Asp Val Tyr His
        115                 120                 125
Ser Pro Gln Tyr His Phe Leu Val Ser Leu Gly Arg Ala Lys Arg Ala
    130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Asp Ser Glu Arg Asp Pro Leu Asn Val
            180                 185                 190
Leu Lys Pro Arg Ala Arg Met Thr Pro Ala Pro Ala Ser Cys Ser Gln
        195                 200                 205
Glu Leu Pro Ser Ala Glu Asp Asn Ser Pro Met Ala Ser Asp Pro Leu
    210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile Gly Gly Gly Gly Ser
```

```
                245                 250                 255
Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
            290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
            370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
            450                 455                 460

Glu Ala Leu His Asn His Tyr Thr Gln Lys Ser Leu Ser Leu Ser Pro
465                 470                 475                 480

Gly Lys

<210> SEQ ID NO 52
<211> LENGTH: 1422
<212> TYPE: DNA
<213> ORGANISM: Homo Sapiens

<400> SEQUENCE: 52
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca gccacagc caggaacagc taccacctgc agatccacaa gaatggccat       180
gtggatggcg cacccatca gaccatctac agtgccctga tgatcagatc agaggatgct     240
ggctttgtgg tgattacagg tgtgatgagc agaagatacc tctgcatgga tttcagaggc     300 aacattttg gatcacacta tttcgacccg gagaactgca ggttccaaca ccagacgctg     360
gaaaacgggt acgacgtcta ccactctcct cagtatcact tcctggtcag tctgggccgg     420
gcgaagagag ccttcctgcc aggcatgaac ccaccccgt actcccagtt cctgtcccgg     480
aggaacgaga tccccctaat tcacttcaac acccccatac acggcggca cacccagagc     540 gccgaggacg actcggagcg ggacccctg aacgtgctga gccccgggc ccggatgacc     600 ccggccccgg cctcctgttc acaggagctc cgagcgccg aggacaacag cccgatggcc     660
agtgacccat taggggtggt caggggcggt cgagtgaaca cgcacgctgg ggaacgggc     720 ccggaaggct gccgccctt cgccaagttc atcggaggtg gaggttcagc cccagaagca    780
```

```
gcaggtggtc catcagtttt tcttttccct cccaaaccca aggatacgct gatgatctct      840
cgcacgcctg aggtgacatg cgtcgtagta cacgtgagcc acgaagatcc cgaggtgaag      900
ttcaattggt atgtggacgg agtagaagtg cataacgcga aaactaagcc gcgcgaggaa      960
caatataaca gtacttacag ggtggtatcc gtgctcacag tcctgcacca ggactggctg     1020
aacggtaagg aatacaagtg caaagtaagc aacaaggcac ttcccgcgcc tattgagaaa     1080
acaatctcca aggcgaaggg acaaccaaga gaacctcagg tttacactct cccgccttcc     1140
agggaagaga tgaccaaaaa tcaagtttcc ctgacttgcc tcgtcaaagg attctaccct     1200
tccgacattg ctgttgaatg ggaaagcaat ggacaaccag agaacaacta caagacaaca     1260
cccccggtgc tggatagtga cggatctttc tttctctact caaagctgac cgtggataag     1320
tccaggtggc agcagggaaa cgtgttttcc tgctctgtca tgcatgaagc gctgcataat     1380
cactataccc agaagtctct gagcttgagc ccaggcaagt aa                        1422
```

<210> SEQ ID NO 53
<211> LENGTH: 473
<212> TYPE: PRT
<213> ORGANISM: Homo Sapiens

<400> SEQUENCE: 53

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255
```

```
Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 54
<211> LENGTH: 1228
<212> TYPE: PRT
<213> ORGANISM: Homo Sapiens

<400> SEQUENCE: 54

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160
```

-continued

Ser Ala Gly Val Pro Asn Arg Glu Gly Leu Arg Tyr Arg Arg Leu
              165                 170                 175

Leu Glu Arg Leu Arg Glu Leu Gly Val Gln Pro Val Val Thr Leu Tyr
         180                 185                 190

His Trp Asp Leu Pro Gln Arg Leu Gln Asp Ala Tyr Gly Gly Trp Ala
             195                 200                 205

Asn Arg Ala Leu Ala Asp His Phe Arg Asp Tyr Ala Glu Leu Cys Phe
         210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                 245                 250                 255

Ile Arg Gly Ser Pro Arg Leu Gly Tyr Leu Val Ala His Asn Leu Leu
             260                 265                 270

Leu Ala His Ala Lys Val Trp His Leu Tyr Asn Thr Ser Phe Arg Pro
         275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                 325                 330                 335

Tyr Pro Glu Ser Met Lys Asn Asn Leu Ser Ser Ile Leu Pro Asp Phe
             340                 345                 350

Thr Glu Ser Glu Lys Lys Phe Ile Lys Gly Thr Ala Asp Phe Phe Ala
         355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                 405                 410                 415

Trp Phe Val Ser Gly Thr Thr Lys Arg Asp Asp Ala Lys Tyr Met Tyr
             420                 425                 430

Tyr Leu Lys Lys Phe Ile Met Glu Thr Leu Lys Ala Ile Lys Leu Asp
         435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                 485                 490                 495

Tyr Gln Lys Leu Ile Glu Lys Asn Gly Phe Pro Pro Leu Pro Glu Asn
             500                 505                 510

Gln Pro Leu Glu Gly Thr Phe Pro Cys Asp Phe Ala Trp Gly Val Val
         515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                 565                 570                 575

-continued

Ala Ile Gln Pro Gln Ile Ala Leu Leu Gln Glu Met His Val Thr His
              580                 585                 590
Phe Arg Phe Ser Leu Asp Trp Ala Leu Ile Leu Pro Leu Gly Asn Gln
          595                 600                 605
Ser Gln Val Asn His Thr Ile Leu Gln Tyr Tyr Arg Cys Met Ala Ser
      610                 615                 620
Glu Leu Val Arg Val Asn Ile Thr Pro Val Ala Leu Trp Gln Pro
625                 630                 635                 640
Met Ala Pro Asn Gln Gly Leu Pro Arg Leu Leu Ala Arg Gln Gly Ala
                  645                 650                 655
Trp Glu Asn Pro Tyr Thr Ala Leu Ala Phe Ala Glu Tyr Ala Arg Leu
              660                 665                 670
Cys Phe Gln Glu Leu Gly His His Val Lys Leu Trp Ile Thr Met Asn
          675                 680                 685
Glu Pro Tyr Thr Arg Asn Met Thr Tyr Ser Ala Gly His Asn Leu Leu
      690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                  725                 730                 735
Pro Ala Cys Pro Phe Ser Gln Lys Asp Lys Glu Val Ala Glu Arg Val
              740                 745                 750
Leu Glu Phe Asp Ile Gly Trp Leu Ala Glu Pro Ile Phe Gly Ser Gly
          755                 760                 765
Asp Tyr Pro Trp Val Met Arg Asp Trp Leu Asn Gln Arg Asn Asn Phe
      770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                  805                 810                 815
Glu Lys Glu Asp Pro Ile Lys Tyr Asn Asp Tyr Leu Glu Val Gln Glu
              820                 825                 830
Met Thr Asp Ile Thr Trp Leu Asn Ser Pro Ser Gln Val Ala Val Val
          835                 840                 845
Pro Trp Gly Leu Arg Lys Val Leu Asn Trp Leu Lys Phe Lys Tyr Gly
850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                  885                 890                 895
Glu Ala Leu Lys Ala His Ile Leu Asp Gly Ile Asn Leu Cys Gly Tyr
              900                 905                 910
Phe Ala Tyr Ser Phe Asn Asp Arg Thr Ala Pro Arg Phe Gly Leu Tyr
          915                 920                 925
Arg Tyr Ala Ala Asp Gln Phe Glu Pro Lys Ala Ser Met Lys His Tyr
      930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                  965                 970                 975
His Thr Arg Lys Ser Leu Gly Ser Gly Gly Gly Ser Gly Gly Gly
              980                 985                 990
Gly Ser Gly Gly Gly Gly Ser Leu  Lys Tyr Pro Asn Ala  Ser Pro Leu

```
                995              1000             1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Cys Arg Pro Phe Ala Lys Phe Ile
    1220                1225

<210> SEQ ID NO 55
<211> LENGTH: 1228
<212> TYPE: PRT
<213> ORGANISM: Homo Sapiens

<400> SEQUENCE: 55

Met Pro Ala Ser Ala Pro Pro Arg Arg Pro Arg Pro Pro Pro Ser
1               5                   10                  15

Leu Ser Leu Leu Leu Val Leu Leu Gly Leu Gly Arg Arg Leu Arg
                20                  25                  30

Ala Glu Pro Gly Asp Gly Ala Gln Thr Trp Ala Arg Phe Ser Arg
                35                  40                  45

Pro Ala Pro Glu Ala Ala Gly Leu Phe Gln Gly Thr Phe Pro Asp Gly
            50                  55                  60

Phe Leu Trp Ala Val Gly Ser Ala Ala Tyr Gln Thr Glu Gly Gly Trp
65                  70                  75              80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
                115                 120                 125
```

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val

```
                545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
                580                 585                 590
Phe Arg Phe Ser Leu Asp Trp Ala Leu Ile Leu Pro Leu Gly Asn Gln
                595                 600                 605
Ser Gln Val Asn His Thr Ile Leu Gln Tyr Tyr Arg Cys Met Ala Ser
                610                 615                 620
Glu Leu Val Arg Val Asn Ile Thr Pro Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
                660                 665                 670
Cys Phe Gln Glu Leu Gly His His Val Lys Leu Trp Ile Thr Met Asn
                675                 680                 685
Glu Pro Tyr Thr Arg Asn Met Thr Tyr Ser Ala Gly His Asn Leu Leu
                690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
                740                 745                 750
Leu Glu Phe Asp Ile Gly Trp Leu Ala Glu Pro Ile Phe Gly Ser Gly
                755                 760                 765
Asp Tyr Pro Trp Val Met Arg Asp Trp Leu Asn Gln Arg Asn Asn Phe
                770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
                820                 825                 830
Met Thr Asp Ile Thr Trp Leu Asn Ser Pro Ser Gln Val Ala Val Val
                835                 840                 845
Pro Trp Gly Leu Arg Lys Val Leu Asn Trp Leu Lys Phe Lys Tyr Gly
                850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
Glu Ala Leu Lys Ala His Ile Leu Asp Gly Ile Asn Leu Cys Gly Tyr
                900                 905                 910
Phe Ala Tyr Ser Phe Asn Asp Arg Thr Ala Pro Arg Phe Gly Leu Tyr
                915                 920                 925
Arg Tyr Ala Ala Asp Gln Phe Glu Pro Lys Ala Ser Met Lys His Tyr
                930                 935                 940
Arg Lys Ile Ile Asp Ser Asn Gly Phe Pro Gly Pro Glu Thr Leu Glu
945                 950                 955                 960
Arg Phe Cys Pro Glu Glu Phe Thr Val Cys Thr Glu Cys Ser Phe Phe
                965                 970                 975
```

```
His Thr Arg Lys Ser Leu Gly Ser Gly Gly Gly Ser Gly Gly Gly
            980             985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010            1015                1020

Ala Arg Asn Ser Tyr His Leu Gln Ile His Lys Asn Gly His Val
    1025            1030                1035

Asp Gly Ala Pro His Gln Thr Ile Tyr Ser Ala Leu Met Ile Arg
    1040            1045                1050

Ser Glu Asp Ala Gly Phe Val Val Ile Thr Gly Val Met Ser Arg
    1055            1060                1065

Arg Tyr Leu Cys Met Asp Phe Arg Gly Asn Ile Phe Gly Ser His
    1070            1075                1080

Tyr Phe Asp Pro Glu Asn Cys Arg Phe Gln His Gln Thr Leu Glu
    1085            1090                1095

Asn Gly Tyr Asp Val Tyr His Ser Pro Gln Tyr His Phe Leu Val
    1100            1105                1110

Ser Leu Gly Arg Ala Lys Arg Ala Phe Leu Pro Gly Met Asn Pro
    1115            1120                1125

Pro Pro Tyr Ser Gln Phe Leu Ser Arg Arg Asn Glu Ile Pro Leu
    1130            1135                1140

Ile His Phe Asn Thr Pro Ile Pro Arg Arg His Thr Gln Ser Ala
    1145            1150                1155

Glu Asp Asp Ser Glu Arg Asp Pro Leu Asn Val Leu Lys Pro Arg
    1160            1165                1170

Ala Arg Met Thr Pro Ala Pro Ala Ser Cys Ser Gln Glu Leu Pro
    1175            1180                1185

Ser Ala Glu Asp Asn Ser Pro Met Ala Ser Asp Pro Leu Gly Val
    1190            1195                1200

Val Arg Gly Gly Arg Val Asn Thr His Ala Gly Gly Thr Gly Pro
    1205            1210                1215

Glu Gly Ser Arg Pro Phe Ala Lys Phe Ile
    1220            1225

<210> SEQ ID NO 56
<211> LENGTH: 1228
<212> TYPE: PRT
<213> ORGANISM: Homo Sapiens

<400> SEQUENCE: 56

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
```

```
            100                 105                 110
Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
            370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
            450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525
```

```
Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
    915                 920                 925

Arg Tyr Ala Ala Asp Gln Phe Glu Pro Lys Ala Ser Met Lys His Tyr
930                 935                 940
```

```
Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Ala Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Thr Gly Pro
    1205                1210                1215

Glu Gly Cys Arg Pro Phe Ala Lys Phe Ile
    1220                1225

<210> SEQ ID NO 57
<211> LENGTH: 1228
<212> TYPE: PRT
<213> ORGANISM: Homo Sapiens

<400> SEQUENCE: 57

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80
```

```
Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495
```

```
Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
```

```
                    915                 920                 925
Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
            995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Ser Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Ser Arg Pro Phe Ala Lys Phe Ile
    1220                1225

<210> SEQ ID NO 58
<211> LENGTH: 1228
<212> TYPE: PRT
<213> ORGANISM: Homo Sapiens

<400> SEQUENCE: 58

Met Pro Ala Ser Ala Pro Pro Arg Arg Pro Arg Pro Pro Pro Ser
1               5                   10                  15

Leu Ser Leu Leu Leu Val Leu Leu Gly Leu Gly Arg Arg Leu Arg
                20                  25                  30

Ala Glu Pro Gly Asp Gly Ala Gln Thr Trp Ala Arg Phe Ser Arg Pro
                35                  40                  45
```

```
Pro Ala Pro Glu Ala Ala Gly Leu Phe Gln Gly Thr Phe Pro Asp Gly
 50                  55                  60

Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
```

```
              465                 470                 475                 480
          Phe Leu Ser Gln Asp Lys Met Leu Leu Pro Lys Ser Ser Ala Leu Phe
                          485                 490                 495
          Tyr Gln Lys Leu Ile Glu Lys Asn Gly Phe Pro Pro Leu Pro Glu Asn
                          500                 505                 510
          Gln Pro Leu Glu Gly Thr Phe Pro Cys Asp Phe Ala Trp Gly Val Val
                          515                 520                 525
          Asp Asn Tyr Ile Gln Val Asp Thr Thr Leu Ser Gln Phe Thr Asp Leu
                          530                 535                 540
          Asn Val Tyr Leu Trp Asp Val His His Ser Lys Arg Leu Ile Lys Val
          545                 550                 555                 560
          Asp Gly Val Val Thr Lys Lys Arg Lys Ser Tyr Cys Val Asp Phe Ala
                              565                 570                 575
          Ala Ile Gln Pro Gln Ile Ala Leu Leu Gln Glu Met His Val Thr His
                          580                 585                 590
          Phe Arg Phe Ser Leu Asp Trp Ala Leu Ile Leu Pro Leu Gly Asn Gln
                          595                 600                 605
          Ser Gln Val Asn His Thr Ile Leu Gln Tyr Tyr Arg Cys Met Ala Ser
                          610                 615                 620
          Glu Leu Val Arg Val Asn Ile Thr Pro Val Val Ala Leu Trp Gln Pro
          625                 630                 635                 640
          Met Ala Pro Asn Gln Gly Leu Pro Arg Leu Leu Ala Arg Gln Gly Ala
                              645                 650                 655
          Trp Glu Asn Pro Tyr Thr Ala Leu Ala Phe Ala Glu Tyr Ala Arg Leu
                          660                 665                 670
          Cys Phe Gln Glu Leu Gly His His Val Lys Leu Trp Ile Thr Met Asn
                          675                 680                 685
          Glu Pro Tyr Thr Arg Asn Met Thr Tyr Ser Ala Gly His Asn Leu Leu
                          690                 695                 700
          Lys Ala His Ala Leu Ala Trp His Val Tyr Asn Glu Lys Phe Arg His
          705                 710                 715                 720
          Ala Gln Asn Gly Lys Ile Ser Ile Ala Leu Gln Ala Asp Trp Ile Glu
                              725                 730                 735
          Pro Ala Cys Pro Phe Ser Gln Lys Asp Lys Glu Val Ala Glu Arg Val
                          740                 745                 750
          Leu Glu Phe Asp Ile Gly Trp Leu Ala Glu Pro Ile Phe Gly Ser Gly
                          755                 760                 765
          Asp Tyr Pro Trp Val Met Arg Asp Trp Leu Asn Gln Arg Asn Asn Phe
                          770                 775                 780
          Leu Leu Pro Tyr Phe Thr Glu Asp Glu Lys Lys Leu Ile Gln Gly Thr
          785                 790                 795                 800
          Phe Asp Phe Leu Ala Leu Ser His Tyr Thr Thr Ile Leu Val Asp Ser
                              805                 810                 815
          Glu Lys Glu Asp Pro Ile Lys Tyr Asn Asp Tyr Leu Glu Val Gln Glu
                          820                 825                 830
          Met Thr Asp Ile Thr Trp Leu Asn Ser Pro Ser Gln Val Ala Val Val
                          835                 840                 845
          Pro Trp Gly Leu Arg Lys Val Leu Asn Trp Leu Lys Phe Lys Tyr Gly
                          850                 855                 860
          Asp Leu Pro Met Tyr Ile Ile Ser Asn Gly Ile Asp Asp Gly Leu His
          865                 870                 875                 880
          Ala Glu Asp Asp Gln Leu Arg Val Tyr Tyr Met Gln Asn Tyr Ile Asn
                              885                 890                 895
```

```
Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
    915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                1000                1005

Leu Gly Ser Ser Trp Gly Gly Leu Ile His Leu Tyr Thr Ala Thr
   1010                1015                1020

Ala Arg Asn Ser Tyr His Leu Gln Ile His Lys Asn Gly His Val
   1025                1030                1035

Asp Gly Ala Pro His Gln Thr Ile Tyr Ser Ala Leu Met Ile Arg
   1040                1045                1050

Ser Glu Asp Ala Gly Phe Val Val Ile Thr Gly Val Met Ser Arg
   1055                1060                1065

Arg Tyr Leu Cys Met Asp Phe Arg Gly Asn Ile Phe Gly Ser His
   1070                1075                1080

Tyr Phe Asp Pro Glu Asn Cys Arg Phe Gln His Gln Thr Leu Glu
   1085                1090                1095

Asn Gly Tyr Asp Val Tyr His Ser Pro Gln Tyr His Phe Leu Val
   1100                1105                1110

Ser Leu Gly Arg Ala Lys Arg Ala Phe Leu Pro Gly Met Asn Pro
   1115                1120                1125

Pro Pro Tyr Ser Ala Phe Leu Ser Arg Arg Asn Glu Ile Pro Leu
   1130                1135                1140

Ile His Phe Asn Thr Pro Ile Pro Arg Arg His Thr Gln Ser Ala
   1145                1150                1155

Glu Asp Asp Ser Glu Arg Asp Pro Leu Asn Val Leu Lys Pro Arg
   1160                1165                1170

Ala Arg Met Thr Pro Ala Pro Ala Ser Ser Gln Glu Leu Pro
   1175                1180                1185

Ser Ala Glu Asp Asn Ser Pro Met Ala Ser Asp Pro Leu Gly Val
   1190                1195                1200

Val Arg Gly Gly Arg Val Asn Thr His Ala Gly Gly Thr Gly Pro
   1205                1210                1215

Glu Gly Ser Arg Pro Phe Ala Lys Phe Ile
   1220                1225

<210> SEQ ID NO 59
<211> LENGTH: 482
<212> TYPE: PRT
<213> ORGANISM: Homo Sapiens

<400> SEQUENCE: 59

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
```

-continued

```
                20                  25                  30
Gly Ser Ser Trp Gly Gly Leu Ile His Leu Tyr Thr Ala Thr Ala Arg
            35                  40                  45
Asn Ser Tyr His Leu Gln Ile His Lys Asn Gly His Val Asp Gly Ala
         50                  55                  60
Pro His Gln Thr Ile Tyr Ser Ala Leu Met Ile Arg Ser Glu Asp Ala
 65                  70                  75                  80
Gly Phe Val Val Ile Thr Gly Val Met Ser Arg Arg Tyr Leu Cys Met
                 85                  90                  95
Asp Phe Arg Gly Asn Ile Phe Gly Ser His Tyr Phe Asp Pro Glu Asn
            100                 105                 110
Cys Arg Phe Gln His Gln Thr Leu Glu Asn Gly Tyr Asp Val Tyr His
            115                 120                 125
Ser Pro Gln Tyr His Phe Leu Val Ser Leu Gly Arg Ala Lys Arg Ala
            130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Asp Ser Glu Arg Asp Pro Leu Asn Val
            180                 185                 190
Leu Lys Pro Arg Ala Arg Met Thr Pro Ala Pro Ala Ser Ser Ser Gln
            195                 200                 205
Glu Leu Pro Ser Ala Glu Asp Asn Ser Pro Met Ala Ser Asp Pro Leu
            210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile Gly Gly Gly Ser
                245                 250                 255
Lys Thr His Thr Cys Pro Pro Cys Pro Ala Pro Glu Ala Ala Gly Gly
                260                 265                 270
Pro Ser Val Phe Leu Phe Pro Pro Lys Pro Lys Asp Thr Leu Met Ile
            275                 280                 285
Ser Arg Thr Pro Glu Val Thr Cys Val Val Val Asp Val Ser His Glu
            290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
            340                 345                 350
Glu Tyr Lys Cys Lys Val Ser Asn Lys Ala Leu Pro Ala Pro Ile Glu
            355                 360                 365
Lys Thr Ile Ser Lys Ala Lys Gly Gln Pro Arg Glu Pro Gln Val Tyr
            370                 375                 380
Thr Leu Pro Pro Ser Arg Glu Glu Met Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
            420                 425                 430
Leu Asp Ser Asp Gly Ser Phe Phe Leu Tyr Ser Lys Leu Thr Val Asp
            435                 440                 445
```

```
Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 60
<211> LENGTH: 482
<212> TYPE: PRT
<213> ORGANISM: Homo Sapiens

<400> SEQUENCE: 60

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335
```

```
Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
            370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
            405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
            450                 455                 460

Glu Ala Leu His Asn His Tyr Thr Gln Lys Ser Leu Ser Leu Ser Pro
465                 470                 475                 480

Gly Lys

<210> SEQ ID NO 61
<211> LENGTH: 482
<212> TYPE: PRT
<213> ORGANISM: Homo Sapiens

<400> SEQUENCE: 61

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
            50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
            85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
            130                 135                 140

Phe Leu Pro Gly Met Asn Pro Pro Tyr Ser Ala Phe Leu Ser Arg
145                 150                 155                 160

Arg Asn Glu Ile Pro Leu Ile His Phe Asn Thr Pro Ile Pro Arg Arg
            165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
            195                 200                 205

Glu Leu Pro Ser Ala Glu Asp Asn Ser Pro Met Ala Ser Asp Pro Leu
            210                 215                 220
```

```
Gly Val Val Arg Gly Arg Val Asn Thr His Ala Gly Gly Thr Gly
225                 230                 235                 240

Pro Glu Gly Cys Arg Pro Phe Ala Lys Phe Ile Gly Gly Gly Ser
            245                 250                 255

Lys Thr His Thr Cys Pro Pro Cys Pro Ala Pro Glu Ala Ala Gly Gly
                260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 62
<211> LENGTH: 482
<212> TYPE: PRT
<213> ORGANISM: Homo Sapiens

<400> SEQUENCE: 62

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110
```

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
                180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
        210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Lys Thr His Thr Cys Pro Pro Cys Pro Ala Pro Glu Ala Ala Gly Gly
        260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
        370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 63
<211> LENGTH: 482
<212> TYPE: PRT
<213> ORGANISM: Homo Sapiens

<400> SEQUENCE: 63

```
Met Leu Gly Ala Arg Leu Arg Leu Trp Val Cys Ala Leu Cys Ser Val
1               5                   10                  15
Cys Ser Met Ser Val Leu Arg Ala Tyr Pro Asn Ala Ser Pro Leu Leu
            20                  25                  30
Gly Ser Ser Trp Gly Gly Leu Ile His Leu Tyr Thr Ala Thr Ala Arg
        35                  40                  45
Asn Ser Tyr His Leu Gln Ile His Lys Asn Gly His Val Asp Gly Ala
    50                  55                  60
Pro His Gln Thr Ile Tyr Ser Ala Leu Met Ile Arg Ser Glu Asp Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asp Pro Glu Asn
            100                 105                 110
Cys Arg Phe Gln His Gln Thr Leu Glu Asn Gly Tyr Asp Val Tyr His
        115                 120                 125
Ser Pro Gln Tyr His Phe Leu Val Ser Leu Gly Arg Ala Lys Arg Ala
    130                 135                 140
Phe Leu Pro Gly Met Asn Pro Pro Tyr Ser Ala Phe Leu Ser Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Ser Glu Arg Asp Pro Leu Asn Val
            180                 185                 190
Leu Lys Pro Arg Ala Arg Met Thr Pro Ala Pro Ala Ser Ser Ser Gln
        195                 200                 205
Glu Leu Pro Ser Ala Glu Asp Asn Ser Pro Met Ala Ser Asp Pro Leu
    210                 215                 220
Gly Val Val Arg Gly Gly Arg Val Asn Thr His Ala Gly Gly Thr Gly
225                 230                 235                 240
Pro Glu Gly Ser Arg Pro Phe Ala Lys Phe Ile Gly Gly Gly Ser
                245                 250                 255
Lys Thr His Thr Cys Pro Pro Cys Pro Ala Pro Glu Ala Ala Gly Gly
            260                 265                 270
Pro Ser Val Phe Leu Phe Pro Pro Lys Pro Lys Asp Thr Leu Met Ile
        275                 280                 285
Ser Arg Thr Pro Glu Val Thr Cys Val Val Val Asp Val Ser His Glu
    290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
            340                 345                 350
Glu Tyr Lys Cys Lys Val Ser Asn Lys Ala Leu Pro Ala Pro Ile Glu
        355                 360                 365
Lys Thr Ile Ser Lys Ala Lys Gly Gln Pro Arg Glu Pro Gln Val Tyr
    370                 375                 380
Thr Leu Pro Pro Ser Arg Glu Glu Met Thr Lys Asn Gln Val Ser Leu
385                 390                 395                 400
Thr Cys Leu Val Lys Gly Phe Tyr Pro Ser Asp Ile Ala Val Glu Trp
                405                 410                 415
```

```
Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 64
<211> LENGTH: 473
<212> TYPE: PRT
<213> ORGANISM: Homo Sapiens

<400> SEQUENCE: 64

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val Leu
            180                 185                 190

Lys Pro Arg Ala Arg Met Thr Pro Ala Pro Ala Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300
```

```
Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 65
<211> LENGTH: 473
<212> TYPE: PRT
<213> ORGANISM: Homo Sapiens

<400> SEQUENCE: 65

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
            50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
            85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
            130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
            165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
            195                 200                 205
```

```
Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 66
<211> LENGTH: 473
<212> TYPE: PRT
<213> ORGANISM: Homo Sapiens

<400> SEQUENCE: 66

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
```

```
            100             105               110
Cys Arg Phe Gln His Gln Thr Leu Glu Asn Gly Tyr Asp Val Tyr His
            115             120             125
Ser Pro Gln Tyr His Phe Leu Val Ser Leu Gly Arg Ala Lys Arg Ala
        130             135             140
Phe Leu Pro Gly Met Asn Pro Pro Tyr Ser Ala Phe Leu Ser Arg
145             150             155             160
Arg Asn Glu Ile Pro Leu Ile His Phe Asn Thr Pro Ile Pro Arg Arg
            165             170             175
His Thr Gln Ser Ala Glu Asp Ser Glu Arg Asp Pro Leu Asn Val
        180             185             190
Leu Lys Pro Arg Ala Arg Met Thr Pro Ala Pro Ala Ser Cys Ser Gln
    195             200             205
Glu Leu Pro Ser Ala Glu Asp Asn Ser Pro Met Ala Ser Asp Pro Leu
    210             215             220
Gly Val Val Arg Gly Gly Arg Val Asn Thr His Ala Gly Gly Thr Gly
225             230             235             240
Pro Glu Gly Cys Arg Pro Phe Ala Lys Phe Ile Gly Gly Gly Ser
            245             250             255
Ala Pro Glu Ala Ala Gly Gly Pro Ser Val Phe Leu Phe Pro Pro Lys
        260             265             270
Pro Lys Asp Thr Leu Met Ile Ser Arg Thr Pro Glu Val Thr Cys Val
        275             280             285
Val Val Asp Val Ser His Glu Asp Pro Glu Val Lys Phe Asn Trp Tyr
    290             295             300
Val Asp Gly Val Glu Val His Asn Ala Lys Thr Lys Pro Arg Glu Glu
305             310             315             320
Gln Tyr Asn Ser Thr Tyr Arg Val Val Ser Val Leu Thr Val Leu His
            325             330             335
Gln Asp Trp Leu Asn Gly Lys Glu Tyr Lys Cys Lys Val Ser Asn Lys
        340             345             350
Ala Leu Pro Ala Pro Ile Glu Lys Thr Ile Ser Lys Ala Lys Gly Gln
    355             360             365
Pro Arg Glu Pro Gln Val Tyr Thr Leu Pro Pro Ser Arg Glu Glu Met
    370             375             380
Thr Lys Asn Gln Val Ser Leu Thr Cys Leu Val Lys Gly Phe Tyr Pro
385             390             395             400
Ser Asp Ile Ala Val Glu Trp Glu Ser Asn Gly Gln Pro Glu Asn Asn
            405             410             415
Tyr Lys Thr Thr Pro Pro Val Leu Asp Ser Asp Gly Ser Phe Phe Leu
        420             425             430
Tyr Ser Lys Leu Thr Val Asp Lys Ser Arg Trp Gln Gln Gly Asn Val
    435             440             445
Phe Ser Cys Ser Val Met His Glu Ala Leu His Asn His Tyr Thr Gln
    450             455             460
Lys Ser Leu Ser Leu Ser Pro Gly Lys
465             470

<210> SEQ ID NO 67
<211> LENGTH: 473
<212> TYPE: PRT
<213> ORGANISM: Homo Sapiens

<400> SEQUENCE: 67
```

-continued

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

-continued

```
                   420                 425                 430
Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 68
<211> LENGTH: 473
<212> TYPE: PRT
<213> ORGANISM: Homo Sapiens

<400> SEQUENCE: 68

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Ala Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 69
<211> LENGTH: 251
<212> TYPE: PRT
<213> ORGANISM: Homo Sapiens

<400> SEQUENCE: 69

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220
```

```
Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 70
<211> LENGTH: 251
<212> TYPE: PRT
<213> ORGANISM: Macaca mulatta

<400> SEQUENCE: 70

```
Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
                100                 105                 110

Cys Arg Phe Arg His Trp Thr Leu Glu Asn Gly Tyr Asp Val Tyr His
            115                 120                 125

Ser Pro Gln His His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
210                 215                 220

Gly Val Val Arg Gly Gly Arg Val Asn Thr His Ala Gly Gly Thr Gly
225                 230                 235                 240

Pro Glu Ala Cys Arg Pro Phe Pro Lys Phe Ile
                245                 250
```

<210> SEQ ID NO 71
<211> LENGTH: 245
<212> TYPE: PRT
<213> ORGANISM: Bos taurus

<400> SEQUENCE: 71

```
Met Leu Gly Ala Arg Leu Gly Leu Trp Val Cys Thr Leu Ser Cys Val
1               5                   10                  15

Val Gln Ala Tyr Pro Asn Ser Ser Pro Leu Leu Gly Ser Ser Trp Gly
                20                  25                  30

Gly Leu Thr His Leu Tyr Thr Ala Thr Ala Arg Asn Ser Tyr His Leu
            35                  40                  45
```

-continued

```
Gln Ile His Gly Asp Gly His Val Asp Gly Ser Pro Gln Gln Thr Val
    50                  55                  60

Tyr Ser Ala Leu Met Ile Arg Ser Glu Asp Ala Gly Phe Val Val Ile
 65                  70                  75                  80

Thr Gly Val Met Ser Arg Arg Tyr Leu Cys Met Asp Phe Thr Gly Asn
                 85                  90                  95

Ile Phe Gly Ser His His Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Arg Ala Lys Arg Ala Phe Leu Pro Gly Thr
    130                 135                 140

Asn Pro Pro Tyr Ala Gln Phe Leu Ser Arg Arg Asn Glu Ile Pro
145                 150                 155                 160

Leu Pro His Phe Ala Ala Thr Ala Arg Pro Arg Arg His Thr Arg Ser
                165                 170                 175

Ala His Asp Ser Gly Asp Pro Leu Ser Val Leu Lys Pro Arg Ala Arg
            180                 185                 190

Ala Thr Pro Val Pro Ala Ala Cys Ser Gln Glu Leu Pro Ser Ala Glu
        195                 200                 205

Asp Ser Gly Pro Ala Ala Ser Asp Pro Leu Gly Val Leu Arg Gly His
    210                 215                 220

Arg Leu Asp Val Arg Ala Gly Ser Ala Gly Ala Glu Arg Cys Arg Pro
225                 230                 235                 240

Phe Pro Gly Phe Ala
                245

<210> SEQ ID NO 72
<211> LENGTH: 251
<212> TYPE: PRT
<213> ORGANISM: Mus musculus

<400> SEQUENCE: 72

Met Leu Gly Thr Cys Leu Arg Leu Leu Val Gly Val Leu Cys Thr Val
  1               5                  10                  15

Cys Ser Leu Gly Thr Ala Arg Ala Tyr Pro Asp Thr Ser Pro Leu Leu
                 20                  25                  30

Gly Ser Asn Trp Gly Ser Leu Thr His Leu Tyr Thr Ala Thr Ala Arg
             35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
 65                  70                  75                  80

Gly Ser Val Val Ile Thr Gly Ala Met Thr Arg Arg Phe Leu Cys Met
                 85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175
```

His Thr Arg Ser Ala Glu Asp Pro Pro Glu Arg Asp Pro Leu Asn Val
                180                 185                 190

Leu Lys Pro Arg Pro Arg Ala Thr Pro Val Pro Val Ser Cys Ser Arg
            195                 200                 205

Glu Leu Pro Ser Ala Glu Glu Gly Gly Pro Ala Ala Ser Asp Pro Leu
        210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250

<210> SEQ ID NO 73
<211> LENGTH: 251
<212> TYPE: PRT
<213> ORGANISM: Rattus norvegicus

<400> SEQUENCE: 73

Met Leu Gly Ala Cys Leu Arg Leu Leu Val Gly Ala Leu Cys Thr Val
1               5                   10                  15

Cys Ser Leu Gly Thr Ala Arg Ala Tyr Ser Asp Thr Ser Pro Leu Leu
                20                  25                  30

Gly Ser Asn Trp Gly Ser Leu Thr His Leu Tyr Thr Ala Thr Ala Arg
            35                  40                  45

Asn Ser Tyr His Leu Gln Ile His Arg Asp Gly His Val Asp Gly Thr
        50                  55                  60

Pro His Gln Thr Ile Tyr Ser Ala Leu Met Ile Thr Ser Glu Asp Ala
65                  70                  75                  80

Gly Ser Val Val Ile Ile Gly Ala Met Thr Arg Arg Phe Leu Cys Met
                85                  90                  95

Asp Leu Arg Gly Asn Ile Phe Gly Ser Tyr His Phe Ser Pro Glu Asn
                100                 105                 110

Cys Arg Phe Arg Gln Trp Thr Leu Glu Asn Gly Tyr Asp Val Tyr Leu
            115                 120                 125

Ser Pro Lys His His Tyr Leu Val Ser Leu Gly Arg Ser Lys Arg Ile
        130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Ala Arg Pro Arg Arg
                165                 170                 175

His Thr Arg Ser Ala Glu Asp Pro Pro Glu Arg Asp Pro Leu Asn Val
                180                 185                 190

Leu Lys Pro Arg Pro Arg Ala Thr Pro Ile Pro Val Ser Cys Ser Arg
            195                 200                 205

Glu Leu Pro Ser Ala Glu Glu Gly Gly Pro Ala Ala Ser Asp Pro Leu
        210                 215                 220

Gly Val Leu Arg Arg Gly Arg Gly Asp Ala Arg Gly Gly Ala Gly Gly
225                 230                 235                 240

Thr Asp Arg Cys Arg Pro Phe Pro Arg Phe Val
                245                 250